US009822385B2

(12) United States Patent
Hara et al.

(10) Patent No.: US 9,822,385 B2
(45) Date of Patent: Nov. 21, 2017

(54) METHOD FOR PRODUCING AN L-GLUTAMIC ACID AND L-ASPARTIC ACID USING A RECOMBINANT MICROORGANISM HAVING ENHANCED EXPRESSION OF A YBJL PROTEIN

(71) Applicant: AJINOMOTO CO., INC., Tokyo (JP)

(72) Inventors: Yoshihiko Hara, Kanagawa (JP); Keita Fukui, Kanagawa (JP); Yoshinori Tajima, Kanagawa (JP); Kazue Kawamura, Kanagawa (JP); Yoshihiro Usuda, Kanagawa (JP); Kazuhiko Matsui, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 46 days.

(21) Appl. No.: 14/723,776

(22) Filed: May 28, 2015

(65) Prior Publication Data

US 2015/0259717 A1 Sep. 17, 2015

Related U.S. Application Data

(60) Division of application No. 12/579,577, filed on Oct. 15, 2009, now abandoned, which is a continuation of application No. PCT/JP2008/057478, filed on Apr. 17, 2008.

(30) Foreign Application Priority Data

Apr. 17, 2007 (JP) ................................ 2007-108631
Sep. 19, 2007 (JP) ................................ 2007-242859

(51) Int. Cl.

| | |
|---|---|
| ***C12P 13/14*** | (2006.01) |
| ***C07K 14/195*** | (2006.01) |
| ***C07K 14/245*** | (2006.01) |
| ***C07K 14/265*** | (2006.01) |
| ***C12P 7/46*** | (2006.01) |
| ***C12P 7/48*** | (2006.01) |
| ***C12P 7/50*** | (2006.01) |
| ***C12P 13/20*** | (2006.01) |

(52) U.S. Cl.
CPC ............ *C12P 13/14* (2013.01); *C07K 14/195* (2013.01); *C07K 14/245* (2013.01); *C07K 14/265* (2013.01); *C12P 7/46* (2013.01); *C12P 7/48* (2013.01); *C12P 7/50* (2013.01); *C12P 13/20* (2013.01)

(58) Field of Classification Search
None
See application file for complete search history.

(56) References Cited

U.S. PATENT DOCUMENTS

| | | | |
|---|---|---|---|
| 3,220,929 | A | 11/1965 | Kinoshita et al. |
| 3,563,857 | A | 2/1971 | Oki et al. |
| 5,142,834 | A | 9/1992 | Laclave et al. |
| 5,504,004 | A | 4/1996 | Guettler et al. |
| 5,573,945 | A | 11/1996 | Ono et al. |
| 6,682,912 | B2 | 1/2004 | Moriya et al. |
| 6,911,332 | B2 | 6/2005 | Usuda et al. |
| 6,979,560 | B1 | 12/2005 | Livshits et al. |
| 7,026,149 | B2 | 4/2006 | Usuda et al. |
| 7,029,893 | B2 | 4/2006 | Usuda et al. |
| 7,060,475 | B2 | 6/2006 | Usuda et al. |
| 7,090,998 | B2 | 8/2006 | Ishikawa et al. |
| 7,192,748 | B2 | 3/2007 | Usuda et al. |
| 7,220,570 | B2 | 5/2007 | Usuda et al. |
| 7,247,459 | B1 | 7/2007 | Izui et al. |
| 7,306,933 | B2 | 12/2007 | Van Dien et al. |
| 7,344,874 | B2 | 3/2008 | Hara et al. |
| 7,468,262 | B2 | 12/2008 | Usuda et al. |
| 7,501,282 | B2 | 3/2009 | Hara et al. |
| 7,919,284 | B2 | 4/2011 | Takikawa et al. |
| 8,058,035 | B2 | 11/2011 | Hara et al. |
| 8,076,111 | B2 | 12/2011 | Fukui et al. |
| 8,080,396 | B2 | 12/2011 | Shiraga et al. |
| 8,512,987 | B2 | 8/2013 | Nagai et al. |
| 8,551,741 | B2 | 10/2013 | Usuda et al. |
| 2001/0009836 | A1 | 7/2001 | Nakanishi et al. |
| 2002/0115159 | A1 | 8/2002 | Farwick et al. |
| 2002/0142404 | A1 | 10/2002 | Farwick et al. |
| 2002/0155556 | A1 | 10/2002 | Imaizumi et al. |
| 2004/0265956 | A1 | 12/2004 | Takikawa et al. |
| 2005/0170482 | A1 | 8/2005 | San et al. |
| 2005/0196846 | A1 | 9/2005 | Hara et al. |
| 2005/0233308 | A1 | 10/2005 | Nishio et al. |
| 2005/0239177 | A1 | 10/2005 | Livshits et al. |
| 2006/0003424 | A1 | 1/2006 | Asakura et al. |
| 2006/0040365 | A1 | 2/2006 | Kozlov et al. |

(Continued)

FOREIGN PATENT DOCUMENTS

| | | |
|---|---|---|
| EP | 1004663 | 5/2000 |
| EP | 1038970 | 9/2000 |
| JP | 32-9393 | 11/1932 |
| JP | 05-244970 | 9/1993 |
| JP | 07-121228 | 12/1995 |
| JP | 11-113588 | 4/1999 |
| JP | 11-196887 | 7/1999 |
| JP | 11-196888 | 7/1999 |
| WO | WO97/23597 | 7/1997 |
| WO | WO00/37647 | 6/2000 |
| WO | WO01/05959 | 1/2001 |
| WO | WO2006/069610 A2 | 7/2006 |
| WO | WO2009/116566 | 9/2009 |

OTHER PUBLICATIONS

Database UniProt [online], Apr. 13, 2004, [retrieved from the internet on Jun. 10, 2008], UniProtKB Entry: P60869, putative transport protein ybjL.

(Continued)

*Primary Examiner* — Sheridan Swope
(74) *Attorney, Agent, or Firm* — Cermak Nakajima & McGowan LLP; Shelly Guest Cermak

(57) ABSTRACT

An acidic substance having a carboxyl group is produced by culturing in a medium a microorganism which has been modified to enhance expression of the ybjL gene, and collecting the acidic substance having a carboxyl group from the medium.

6 Claims, 5 Drawing Sheets

(56) References Cited

U.S. PATENT DOCUMENTS

| | | | |
|---|---|---|---|
| 2006/0088919 | A1 | 4/2006 | Rybak et al. |
| 2006/0234356 | A1 | 10/2006 | Usuda et al. |
| 2006/0234357 | A1 | 10/2006 | Usuda et al. |
| 2007/0134773 | A1 | 6/2007 | Izui et al. |
| 2007/0249017 | A1 | 10/2007 | Usuda et al. |
| 2007/0254345 | A1 | 11/2007 | Fukui et al. |
| 2009/0068712 | A1 | 3/2009 | Terashita et al. |
| 2009/0093029 | A1 | 4/2009 | Usuda et al. |
| 2009/0104659 | A1 | 4/2009 | Smirnov et al. |
| 2009/0148915 | A1 | 6/2009 | Van Dien et al. |
| 2009/0203090 | A1 | 8/2009 | Ptitsyn et al. |
| 2009/0215131 | A1 | 8/2009 | Hara et al. |
| 2009/0226981 | A1 | 9/2009 | Hara et al. |
| 2009/0239269 | A1 | 9/2009 | Tajima et al. |
| 2009/0246835 | A1 | 10/2009 | Iwatani et al. |
| 2010/0068774 | A1 | 3/2010 | Fukui et al. |
| 2010/0112647 | A1 | 5/2010 | Hara et al. |
| 2011/0111458 | A1 | 5/2011 | Masuda et al. |

OTHER PUBLICATIONS

Hayashi, K., et al., "Highly accurate genome sequences of *Escherichia coli* K-12 strains MG1655 and W3110," Mol. Sys. Biol. 2006, vol. 2, Article No. 2006.0007, pp. 1-5.

International Search Report for PCT Patent App. No. PCT/JP2008/057478 (Jun. 24, 2008).

Blattner, F. R., et al., "The Complete Genome Sequence of *Escherichia coli* K-12," Science 1997;277:1453-1474.

Guettler, M. V., et al., "*Actinobacillus succinogenes* sp. Nov., a novel succinic-acid-producing strain from the bovine rumen," Int. J. Systemic Bacteriol. 1999;49:207-216.

Kikuchi, M., et al., "Glutamic Acid," Biotechnology of Amino Acid Production, Progress in Industrial Microbiology, vol. 24, 1986, pp. 101-116.

Vemuri, G. N., et al., "Succinate production in dual-phase *Escherichia coli* fermentations depends on the time of transition from aerobic to anaerobic conditions," J. Industrial Microbiol. Biotechnol. 2002;28:325-332.

International Preliminary Report on Patentability for PCT Patent App. No. PCT/JP2008/057478 (Nov. 19, 2009).

Kitagawa, M., et al., "Complete set of ORF clones of *Escherichia coli* ASKA library (A Complete Set of *E. coli* K-12 ORF Archive): Unique Resources for Biological Research," DNA Research 2005;12(5):291-299.

Notice of Reason for Rejection for Japanese Patent App. No. 2009-511838 (Nov. 13, 2012) with English translation thereof.

Galye et al., "Identification of regions in interleukin-1 alpha important for activity," J. Biol. Chem. 1993;26(29):22105-22111.

Whisstock et al., "Prediction of protein function from protein sequence and structure," Q. Rev. Biophys. 2003;36(3):307-340.

Abe et al., "Plasmid-Encoded asp Operon Confers a Proton Motive Metabolic Cycle Catalyzed by an Aspartate-Alanine Exchange Reaction," J. Bacteriol. Jun. 2002;2906-2913.

Nanatani et al., "Topology of AspT, the Aspartate:Alanine Antiporter of Tetragenococcus halophilus, Determined by Site-Directed Fluorescence Labeling," J. Bacteriol. 2007;189(19):7089-7097.

Brenda 2.6.1.1 aspartate transaminase. Retrieved Jan. 23, 2014.

Kegg Alanine, Aspartate, and Glutamate Metabolism. Retrieved Jan. 23, 2014.

Andersson, D. I., et al., "Gene Amplification and Adaptive Evolution in Bacteria," Annual Review of Genetics 2009; 43:167-195.

Supplementary European Search Report for European Patent App. No. 08740548.6 dated Apr. 22, 2010.

METHOD FOR PRODUCING AN L-GLUTAMIC ACID AND L-ASPARTIC ACID USING A RECOMBINANT MICROORGANISM HAVING ENHANCED EXPRESSION OF A YBJL PROTEIN

This application is a Divisional of, and claims priority under 35 U.S.C. §120 to, U.S. patent application Ser. No. 12/579,577, filed Oct. 15, 2009, which was a Continuation under 35 U.S.C. §120 of PCT Patent Application No. PCT/JP2008/057478, filed Apr. 17, 2008, which claimed priority under 35 U.S.C. §119 to Japanese Patent Application No. 2007-108631, filed on Apr. 17, 2007, and Japanese Patent Application No. 2007-242859, filed on Sep. 19, 2007, which are incorporated in their entireties by reference herein. Also, the Sequence Listing filed electronically herewith is hereby incorporated by reference (File name: 2015-05-28T_US-408D_Seq_List; File size: 240 KB; Date recorded: May 28, 2015).

BACKGROUND OF THE INVENTION

Field of the Invention

The present invention relates to a method for producing an acidic substance having a carboxyl group. L-Glutamic acid and L-aspartic acid are widely used as raw materials in making seasonings and so forth. Succinic acid is widely used as a raw material in making seasonings and biodegradable plastics.

Brief Description of the Related Art

L-Glutamic acid is mainly produced by fermentation utilizing L-glutamic acid-producing bacteria of the so-called coryneform bacteria belonging to the genus *Brevibacterium, Corynebacterium* or *Microbacterium*, or their mutant strains (see, for example, Kunihiko Akashi et al., Amino Acid Fermentation, Japan Scientific Societies Press (Gakkai Shuppan Center), pp. 195-215, 1986). Methods are known for producing L-glutamic acid by fermentation using other bacterial strains, including microorganisms belonging to the genera *Bacillus, Streptomyces, Penicillium* or the like (see, for example, U.S. Pat. No. 3,220,929), microorganisms belonging to the genera *Pseudomonas, Arthrobacter, Serratia, Candida* or the like (see, for example, U.S. Pat. No. 3,563,857), microorganisms belonging to the genera *Bacillus, Pseudomonas, Serratia, Aerobacter aerogenes* (currently referred to as *Enterobacter aerogenes*) or the like (see, for example, Japanese Patent Publication (KOKOKU) No. 32-9393), a mutant strain of *Escherichia coli* (see, for example, Japanese Patent Laid-open (KOKAI) No. 5-244970), and the like. In addition, methods for producing L-glutamic acid have also been disclosed using microorganisms belonging to the genera *Klebsiella, Erwinia, Pantoea* or *Enterobacter* (see, for example, Japanese Patent Laid-open No. 2000-106869 (U.S. Pat. No. 6,682,912), Japanese Patent Laid-open No. 2000-189169 (U.S. Patent Published Application No. 2001009836), Japanese Patent Laid-open No. 2000-189175 (U.S. Pat. No. 7,247,459)).

Furthermore, various techniques have been disclosed for increasing the L-glutamic acid-producing ability by enhancing the L-glutamic acid biosynthetic enzymes using recombinant DNA techniques. For example, it has been reported for *Corynebacterium* or *Brevibacterium* bacteria that introduction of a gene coding for citrate synthase derived from *Escherichia coli* or *Corynebacterium glutamicum* was effective to enhance the L-glutamic acid-producing ability of coryneform bacteria (see, for example, Japanese Patent Publication No. 7-121228). Furthermore, it has also been reported that introduction of a citrate synthase gene derived from a coryneform bacterium into enterobacteria belonging to the genera *Enterobacter, Klebsiella, Serratia, Erwinia* or *Escherichia* was effective to enhance the bacteria's L-glutamic acid-producing ability (see, for example, Japanese Patent Laid-open No. 2000-189175 (U.S. Pat. No. 7,247,459)).

Methods for improving the production of target substances such as amino acids are also known, including by modifying the uptake or secretion systems of target substances. Such methods include, for example, by deleting or attenuating the system for uptake of a target substance into cells. Specifically, known methods to improve production of L-glutamic acid include deleting the gluABCD operon, or a part thereof, to eliminate or attenuate uptake of L-glutamic acid into cells (see, for example, European Patent Application Laid-open No. 1038970), and enhancing production of purine nucleotides by attenuating uptake of purine nucleotides into cells (see, for example, European Patent Application Laid-open No. 1004663), and the like.

Furthermore, methods of enhancing the secretion system for a target substance, and methods of deleting or attenuating the secretion system for an intermediate or substrate in the biosynthetic system of a target substance are known. Known methods of enhancing the secretion system of a target substance include, for example, production of L-lysine by utilizing a *Corynebacterium* strain in which the L-lysine secretion gene (lysE) is enhanced (see, for example, WO2001/5959), and production of L-glutamic acid by using an enterobacterium in which the L-glutamic acid secretion system gene (yhfK) is enhanced (see, for example, Japanese Patent Laid-open No. 2005-278643 (U.S. Patent Published Application No. 2005196846)). Furthermore, methods for producing an L-amino acid using the rhtA, B, C genes, which have been suggested to be involved in the secretion of L-amino acids, have also been reported (see, for example, Japanese Patent Laid-open No. 2000-189177 (U.S. Patent Published Application No. 2005239177)). Known methods for, for example, deleting a secretion system for an intermediate or substrate in a biosynthesis system of a target substance include, for L-glutamic acid, mutating or disrupting the 2-oxoglutarate permease gene to attenuate secretion of 2-oxoglutarate, which is an intermediate of the target substance (see, for example, WO97/23597).

Furthermore, use of the gene coding for the ATP binding cassette superfamily (ABC transporter), which is involved in transportation of substances through cell membranes, in the breeding of microorganisms in which transmembrane transportation of amino acids is modified has been suggested (see, for example, WO00/37647).

Furthermore, it has also been reported that L-glutamic acid production efficiency can be improved in *Escherichia* bacteria by enhancing the expression of genes thought to participate in secretion of L-amino acids such as yfiK (see, for example, Japanese Patent Laid-open No. 2000-189180 (U.S. Pat. No. 6,979,560)). Moreover, it has also been reported that L-glutamic acid-producing ability can be improved by enhancing expression of the yhfK gene (see, for example, Japanese Patent Laid-open No. 2005-278643 (U.S. Patent Published Application No. 2005196846)).

Moreover, methods are known for producing L-glutamic acid by culturing a microorganism under acidic conditions to precipitate the L-glutamic acid (see, for example, Japanese Patent Laid-open No. 2001-333769 (U.S. Patent Published Application No. 2007134773)). When the pH is kept low, L-glutamic acid is precipitated, and the ratio of L-glutamic acid in free form with no electrical charge increases. As a result, the L-glutamic acid easily penetrates cell membranes. When L-glutamic acid is taken up into cells, it is converted into an intermediate of the TCA cycle, 2-oxoglutaric acid, in one step by glutamate dehydrogenase, and therefore it is generally thought that L-glutamic acid taken up into cells is easily metabolized. However, 2-oxoglutarate dehydrogenase activity can be deleted or attenuated, or the like, in the fermentative production of L-glutamic acid (for example, Japanese Patent Laid-open No. 2001-333769 (U.S. Patent Published Application No. 2007134773), Japanese Patent Laid-open No. 7-203980 (U.S. Pat. No. 5,573,945)), but then 2-oxoglutaric acid is not degraded, intracellular 2-oxoglutaric acid concentration increases which inhibits the growth of the microorganism. Thus, the culture fails. Therefore, as described in Japanese Patent Laid-open No. 2001-333769 (U.S. Patent Published Application No. 2007134773), a strain was bred using a mutation that is deficient in 2-oxoglutarate dehydrogenase activity and can produce L-glutamic acid accompanying precipitation, and this strain can be used for the production of L-glutamic acid.

For fermentative production of non-amino organic acids, including succinic acid, anaerobic bacteria including those belonging to the genus *Anaerobiospirillum* or *Actinobacillus* are usually used (U.S. Pat. Nos. 5,142,834 and 5,504,004, Guettler, M. V. et al., 1999, International Journal of Systematic Bacteriology, 49:207-216). Although the use of such anaerobic bacteria provides high product yields, many nutrients are required for sufficient proliferation, and therefore, it is necessary to add large amounts of organic nitrogen sources such as corn steep liquor (CSL) into the culture medium. The addition of large amounts of organic nitrogen sources can result in not only an increase in the cost of the culture, but also an increase in the cost for isolating or purifying the product, and therefore, their use is not economical.

In addition, methods are known in which aerobic bacteria such as coryneform bacteria are cultured once under aerobic conditions, then harvested, washed, and allowed to rest, producing a non-amino organic acid in the absence of supplied oxygen (Japanese Patent Laid-open Nos. 11-113588 and 11-196888). These methods are economical since a smaller amount of organic nitrogen can be added, and the bacteria will sufficiently grow in a simple culture medium. However, there is still a room for improvement in terms of production amount, concentration, and production rate per cell of the target organic acids, as well as simplification of the production process, and the like. Furthermore, the production of a non-amino organic acid by fermentation using a bacterium in which phosphoenolpyruvate carboxylase activity is enhanced (for example, Japanese Patent Laid-open No. 11-196887), and the like have also been reported.

Furthermore, as for *Escherichia coli*, which is a facultative anaerobic gram negative bacterium, methods for producing a non-amino organic acid by culturing it once under aerobic conditions, and then allowing the cells to rest in the absence of supplied oxygen, resulting in an anaerobically produced non-amino organic acid (Vemuri G. N. et al., 2002, Journal of Industrial Microbiology and Biotechnology, 28(6):325-332). This is similar to the methods using coryneform bacteria. Alternatively, *E. coli* can be aerobically cultured to aerobically produce the non-amino organic acid (U.S. Patent Published Application No. 20050170482). However, since *Escherichia coli* is a gram negative bacterium, it is vulnerable to osmotic pressure, and there remains room for improvement in productivity per cell etc.

The ybjL gene is located on the genome of *Escherichia coli* (see, for example, Blattner, F. R. et al., 1997, Science, 277(5331):1453-74), and it is also thought to code for a transporter on the basis of the motifs, topology etc. of the deduced amino acid sequence. However, cloning of the gene, as well as expression of the gene and analysis of the expression product have not been reported, and the actual functions of the gene remained unknown.

SUMMARY OF THE INVENTION

An aspect of the present invention is to provide a bacterial strain that can efficiently produce an acidic substance having a carboxyl group, especially L-glutamic acid, L-aspartic acid, and succinic acid, and to provide a method for efficiently producing an acidic substance having a carboxyl group by using such a strain.

The ybjL gene was isolated and shown to be involved in L-glutamic acid resistance. Also, it has been found that when the expression of the ybjL gene is enhanced, L-glutamic acid fermentation yield is improved and the production rate or yield of succinic acid is improved.

It is an aspect of the present invention to provide a microorganism that has an ability to produce an acidic substance having a carboxyl group and has been modified to enhance expression of the ybjL gene.

It is a further aspect of the present invention to provide the aforementioned microorganism, wherein enhanced expression is obtained by a method selected from the group consisting of: A) increasing copy number of the ybjL gene, B) modifying an expression control sequence of the ybjL gene, and C) combinations thereof.

It is a further aspect of the present invention to provide the aforementioned microorganism, wherein the ybjL gene encodes a protein: (A) a protein comprising an amino acid sequence selected from the group consisting of SEQ ID NO: 2, 4 and 87; (B) a protein comprising an amino acid sequence selected from the group consisting of SEQ ID NO: 2, 4 and 87, but wherein one or several amino acid residues are substituted, deleted, inserted or added, and the protein improves the ability of the microorganism to produce an acidic substance having a carboxyl group when expression of the gene encoding the protein is enhanced in the microorganism.

It is a further aspect of the present invention to provide the aforementioned microorganism, wherein the ybjL gene encodes the protein selected from the group consisting of SEQ ID NO: 5 and 88.

It is a further aspect of the present invention to provide the aforementioned microorganism, wherein the microorganism is a bacterium belonging to the family Enterobacteriaceae.

It is a further aspect of the present invention to provide the aforementioned microorganism, wherein the bacterium belongs to a genus selected from the group consisting of *Escherichia, Enterobacter, Raoultella, Pantoea*, and *Klebsiella.*

It is a further aspect of the present invention to provide the aforementioned microorganism, wherein the microorganism is a rumen bacterium.

It is a further aspect of the present invention to provide the aforementioned microorganism, wherein the microorganism is *Mannheimia succiniciproducens.*

It is a further aspect of the present invention to provide the aforementioned microorganism, wherein the acidic substance is an organic acid selected from the group consisting of succinic acid, fumaric acid, malic acid, oxalacetic acid, citric acid, isocitric acid, α-ketoglutaric acid, and combinations thereof.

It is a further aspect of the present invention to provide the aforementioned microorganism, wherein the acidic substance is L-glutamic acid and/or L-aspartic acid.

It is a further aspect of the present invention to provide a method for producing an acidic substance having a carboxyl group comprising culturing the aforementioned microorganism in a medium to produce and accumulate the acidic substance having a carboxyl group in the medium, and collecting the acidic substance having a carboxyl group from the medium.

It is a further aspect of the present invention to provide the aforementioned method, wherein the acidic substance is an organic acid selected from the group consisting of succinic acid, fumaric acid, malic acid, oxalacetic acid, citric acid, isocitric acid, α-ketoglutaric acid, and combinations thereof.

It is a further aspect of the present invention to provide the aforementioned method, wherein the acidic substance is L-glutamic acid and/or L-aspartic acid.

It is a further aspect of the present invention to provide a method for producing an acidic substance having a carboxyl group comprising: A) allowing a substance to act on an organic raw material in a reaction mixture containing carbonate ions, bicarbonate ions, or carbon dioxide gas, wherein the substance is selected from the group consisting of i) the microorganism as described above, ii) a product obtained by processing the microorganism of i), and iii) combinations thereof, and collecting the acidic substance having a carboxyl group.

It is a further aspect of the present invention to provide the aforementioned method, wherein the acidic substance is an organic acid selected from the group consisting of succinic acid, fumaric acid, malic acid, oxalacetic acid, citric acid, isocitric acid, α-ketoglutaric acid, and combinations thereof.

It is a further aspect of the present invention to provide a method for producing a polymer comprising succinic acid comprising A) producing succinic acid by the aforementioned method, and B) polymerizing the succinic acid.

DETAILED DESCRIPTION OF THE PREFERRED EMBODIMENTS

Figure 1:
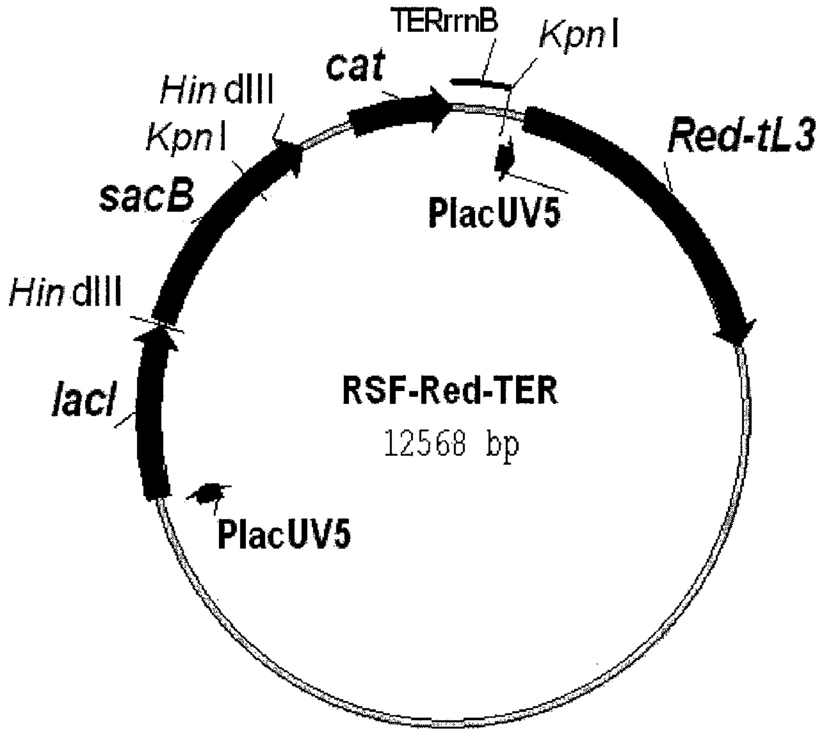
FIG. 1 shows the structure of helper plasmid RSF-Red-TER.

Hereinafter, the present invention will be explained in detail.

<1> Microorganism Having Ability to Produce Acidic Substance Having a Carboxyl Group The microorganism in accordance with the presently disclosed subject matter has an ability to produce an acidic substance having a carboxyl group and has been modified so that expression of the ybjL gene is enhanced. The term "ability to produce an acidic substance having a carboxyl group" can mean the ability of a microorganism to produce and cause accumulation of an acidic substance having a carboxyl group in a medium or cells to such a degree that the acidic substance having a carboxyl group can be collected from the cells or medium when the microorganism of the present invention is cultured in the medium. The microorganism can originally have the ability to produce an acidic substance having a carboxyl group, or the ability to produce an acidic substance can be obtained by modifying a microorganism such as those described below using mutation or recombinant DNA techniques. Also, a microorganism can be imparted with the ability to produce an acidic substance having a carboxyl group, or the ability to produce an acidic substance having a carboxyl group can be enhanced by introducing the gene described herein.

In the present invention, the "acidic substance having a carboxyl group" can mean an organic compound having one or more carboxyl groups and which is acidic when the substance is in the free form, and not in the salt form. Specifically, examples include organic acids and L-amino acids having two carboxyl groups, for example, acidic amino acids. Examples of the L-amino acids include L-glutamic acid and L-aspartic acid, and examples of the organic acids include succinic acid, fumaric acid, malic acid, oxalacetic acid, citric acid, isocitric acid, α-ketoglutaric acid, and the like.

The parent strain which can be used to derive the microorganism in accordance with the presently disclosed subject matter is not particularly limited, and can include bacteria, for example, Enterobacteriaceae, rumen bacteria, and coryneform bacteria.

The Enterobacteriaceae family encompasses bacteria belonging to the genera *Escherichia, Enterobacter, Erwinia, Klebsiella, Pantoea, Photorhabdus, Providencia, Raoultella, Salmonella, Serratia, Shigella, Morganella, Yersinia*, and the like. In particular, bacteria classified into the family Enterobacteriaceae according to the taxonomy used by the NCBI (National Center for Biotechnology Information) database are examples. Among these, bacteria belonging to the genus *Escherichia, Enterobacter, Raoultella, Pantoea, Klebsiella*, or *Serratia* are particular examples.

A "bacterium belonging to the genus *Escherichia*" means that the bacterium is classified into the genus *Escherichia* according to the classification known to a person skilled in the art of microbiology, although the bacterium is not particularly limited. Examples of the bacterium belonging to the genus *Escherichia* include, but are not limited to, *Escherichia coli* (*E. coli*). Other examples include, for example, the bacteria of the phyletic groups described in the work of Neidhardt et al. (Neidhardt F. C. Ed., 1996, *Escherichia coli* and *Salmonella*: Cellular and Molecular Biology/Second Edition, pp. 2477-2483, Table 1, American Society for Microbiology Press, Washington, D.C.). Specific examples include *Escherichia coli* W3110 (ATCC 27325), *Escherichia coli* MG1655 (ATCC 47076), and the like, and others derived from the prototype wild-type strain, the K12 strain.

These strains are available from, for example, the American Type Culture Collection (Address: 12301 10801 University Boulevard, Manassas, Va. 20108, United States of America). That is, registration numbers are given to each of the strains, and the strains can be ordered by using these numbers. The registration numbers of the strains are listed in the catalogue of the American Type Culture Collection.

*Pantoea, Erwinia*, and *Enterobacter* bacteria are classified as γ-proteobacteria, and they are taxonomically very close to one another (J. Gen. Appl. Microbiol., 1997, 43, 355-361; Int. J. Syst. Bacteriol., 1997, 43, 1061-1067). In recent years, some bacteria belonging to the genus *Enterobacter* were reclassified as *Pantoea agglomerans, Pantoea dispersa*, or the like, on the basis of DNA-DNA hybridization experiments etc. (Int. J. Syst. Bacteriol., 1989, 39:337-345). Furthermore, some bacteria belonging to the genus *Erwinia* were reclassified as *Pantoea ananas* or *Pantoea stewartii* (refer to Int. J. Syst. Bacteriol., 1993, 43:162-173).

Examples of the *Enterobacter bacteria* include *Enterobacter agglomerans, Enterobacter aerogenes*, and the like. Specifically, the strains exemplified in European Patent Application Laid-open No. 952221 can be used. Typical strains of the genus *Enterobacter* include *Enterobacter agglomerans* ATCC 12287, *Enterobacter aerogenes* ATCC 13048, *Enterobacter aerogenes* NBRC 12010 (Biotechnol Bioeng., 2007, Mar. 27; 98(2):340-348), and *Enterobacter aerogenes* AJ110637 (FERM ABP-10955), and the like. The AJ110637 strain was obtained from the soil at the seashore of Susuki Kaigan, Makinohara-shi, Shizuoka-ken on March, 2006 by cumulative liquid culture using glycerol as the carbon source. The full-length 16S rDNA sequence was then determined, and it was found to be 99.9% homologous to that from *Enterobacter aerogenes* NCTC 10006. Moreover, in a physiological test using an API kit, the strain gave results similar to the prototype species of *Enterobacter aerogenes*, and therefore it was identified as *Enterobacter aerogenes*. This strain was deposited at International Patent Organism Depository, Agency of Industrial Science and Technology (Central 6, 1-1, Higashi 1-Chome, Tsukuba-shi, Ibaraki-ken, 305-8566, Japan) on Aug. 22, 2007, and assigned an accession number of FERM P-21348. Then, the deposit was converted to an international deposit based on the Budapest Treaty on Mar. 13, 2008, and assigned an accession number of FERM ABP-10955.

Typical strains of the *Pantoea* bacteria include *Pantoea ananatis, Pantoea stewartii, Pantoea agglomerans*, and *Pantoea citrea*. Specific examples include the following strains:

*Pantoea ananatis* AJ13355 (FERM BP-6614, European Patent Laid-open No. 0952221)

*Pantoea ananatis* AJ13356 (FERM BP-6615, European Patent Laid-open No. 0952221)

Although these strains are described as *Enterobacter agglomerans* in European Patent Laid-open No. 0952221, they are currently classified as *Pantoea ananatis* on the basis of nucleotide sequence analysis of the 16S rRNA etc., as described above.

Examples of the *Erwinia* bacteria include *Erwinia amylovora* and *Erwinia carotovora*, examples of the *Klebsiella* bacteria include *Klebsiella planticola*, and examples of the *Raoultella* bacteria include *Raoultella planticola*. Specific examples include the following strains:

*Erwinia amylovora* ATCC 15580 strain

*Erwinia carotovora* ATCC 15713 strain

*Klebsiella planticola* AJ13399 strain (FERM BP-6600, European Patent Laid-open No. 955368)

*Klebsiella planticola* AJ13410 strain (FERM BP-6617, European Patent Laid-open No. 955368).

*Raouhella planticola* ATCC 33531 strain

Although the AJ13399 strain and the AJ13410 strain were classified as *Klebsiella planticola* at the time of the deposit, *Klebsiella planticola* is currently classified into *Raoultella planticola* (Drancourt, M., 2001, Int. J. Syst. Evol. Microbiol, 51:925-32).

Examples of rumen bacteria include *Mannheimia, Actinobacillus, Anaerobiospirillum, Pyrobacterium*, and *Selenomonas*. Bacteria including *Mannheimia succiniciproducens, Actinobacillus succinogenes, Selenomonas ruminantium, Veillonella parvula, Wolnella succino genes, Anaerobiospirillum succiniciproducens*, and the like, can be used. Specific strains include *Mannheimia* sp. 55E (KCTC0769BP strain, U.S. Patent Published Application No. 20030113885, International Patent Publication WO2005/052135).

<1-1> Imparting an Ability to Produce an Acidic Substance Having a Carboxyl Group Hereinafter, methods for imparting an ability to produce an acidic substance having a carboxyl group to bacteria, or methods for enhancing the ability to produce an acidic substance having a carboxyl group are described.

To impart an ability to produce an acidic substance having a carboxyl group, methods conventionally employed in the breeding of bacteria for producing substances by fermentation (see "Amino Acid Fermentation", Japan Scientific Societies Press, 1st Edition, published May 30, 1986, pp. 77-100) can be applied. Such methods include the acquisition of an auxotrophic mutant, an analogue-resistant strain, or a metabolic regulation mutant, or construction of a recombinant strain having enhanced expression of an enzyme involved in biosynthesis of acidic substances having a carboxyl group. In the breeding of bacteria that produce an acidic substance having a carboxyl group, one or more properties, such as auxotrophic mutation, analogue resistance, or metabolic regulation mutation, can be imparted. The expression of one or two or more enzymes involved in the biosynthesis of an acidic substance having a carboxyl group can be enhanced. Furthermore, the impartation of properties such as auxotrophic mutation, analogue resistance, or metabolic regulation mutation can be combined with the enhancement of the biosynthetic enzymes.

A mutant strain auxotrophic for an acidic substance having a carboxyl group, a strain resistant to an analogue of an acidic substance having a carboxyl group, or a metabolic regulation mutant strain can be obtained by subjecting a parent or wild-type strain to a conventional mutagenesis, such as exposure to X-rays or UV irradiation, or a treatment with a mutagen such as N-methyl-N'-nitro-N-nitrosoguanidine, and then selecting bacteria which exhibit an autotrophy, analogue resistance, or metabolic regulation mutation and which also have the ability to produce an acidic substance having a carboxyl group.

Methods for imparting an amino acid- or organic acid-producing ability to microorganisms, and amino acid- or organic acid-producing bacteria will be specifically exemplified below.

<L-Glutamic Acid-Producing Bacteria>

Examples of the method of modifying a microorganism to impart L-glutamic acid-producing ability to the microorganism include, for example, enhancing expression of a gene coding for an enzyme involved in L-glutamic acid biosynthesis. Examples of an enzyme involved in L-glutamic acid biosynthesis include glutamate dehydrogenase ("GDH") (gdh), glutamine synthetase (glnA), glutamate synthetase (gltAB), isocitrate dehydrogenase (icdA), aconitate hydratase (acnA, acnB), citrate synthase ("CS") (gltA), methylcitrate synthase (hereinafter also referred to as "PRPC" (prpC), phosphoenolpyruvate carboxylase ("PEPC") (ppc), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgml), phosphoglycerate kinase (pgk), glyceraldehyde-3-phosphate dehydrogenase (gapA), triose phosphate isomerase (tpiA), fructose bisphosphate aldolase (fbp), phosphofructokinase (pfkA, pfkB), and glucose phosphate isomerase (pgi), and the like. The capital letter abbreviations in parentheses after the enzyme names are the enzyme abbreviation, while the lower case abbreviations indicate the name of the gene encoding the enzyme.

Methods for modifying a microorganism to increase expression of a target gene will be explained below.

The first method is to increase the copy number of the target gene by cloning the target gene on an appropriate plasmid and transforming the chosen host bacterium with the obtained plasmid. For example, when the target gene is the gene coding for CS (gltA gene), the gene coding for PEPC (ppc gene) or the gene coding for GDH (gdhA gene), nucleotide sequences of these genes from *Escherichia* bacteria and *Corynebacterium* bacteria have already been reported (Ner, S. et al., 1983, Biochemistry, 22:5243-5249; Fujita, N. et al., 1984, J. Biochem., 95:909-916; Valle, F. et al., 1984, Gene, 27:193-199; Microbiology, 140:1817-1828, 1994; Eikmanns, B. J. et al., 1989, Mol. Gen. Genet., 218:330-339; Bormann, E. R. et al., 1992, Molecular Microbiology, 6:317-326), and therefore they can be obtained by synthesizing primers based on their respective nucleotide sequences, and performing PCR using chromosomal DNA as the template.

Examples of plasmids which can be used for transformation include a plasmid which autonomously replicates in the host bacterium belonging to the family Enterobacteriaceae, such as pUC19, pUC18, pBR322, RSF1010, pHSG299, pHSG298, pHSG399, pHSG398, pSTV28, pSTV29 (pHSG and pSTV are available from Takara Bio), pMW119, pMW118, pMW219, pMW218 (pMW vectors are available from Nippon Gene), and the like. Moreover, a phage DNA can also be used as the vector instead of a plasmid. Examples of plasmids for simultaneously enhancing the activities of CS or PRPC, PEPC, and GDH as described above include RSFCPG which includes the gltA gene, ppc gene, and gdhA gene (refer to European Patent Laid-open No. 0952221), and RSFPPG which is the same as RSFCPG, but the gltA gene is replaced with the prpC gene.

Examples of transformation methods include treating recipient cells with calcium chloride so to increase permeability for DNA, which has been reported for *Escherichia coli* K-12 (Mandel, M. and Higa, A., 1970, J. Mol. Biol., 53:159-162), and preparing competent cells from cells which are in the growth phase, followed by transformation with DNA, which has been reported for *Bacillus subtilis* (Duncan, C. H., et al., 1977, Gene, 1:153-167). Alternatively, a method of making potential host cells into protoplasts or spheroplasts, which can easily take up recombinant DNA, followed by introducing the recombinant DNA into the cells. This method is known to be applicable to *Bacillus subtilis*, actinomycetes and yeasts (Chang, S. and Choen, S. N., 1979, Molec. Gen. Genet., 168:111-115; Bibb, M. J. et al., 1978, Nature, 274:398-400; Hinnen, A., et al., 1978, Proc. Natl. Sci., USA, 75:1929-1933). In addition, microorganisms can also be transformed by the electric pulse method (Japanese Patent Laid-open No. 2-207791).

The copy number of a target gene can also be increased by introducing multiple copies of the gene into the chromosomal DNA of the microorganism. Multiple copies of a gene can be introduced into the chromosomal DNA by homologous recombination (Experiments in Molecular Genetics, 1972, Cold Spring Harbor Laboratory) using multiple copies of a sequence as targets in the chromosomal DNA. Sequences, which are present in multiple copies on the chromosomal DNA, repetitive DNAs, and inverted repeats present at the end of a transposable element, are exemplary. Also, as disclosed in Japanese Patent Laid-open No. 2-109985, it is possible to incorporate a target gene into a transposon, and allow it to be transferred to introduce multiple copies of the gene into the chromosomal DNA. The target gene can also be introduced into the bacterial chromosome by using Mu phage (Japanese Patent Laid-open No. 2-109985).

The second method is to increase expression of the target gene by replacing an expression regulatory sequence of the target gene, such as promoter, on the chromosomal DNA or plasmid with a stronger promoter. For example, the lac promoter, trp promoter, trc promoter, etc. are known as strong promoters. Moreover, it is also possible to substitute several nucleotides in the promoter region of a gene so that the promoter is stronger, or to modify the SD sequence as disclosed in International Patent Publication WO00/18935. Examples of methods for evaluating the strength of promoters and strong promoters are described in the article of Goldstein et al. (Goldstein, M. A., and Doi, R. H., 1995, Biotechnol. Annu. Rev., 1:105-128), etc.

Substitution of an expression regulatory sequence can be performed, for example, in the same manner as for gene substitution using a temperature-sensitive plasmid. Examples of vectors having a temperature-sensitive replication origin and are usable for *Escherichia coli* and *Pantoea ananatis* include, for example, the pMAN997 plasmid described in International Publication WO99/03988, and the like. Furthermore, an expression regulatory sequence can also be substituted by the method called "Red-driven integration" using Red recombinase of λ phage (Datsenko, K. A. and Wanner, B. L., 2000, Proc. Natl. Acad. Sci. USA. 97:6640-6645), or by combining the Red-driven integration method and the λ phage excisive system (Cho, E. H., et al., 2002, J. Bacteriol., 184:5200-5203) (WO2005/010175), and the like. Modification of an expression regulatory sequence can be combined with increasing the gene copy number.

As shown in Reference Example 1, a strain resistant to a λ Red gene product, for example, *Pantoea ananatis* SC17 (0), can be used for the Red driven integration. The SC17(0) strain was deposited at the Russian National Collection of Industrial Microorganisms (VKPM), GNII Genetika (Russia, 117545 Moscow 1, Dorozhny proezd. 1) on Sep. 21, 2005 under an accession number of VKPM B-9246.

Examples of microorganisms modified by the method described above so that expression of citrate synthase gene, methylcitrate synthase gene, phosphoenolpyruvate carboxylase gene and/or glutamate dehydrogenase gene are enhanced include the microorganisms disclosed in Japanese Patent Laid-open Nos. 2001-333769, 2000-106869, 2000-189169, 2000-333769, 2006-129840, WO2006/051660, and the like.

Furthermore, L-glutamic acid-producing ability can also be imparted by enhancing the 6-phosphogluconate dehydratase activity, 2-keto-3-deoxy-6-phosphogluconate aldolase activity, or both. Examples of the microorganism in which 6-phosphogluconate dehydratase activity and 2-keto-3-deoxy-6-phosphogluconate aldolase activity are increased include the microorganism disclosed in Japanese Patent Laid-open No. 2003-274988.

L-glutamic acid-producing ability can also be imparted by decreasing or eliminating the activity of an enzyme that catalyzes a reaction that branches off from the L-glutamic acid biosynthesis pathway, producing a compound other than L-glutamic acid. Examples of these include 2-oxoglutarate dehydrogenase (sucA), isocitrate lyase (aceA), phosphate acetyltransferase (pta), acetate kinase (ack), acetohydroxy acid synthase (ilvG), acetolactate synthase (ilvI), formate acetyltransferase (pfl), lactate dehydrogenase (ldh), glutamate decarboxylase (gadAB), 1-pyrroline-5-carboxylate dehydrogenase (putA), and the like. Gene names are indicated in the parentheses after the enzyme names. The activity of 2-oxoglutarate dehydrogenase can be decreased or completely eliminated.

In order to decrease or eliminate the activities of the aforementioned enzymes, methods similar to the method for decreasing or eliminating the activity of lactate dehydrogenase (LDH) described later can be used.

A decrease in the intracellular activity of the target enzyme and the degree by which the activity is decreased, including if it is completely eliminated, can be confirmed by measuring the enzyme activity of a cell extract or a purified fraction thereof obtained from a candidate strain and comparing it with that of a wild-type strain. For example, 2-oxoglutarate dehydrogenase activity can be measured by the method of Reed et al. (Reed L. J. and Mukherjee B. B., 1969, Methods in Enzymology, 13, pp. 55-61).

Methods of eliminating or decreasing the 2-oxoglutarate dehydrogenase activity in *Escherichia* bacteria are disclosed in Japanese Patent Laid-open Nos. 5-244970, 7-203980 and the like. A method of eliminating or decreasing 2-oxoglutarate dehydrogenase activity in coryneform bacteria is disclosed in International Patent Publication WO95/34672. Furthermore, such a method for *Enterobacter* bacteria is disclosed in Japanese Patent Laid-open No. 2001-333769.

Specific examples of *Escherichia* bacteria which are deficient in 2-oxoglutarate dehydrogenase activity or in which the 2-oxoglutarate dehydrogenase activity is decreased include the following strains (U.S. Pat. Nos. 5,378,616 and 5,573,945).

*E. coli* W3110sucA::Kmr

*E. coli* AJ12624 (FERM BP-3853)

*E. coli* AJ12628 (FERM BP-3854)

*E. coli* AJ12949 (FERM BP-4881)

*E. coli* W3110sucA::Kmr is obtained by disrupting the 2-oxoglutarate dehydrogenase gene (sucA gene) of *Escherichia coli* W3110. This strain is completely deficient in 2-oxoglutarate dehydrogenase.

Other specific examples of bacteria wherein the activity of 2-oxoglutarate dehydrogenase is deleted or decreased include the following strains:

*Pantoea ananatis* AJ13601 (FERM BP-7207, European Patent Laid-open No. 1078989)

*Pantoea ananatis* AJ13356 (FERM BP-6615, U.S. Pat. No. 6,331,419)

*Pantoea ananatis* SC17sucA (FERM BP-8646, WO2005/085419)

*Klebsiella planticola* AJ13410 strain (FERM BP-6617, U.S. Pat. No. 6,197,559)

*Brevibacterium lactofermentum* ΔS strain (refer to International Patent Publication WO95/34672)

The SC17sucA strain is obtained by obtaining a low phlegm production mutant strain (SC17) from the AJ13355 strain, which was isolated from nature as a strain that could proliferate in a medium containing L-glutamic acid and a carbon source at low pH, and disrupting the 2-oxoglutarate dehydrogenase gene (sucA) in the mutant strain. The AJ13601 strain is obtained by introducing the plasmid RSFCPG containing the gltA, ppc and gdhA genes derived from *Escherichia coli* and the plasmid pSTVCB containing the gltA gene derived from *Brevibacterium lactofermentum* into the SC17sucA strain to obtain the SC17sucA/RSFCPG+pSTVCB strain, and selecting a high concentration L-glutamic acid-resistant strain at a low pH and a strain showing a high proliferation degree and a high L-glutamic acid-producing ability (European Patent Laid-open No. 0952221). The AJ13356 strain was obtained by deleting the αKGDH-E1 subunit gene (sucA) from the AJ13355 strain.

The SC17sucA strain was assigned a private number of AJ417, deposited in the International Patent Organism Depositary, National Institute of Advanced Industrial Science and Technology (Central 6, 1-1, Higashi 1-Chome, Tsukuba-shi, Ibaraki-ken, Japan, postal code: 305-8566) on Feb. 26, 2004, and assigned an accession number of FERM BP-08646.

The AJ13410 strain was deposited in the International Patent Organism Depositary, National Institute of Advanced Industrial Science and Technology (Central 6, 1-1, Higashi 1-Chome, Tsukuba-shi, Ibaraki-ken, Japan, postal code: 305-8566) on Feb. 19, 1998, and assigned an accession number of FERM P-16647. The deposit was then converted to an international deposition under the provisions of Budapest Treaty on Jan. 11, 1999 and assigned an accession number of FERM BP-6617.

The aforementioned *Pantoea ananatis* AJ13355, AJ13356, and AJ13601 strains and the *Klebsiella planticola* AJ13399 strain have an ability to accumulate L-glutamic acid in a concentration which exceeds the saturation concentration of L-glutamic acid in a liquid medium when it is cultured under acid conditions.

Furthermore, in order to improve the L-glutamic acid-producing ability of Enterobacteriaceae bacteria, the method of deleting the arcA gene (U.S. Pat. No. 7,090,998), and the method of amplifying the yhfK gene, which is a glutamic acid secretion gene (WO2005/085419) can also be used.

Other than the above, examples of coryneform bacteria having L-glutamic acid-producing ability include the following strains:

*Brevibacterium flavum* AJ11573 (FERM P-5492, refer to Japanese Patent Laid-open No. 56-151495)

*Brevibacterium flavum* AJ12210 (FERM P-8123, refer to Japanese Patent Laid-open No. 61-202694)

*Brevibacterium flavum* AJ12212 (FERM P-8123, refer to Japanese Patent Laid-open No. 61-202694)

*Brevibacterium flavum* AJ12418 (FERM-BP2205, refer to Japanese Patent Laid-open No. 2-186994)

*Brevibacterium flavum* DH18 (FERM P-11116, refer to Japanese Patent Laid-open No. 3-232497)

*Corynebacterium melassecola* DH344 (FERM P-11117, refer to Japanese Patent Laid-open No. 3-232497)

*Corynebacterium glutamicum* AJ11574 (FERM P-5493, refer to Japanese Patent Laid-open No. 56-151495)

Microorganisms having L-glutamic acid-producing ability include the *Brevibacterium lactofermentum* AJ13029 strain (FERM BP-5189, refer to WO96/06180), which was made to be able to produce L-glutamic acid in a medium containing an excessive amount of biotin in the absence of biotin action inhibitor, such as surfactant, by introducing a mutation which imparts temperature sensitivity to the biotin action inhibitor. Examples further include microorganisms that belong to the genus *Alicyclobacillus* and are resistant to a L-glutamic acid antimetabolite (Japanese Patent Laid-open No. 11-262398).

Furthermore, the microorganism having a L-glutamic acid producing ability can also be unable to degrade L-glutamic acid, or express the maleate synthase (aceB).isocitrate lyase (aceA).isocitrate dehydrogenase kinase/phosphatase (aceK) operon (henceforth abbreviated as "ace operon") constitutively. Examples of such microorganisms include, for example, the following:

*Escherichia coli* AJ12628 (FERM BP-3854)

*Escherichia coli* AJ12624 (FERM BP-3853)

The former is a mutant strain in which 2-oxoglutarate dehydrogenase activity is decreased and expression of the ace operon has become constitutive. The latter is a mutant strain in which 2-oxoglutarate dehydrogenase activity is decreased and the ability to degrade L-glutamic acid is decreased (refer to French Patent No. 2680178).

When a *Pantoea* bacterium is used, a mutation can be imparted that results in production of less extracellular phlegm as compared to a wild-type strain when it is cultured in a medium containing a saccharide. In order to introduce such a mutation, bacterial strains can be screened for their ability to produce viscous materials on the solid medium (Japanese Patent Laid-open No. 2001-333769), and the ams operon that is involved in polysaccharide synthesis can be disrupted. The nucleotide sequence of the ams operon is shown in SEQ ID NO: 66, and the amino acid sequences of AmsH, I, A, C and B encoded by this operon are shown in SEQ ID NOS: 67, 68, 69, 70 and 71, respectively.

<Succinic Acid-Producing Bacteria>

As succinic acid-producing bacteria, strains which are unable to form acetic acid, lactic acid, ethanol, and formic acid can be used, and specific examples include the *Escherichia coli* SS373 strain (International Patent Publication WO99/06532).

Strains deficient in their abilities to form acetic acid, lactic acid, ethanol and formic acid can be obtained by using a strain that cannot assimilate acetic acid and lactic acid in a minimal medium, or by decreasing the activities of the lactic acid or acetic acid biosynthetic enzymes described below (International Patent Publication WO2005/052135).

Moreover, such strains as described above can also be obtained by imparting monofluoroacetic acid resistance (U.S. Pat. No. 5,521,075).

Other examples of methods for obtaining a strain with improved succinic acid-producing ability include culturing a strain which is deficient in both formate lyase and lactate dehydrogenase and cannot assimilate pyruvic acid in a glucose-enriched medium under anaerobic conditions, and isolating a mutant strain having the ability to assimilate pyruvic acid (International Patent Publication WO97/16528).

The ability to produce succinic acid can also be imparted by amplifying a gene encoding an enzyme which is involved in the succinic acid biosynthesis system described below, or deleting a gene encoding an enzyme which catalyzes a reaction which branches away from the succinic acid biosynthesis system to produce another compound.

The ability to produce succinic acid can also be imparted by modifying a microorganism to decrease the enzymatic activity of lactate dehydrogenase (LDH), which is a lactic acid biosynthesis system enzyme (International Patent Publications WO2005/052135, WO2005/116227, U.S. Pat. No. 5,770,435, U.S. Patent Published Application No. 20070054387, International Patent Publication WO99/53035, Alam, K. Y. and Clark, D. P., 1989, J. Bacteriol., 171:6213-6217). Some microorganisms can have both L-lactate dehydrogenase and D-lactate dehydrogenase, and can be modified to decrease the activity of either one of the enzymes, or the activities of both the enzymes, in another example.

The ability to produce succinic acid can also be imparted by modifying a microorganism to decrease the enzymatic activity of the formic acid biosynthesis system enzyme, pyruvate-formate lyase (PFL) (U.S. Patent Published Application No. 20070054387, International Patent Publications WO2005/116227, WO2005/52135, Donnelly, M. I. et al., 1998, Appl. Biochem. Biotechnol., 70-72:187-198).

The ability to produce succinic acid can also be imparted by modifying a microorganism to decrease the enzymatic activities of phosphate acetyltransferase (PTA), acetate kinase (ACK), pyruvate oxidase (POXB), acetyl-CoA synthetase (ACS) and acetyl-CoA hydrolase (ACH), which are acetic acid biosynthesis system enzymes (U.S. Patent Published Application No. 20070054387, International Patent Publications WO2005/052135, WO99/53035, WO2006/031424, WO2005/113745, and WO2005/113744).

The ability to produce succinic acid can also be enhanced by modifying a microorganism to decrease the enzymatic activity of alcohol dehydrogenase (ADH), which is an ethanol biosynthesis system enzyme (refer to International Patent Publication WO2006/031424).

The ability to produce succinic acid can also be enhanced by decreasing the activities of pyruvate kinase, glucose PTS (ptsG), ArcA protein, IclR protein (iclR), glutamate dehydrogenase (gdh) and/or glutamine synthetase (glnA), and glutamate synthase (gltBD) (International Patent Publication WO2006/107127, WO2007007933, Japanese Patent Laid-open No. 2005-168401). The gene names are indicated in the parentheses following the enzyme names.

The ability to produce succinic acid can also be imparted by enhancing a biosynthesis system enzyme involved in the succinic acid production.

The ability to produce succinic acid can also be enhanced by increasing the enzymatic activities of pyruvate carboxylase, malic enzyme, phosphoenolpyruvate carboxylase, fumarase, fumarate reductase, malate dehydrogenase and phosphoenolpyruvate carboxykinase (Japanese Patent Laid-open No. 11-196888, International Patent Publication WO99/53035, Hong, S. H., and S. Y. Lee, 2001, Biotechnol. Bioeng., 74:89-95, Millard, C. S. et al., 1996, Appl. Environ. Microbiol., 62:1808-1810, International Patent Publication WO2005/021770, Japanese Patent Laid-open No. 2006-320208, Kim, P. et al., 2004, Appl. Environ. Microbiol., 70:1238-1241). Increasing the enzymatic activities of these target enzymes can be performed by referring to the methods for enhancing expression of a target gene described herein, and the methods for enhancing expression of ybjL gene described later.

Specific examples of succinic acid-producing bacteria belonging to the family Enterobacteriaceae include the following strains:

*Escherichia coli* SS373 strain (International Patent Publication WO99/06532)

*Escherichia coli* AFP111 strain (International Patent Publication WO97/16528)

*Escherichia coli* NZN111 strain (U.S. Pat. No. 6,159,738)

*Escherichia coli* AFP184 strain (International Patent Publication WO2005/116227)

*Escherichia coli* SBS100MG strain, SBS110MG strain, SBS440MG strain, SBS550MG strain, and SBS660MG strain (International Patent Publication WO2006/031424)

Examples of succinic acid-producing bacteria belonging to coryneform bacteria include the following strains.

*Brevibacterium flavum* AB-41 strain (Japanese Patent Laid-open No. 11-113588)

*Brevibacterium flavum* AB-41 strain (PC-amplified strain, Japanese Patent Laid-open No. 11-196888)

*Corynebacterium glutamicum* AJ110655 strain (FERM BP-10951)

*Brevibacterium flavum* MJ233Δldh strain (International Patent Publication WO2005/021770)

*Brevibacterium lactofermentum* (*Corynebacterium glutamicum*) 2256Δ(ldh, ach, pta, ack) (International Patent Publication WO2005/113744)

*Brevibacterium lactofermentum* 2256Δ(ldh, pta, ack, poxB) (International Patent Publication WO2005/113745)

*Corynebacterium glutamicum* Rldh-/pCRB-1 PC strain (International Patent Publication WO2005/010182)

Examples of succinic acid-producing rumen bacteria include the following strains.

*Mannheimia succiniciproducens* LPK, LPK7 and LPK4 (International Patent Publication WO2005/052135)

*Actinobacillus succinogenes* 130Z (U.S. Pat. No. 5,504,004)

*Anaerobiospirillum succiniciproducens* FZ10 (U.S. Pat. No. 5,521,075)

*Anaerobiospirillum succiniciproducens* FZ53 (U.S. Pat. No. 5,573,931)

<1-2> Enhancement of Expression of ybjL Gene

A microorganism that has an ability to produce an acidic substance having a carboxyl group can be modified such as those described above so that expression of the ybjL gene is enhanced. However, the modification to enhance expression of the ybjL gene is performed first, and then the ability to produce an acidic substance having a carboxyl group can be imparted. Furthermore, the microorganism can already have the ability to produce an acidic substance having a carboxyl group, or the ability to produce an acidic substance having a carboxyl group can be enhanced by amplification of the ybjL gene.

The "ybjL gene" refers to the ybjL gene of *Escherichia coli* or a homologue thereof, the ybjL gene of *Pantoea ananatis* or a homologue thereof, or the ybjL gene of *Enterobacter aerogenes* or a homologue thereof. Examples of the ybjL gene of *Escherichia coli* include a gene coding for a protein having the amino acid sequence of SEQ ID NO: 4, for example, a gene having the nucleotide sequence of the nucleotides 101 to 1783 in SEQ ID NO: 3. Furthermore, examples of the ybjL gene derived from *Pantoea ananatis* include a gene coding for a protein having the amino acid sequence of SEQ ID NO: 2, for example, a gene having the nucleotide sequence of the nucleotides 298 to 1986 in SEQ ID NO: 1. Furthermore, examples of the ybjL gene derived from the *Enterobacter aerogenes* AJ110673 strain include a gene coding for a protein having the amino acid sequence of SEQ ID NO: 87, for example, a gene having the nucleotide sequence of the nucleotides 19 to 1704 in SEQ ID NO: 86. Furthermore, examples of the ybjL gene derived from *Salmonella typhimurium* include a gene coding for a protein having the amino acid sequence of SEQ ID NO: 25 (SEQ ID NO: 24). Examples of the ybjL gene derived from *Yersinia pestis* include a gene coding for a protein having the amino acid sequence of SEQ ID NO: 27 (SEQ ID NO: 26). Examples of the ybjL gene derived from *Erwinia carotovora* include a gene coding for a protein having the amino acid sequence of SEQ ID NO: 29 (SEQ ID NO: 28). Examples of the ybjL gene derived from *Vibrio cholerae* include a gene coding for a protein having the amino acid sequence of SEQ ID NO: 31 (SEQ ID NO: 30). Examples of the ybjL gene derived from *Aeromonas hydrophila* include a gene coding for a protein having the amino acid sequence of SEQ ID NO: 33 (SEQ ID NO: 32). Examples of the ybjL gene derived from *Photobacterium profundum* include a gene coding for a protein having the amino acid sequence of SEQ ID NO: 35 (SEQ ID NO: 34). Furthermore, the ybjL gene can be cloned from a coryneform bacterium such as *Corynebacterium glutamicum* and *Brevibacterium lactofermentum*, *Pseudomonas* bacterium such as *Pseudomonas aeruginosa*, *Mycobacterium* bacterium such as *Mycobacterium tuberculosis* or the like, on the basis of homology to the genes exemplified above. The amino acid sequences of the proteins encoded by the ybjL genes of *Salmonella typhimurium, Yersinia pestis, Erwinia carotovora, Vibrio cholerae, Aeromonas hydrophila* and *Photobacterium profundum* described above are 96%, 90%, 88%, 64%, 60% and 68% homologous to the amino acid sequence of SEQ ID NO: 4, respectively, and 86%, 90%, 84%, 63%, 60% and 67% homologous to the amino acid sequence of SEQ ID NO: 2, respectively. The amino acid sequences of SEQ ID NOS: 2 and 4 are 86% homologous. The consensus sequence of SEQ ID NOS: 2 and 4 is shown in SEQ ID NO: 5. The amino acid sequences of SEQ ID NOS: 4 and 87 re 92% homologous, and the amino acid sequences of SEQ ID NOS: 2 and 87 are 83% homologous. The sequence of the ybjL gene from the *Enterobacter aerogenes* AJ110637 strain (SEQ ID NO: 86) and the encoded amino acid sequence (SEQ ID NO: 87) have not been previously reported. The consensus sequence for the amino acid sequences of SEQ ID NOS: 2, 4 and 87 is shown in SEQ ID NO: 88.

The term "ybjL gene homologue" refers to a gene derived from a microorganism other than *Escherichia coli, Pantoea ananatis*, and *Enterobacter aerogenes*, which exhibits high structural similarity to the ybjL gene of *Escherichia coli, Pantoea ananatis*, or *Enterobacter aerogenes* and codes for a protein that improves an ability of a microorganism to produce an acidic substance having a carboxyl group when expression of the gene is enhanced in the microorganism. Examples of ybjL gene homologues include genes coding for a protein having a homology of 70% or more, 80% or more in another example, 90% or more in another example, 95% or more in another example, 97% or more in another example, to the entire amino acid sequence of SEQ ID NO: 2, 4 or 87 or the amino acid sequence of SEQ ID NO: 2, 4 or 87, and which improves an ability to produce an acidic substance having a carboxyl group of a microorganism when expression of the gene is enhanced in the microorganism. The ybjL gene homologue can code for a protein having a homology of 70% or more, 80% or more in another example, 90% or more in another example, 95% or more in another example, or 97% or more in another example, to any of the aforementioned amino acid sequences, and the consensus sequences of the SEQ ID NOS: 5 or 88. Homology of the amino acid sequences and nucleotide sequences can be determined by using, for example, the algorithm BLAST of Karlin and Altschul (Pro. Natl. Acad. Sci. USA, 90, 5873 (1993)) or FASTA (Methods Enzymol., 183, 63 (1990)). Programs called BLASTN and BLASTX were developed on the basis of the algorithm BLAST (refer to www.ncbi.nlm-.nih.gov). The term "homology" can also be used to mean "identity".

The ybjL gene can have one or more conservative mutations, and can be artificially modified, so long as enhancement of the tbjL gene's expression results in an improved ability to produce a target substance by a microorganism. That is, the ybjL gene can encode for an amino acid sequence of a known protein, for example, a protein having an amino acid sequence of SEQ ID NO: 2, 4, 25, 27, 29, 31, 33, 35 or 87, but which includes a conservative mutation, specifically, substitution, deletion, insertion or addition, of one or several amino acid residues at one or several positions. Although the number meant by the term "several" can differ depending on the position in the three-dimensional structure of the protein, or the type of amino acid residue. For example, it can be 1 to 20, 1 to 10 in another example, 1 to 5 in another example. Furthermore, the ybjL gene can encode for a protein having a homology of 70% or more, 80% or more in another example, 90% or more in another example, 95% or more in another example, or 97% or more in another example, to the entire amino acid sequence of SEQ ID NO: 2, 4, 25, 27, 29, 31, 33, 35 or 87, and which improves an ability to produce a target substance by a microorganism when expression of the gene is enhanced in the microorganism.

The aforementioned conservative substitution can be neutral, in that the function of the protein is not changed. The conservative mutation can take place mutually among Phe, Trp and Tyr, if the substitution site is an aromatic amino acid; among Leu, Ile and Val, if the substitution site is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having hydroxyl group. Specific examples of substitution considered conservative substitution include: substitution of Ser or Thr for Ala; substitution of Gln, His or Lys for Arg; substitution of Glu, Gln, Lys, His or Asp for Asn; substitution of Asn, Glu or Gln for Asp; substitution of Ser or Ala for Cys; substitution of Asn, Glu, Lys, His, Asp or Arg for Gln; substitution of Gly, Asn, Gln, Lys or Asp for Glu; substitution of Pro for Gly; substitution of Asn, Lys, Gln, Arg or Tyr for His; substitution of Leu, Met, Val or Phe for Ile; substitution of Be, Met, Val or Phe for Leu; substitution of Asn, Glu, Gln, His or Arg for Lys; substitution of Ile, Leu, Val or Phe for Met; substitution of Trp, Tyr, Met, Ile or Leu for Phe; substitution of Thr or Ala for Ser; substitution of Ser or Ala for Thr; substitution of Phe or Tyr for Trp; substitution of His, Phe or Trp for Tyr; and substitution of Met, Ile or Leu for Val.

Such a gene can be obtained by modifying the nucleotide sequence of the nucleotides 298 to 1986 in SEQ ID NO: 1, the nucleotide sequence of the nucleotides 101 to 1783 in SEQ ID NO: 3, the nucleotide sequence of the nucleotides 19 to 1704 in SEQ ID NO: 86, or the nucleotide sequence of SEQ ID NO: 24, 26, 28, 30, 32 or 34 by, for example, site-specific mutagenesis, so that substitution, deletion, insertion or addition of an amino acid residue or residues occurs at a specific site in the encoded protein. Furthermore, such a gene can also be obtained by a known mutation treatment, examples of which include treating a gene having any of the nucleotide sequences described above with hydroxylamine or the like in vitro, and treating a microorganism, for example, an *Escherichia* bacterium, containing the gene with ultraviolet ray irradiation or a mutagen used in a usual mutation treatment such as N-methyl-N'-nitro-N-nitrosoguanidine (NTG) or EMS (ethyl methanesulfonate). The mutation for the substitutions, deletions, insertions, additions, inversions or the like of amino acid residues described above also includes a naturally occurring mutation based on individual difference, difference in species of microorganisms that contain the ybjL gene (mutant or variant), and the like.

The ybjL gene can also be a DNA hybridizable with a complementary strand of DNA having the nucleotide sequence of the nucleotides 298 to 1986 in SEQ ID NO: 1, a DNA having the nucleotide sequence of the nucleotides 101 to 1783 in SEQ ID NO: 3, a DNA having the nucleotide sequence of the nucleotides 19 to 1704 in SEQ ID NO: 86, or a DNA having the nucleotide sequence of SEQ ID NO: 1, 3, 24, 26, 28, 30, 32, 34 or 86, or a probe that can be prepared from the DNAs having these sequences under stringent conditions and which codes for a protein which improves an ability to produce a substance of a microorganism when expression of the gene is enhanced in the microorganism.

The "stringent conditions" can be conditions under which a so-called specific hybrid is formed, and non-specific hybrid is not formed. It is difficult to clearly express this condition by using any numerical value. However, the stringent conditions include, for example, when DNAs having high homology to each other, for example, DNAs having a homology of, for example, not less than 80%, not less than 90% in another example, not less than 95% in another example, or not less than 97% in another example, hybridize with each other, and DNAs having homology lower than the above level do not hybridize with each other, and when washing in ordinary Southern hybridization, i.e., washing once, twice or three times in another example, at salt concentrations and temperature of 1×SSC, 0.1% SDS at 60° C., 0.1×SSC, 0.1% SDS at 60° C. in another example, 0.1×SSC, 0.1% SDS at 65° C., 0.1×SSC in another example, or 0.1% SDS at 68° C. in another example.

The probe can have a partial sequence of the ybjL gene. Such a probe can be produced by PCR using oligonucleotides prepared on the basis of the nucleotide sequence of the gene and a DNA fragment including the gene as the template and performed in a manner well known to those skilled in the art. When a DNA fragment having a length of about 300 bp is used as the probe, the washing conditions after hybridization can be exemplified by 2×SSC, 0.1% SDS at 50° C.

The aforementioned descriptions concerning the gene homologue and conservative mutations can be similarly applied to the other enzyme genes described herein.

The expression of the ybjL gene can be enhanced by increasing the copy number of the ybjL gene, modifying an expression control sequence of the ybjL gene, amplifying a regulator that increases expression of the ybjL gene, or deleting or attenuating a regulator that decreases expression of the ybjL gene. Expression can be enhanced or increased using transformation or homologous recombination performed in the same manner as the methods for enhancing expression of a target gene described above for L-glutamic acid-producing bacteria.

In the microorganism, an activity for secreting an acidic substance having a carboxyl group can be improved by enhancing the expression of the ybjL gene. Whether "the activity for secreting an acidic substance having a carboxyl group is improved" can be confirmed by comparing the amount of the acidic substance having a carboxyl group which has been secreted into the medium in which the microorganism is cultured with the amount obtained by culturing a control microorganism into which the ybjL gene is not introduced. That is, the "improvement in the activity for secreting the acidic substance having a carboxyl group" is observed as an increase in the concentration of the acidic substance having a carboxyl group in the medium in which the microorganism is cultured as compared to the concentration obtained with a control microorganism. Furthermore, the "improvement in the activity for secreting an acidic substance having a carboxyl group" is also observed as a decrease in intracellular concentration of the acidic substance having a carboxyl group in the microorganism. As for the improvement of the "activity for secreting an acidic substance having a carboxyl group", the intracellular concentration of the acidic substance having a carboxyl group can be decreased by 10% or more, 20% or more in another example, 30% or more in another example, as compared to the concentration in a strain in which expression of the ybjL gene is not enhanced. The absolute "activity for secreting an acidic substance having a carboxyl group" of a microorganism can be detected by measuring the difference between the intracellular and extracellular concentrations of the acidic substance having a carboxyl group. Furthermore, the "activity for secreting an acidic substance having a carboxyl group" can also be detected by measuring the activity for taking up amino acids into the cells using reverted membrane vesicles with a radioisotope (J. Biol. Chem., 2002, vol. 277, No. 51, pp. 49841-49849). For example, the activity can be measured by preparing reverted membrane vesicles from cells in which the ybjL gene is expressed, adding a substrate which can act as a driving force such as ATP, and measuring the uptake activity for RI-labeled glutamic acid. Moreover, the activity can also be measured by detecting an exchange reaction rate of a labeled acidic substance having a carboxyl group and unlabeled acidic substance having a carboxyl group in live bacteria.

The microorganism can have an ability to accumulate L-glutamic acid in the liquid medium in an amount which is more than the amount at the saturation concentration of L-glutamic acid when it is cultured under acidic conditions (this ability is also referred to as the "L-glutamic acid accumulation ability under acidic conditions"). Such a microorganism can have the L-glutamic acid accumulation ability under acidic conditions by enhancing the expression of the ybjL gene. Alternatively, the microorganism can have a native ability to accumulate L-glutamic acid under acidic conditions.

Specific examples of microorganisms having L-glutamic acid accumulation ability under acidic conditions include the aforementioned *Pantoea ananatis* AJ13355 strain (FERM BP-6614), AJ13356 strain (FERM BP-6615), AJ13601 strain (FERM BP-7207) (for these, refer to Japanese Patent Laid-open No. 2001-333769), and the like. The *Pantoea ananatis* AJ13355 and AJ13356 strains were deposited at the National Institute of Bioscience and Human-Technology, Agency of Industrial Science and Technology, Ministry of International Trade and Industry (currently, National Institute of Bioscience and Human-Technology, National Institute of Advanced Industrial Science and Technology, Address: Central 6, 1-1, Higashi 1-Chome, Tsukuba-shi, Ibaraki-ken, 305-8566, Japan) on Feb. 19, 1998 and given accession numbers of FERM P-16644 and FERM P-16645. The deposits were then converted to international deposits under the provisions of Budapest Treaty on Jan. 11, 1999 and given accession numbers of FERM BP-6614 and FERM BP-6615. The AJ13601 strain was deposited at the National Institute of Bioscience and Human-Technology, Agency of Industrial Science and Technology (currently, International Patent Organism Depository, National Institute of Advanced Industrial Science and Technology) on Aug. 18, 1999 and given an accession number of FERM P-17516. The deposit was converted to an international deposit under the provisions of the Budapest Treaty on Jul. 6, 2000 and given an accession number of FERM BP-7207. These strains were identified as *Enterobacter agglomerans* when they were isolated and deposited as *Enterobacter agglomerans* AJ13355, AJ13356, and AJ13601 strains. However, they were recently re-classified as *Pantoea ananatis* on the basis of nucleotide sequencing of 16S rRNA and the like.

When an organic acid, especially succinic acid, is produced, using a microorganism which is modified to decrease the activities of one or more enzymes among lactate dehydrogenase (LDH), alcohol dehydrogenase (ADH), and pyruvate formate lyase (PFL), in addition to increasing the expression of the ybjL gene, is more effective.

The expression "modified so that lactate dehydrogenase activity is decreased" can mean that the lactate dehydrogenase activity is decreased as compared to that of a strain in which lactate dehydrogenase is unmodified. The lactate dehydrogenase activity can be decreased to 10% per cell or lower as compared to that of a lactate dehydrogenase-unmodified strain. The lactate dehydrogenase activity can also be completely deleted. Decrease of the lactate dehydrogenase activity can be confirmed by measuring the lactate dehydrogenase activity by a known method (Kanarek, L. and Hill, R. L., 1964, J. Biol. Chem., 239:4202). Specific examples of the method for producing a mutant strain of *Escherichia coli* in which the lactate dehydrogenase activity is decreased include the method described in Alam, K. Y., and Clark, D. P., 1989, J. Bacteriol., 171:6213-6217, and the like. The microorganism with decreased lactate dehydrogenase activity and enhanced expression of the ybjL gene can be obtained by, for example, preparing a microorganism in which the LDH gene is disrupted, and transforming this microorganism with a recombinant vector containing the ybjL gene, as described in Example 1. However, either the modification for decreasing the LDH activity or the modification for enhancing expression of the ybjL gene can be performed first. In *Escherichia coli*, LDH is encoded by the ldhA and lldD genes. The DNA sequence of the ldhA gene is shown in SEQ ID NO: 36, the amino acid sequence encoded thereby is shown in SEQ ID NO: 37, the DNA sequence of the lldD gene is shown in SEQ ID NO: 38, and the amino acid sequence encoded thereby is shown in SEQ ID NO: 39.

In order to decrease or delete activity of LDH, a mutation that decreases or deletes the intracellular activity of LDH can be introduced into the LDH gene on the chromosome by a known mutagenesis method. For example, the gene coding for LDH on the chromosome can be deleted, or an expression control sequence such as a promoter and the Shine-Dalgarno (SD) sequence can be modified by gene recombination. Furthermore, a mutation can also be introduced to cause an amino acid substitution (missense mutation), a stop codon (nonsense mutation), or a frame shift mutation that adds or deletes one or two nucleotides into the coding region of the LDH on the chromosome, or a part of, or the entire gene can be deleted (Qiu Z. and Goodman M. F., 1997, J. Biol. Chem., 272:8611-8617). Furthermore, the LDH activity can also be decreased or deleted by gene disruption, for example, by deleting the coding region of the LDH gene in a DNA construct, and replacing the normal LDH gene with the DNA construct on the chromosome by homologous recombination or the like, or by introducing a transposon or IS factor into the gene.

In order to introduce a mutation which results in decreasing or deleting the LDH activity by genetic recombination, for example, the following methods are used. The chromosomal LDH gene can be replaced with a mutant gene by preparing a mutant LDH gene in which a partial sequence of the LDH gene is modified so that it does not produce an enzyme that can function normally, and transforming a bacterium with a DNA containing the mutant gene to cause homologous recombination between the mutant gene and the gene on a chromosome. Such site-specific mutagenesis based on gene substitution utilizing homologous recombination has been already reported, and include a method called Red driven integration developed by Datsenko and Wanner (Datsenko, K. A, and Wanner, B. L., 2000, Proc. Natl. Acad. Sci. USA, 97:6640-6645), a method of using a linear DNA such as by utilizing Red driven integration in combination with an excision system derived from λ phage (Cho, E. H., et al., 2002, J. Bacteriol., 184:5200-5203), a method of using a plasmid containing a temperature sensitive replication origin (U.S. Pat. No. 6,303,383, Japanese Patent Laid-open No. 05-007491, WO2005/010175), and the like. Such site-specific mutagenesis based on gene substitution using homologous recombination as described above can also be performed by using a plasmid that is unable to replicate in a host.

The expression "modified so that alcohol dehydrogenase activity is decreased" can mean that the alcohol dehydrogenase activity is decreased as compared to that of a strain in which alcohol dehydrogenase is unmodified. The alcohol dehydrogenase activity can be decreased to 10% per cell or lower as compared to an alcohol dehydrogenase-unmodified strain. The alcohol dehydrogenase activity can also be completely deleted. Decrease in the alcohol dehydrogenase activity can be confirmed by measuring the alcohol dehydrogenase activity by a known method (Lutstorf, U. M. et al., 1970, Eur. J. Biochem., 17:497-508). Specific examples of the method for producing a mutant strain of *Escherichia coli* in which the alcohol dehydrogenase activity is decreased include the method described in Sanchez A. M. et al., 2005, Biotechnol. Prog., 21:358-365, and the like. The microorganism in which alcohol dehydrogenase activity is decreased and expression of the ybjL gene is enhanced can be obtained by, for example, preparing a microorganism in which the gene coding for alcohol dehydrogenase (ADH) is disrupted, and transforming this microorganism with a recombinant vector containing the ybjL gene. However, either the modification for decreasing the ADH activity or the modification for enhancing expression of the ybjL gene can be performed first. The alcohol dehydrogenase activity can be decreased by a method similar to that for decreasing the lactate dehydrogenase activity described above. The nucleotide sequence (partial sequence) of the ADH gene from the *Enterobacter aerogenes* AJ110637 strain (FERM ABP-10955) is shown in SEQ ID NO: 74. The entire nucleotide sequence of this gene can be determined by, for example, isolating the ADH gene (adhE) from the chromosomal DNA of *Enterobacter aerogenes* on the basis of this partial sequence.

The expression "modified so that pyruvate formate lyase activity is decreased" can mean that the pyruvate formate lyase activity is decreased as compared to that of a strain in which the pyruvate formate lyase is unmodified. The pyruvate formate lyase activity can be decreased to 10% per cell or lower as compared to a pyruvate formate lyase-unmodified strain. The pyruvate formate lyase activity can also be completely deleted. A decrease in the pyruvate formate lyase activity can be confirmed by measuring the pyruvate formate lyase activity by a known method (Knappe, J. and Blaschkowski, H. P., 1975, Meth. Enzymol., 41:508-518). The microorganism in which pyruvate formate lyase activity is decreased and expression of the ybjL gene is enhanced can be obtained by, for example, preparing a microorganism in which the PFL gene is disrupted, and transforming this microorganism with a recombinant vector containing the ybjL gene. However, either the modification for decreasing the PFL activity or the modification for enhancing expression of ybjL can be performed first. The pyruvate formate lyase activity can be decreased by a method similar to the method for decreasing the lactate dehydrogenase activity described above.

A bacterium modified so that the pyruvate carboxylase (PC) activity is enhanced, in addition to the enhanced the expression of the ybjL gene, can also be used to produce an organic acid, especially succinic acid. Enhancing the pyruvate carboxylase activity can be combined with decreasing the lactate dehydrogenase activity, alcohol dehydrogenase activity, and/or pyruvate formate lyase activity. The expression "modified so that pyruvate carboxylase activity is enhanced" can mean that the pyruvate carboxylase activity is increased as compared to that of an unmodified strain such as a wild-type strain or parent strain. The pyruvate carboxylase activity can be measured by, for example, a method of measuring a decrease of NADH as described later.

The nucleotide sequence of the PC gene can be a reported sequence or can be obtained by isolating a DNA fragment encoding a protein having the PC activity from the chromosome of a microorganism, animal, plant, or the like, and then the nucleotide sequence can be determined. After the nucleotide sequence is determined, a gene synthesized on the basis of that sequence can also be used.

The PC gene can be derived from a coryneform bacterium, such as *Corynebacterium glutamicum* (Peters-Wendisch, P. G. et al., 1998, Microbiology, vol. 144:915-927). Furthermore, so long as the functions of the encoded PC protein, such as its involvement in carbon dioxide fixation, are not substantially degraded, nucleotides in the PC gene can be replaced with other nucleotides or deleted, or other nucleotides can be inserted into the sequence. Alternatively, a part of the nucleotide sequence can be transferred.

PC genes obtained from bacteria other than *Corynebacterium glutamicum*, including from other microorganisms, animals, and plants, can also be used. In particular, the sequences of PC genes derived from other microorganisms, animals and plants described below are known (references are indicated below), and they can be obtained by hybridization or amplification by PCR of the ORF portions in the same manner as described above.

Human [Biochem. Biophys. Res. Comm., 202, 1009-1014, (1994)]
Mouse [Proc. Natl. Acad. Sci. USA., 90, 1766-1779, (1993)]
Rat [GENE, 165, 331-332, (1995)]
Yeast: *Saccharomyces cerevisiae* [Mol. Gen. Genet., 229, 307-315, (1991)], *Schizosaccharomyces pombe* [DDBJ Accession No.; D78170]
*Bacillus stearothermophilus* [GENE, 191, 47-50, (1997)]
*Rhizobium etli* [J. Bacteriol., 178, 5960-5970, (1996)]

The PC gene can be enhanced in the same manner as when enhancing expression of a target gene described above for L-glutamic acid-producing bacteria and enhancing expression of the ybjL gene.

<2> Method for Producing an Acidic Substance Having a Carboxyl Group

An acidic substance having a carboxyl group can be produced by culturing the microorganism in a medium to produce and cause accumulation of an acidic substance having a carboxyl group in the medium and collecting the substance from the medium. Furthermore, the acidic substance having a carboxyl group can also be produced by allowing the microorganism, or a product obtained by processing the microorganism, to act on an organic raw material in a reaction mixture containing carbonate ions, bicarbonate ions, or carbon dioxide gas to produce the acidic substance having a carboxyl group, and collecting the substance. The former method is exemplary for producing an acidic amino acid. The latter method is exemplary for producing an organic acid. Hereinafter, further examples methods for producing an acidic amino acid and an organic acid will be exemplified.

<2-1> Production of Acidic Amino Acid

An acidic amino acid can be produced by culturing the microorganism in a medium to produce and cause accumulation of an acidic amino acid in the medium and collecting the acidic amino acid from the medium.

As the medium used for the culture, a known medium containing a carbon source, nitrogen source, and inorganic salts, as well as trace amounts of organic nutrients such as amino acids and vitamins as required can be used. Either a synthetic medium or natural medium can be used. The carbon source and nitrogen source used in the medium can be of any type so long as substances that can be utilized by the chosen strain to be cultured.

As the carbon source, saccharides such as glucose, glycerol, fructose, sucrose, maltose, mannose, galactose, starch hydrolysate and molasses can be used. In addition, alcohols such as ethanol can be used independently or in combination with another carbon source. Furthermore, organic acids such as acetic acid and citric acid other than the target substance can also be used as the carbon source. As the nitrogen source, ammonia, ammonium salts such as ammonium sulfate, ammonium carbonate, ammonium chloride, ammonium phosphate and ammonium acetate, nitrates and the like can be used. As the trace amount organic nutrients, amino acids, vitamins, fatty acids, nucleic acids, those containing these substances such as peptone, casamino acid, yeast extract and soybean protein decomposition products can be used. When an auxotrophic mutant strain that requires an amino acid or the like for growth is used, the required nutrient can be supplemented. As mineral salts, phosphates, magnesium salts, calcium salts, iron salts, manganese salts and the like can be used.

The culture can be performed as an aeration culture, while the fermentation temperature can be controlled to be 20 to 45° C., and pH to be 3 to 9. When pH drops during the culture, the medium can be neutralized by addition of, for example, calcium carbonate, or with an alkali such as ammonia gas. An acidic amino acid can accumulate in the culture broth, for example, after 10 to 120 hours of culture under such conditions as described above.

When the acidic amino acid is L-glutamic acid, L-glutamic acid can precipitate into the medium by using a liquid medium, the pH of which is adjusted so that L-glutamic acid precipitates. L-glutamic acid precipitates around, for example, pH 5.0 to 4.0, pH 4.5 to 4.0 in another example, pH 4.3 to 4.0 in another example, or pH 4.0 in another example.

After completion of the culture, L-glutamic acid can be collected from the culture medium by any known collection method. For example, after cells are removed from the culture medium, L-glutamic acid can be collected by concentrating the culture medium so it crystallizes, or by ion exchange chromatography, or the like. When the culture is performed so that L-glutamic acid precipitates, the L-glutamic acid that has precipitated in the medium can be collected by centrifugation, filtration, or the like. In this case, it is also possible to crystallize L-glutamic acid that has dissolved in the medium, and then collect the precipitated L-glutamic acid in the culture broth together with the crystallized L-glutamic acid.

<2-2> Production of Organic Acid

An organic acid can be produced by allowing the microorganism, or a product obtained by processing the microorganism, to act on an organic raw material in a reaction mixture containing carbonate ions, bicarbonate ions, or carbon dioxide gas, and collecting the organic acid.

In a first example, by culturing the microorganism in a medium containing carbonate ions, bicarbonate ions, or carbon dioxide gas, and an organic raw material, proliferation of the microorganism and production of the organic acid simultaneously occur. In this example, the medium can be the reaction mixture. Proliferation of the microorganism and production of the organic acid can simultaneously occur, or there can be a period during the culture in which proliferation of the microorganism mainly occurs, and a period in which production of the organic acid mainly occurs.

In a second example, by allowing cells that have proliferated in the medium to coexist with a reaction mixture containing carbonate ions, bicarbonate ions, or carbon dioxide gas, and an organic raw material, and thereby allowing the microorganism to act on the organic raw material in the reaction mixture, an organic acid can be produced. In this example, a product obtained by processing the cells of the microorganism can also be used. Examples of the product obtained by processing cells include, for example, immobilized cells obtained with acrylamide, carragheenan, or the like, a disrupted cellular product, a centrifugation supernatant of the disrupted product, a fraction obtained by partial purification of the supernatant by ammonium sulfate treatment or the like, and the like.

Although the bacteria can be obtained on a solid medium such as an agar medium by slant culture, bacteria previously cultured in a liquid medium (seed culture) are examples.

A medium usually used for culture of microorganisms can be used. For example, a typical medium obtained by adding natural nutrients such as meat extract, yeast extract and peptone, to a composition comprising inorganic salts such as ammonium sulfate, potassium phosphate and magnesium sulfate can be used.

In the aforementioned first example, the carbon source added to the medium also serves as the organic raw material for the production of the organic acid.

In the aforementioned second example, the cells after the culture are collected by centrifugation, membrane separation, or the like, and used for the organic acid production reaction.

The organic raw material is not particularly limited so long as the chosen microorganism can assimilate it to produce succinic acid. However, fermentable carbohydrates including carbohydrates such as galactose, lactose, glucose, fructose, glycerol, sucrose, saccharose, starch and cellulose, polyalcohols such as glycerin, mannitol, xylitol and ribitol, and the like are typically used. Glucose, fructose and glycerol are examples, and glucose is a particular example. When the organic acid is succinic acid, fumaric acid or the like can be added in order to efficiently produce succinic acid as described in Japanese Patent Laid-open No. 5-68576, and malic acid can be added instead of fumaric acid.

Furthermore, a saccharified starch solution, molasses, or the like containing the aforementioned fermentable carbohydrates can also be used. The fermentable carbohydrates can be used independently or in combination. Although concentration of the aforementioned organic raw material is not particularly limited, it is more advantageous that the concentration is as high as possible and within such a range that the culture of the microorganism and production of the organic acid are not inhibited. In the aforementioned first example, the concentration of the organic raw material in the medium is generally in the range of 5 to 30% (w/v), or 10 to 20% (w/v) in another example. Furthermore, in the aforementioned second example, the concentration of the organic raw material in the reaction mixture is generally in the range of 5 to 30% (w/v), or 10 to 20% (w/v) in another example. Furthermore, it may be necessary to add additional organic raw material as the concentration of the organic raw material decreases with the progress of the culture or reaction.

The aforementioned reaction mixture containing carbonate ions, bicarbonate ions, or carbon dioxide gas and the organic raw material is not particularly limited, and it can be, for example, a typical medium for culturing microorganisms, or it can be a buffer such as phosphate buffer. The reaction mixture can be an aqueous solution containing a nitrogen source, inorganic salts, and the like. The nitrogen source is not particularly limited so long the chosen microorganism can assimilate it to produce an organic acid, and specific examples include various organic or inorganic nitrogen compounds such as ammonium salts, nitrates, urea, soybean hydrolysate, casein degradation products, peptone, yeast extract, meat extract, and corn steep liquor. Examples of the inorganic salts include various phosphates, sulfates, and metallic salts such as those of magnesium, potassium, manganese, iron, and zinc. If necessary, growth-promoting factors including vitamins such as biotin, pantothenic acid, inositol, and nicotinic acid, nucleotides, amino acids and the like can be added. In order to suppress foaming during the reaction, an appropriate amount of a commercially available antifoam can be added to the medium.

The pH of the reaction mixture can be adjusted by adding sodium carbonate, sodium bicarbonate, potassium carbonate, potassium bicarbonate, magnesium carbonate, sodium hydroxide, calcium hydroxide, magnesium hydroxide, or the like. Since the pH for the reaction is usually 5 to 10, or 6 to 9.5 in another example, the pH of the reaction mixture can be adjusted to be within the aforementioned range with an alkaline substance, carbonate, urea, or the like, even during the reaction, if needed.

Water, buffer, medium or the like can be used as the reaction mixture, but a medium is a particular example. The medium can contain, for example, the aforementioned organic raw material, and carbonate ions, bicarbonate ions, or carbon dioxide gas, and the reaction can be performed under anaerobic conditions. Magnesium carbonate, sodium carbonate, sodium bicarbonate, potassium carbonate, or potassium bicarbonate can be the source of the carbonate or bicarbonate ions, and these can also be used as a neutralizing agent. However, if necessary, carbonate or bicarbonate ions can also be supplied from carbonic acid or bicarbonic acid or salts thereof or carbon dioxide gas. Specific examples of salts of carbonic acid or bicarbonic acid include, for example, magnesium carbonate, ammonium carbonate, sodium carbonate, potassium carbonate, ammonium bicarbonate, sodium bicarbonate, potassium bicarbonate, and the like. Carbonate ions or bicarbonate ions can be added at a concentration of 0.001 to 5 M, 0.1 to 3 M in another example, or 1 to 2 M in another example. When carbon dioxide gas is present, it can be in an amount of 50 mg to 25 g, 100 mg to 15 g in another example, or 150 mg to 10 g in another example, per liter of the solution.

The optimal growth temperature of the chosen microorganism is generally in the range of 25 to 40° C. Therefore, the reaction temperature is generally in the range of 25 to 40° C., or in the range of 30 to 37° C. in another example. The amount of bacterial cells in the reaction mixture is, although it is not particularly limited, 1 to 700 g/L, 10 to 500 g/L in another example, or 20 to 400 g/L in another example. The reaction time can be 1 to 168 hours, or 3 to 72 hours in another example. The reaction can be performed batchwise or on a column.

The culture of the bacteria can be performed under aerobic conditions. On the other hand, the organic acid production reaction can be performed under aerobic conditions, microaerobic conditions, or anaerobic conditions. When performed under microaerobic conditions or anaerobic conditions, the reaction can be performed in a sealed reaction vessel without aeration, with a supplied inert gas such as nitrogen gas, or with a supplied inert gas containing carbon dioxide gas, and the like.

The organic acid can accumulate in the reaction mixture (culture medium) and can be separated and purified from the reaction mixture in a conventional manner. Specifically, solids such as bacterial cells can be removed by centrifugation, filtration, or the like, then the resulting solution can be desalted with an ion exchange resin or the like, and the organic acid can be separated and purified from the solution by crystallization or column chromatography.

Furthermore, when the target organic acid is succinic acid, and after the production, a polymerization reaction can be carried out by using the produced succinic acid as a raw material to produce a polymer containing succinic acid. In recent years, with the increase of environmentally friendly industrial products, polymers prepared from raw materials of plant origin have been attracting attention. The produced succinic acid can be converted into polymers such as polyesters and polyamides and used (Japanese Patent Laid-open No. 4-189822). Specific examples of succinic acid-containing polymers include succinic acid polyesters obtained by polymerizing a diol such as butanediol and ethylene glycol and succinic acid, succinic acid polyamides obtained by polymerizing a diamine such as hexamethylenediamine and succinic acid, and the like. In addition, succinic acid and succinic acid-containing polymers obtained by the production method described herein, and compositions containing these can be used for food additives, pharmaceutical agents, cosmetics, and the like.

EXAMPLES

Hereinafter, the present invention will be explained more specifically with reference to the following non-limiting examples.

Reference Example 1: Construction of *Pantoea ananatis* Strain Resistant to λ Red Gene Product In order to disrupt the sdhA gene in *Pantoea ananatis*, a recipient strain for efficiently carrying out the method called "Red-driven integration" or "Red-mediated integration" (Datsenko, K A. and Wanner, B. L., 2000, Proc. Natl. Acad. Sci. USA., 97, 6640-6645) was constructed.

First, the novel helper plasmid RSF-Red-TER which expresses the gam, bet and exo genes of λ("λ Red genes") was constructed (FIG. 1). The details of this construction are described in Reference Example 2.

This plasmid can be used in a wide range of hosts having different genetic backgrounds. This is because 1) this plasmid has the replicon of the RSF1010 wide host spectrum plasmid (Scholz, et al., 1989, Gene, 75:271-288; Buchanan-Wollaston et al., 1987, Nature, 328:172-175), which is stably maintained by many types of gram negative and gram positive bacteria, and even plant cells, 2) the λ Red genes, gam, bet and exo, are under the control of the PlacUV5 promoter, which is recognized by the RNA polymerases of many types of bacteria (for example, Brunschwig, E. and Darzins, A., 1992, Gene, 111, 1, 35-41; Dehio, M. et al, 1998, Gene, 215, 2, 223-229), and 3) the autoregulation factor PlacUV5-lacI and the ρ-non-dependent transcription terminator (TrrnB) of the rrnB operon of *Escherichia coli* lower the basal expression level of the λ Red genes (Skorokhodova, A. Y. et al, 2004, Biotekhnologiya (Rus), 5, 3-21). Furthermore, the RSF-Red-TER plasmid contains the levansucrase gene (sacB), and by the expression of this gene, the plasmid can be collected from cells in a medium containing sucrose.

In *Escherichia coli*, the frequency of integration of a PCR-generated DNA fragment along with the short flanking region provided by the RSF-Red-TER plasmid is as high as the frequency obtained when using the pKD46 helper plasmid (Datsenko, K. A., Wanner, B. L., 2000, Proc. Natl. Acad. Sci. USA, 97, 6640-6645). However, expression of the λ Red genes is toxic to *Pantoea ananatis*. Cells transformed with the RSF-Red-TER helper plasmid grow extremely slowly in LB medium containing IPTG (isopropyl-β-D-thiogalactopyranoside, 1 mM) and an appropriate antibiotic (25 μg/ml of chloramphenicol or 40 μg/ml of kanamycin), and the efficiency of λ Red-mediated recombination is extremely low ($10^{-8}$), if observed at all.

A variant strain of *Pantoea ananatis* which is resistant to expression of all three of the λ Red genes was selected. For this purpose, the RSF-Red-TER plasmid was introduced into the *Pantoea ananatis* SC17 strain (U.S. Pat. No. 6,596,517) by electroporation. After an 18-hour culture, about $10^6$ transformants were obtained, and among these, 10 clones formed colonies of a large size, and the remainder formed extremely small colonies. After an 18 hour culture, the large colonies were about 2 mm, and the small colonies were about 0.2 mm. While the small colonies did not grow any more even when the culture was extended up to 24 hours, the large colonies continued to grow. One of the large colony *Pantoea ananatis* mutant strains which was resistant to expression of all three of the λ Red genes (gam, bet, and exo) was used for further analysis.

The RSF-Red-TER plasmid DNA was isolated from one clone of the large colony clones, and from several clones of the small colony clones, and transformed again into *Escherichia coli* MG1655 to examine the ability of the plasmid to synthesize an active Red gene product. A control experiment for Red-dependent integration in the obtained transformants was used to demonstrate that only the plasmid isolated from the large colony clone induced expression of the λ Red genes required for the Red-dependent integration. In order to investigate whether the Red-mediated integration occurs in the selected large colony clone, electroporation was performed using a linear DNA fragment produced by PCR. This fragment was designed so that it contains a $Km^R$ marker and a flanking region of 40 bp homologous to the hisD gene, and is integrated into the hisD gene of *Pantoea ananatis* at the SmaI recognition site. Two small colony clones were used as control. The nucleotide sequence of the hisD gene of *Pantoea ananatis* is shown in SEQ ID NO: 40. For PCR, the oligonucleotides of SEQ ID NOS: 41 and 42 were used as primers, and the pMW118-(λatt-$Km^r$-λatt) plasmid was used as the template. The two small colony clones which were not resistant to the λ Red genes were used as the control. Construction of the pMW118-(λattL-Kmr-λattR) plasmid will be explained in detail in Reference Example 3.

The RSF-Red-TER plasmid can induce expression of the Red genes by the lacI gene carried on the plasmid. Two kinds of induction conditions were investigated. In the first group, IPTG (1 mM) was added 1 hour before the electroporation, and in the second group, IPTG was added at the start of the culture to prepare cells in which electroporation is possible. The growth rate of the progeny of the SC17 strain harboring RSF-Red-TER derived from the large colony clone was not significantly lower than that of a strain not having the RSF-Red-TER plasmid. The addition of IPTG only slightly decreased the growth rate of these cultures. On the other hand, the RSF-Red-TER-introduced SC17 strain derived from the progeny of the small colony clones grew extremely slowly even without the addition of IPTG, and after induction, growth was substantially arrested. After electroporation of RSF-Red-TER isolated from the cells of the progeny of the large colony clone, many $Km^R$ clones grew (18 clones after a short induction time, and about 100 clones after an extended induction time). All of the 100 clones that were investigated had a His phenotype, and about 20 clones were confirmed by PCR to have the expected structure of the chromosome in the cells. On the other hand, even when electroporation was performed with RSF-Red-TER isolated from cells of the progeny of the small colony clones, an integrated strain was not obtained.

The large colony clone was grown on a plate containing 7% sucrose to eliminate the plasmid, and transformed again with RSF-Red-TER. The strain without the plasmid was designated SC17(0). This strain was deposited at the Russian National Collection of Industrial Microorganisms (VKPM), GNII Genetica (Address: 1 Dorozhny proezd., 1 Moscow 117545, Russia) on Sep. 21, 2005, and assigned an accession number of VKPM B-9246.

All the clones which grew after the aforementioned re-transformation were large like the parent strain clone SC17(0). The Red-mediated integration experiment was performed in the SC17(0) strain which had been re-transformed with the RSF-Red-TER plasmid. Three of the independent transformants obtained were investigated using the same DNA fragment as that used for the previous experiment. A short induction time (1 hour before electroporation) was employed. $Km^R$ clones exceeding ten clones grew in each experiment. All the examined clones had the His phenotype. In this way, a mutant strain designated SC17(0) which is resistant to the expression of the λ Red genes was selected. This strain can be used as a recipient strain suitable for the Red-dependent integration into the *Pantoea ananatis* chromosome.

Reference Example 2: Construction of Helper Plasmid RSF-Red-TER

Figure 2:
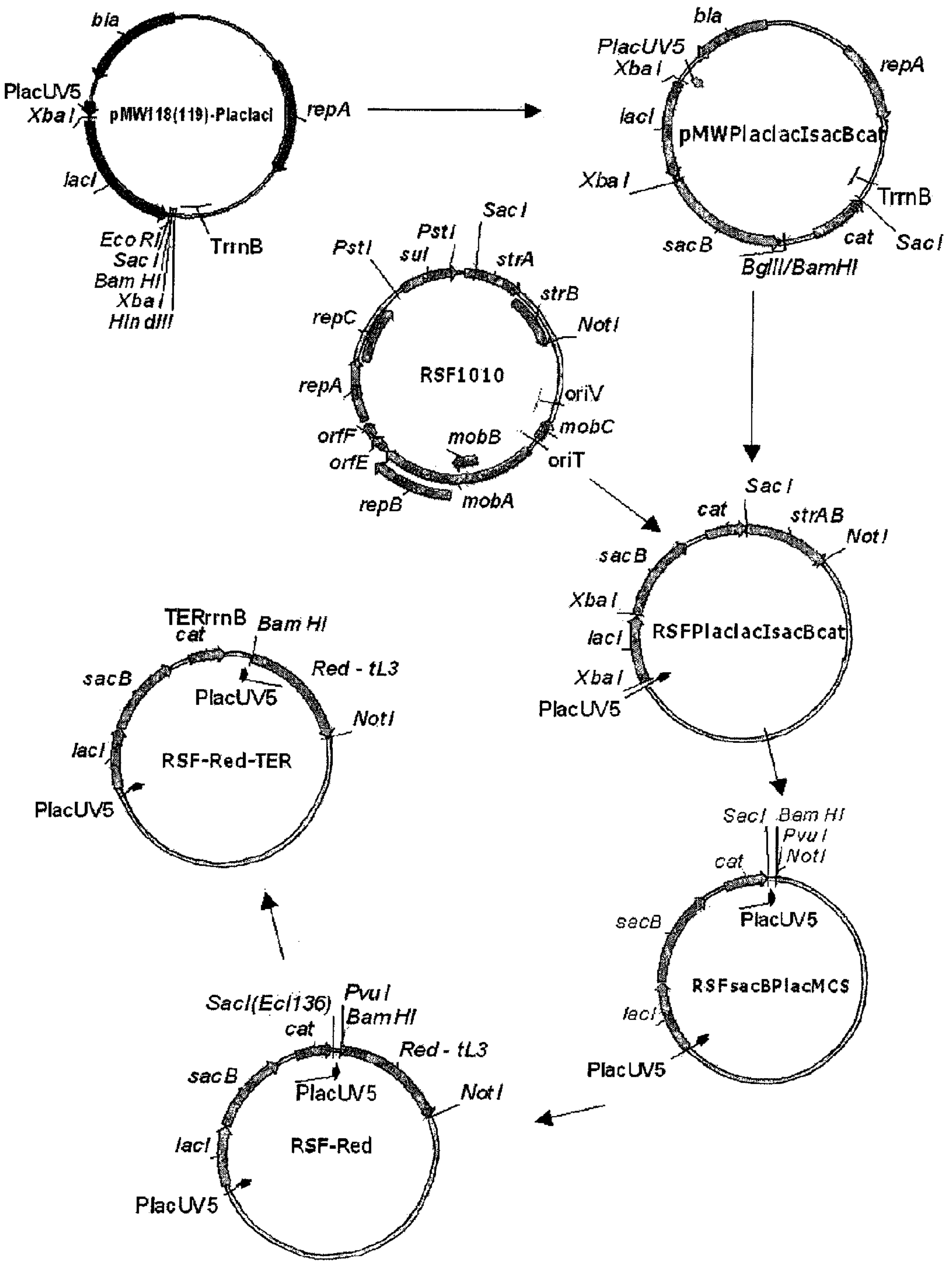
FIG. 2 shows construction of helper plasmid RSF-Red-TER.

The scheme for constructing the helper plasmid RSF-Red-TER is shown in FIG. 2.

As the first step in the construction, an RSFsacBPlacMCS vector was designed. For this purpose, DNA fragments containing the cat gene of the pACYC184 plasmid and the structural region of the sacB gene of *Bacillus subtilis* were amplified by PCR using the oligonucleotides of SEQ ID NOS: 43 and 44, and 45 and 46, respectively. These oligonucleotides contained the BglII, SacI, XbaI and BamHI restriction enzyme sites in the 5' end regions. These sites are required and convenient for further cloning. The obtained sacB fragment of 1.5 kb was cloned into the previously obtained pMW119-$P_{lac}$lacI vector at the XbaI-BamHI site. This vector was constructed in the same manner as that described for the pMW118-$P_{lac}$lacI vector (Skorokhodova, A. Y. et al, 2004, Biotekhnologiya (Rus), 5:3-21). However, this vector contained a polylinker moiety derived from pMW219 instead of the pMW218 plasmid.

Then, the aforementioned cat fragment of 1.0 kb was treated with BglII and SacI, and cloned into the RSF-$P_{lac}$lacIsacB plasmid obtained in the previous step at the BamHI-SacI site. The obtained plasmid pMW-$P_{lac}$lacIsacB-cat contained the PlacUV5-lacI-sacB-cat fragment. In order to subclone this fragment into the RSF1010 vector, pMW-$P_{lac}$lacIsacBcat was digested with BglII, blunt-ended with DNA polymerase I Klenow fragment, and successively digested with SacI. A 3.8 kb BglII-SacI fragment of the pMWP$_{lac}$lacIsacBcat plasmid was eluted from a 1% agarose gel, and ligated with the RSF1010 vector which had been treated with PstI and SacI. *Escherichia coli* TG1 was transformed with the ligation mixture, and plated on the LB medium containing chloramphenicol (50 mg/L). The plasmids isolated from the grown clones were analyzed with restriction enzymes to obtain an RSFsacB plasmid. In order to construct an RSFsacBPlacMCS vector, a DNA fragment containing the PlacUV5 promoter was amplified by PCR using the oligonucleotides of SEQ ID NOS: 47 and 48 as primers and the pMW119-$P_{lac}$lacI plasmid as a template. The obtained fragment of 146 bp was digested with SacI and NotI, and ligated with the SacI-NotI large fragment of the RSFsacB plasmid. Then, by PCR using the oligonucleotides of SEQ ID NOS: 49 and 50 as primers, and the pKD46 plasmid (Datsenko, K. A., Wanner, B. L., 2000, Proc. Natl. Acad. Sci. USA, 97, 6640-6645) as a template, a DNA fragment of 2.3 kb containing the λRedαβγ genes and the transcription terminator tL3 was amplified. The obtained fragment was cloned into the RSFsacBPlacMCS vector at the PvuI-NotI site. In this way, the RSFRed plasmid was designed.

In order to eliminate read through transcription of the Red genes, a ρ-dependent transcription terminator of the rrnB operon of *Escherichia coli* was inserted at a position between the cat gene and the PlacUV5 promoter. For this purpose, a DNA fragment containing the PlacUV5 promoter and the TrrnB terminator was amplified by PCR using the oligonucleotides of SEQ ID NOS: 51 and 48 as primers and the chromosome of *Escherichia coli* BW3350 as the template. These obtained fragments were treated with KpnI and ligated. Then, the 0.5 kb fragment containing both PlacUV5 and TrrnB was amplified by PCR using the oligonucleotides of SEQ ID NOS: 48 and 52 as primers. The obtained DNA fragment was digested with EcoRI, blunt-ended by a treatment with DNA polymerase I Klenow fragment, digested with BamHI, and ligated with the Ecl136II-BamHI large fragment of the RSFsacBPlacMCS vector. The obtained plasmid was designated RSF-Red-TER.

Reference Example 3: Construction of the pMW118-(λattL-$Km^r$-λattR) Plasmid

The pMW118-(λattL-$Km^r$-λattR) plasmid was constructed from the pMW118-attL-Tc-attR (WO2005/010175) plasmid by replacing the tetracycline resistance marker gene with the kanamycin resistance gene of the pUC4K plasmid. For that purpose, the EcoRI-HindIII large fragment from pMW118-attL-Tc-attR was ligated to two fragments from the pUC4K plasmid: the HindIII-PstI fragment (676 bp) and EcoRI-HindIII fragment (585 bp). Basic pMW118-attL-Tc-attR was obtained by ligation of the following four fragments.

1) The BglII-EcoRI fragment (114 bp) including attL (SEQ ID NO: 55) which was obtained by PCR amplification of the region corresponding to attL of the *Escherichia coli* W3350 (containing λ prophage) chromosome using the primers P1 and P2 (SEQ ID NOS: 53 and 54) (these primers contained the subsidiary recognition sites for BglII and EcoRI).

2) The PstI-HindIII fragment (182 bp) including attR (SEQ ID NO: 58) which was obtained by PCR amplification of the region corresponding to attR of the *Escherichia coli* W3350 (containing λ prophage) chromosome using the primers P3 and P4 (SEQ ID NOS: 56 and 57) (these primers contained the subsidiary recognition sites for PstI and HindIII).

3) The BglII-HindIII large fragment (3916 bp) of pMW118-ter_rrnB. The plasmid pMW118-ter_rrnB was obtained by ligation of the following three DNA fragments:

The large DNA fragment (2359 bp) including the AatII-EcoRI fragment of pMW118 that was obtained by digesting pMW118 with EcoRI, treated with DNA polymerase I Klenow fragment, and then digested with AatII;

The small AatII-BglII fragment (1194 bp) of pUC19 including the bla gene for ampicillin resistance (ApR), which was obtained by PCR amplification of the corresponding region of the pUC19 plasmid using the primers P5 and P6 (SEQ ID NOS: 59 and 60) (these primers contained the subsidiary recognition sites for PstI, AatII and BglII);

The small BglII-PstI fragment (363 bp) of the transcription terminator ter_rrnB, which was obtained by PCR amplification of the corresponding region of the *Escherichia coli* MG1655 chromosome using the primers P7 and P8 (SEQ ID NOS: 61 and 62) (these primers contained the subsidiary recognition sites for PstI, BglII and PstI).

4) The small EcoRI-PstI fragment (1388 bp) (SEQ ID NO: 63) of pML-Tc-ter_thrL including the tetracycline resistance gene and the ter_thrL transcription terminator; the pML-Tc-ter_thrL plasmid was obtained by the following two steps:

the pML-ter_thrL plasmid was obtained by digesting the pML-MCS plasmid (Mashko, S. V. et al., 2001, Biotekhnologiya (in Russian), no. 5, 3-20) with XbaI and BamHI, followed by ligation of the large fragment (3342 bp) with the XbaI-BamHI fragment (68 bp) carrying ter_thrL terminator obtained by PCR amplification of the corresponding region of the *Escherichia coli* MG1655 chromosome using the primers P9 and P10 (SEQ ID NOS: 64 and 65) (these primers contained the subsidiary recognition sites for PstI, XbaI and BamHI);

the pML-Tc-ter_thrL plasmid was obtained by digesting the pML-ter_thrL plasmid with KpnI and XbaI followed by treatment with Klenow fragment of DNA polymerase I and ligated with the small EcoRI-Van91I fragment (1317 bp) of pBR322 including the tetracycline resistance gene (pBR322 was digested with EcoRI and Van91I and then treated with DNA polymerase I Klenow fragment).

Example 1: Search of L-Glutamic Acid Secretion Gene

A search for an L-glutamic acid secretion gene was performed as follows. Since L-glutamic acid is converted into an intermediate of the tricarboxylic acid cycle, 2-oxoglutarate, in one step by glutamate dehydrogenase, L-glutamic acid is thought to be easily metabolized in many microorganisms having glutamate dehydrogenase or the tricarboxylic acid cycle. However, since a strain in which 2-oxoglutarate dehydrogenase is deleted cannot degrade L-glutamic acid, growth of the cells is inhibited in the presence of a high concentration glutamic acid. In this example, the SC17sucAams strain derived from the *Pantoea ananatis* SC17sucA strain (refer to Japanese Patent Laid-open No. 2001-333769) is deficient in the extracellular polysaccharide biosynthesis system, and is also deficient in 2-oxoglutarate dehydrogenase. Therefore, this strain was used to try to obtain an L-glutamic acid excretion gene utilizing resistance to a high concentration of L-glutamic acid as a marker.

Since the SC17sucA strain produced a marked amount of extracellular polysaccharides when grown on an agar medium containing a sugar source, the handling of this strain is extremely difficult. Therefore, by deleting the ams operon coding for the extracellular polysaccharide biosynthesis system genes, production of extracellular polysaccharides was suppressed. PCR was performed by using pMW118-λattL-$Km^r$-λattR as the template and the primers of SEQ ID NOS: 6 and 7 to amplify a gene fragment containing a kanamycin resistance gene, attL and attR sequences of λ phage at the both ends of the resistance gene, and 50 bp upstream sequence of amsI and 50 bp downstream sequence of the amsC gene added to the outer ends of the λ phage sequences. This fragment was purified by using Wizard PCR Prep DNA Purification System (Promega).

Then, the SC17(0) strain was transformed with RSF-Red-TER to obtain an SC17(0)/RSF-Red-TER strain. This strain was cultured overnight in L medium (10 g of Bacto tryptone, 5 g of yeast extract and 5 g of NaCl in 1 L of pure water, pH 7.0) containing 25 mg/L of chloramphenicol, and then the culture medium after the overnight culture was inoculated in 1/100 volume into 100 mL of the L medium containing 25 mg/L of chloramphenicol and 1 mM isopropyl-β-D-thiogalactopyranoside, and culture was performed at 34° C. for 3 hours. The cells prepared as described above were collected, washed three times with ice-cooled 10% glycerol, and finally suspended in 0.5 mL of 10% glycerol. The suspended cells were used as competent cells, and 100 ng of the PCR fragment prepared in the above section was introduced into the cells by using GENE PULSER II (BioRad) with a field strength of 18 kV/cm, capacitor capacity of 25 μF and resistance of 200Ω. Ice-cooled SOC medium (20 g/L of Bacto tryptone, 5 g/L of yeast extract, 0.5 g/L of NaCl and 10 g/L of glucose) was added to the cell suspension, and culture was performed at 34° C. for 2 hours with shaking. The culture was applied to a medium prepared by adding ingredients of minimal medium (5 g of glucose, 2 mM magnesium sulfate, 3 g of monopotassium phosphate, 0.5 g of sodium chloride, 1 g of ammonium chloride and 6 g of disodium phosphate in 1 L) and 40 mg/L of kanamycin to the L medium (10 g of Bacto tryptone, 5 g of yeast extract, 5 g of NaCl and 15 g of agar in 1 L of pure water, pH 7.0). The colonies that appeared were purified with the same medium, and then it was confirmed by PCR that the ams gene had been replaced with the kanamycin resistance gene.

The chromosome was extracted from the ams gene-deficient strain using a Bacterial Genomic DNA Purification Kit (Edge Biosystems). Separately, the SC17sucA strain was cultured overnight on an agar medium obtained by adding the ingredients of the minimal medium described above to the L medium. The cells were scraped with a loop, washed three times with ice-cooled 10% glycerol, and finally suspended in 10% glycerol to a final volume of 500 μL. The suspended cells were used as competent cells, and 600 ng of the aforementioned chromosome DNA was introduced into the competent cells using GENE PULSER II (BioRad) with a field strength of 17.5 kV/cm, capacitor capacity of 25 μF and resistance of 200Ω. Ice-cooled SOC medium was added to the cell suspension, and culture was performed at 34° C. for 2 hours with shaking. Then, the culture was applied on an agar medium prepared by adding ingredients of the minimal medium described above and 40 mg/L of kanamycin to the L medium. The colonies that appeared were purified with the same medium, and then it was confirmed by PCR that the ams gene had been replaced with the kanamycin resistance gene. This strain was designated as SC17sucAams.

Chromosomal DNA extracted from the *Pantoea ananatis* AJ13355 strain was partially digested with the restriction enzyme Sau3AI. Then, fragments of about 10 kb were collected and introduced into the BamHI site of pSTV28 (Takara Bio) to prepare a plasmid library. This plasmid library was introduced into competent cells of the SC17sucAams strain prepared in a conventional manner by electroporation.

Selection was performed for the SC17sucAams strain which had been introduced with a plasmid library on a plate of the L medium (10 g of Bacto tryptone, 5 g of yeast extract, 5 g of NaCl and 15 g of agar in 1 L of pure water, pH 7.0) added with ingredients of minimal medium (5 g of glucose, 2 mM magnesium sulfate, 3 g of monopotassium phosphate, 0.5 g of sodium chloride, 1 g of ammonium chloride and 6 g of disodium phosphate in 1 L of pure water) using chloramphenicol resistance as a marker to obtain transformants. These transformants were plated on a glucose minimal medium containing a high concentration L-glutamic acid (the glucose minimal medium mixed with 0.2 M L-glutamic acid, 100 mg/L each of lysine, methionine and diaminopimelic acid as final concentrations), in which SC17sucAams cannot form colonies.

The transformants were cultured at 34° C. for 3 days, and 64 clones among the colonies that appeared were allowed to again form single colonies on the same plate. As a result, 11 clones were found to form colonies after 48 hours, and the remaining colonies formed colonies after 72 hours.

Then, the genes inserted into the vectors harbored by the transformants were analyzed. Plasmids were extracted from the transformants, and nucleotide sequences were determined. It was found that among the 11 clones that formed colonies within 48 hours, 10 clones had the same loci, and all contained genes showing homology to ybjL, which was an *Escherichia coli* gene of unknown function. In addition, this ybjL gene could not be obtained under the same conditions that the glutamic acid secretion system gene described in WO2005/085419, yhfK, was obtained, and conversely, the yhfK gene could not be obtained under the selection conditions used in this example.

In order to confirm that the factor which imparts glutamic acid resistance is ybjL, the ybjL gene was cloned. PCR was performed using the chromosomal DNA of AJ13355 strain as the template and oligonucleotides ybjL-F1 and ybjL-R2 shown in SEQ ID NOS: 8 and 9 to amplify the fragment of about 1.8 kb containing the ybjL gene of *P. ananatis*. This fragment was purified using Wizard PCR Prep DNA Purification System (Promega), and then treated with the restriction enzymes KpnI and SphI, and the product was ligated with pSTV28 (Takara Bio) which had been treated with the same enzymes to obtain pSTV-PanybjL. The SC17sucA strain was transformed with this pSTV-PanybjL plasmid, and using pSTV28 as a control for comparison (Takara Bio) to construct the SC17sucA/pSTV-PanybjL and SC17sucA/pSTV28 strains.

The SC17sucA/pSTV-ybjL strain was plated on minimal medium (5 g of glucose or sucrose, 2 mM magnesium sulfate, 3 g of monopotassium phosphate, 0.5 g of sodium chloride, 1 g of ammonium chloride, 6 g of disodium phosphate, 0.2 M sodium L-glutamate, 100 mg/L each of lysine, methionine and diaminopimelic acid and 15 g of agar in 1 L of pure water) containing glutamic acid. Culture was performed at 34° C. for 2 days. As a result, it was confirmed that whereas the control vector-introduced strain, SC17sucA/pSTV28, could not form colonies, SC17sucA/pSTV-ybjL could form colonies on the minimal medium.

Then, the SC17sucA/pSTV-PanybjL strain was cultured in liquid minimal medium (5 g of glucose, 2 mM magnesium sulfate, 3 g of monopotassium phosphate, 0.5 g of sodium chloride, 1 g of ammonium chloride, 6 g of disodium phosphate, 0.2 M sodium L-glutamate, 100 mg/L each of lysine, methionine and diaminopimelic acid in 1 L of pure water) containing glutamic acid to examine growth of the strain in the presence of a high concentration of L-glutamic acid.

Figure 3:
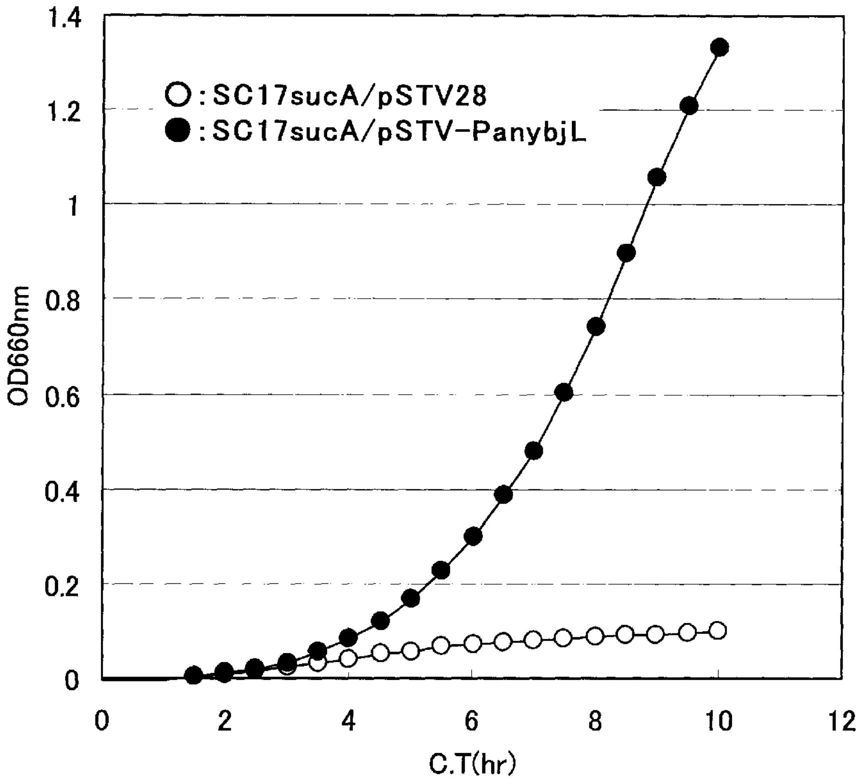
FIG. 3 shows the growth of the ybjL-amplified strain in the presence of a high concentration L-glutamic acid. C.T. (hr) stands for 'culture time' in hours. $OD_{660\ nm}$ stands for the optical density at 660 nm, which is a measure of growth of the respective strains of bacteria as identified in the graph.

The results are shown in FIG. 3. It was found that growth of SC17sucA/pSTV-PanybjL in which the ybjL gene had been enhanced was markedly improved in the presence of high concentration L-glutamic acid as compared to the control strain SC17sucA/pSTV28. Accordingly, it was confirmed that ybjL is a factor which imparts resistance to L-glutamic acid.

Example 2: Effect of ybjL Gene Amplification on L-Glutamic Acid Production at Neutral pH Then, in order to examine the effect of this gene on L-glutamic acid production, the plasmid for ybjL amplification, pSTV-PanybjL, was introduced into the L-glutamic acid producing bacterium SC17sucA/RSFCPG having the plasmid for L-glutamic acid production, RSFCPG, shown in SEQ ID NO: 10 (refer to Japanese Patent Laid-open No. 2001-333769), and L-glutamic acid productivity thereof was examined.

pSTV-PanybjL and the control plasmid, pSTV28 (Takara Bio), were each introduced into SC17sucA/RSFCPG by electroporation, and transformants were obtained using chloramphenicol resistance as a marker. After confirmation of the presence of the plasmids, the strain with the plasmid for ybjL amplification was designated SC17sucA/RSFCPG+pSTV-PanybjL, and the strain with pSTV29 was designated SC17sucA/RSFCPG+pSTV28.

Then, SC17sucA/RSFCPG+pSTV-PanybjL and the control strain SC17sucA/RSFCPG+pSTV28 were cultured to examine the L-glutamic acid producing ability of the strains. The medium had the following composition:

Composition of Culture Medium:

Section A:

| | |
|---|---|
| Sucrose | 30 g/L |
| $MgSO_4 \cdot 7H_2O$ | 0.5 g/L |

[[Group B:

| | |
|---|---|
| $KH_2PO_4$ | 2.0 g/L |
| Yeast Extract | 2.0 g/L |
| $FeSO_4 \cdot 7H_2O$ | 0.02 g/L |
| $MnSO_4 \cdot 5H_2O$ | 0.02 g/L |
| L-Lysine hydrochloride | 0.2 g/L |
| DL-Methionine | 0.2 g/L |
| Diaminopimelic acid | 0.2 g/L |
| (adjusted to pH 7.0 with KOH) | |

Group C:

| | |
|---|---|
| $CaCO_3$ | 20 g/L |

The ingredients of groups A and B were sterilized at 115° C. for 10 minutes by autoclaving, and the ingredient of group C was sterilized at 180° C. for 3 hours with dry heat. Then, the ingredients of the three groups were mixed, and 12.5 mg/L of tetracycline hydrochloride and 25 mg/L of chloramphenicol were added to the mixture.

SC17sucA/RSFCPG+pSTV29 and SC17sucA/RSFCPG+pSTV-PanybjL were each precultured on a medium obtained by adding ingredients of the minimal medium (medium containing 5 g of glucose, 2 mM magnesium sulfate, 3 g of monopotassium phosphate, 0.5 g of sodium chloride, 1 g of ammonium chloride and 6 g of disodium phosphate in 1 L of pure water), 25 mg/L of chloramphenicol and 12.5 mg/L tetracycline to the L medium (medium containing 10 g of Bacto tryptone, 5 g of yeast extract, 5 g of NaCl and 15 g of agar in 1 L of pure water, pH 7.0), and inoculated into an appropriate amount to 5 ml of the aforementioned medium in a test tube.

The cells were cultured for 17.5 hours, and then cell density, L-glutamic acid concentration, and the amount of residual saccharide in the culture medium were measured. The cell density was examined by measuring turbidity at 620 nm of the medium diluted 51 times using a spectrophotometer (U-2000A, Hitachi). The L-glutamic acid concentration was measured in culture supernatant appropriately diluted with water by using Biotech Analyzer (AS-210, Sakera SI). The results are shown in Table 1. L-Glutamic acid accumulation was increased by about 3 g/L, and the yield based on saccharide increased by about 9% in the ybjL-amplified strain, SC17sucA/RSFCPG+pSTV-PanybjL, as compared to the control strain, SC17sucA/RSFCPG+pSTV28.

TABLE 1

| | OD 620 nm (×51) | L-Glutamic acid (g/L) | Yield based on saccharide (%) |
|---|---|---|---|
| SC17sucA/RSFCPG + pSTV28 | 0.385 | 15.0 | 44.5 |
| SC17sucA/RSFCPG + pSTV-PanybjL | 0.280 | 18.0 | 53.7 |

Example 3: Effect of Amplification of the ybjL Gene Derived from *Escherichia coli*

Then, the ybjL gene from *Escherichia coli* was introduced into the *Pantoea ananatis* SC17sucA/RSFCPG strain, and the effect of this amplification on glutamic acid production was examined.

PCR was performed using the oligonucleotides shown in SEQ ID NOS: 11 and 12 prepared on the basis of the sequence of the ybjL of *Escherichia coli* registered at GeneBank as AP009048 (SEQ ID NO: 3) and the chromosome from the *Escherichia coli* W3110 strain (ATCC 27325) as the template to obtain a fragment of about 1.7 kb containing the ybjL gene. This fragment was treated with SphI and KpnI, and ligated with pSTV28 (Takara Bio) at the corresponding site. The plasmid for amplification of ybjL of *Escherichia coli* was designated as pSTV-EcoybjL.

The plasmid pSTV-EcoybjL for ybjL amplification was introduced into the aforementioned SC17sucA/RSFCPG strain by electroporation, and a transformant was obtained using chloramphenicol resistance as a marker. The obtained *Escherichia coli* ybjL gene-amplified strain was designated as SC17sucA/RSFCPG+pSTV-EcoybjL.

Then, SC17sucA/RSFCPG+pSTV-EcoybjL and the control strain, SC17sucA/RSFCPG+pSTV28, were cultured to examine their L-glutamic acid producing ability. The medium had the following composition.

Composition of Culture Medium:

Group A:

| | |
|---|---|
| Sucrose | 30 g/L |
| $MgSO_4 \cdot 7H_2O$ | 0.5 g/L |

Group B:

| | |
|---|---|
| $KH_2PO_4$ | 2.0 g/L |
| Yeast Extract | 2.0 g/L |

-continued

| | |
|---|---|
| $FeSO_4 \cdot 7H_2O$ | 0.02 g/L |
| $MnSO_4 \cdot 5H_2O$ | 0.02 g/L |
| L-Lysine hydrochloride | 0.2 g/L |
| DL-Methionine | 0.2 g/L |
| Diaminopimelic acid | 0.2 g/L |
| (adjusted to pH 7.0 with KOH) | |

Group C:

| | |
|---|---|
| $CaCO_3$ | 20 g/L |

The ingredients of groups A and B were sterilized at 115° C. for 10 minutes by autoclaving, and the ingredient of group C was sterilized at 180° C. for 3 hours with dry heat. Then, the ingredients of the three groups were mixed, and 12.5 mg/L of tetracycline hydrochloride and 25 mg/L of chloramphenicol were added to the mixture.

SC17sucA/RSFCPG+pSTV28 and SC17sucA/RSFCPG+pSTV-EcoybjL were each precultured on a medium obtained by adding ingredients of the minimal medium (5 g of glucose, 2 mM magnesium sulfate, 3 g of monopotassium phosphate, 0.5 g of sodium chloride, 1 g of ammonium chloride and 6 g of disodium phosphate in 1 L of pure water), 25 mg/L of chloramphenicol, and 12.5 mg/L tetracycline to the L medium (10 g of Bacto tryptone, 5 g of yeast extract, 5 g of NaCl and 15 g of agar in 1 L of pure water, pH 7.0), and inoculated in an appropriate amount to 5 ml of the aforementioned medium in a test tube.

The cells were cultured for 17.5 hours, and then cell density and L-glutamic acid concentration in the culture medium were measured in the same manner as shown in Example 2. The results are shown in Table 2. L-Glutamic acid accumulation was increased by about 2 g/L, and the yield based on saccharide increased by about 7% in the ybjL-amplified strain, SC17sucA/RSFCPG+pSTV-EcoybjL, as compared to the control strain, SC17sucA/RSFCPG+pSTV28.

TABLE 2

| | OD 620 nm (×51) | L-Glutamic acid (g/L) | Yield based on saccharide (%) |
|---|---|---|---|
| SC17sucA/RSFCPG + pSTV28 | 0.385 | 15.0 | 44.5 |
| SC17sucA/RSFCPG + pSTV-EcoybjL | 0.348 | 17.2 | 51.2 |

Example 4: Effect of Amplification of ybjL Gene on L-Amino Acid Production in *Escherichia coli*

Then, the ybjL gene derived from *Pantoea ananatis* and the ybjL gene derived from *Escherichia coli* were each introduced into *Escherichia coli*, and the effect of the amplification was examined.

The aforementioned vector for amplification of the ybjL gene derived from *Pantoea ananatis*, pSTV-PanybjL, vector for amplification of ybjL gene derived from *Escherichia coli*, pSTV-EcoybjL, and the control plasmid pSTV28 were each introduced into an *Escherichia coli* wild-type strain, W3110, by electroporation to obtain transformants resistant to chloramphenicol. The strain in which ybjL derived from *Pantoea ananatis* had been amplified was designated W3110/pSTV-PanybjL, the strain in which ybjL derived from *Escherichia coli* had been amplified was designated W3110/pSTV-EcoybjL, and the control strain with pSTV28 was designated W3110/pSTV28.

Then, the ability to produce L-glutamic acid of the ybjL-amplified strains, W3110/pSTV-PanybjL and W3110/pSTV-EcoybjL, and the control strain W3110/pSTV28 were examined. W3110/pSTV-PanybjL, W3110/pSTV-EcoybjL, and W3110/pSTV28 were each precultured on L medium (10 g of Bacto tryptone, 5 g of yeast extract, 5 g of NaCl and 15 g of agar in 1 L of pure water, pH 7.0) containing chloramphenicol, and one loop of cells were inoculated by using a 1-mL volume loop (Nunc) to 5 mL of a medium having the following composition in a test tube, and cultured at 37° C. for 11.5 hours with shaking. Cell density and L-glutamic acid concentration in the culture medium were measured in the same manners as those in Example 2. The results are shown in Table 3.

Composition of Culture Medium:

Group A:

| | |
|---|---|
| Glucose | 30 g/L |
| $MgSO_4 \cdot 7H_2O$ | 0.5 g/L |

Group B:

| | |
|---|---|
| $(NH_4)_2SO_4$ | 20 g/L |
| $KH_2PO_4$ | 2.0 g/L |
| Yeast Extract | 2.0 g/L |
| $FeSO_4 \cdot 7H_2O$ | 20 mg/L |
| $MnSO_4 \cdot 5H_2O$ | 20 mg/L |
| (adjusted to pH 7.0 with KOH) | |

Group C:

| | |
|---|---|
| Calcium carbonate | 20 g/L |

The ingredients of groups A and B were sterilized at 115° C. for 10 minutes by autoclaving, and the ingredient of group C was sterilized at 180° C. for 3 hours with dry heat. Then, the ingredients of the three groups were mixed, and 25 mg/L of chloramphenicol was added to the mixture.

TABLE 3

| | OD 620 nm (×51) | L-Glutamic acid (g/L) | Yield based on saccharide (%) |
|---|---|---|---|
| W3110/pSTV28 | 0.341 | 1.2 | 6.5 |
| W3110/pSTV-PanybjL | 0.303 | 5.7 | 28.8 |
| W3110/pSTV-EcoybjL | 0.310 | 4.8 | 25.2 |

The L-glutamic acid producing ability was markedly improved in the *Escherichia coli* W3110/pSTV-PanybjL strain, which is a *Pantoea ananatis* in which the ybjL gene has been amplified, and the *Escherichia coli* W3110/pSTV-EcoybjL strain, which is an *Escherichia coli* in which the ybjL gene has been amplified, as compared to the control strain W3110/pSTV28 strain.

Then, the ability of the ybjL-amplified strain to produce other amino acids was examined. W3110/pSTV-PanybjL, and the control strain W3110/pSTV28 were precultured in L medium (10 g of Bacto tryptone, 5 g of yeast extract, 5 g of NaCl and 15 g of agar in 1 L of pure water, pH 7.0) containing chloramphenicol, and one loop of cells were inoculated by using a 5-mL volume loop (Nunc) to 5 mL of a medium having the following composition in a test tube, and cultured at 37° C. for 7 hours with shaking. Cell densities and L-amino acid concentrations in the culture medium were measured in the same manner as in Example 2. The results are shown in Table 4.

Composition of Culture Medium:

Group A:

| | |
|---|---|
| Glucose | 40 g/L |
| $MgSO_4 \cdot 7H_2O$ | 0.5 g/L |

Group B:

| | |
|---|---|
| $(NH_4)_2SO_4$ | 20 g/L |
| $KH_2PO_4$ | 2.0 g/L |
| Yeast Extract | 2.0 g/L |
| $FeSO_4 \cdot 7H_2O$ | 20 mg/L |
| $MnSO_4 \cdot 5H_2O$ | 20 mg/L |
| (adjusted to pH 7.0 with KOH) | |

Group C:

| | |
|---|---|
| Calcium carbonate | 30 g/L |

The ingredients of groups A and B were sterilized at 115° C. for 10 minutes by autoclaving, and the ingredient of group C was sterilized at 180° C. for 3 hours with dry heat. Then, the ingredients of the three groups were mixed, and 25 mg/L of chloramphenicol was added to the mixture.

TABLE 4

| | W3110/pSTV28 | W3110/pSTV-PanybjL | MS medium* |
|---|---|---|---|
| Asp | 26.69 | 62.35 | 40.21 |
| Thr | 0.00 | 0.00 | 36.23 |
| Ser | 0.00 | 0.00 | 56.03 |
| Glu | 1258.75 | 3702.74 | 127.50 |
| Gly | 0.00 | 0.00 | 27.28 |
| Ala | 5.49 | 9.79 | 77.61 |
| $(Cys)_2$ | 16.49 | 13.72 | 10.13 |
| Val | 3.30 | 8.02 | 59.32 |
| Met | 0.00 | 0.00 | 85.06 |
| Ile | 0.00 | 0.00 | 50.51 |
| Leu | 0.00 | 0.00 | 80.02 |
| Tyr | 48.20 | 0.00 | 38.80 |
| Phe | 2.88 | 4.47 | 70.49 |
| Lys | 8.07 | 8.00 | 50.50 |
| His | 0.00 | 0.00 | 20.95 |
| Arg | 0.00 | 0.00 | 35.80 |
| OD 620 nm (×51) | 0.245 | 0.197 | — |
| Residual glucose (g/L) | 28.9 | 28.3 | 40.0 |

*Blank inoculated with no cells

Not only did the amount of L-glutamic acid increase, but the L-aspartic acid amount also increased in the *Escherichia coli* W3110/pSTV-PanybjL, which is a ybjL gene-amplified strain, as compared to the vector-introduced control strain, W3110/pSTV28 strain.

Example 5: Effect of Amplification of the ybjL Gene on L-Glutamic Acid Production in *Klebsiella planticola*

The ybjL gene derived from *Pantoea ananatis* was introduced into *Klebsiella planticola*, and the effect of the amplification of the gene was examined.

The aforementioned vector for amplification of ybjL gene derived from *Pantoea ananatis*, pSTV-PanybjL, and the control plasmid pSTV28 were each introduced into a *Klebsiella planticola* L-glutamic acid-producing strain, AJ13410 (Japanese Patent Application No. 11-68324), by electroporation to obtain transformants which are resistant to chloramphenicol. The strain in which ybjL derived from *Pantoea ananatis* had been amplified was designated as AJ13410/pSTV-PanybjL, and the control strain with pSTV28 was designated as AJ13410/pSTV28.

Then, the ability to produce L-glutamic acid of the ybjL-amplified strain, AJ13410/pSTV-PanybjL, and the control strain AJ13410/pSTV28 were examined. AJ13410/pSTV-PanybjL and AJ13410/pSTV28 were precultured on L medium (10 g of Bacto tryptone, 5 g of yeast extract, 5 g of NaCl and 15 g of agar in 1 L of pure water, pH 7.0) containing chloramphenicol, and one loop of cells were inoculated by using a 1-mL volume loop (Nunc) to 5 mL of a medium having the following composition in a test tube, and cultured at 37° C. for 17 hours with shaking. Cell density and L-glutamic acid concentration in the culture medium were measured in the same manner as in Example 2. The results are shown in Table 5.

Composition of Culture Medium:

Group A:

| | |
|---|---|
| Sucrose | 30 g/L |
| $MgSO_4 \cdot 7H_2O$ | 0.5 g/L |

Group B:

| | |
|---|---|
| $KH_2PO_4$ | 2.0 g/L |
| Yeast Extract | 2.0 g/L |
| $FeSO_4 \cdot 7H_2O$ | 0.02 g/L |
| $MnSO_4 \cdot 5H_2O$ | 0.02 g/L |
| L-Lysine hydrochloride | 0.2 g/L |
| DL-Methionine | 0.2 g/L |
| Diaminopimelic acid | 0.2 g/L |
| (adjusted to pH 7.0 with KOH) | |

Group C:

| | |
|---|---|
| $CaCO_3$ | 20 g/L |

The ingredients of groups A and B were sterilized at 115° C. for 10 minutes by autoclaving, and the ingredient of group C was sterilized at 180° C. for 3 hours with dry heat. Then, the ingredients of the three groups were mixed, and 25 mg/L of chloramphenicol was added to the mixture.

TABLE 5

| | OD 620 nm (×51) | L-Glutamic acid (g/L) | Yield based on saccharide (%) |
|---|---|---|---|
| AJ13410/pSTV28 | 0.236 | 5.3 | 23.3 |
| AJ13410/pSTV-PanybjL | 0.220 | 12.1 | 48.7 |

L-glutamic acid-producing ability was markedly improved in the *Klebsiella planticola* AJ13410/pSTV-PanybjL, which is a *Pantoea ananatis* ybjL gene-amplified strain, as compared to the control strain, AJ13410/pSTV28.

Reference Example 4: Construction of an *Escherichia coli* Strain Deficient in the L,D-Lactate Dehydrogenase Gene This gene was deleted by using the method called "Red-driven integration" developed by Datsenko and Wanner (Datsenko, K. A. and Wanner, B. L., 2000, Proc. Natl. Acad. Sci. USA, vol. 97, No. 12, pp. 6640-6645), and the λ phage excision system (Cho, E. H., Gumport, R. I., and Gardner, J. F., 2002, J. Bacteriol., 184 (18):5200-5203). According to this method, it is possible, to construct a gene-disrupted strain in a single step by using a PCR product obtained with synthetic oligonucleotide primers in which a part of the target gene is designed in the 5' end and a part of an antibiotic resistance gene is designed in the 3' end. Furthermore, by using the λ phage excision system in combination, the antibiotic resistance gene which is integrated into the gene-disrupted strain can be removed.

<1-1> Construction of a Strain Deficient in the ldhA Gene Coding for D-Lactate Dehydrogenase According to the description of WO2005/010175, PCR was performed by using synthetic oligonucleotides having sequences corresponding to parts of the ldhA gene in the 5' end and sequences corresponding to both ends of attL and attR of λ phage at the 3' end as primers and plasmid pMW118-attL-Cm-attR as the template. pMW118-attL-Cm-attR is a plasmid obtained by inserting attL and attR genes, which are the attachment sites for λ phage, and the cat gene, which is an antibiotic resistance gene, into pMW118 (Takara Bio), and the genes are inserted in the order of attL-cat-attR. The sequences of the synthetic oligonucleotides used as the primers are shown in SEQ ID Nos. 13 and 14. The amplified PCR product was purified on an agarose gel and introduced into *Escherichia coli* MG1655 strain containing the plasmid pKD46, which is capable of temperature-sensitive replication by electroporation. Then, an ampicillin-sensitive strain not harboring pKD46 was obtained, and the deletion of the ldhA gene was confirmed by PCR. PCR was performed by using the synthetic oligonucleotides shown in SEQ ID NOS: 15 and 16 as primers. Whereas the PCR product obtained for the parent strain was about 1.2 kb, the deficient strain was about 1.9 kb.

To eliminate the att-cat gene introduced into the ldhA gene, the strain was transformed with helper plasmid pMW-intxis-ts, and an ampicillin resistant strain was selected. The pMW-intxis-ts contains the λ phage integrase (Int) gene and excisionase (Xis) gene and shows temperature-sensitive replication. Then, the strain in which att-cat and pMW-intxis-ts had been eliminated was confirmed by PCR on the basis of ampicillin sensitivity and chloramphenicol sensitivity. PCR was performed by using the synthetic oligonucleotides shown in SEQ ID NOS: 15 and 16 as primers. Whereas the PCR product obtained for the strain in which att-cat remained was about 1.9 kb, a band of about 0.3 kb was observed for the strain in which att-cat was eliminated. The ldhA deficient strain obtained as described above was designated as MG1655ΔldhA strain.

<1-2> Construction of a Strain Deficient in the lldD Gene Coding for L-Lactate Dehydrogenase A strain was constructed in the same manner as that of the construction of the ldhA gene-deficient strain. PCR was performed using synthetic oligonucleotides having sequences corresponding to parts of the lldD gene in the 5' end and sequences corresponding to both ends of attL and attR of λ phage in the 3' end as primers and plasmid pMW118-attL-Cm-attR as the template. The sequences of the synthetic oligonucleotides used as the primers are shown in SEQ ID Nos. 17 and 18. The amplified PCR product was purified on an agarose gel and introduced into the *Escherichia coli* MG1655ΔldhA strain containing plasmid pKD46 capable of temperature-sensitive replication by electroporation. Then, an ampicillin-sensitive strain not harboring pKD46 was obtained, and the deletion of the lldD gene was confirmed by PCR. PCR was performed by using the synthetic oligonucleotides shown in SEQ ID NOS: 19 and 20 as primers. Whereas the PCR product obtained for the parent strain was about 1.4 kb, a band of about 1.9 kb was observed for the deficient strain.

To eliminate the att-cat gene introduced into the lldD gene, the strain was transformed with helper plasmid pMW-intxis-ts, and an ampicillin resistant strain was selected. Then, the strain from which att-cat and pMW-intxis-ts had been eliminated was obtained and confirmed by PCR on the basis of ampicillin sensitivity and chloramphenicol sensitivity. PCR was performed by using the synthetic oligonucleotides shown in SEQ ID NOS: 19 and 20 as primers. Whereas the PCR product obtained for the strain in which att-cat remained was about 1.9 kb, a band of about 0.3 kb was observed for the strain in which att-cat was eliminated. The lldD deficient strain obtained as described above was designated as MG1655ΔldhΔlldD strain.

Example 6: Construction of ybjL Gene-Enhanced Strain of Succinic Acid-Producing Bacterium <6-1> Construction of Plasmid for Gene Amplification In order to amplify the ybjL gene, plasmid pMW219::Pthr was used. This plasmid corresponds to the vector pMW219 (Nippon Gene) having the promoter region of the threonine operon (thrLABC) in the genome of the *Escherichia coli* shown in SEQ ID NO: 21 at the HindIII site and BamHI site, and enables amplification of a gene by cloning the gene at a position in the plasmid downstream from that promoter.

<6-2> Construction of Plasmid for Enhancing ybjL

PCR was performed by using the synthetic oligonucleotide having a BamHI site shown in SEQ ID NO: 22 as a 5' primer, and the synthetic oligonucleotide having a BamHI site shown in SEQ ID NO: 23 as a 3' primer, which were prepared on the basis of the nucleotide, sequence of the ybjL gene in the genome sequence of *Escherichia coli* (GenBank Accession No. U00096), and the genomic DNA of *Escherichia coli* MG1655 strain as the template. The product was treated with the restriction enzyme BamHI to obtain a gene fragment containing the ybjL gene. The PCR product was purified and ligated with the vector pMW219::Pthr which had been treated with BamHI to construct plasmid pMW219::Pthr::ybjL for ybjL amplification.

<6-3> Production of ybjL-Amplified Strain pMW219::Pthr::ybjL obtained in <6-2> described above and pMW219 were used to transform the *Escherichia coli* MG1655ΔldhΔlldD strain by the electric pulse method, and the transformants were applied to the LB agar medium containing 25 μg/ml of kanamycin, and cultured at 37° C. for about 18 hours. The colonies which appeared were purified, and plasmids were extracted from them in a conventional manner to confirm introduction of the target plasmid. The obtained strains were designated as MG1655ΔldhΔlldD/pMW219::Pthr::ybjL and MG1655ΔldhΔlldD/pMW219 respectively. The *Enterobacter aerogenes* AJ110637 strain was also transformed with pMW219::Pthr::ybjL and pMW219 by the electric pulse method, and the transformants were applied to the LB agar medium containing 50 μg/ml of kanamycin, and cultured at 37° C. for about 18 hours. The colonies which appeared were purified, and plasmids were extracted from them in a conventional manner to confirm introduction of the target plasmid. The obtained strains were designated as AJ110637/pMW219::Pthr::ybjL and AJ110637/pMW219, respectively.

Example 7: Effect of ybjL Amplification in Succinic Acid-Producing Strain of *Escherichia* Bacterium MG1655ΔldhΔlldD/pMW219::Pthr::ybjL and MG1655ΔldhΔlldD/pMW219 were each uniformly applied to an LB plate containing 25 µg/ml of kanamycin, and cultured at 37° C. for 16 hours. Then, each plate was incubated at 37° C. for 16 hours under an anaerobic condition by using Anaeropack (Mitsubishi Gas Chemical). The cells on the plate were washed with 0.8% brine, and then diluted 51 times, and thereby a cell suspension having OD=1.0 (600 nm) was prepared. This cell suspension in a volume of 100 µl and a production medium (10 g/l of glucose, 10 g/l 2Na malate, 45.88 g/l of TES, 6 g/l of $Na_2HPO_4$, 3 g/l of $KH_2PO_4$, 1 g/l of $NH_4Cl$, adjusted to pH 7.3 with KOH and filtered) in a volume of 1.3 ml in which the dissolved gases in the medium were replaced with nitrogen gas by bubbling nitrogen gas beforehand were put into 1.5-ml volume micro tubes, and the cells were cultured at 31.5° C. for 10 hours by using a stirrer for micro tubes. After the culture, the amount of succinic acid which had accumulated in the medium was analyzed by liquid chromatography. Two Shim-pack SCR-102H (Shimadzu) connected in series were used as the column, and a sample was eluted at 50° C. with 5 mM p-toluenesulfonic acid. The eluate was neutralized with 20 mM Bis-Tris aqueous solution containing 5 mM p-toluenesulfonic acid and 100 µM EDTA, and succinic acid was quantified by measuring electric conductivity with CDD-10AD (Shimadzu).

Figure 4:
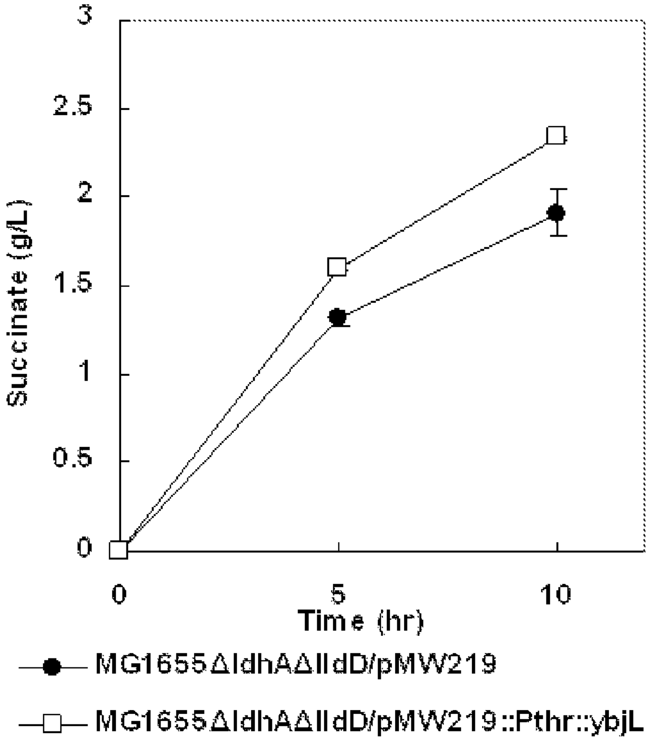
FIG. 4 shows accumulation of succinic acid obtained with the ybjL-amplified strain of *Escherichia* bacterium (open squares) vs. control (closed circles).

The amounts of succinic acid which had accumulated after 10 hours are shown in Table 6, and the change in succinic acid accumulation is shown in FIG. 4.

Succinic acid accumulation was markedly increased in the ybjL gene-amplified strain MG1655ΔldhΔlldD/pMW219::Pthr::ybjL as compared to the control strain MG1655ΔldhΔlldD/pMW219.

TABLE 6

Effect of ybjL amplification in succinic acid-producing strain, MG1655ΔldhAΔlldD

| Strain | Succinate (g/L) |
| --- | --- |
| MG1655ΔldhAΔlldD/pMW219 | 1.91 (±0.13) |
| MG1655ΔldhAΔlldD/pMW219::Pthr::ybjL | 2.34 (±0.01) |

Example 8: Effect of ybjL Amplification in a Succinic Acid-Producing Strain of *Enterobacter* Bacterium AJ110637/pMW219::Pthr::ybjL and AJ110637/pMW219 were each uniformly applied to an LB plate containing 50 µg/ml of kanamycin, and cultured at 37° C. for 16 hours. Then, each plate was incubated at 37° C. for 16 hours under an anaerobic condition by using Anaeropack (Mitsubishi Gas Chemical). The cells on the plate were washed with 0.8% brine, and then diluted 51 times, and thereby a cell suspension having OD=1.0 (60 nm) was prepared. This cell suspension in a volume of 100 µl and a production medium (10 g/l of glucose, 10 g/l 2Na malate, 45.88 g/l of TES, 6 g/l of $Na_2HPO_4$, 3 g/l of $KH_2PO_4$, 1 g/l of $NH_4Cl$, adjusted to pH 7.3 with KOH and filtered) in a volume of 1.3 ml in which the dissolved gases in the medium were replaced with nitrogen gas by bubbling nitrogen gas beforehand were put into 1.5-ml volume micro tubes, and the cells were cultured at 31.5° C. for 6 hours by using a stirrer for micro tubes. After the culture, the amount of succinic acid which had accumulated in the medium was analyzed by liquid chromatography. Two Shim-pack SCR-102H Shimadzu) connected in series were used as the column, and a sample was eluted at 50° C. with 5 mM p-toluenesulfonic acid. The eluate was neutralized with 20 mM Bis-Tris aqueous solution containing 5 mM p-toluenesulfonic acid and 100 µM EDTA, and succinic acid was quantified by measuring electric conductivity with CDD-10AD (Shimadzu).

Figure 5:
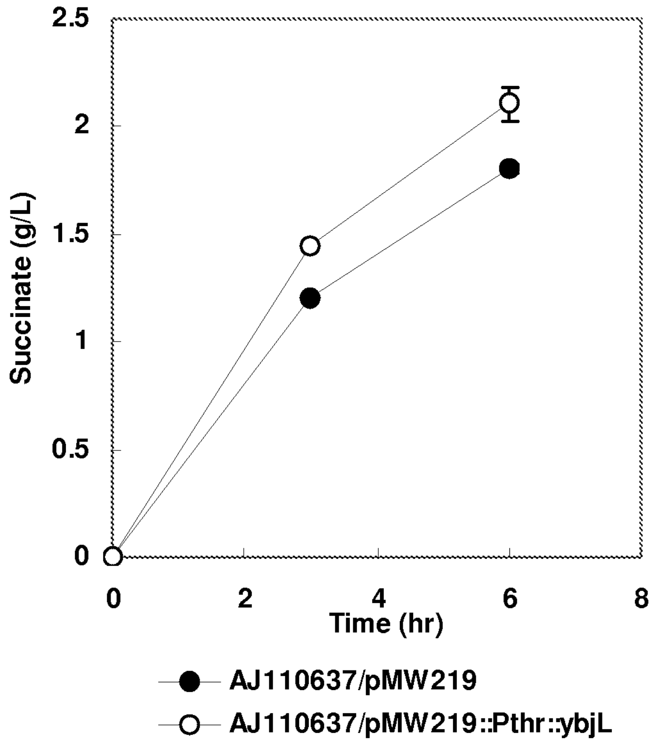
FIG. 5 shows accumulation of succinic acid obtained with the ybjL-amplified strain of *Enterobacter* bacterium (open squares) vs. control (closed circles).

The amounts of succinic acid which had accumulated after 6 hours are shown in Table 7, and change of succinic acid accumulation is shown in FIG. 5.

Succinic acid accumulation was markedly increased in the ybjL gene-amplified strain AJ110637/pMW219::Pthr::ybjL as compared to the control strain AJ110637/pMW219.

TABLE 7

Effect of ybjL amplification in AJ110637 strain

| Strain | Succinate (g/L) |
| --- | --- |
| AJ110637/pMW219 | 1.81 (±0.04) |
| AJ110637/pMW219::Pthr::ybjL | 2.11 (±0.02) |

Example 9

<9-1> Construction of an adhE-Deficient Strain of *Enterobacter aerogenes* AJ110637

When *Enterobacter aerogenes* AJ110637 is grown in a medium containing a sugar source under anaerobic conditions, it produces a marked amount of ethanol. Therefore, adhE coding for alcohol dehydrogenase was deleted to suppress the generation of ethanol.

A gene fragment for deleting adhE was prepared by PCR using the plasmid pMW-attL-Tc-attR described in WO2005/010175 as the template and oligonucleotides of SEQ ID NOS: 72 and 73 as primers, pMW118-attL-Tc-attR is a plasmid obtained by inserting attL and attR genes, which are the attachment sites of λ phage, and the Tc gene, which is a tetracycline resistance gene, into pMW118 (Takara Bio), and the genes are inserted in the order of attL-Tc-attR. By PCR described above, a gene fragment containing a tetracycline resistance gene, attL and attR sites of λ phage at the both ends of the resistance gene, and 60 bp upstream sequence and 59 bp downstream sequence of the adhE gene added to the outer ends of the λ phage sequences was amplified. This fragment was purified by using Wizard PCR Prep DNA Purification System (Promega).

Then, the *Enterobacter aerogenes* AJ110637 strain was transformed with RSF-Red-TER to obtain the *Enterobacter aerogenes* AJ110637/RSF-Red-TER strain. This strain was cultured overnight in LB medium containing 40 µg/mL of chloramphenicol, the culture medium was inoculated in a 1/100 volume to 50 mL of the LB medium containing 40 µg/mL of chloramphenicol and 0.4 mM isopropyl-β-D-thiogalactopyranoside, and culture was performed at 31° C. for 4 hours. The cells were collected, washed three times with ice-cooled 10% glycerol, and finally suspended in 0.5 mL of 10% glycerol. The suspended cells were used as competent cells, and the PCR fragment prepared in the above section was introduced into the cells by using GENE PULSER II (BioRad) under the conditions of a field strength of 20 kV/cm, capacitor capacity of 25 µF and resistance of 200Ω. Ice-cooled LB medium was added to the cell suspension, and culture was performed at 31° C. for 2 hours with shaking. Then, the culture was applied to a LB plate containing 25 µg/mL of tetracycline. The colonies that appeared were purified with the same plate, and then it was confirmed by PCR that the adhE gene had been replaced with the tetracycline resistance gene.

<9-2> Construction of Pyruvate Carboxylase Gene-Enhanced Strain of AJ110637ΔadhE Strain The ability to produce succinic acid was imparted to the *Enterobacter aerogenes* AJ110637ΔadhE strain by amplifying pyc coding for pyruvate carboxylase derived from *Corynebacterium glutamicum*.

In order to express pyc derived from *Corynebacterium glutamicum* in the AJ110637ΔadhE strain, it was attempted to obtain a threonine operon promoter fragment of the *Escherichia coli* MG1655 strain. The total genomic sequence of *Escherichia coli* (*Escherichia coli* K-12 strain) has already been elucidated (Genbank Accession No. U00096, Science, 277, 1453-4474 (1997)). On the basis of this sequence, PCR amplification of the promoter region of the threonine operon (thrLABC) was performed. PCR was performed by using the synthetic oligonucleotide having an SacI site shown n SEQ ID NO: 75 as a 5' primer, the synthetic oligonucleotide shown in SEQ ID NO: 76 as a 3' primer, and the genomic DNA of *Escherichia coli* MG1655 strain (ATCC 47076, ATCC 700926) as the template to obtain a threonine operon promoter fragment (A) (SEQ ID NO: 77).

Furthermore, a pyc gene fragment derived from the *Corynebacterium glutamicum* 2256 strain (ATCC 13869) was obtained. PCR was performed by using the synthetic oligonucleotide shown in SEQ ID NO: 78 as a 5' primer, the synthetic oligonucleotide having an SacI site shown SEQ ID NO: 79 as a 3' primer, and the genomic DNA of the *Corynebacterium glutamicum* 2256 strain (ATCC 13869) as a template to obtain a pyc gene fragment (B) (SEQ ID NO: 80).

PCR was performed by using the fragments (A) and (B) as templates, the primers of SEQ ID NOS: 75 and 79 to obtain a gene fragment (C) including the fragments (A) and (B) ligated to each other. This gene fragment (C) was treated with the restriction enzyme SacI, and purified, and the product was ligated with the plasmid vector pSTV28 (Takara Bio) which had been digested with the restriction enzyme SacI to construct a plasmid pSTV28::Pthr::pyc for pyc amplification.

The plasmid pSTV28::Pthr::pyc for pyc amplification was introduced into the aforementioned *Enterobacter aerogenes* AJ110637ΔadhE strain by electroporation to obtain a transformant which are resistant to tetracycline and chloramphenicol. This pyc-amplified strain of *Enterobacter aerogenes* AJ110637ΔadhE was designated as AJ110637ΔadhE/pSTV28::Pthr::pyc.

<9-3> Construction of *Enterobacter aerogenes* ybjL Gene-Enhanced Strain of AJ110637ΔadhE/pSTV28::Pthr:pyc In the same manner as that described above, PCR amplification of the promoter region of the threonine operon (thrLABC) of *Escherichia coli* (*Escherichia coli* K-12 strain) was performed. PCR was performed by using the synthetic oligonucleotide shown in SEQ ID NO: 81 as a 5' primer, the synthetic oligonucleotide shown in SEQ ID NO: 82 as a 3' primer, and the genomic DNA of *Escherichia coli* MG1655 strain (ATCC 47076, ATCC 700926) as a template to obtain a threonine operon promoter fragment (A) (SEQ ID NO: 83).

Furthermore, in order to clone the ybjL gene of the *Enterobacter aerogenes* AJ110637 strain, PCR was performed by using the synthetic oligonucleotide shown in SEQ ID NO: 84 as a 5' primer, the synthetic oligonucleotide shown in SEQ ID NO: 85 as a 3' primer, and the genomic DNA of the *Enterobacter aerogenes* AJ110637 strain as the template to obtain a ybjL gene fragment (B) (SEQ ID NO: 86).

PCR was performed by using the fragments (A) and (B) as templates, and the primers of SEQ ID NOS: 81 and 85 to obtain a gene fragment (C) with the fragments (A) and (B) ligated to each other. This gene fragment (C) was blunt-ended by using TaKaRa BKL Kit (Takara Bio), and the 5' end was phosphorylated. Then, the fragment was digested with the restriction enzyme SmaI, and the product was ligated with the plasmid vector pMW218 dephosphorylated with alkaline phosphatase to construct a plasmid pMW218::Pthr::Ent-ybjL for ybjL amplification.

The aforementioned vector pMW218::Pthr::Ent-ybjL for amplification of the ybjL gene derived from the *Enterobacter aerogenes* AJ110637 strain, and the control plasmid pMW218 were each introduced into the *Enterobacter aerogenes* AJ110637ΔadhE/pSTV28::Pthr::pyc strain by electroporation to obtain transformants which are resistant to tetracycline, chloramphenicol and kanamycin. The ybjL-amplified strain derived from the *Enterobacter aerogenes* AJ110637ΔadhE/pSTV28::Pthr::pyc strain was designated as AJ110637ΔadhE/pSTV28::Pthr::pyc/pMW218::Pthr::Ent-ybjL, and the control strain as with pMW218 was designated as AJ110637ΔadhE/pSTV28::Pthr::pyc/pMW218.

<9-4> Effect of Amplification of ybjL Derived from *Enterobacter aerogenes* in *Enterobacter* Bacterium AJ110637ΔadhE/pSTV28::Pthr::pyc/pMW218::Pthr::Ent-ybjL, and AJ110637ΔadhE/pSTV28::Pthr::pyc/pMW218 were each uniformly applied to an LB plate containing 50 µg/ml of kanamycin, 25 µg/ml of tetracycline, and 40 µg/ml of chloramphenicol, and cultured at 31.5° C. for 16 hours. Then, the cells were inoculated into 3 ml of a seed medium (20 g/l of Bacto tryptone, 10 g/l of yeast extract, 20 g/L of NaCl) in a test tube, and cultured at 31.5° C. for 16 hours with shaking. A succinic acid production medium (100 g/l of glucose, 50 g/L of calcium carbonate subjected to hot air sterilization for 3 hours or more) in a volume of 3 ml was added to the medium obtained above, then the tube was sealed with a silicone stopper, and culture was performed at 31.5° C. for 24 hours with shaking. After the culture, the amount of succinic acid which had accumulated in the medium was analyzed by liquid chromatography, Two Shim-pack SCR-102H (Shimadzu) connected in series were used as the column, and a sample was eluted at 50° C. with 5 mM p-toluenesulfonic acid. The eluate was neutralized with 20 mM Bis-Tris aqueous solution containing 5 mM p-toluenesulfonic acid and 100 µM EDTA, and succinic acid was quantified by measuring electric conductivity with CDD-10AD (Shimadzu).

The amounts of succinic acid which had accumulated after 24 hours are shown in Table 8.

Succinic acid accumulation and succinic acid yield based on consumed glucose were markedly increased in the ybjL gene-amplified strain 110637ΔadhE/pSTV28::Pthr::pyc/pMW218::Pthr::Ent-ybjL as compared to control AJ110637ΔadhE/pSTV28::Pthr::pyc/pMW218.

TABLE 8

| | AJ110637ΔadhE/pSTV28::Pthr::pyc/pMW218 | AJ110637ΔadhE/pSTV28::Pthr::pyc/pMW218::Pthr::Ent-ybjL |
|---|---|---|
| Consumed glucose amount (g/L) | 9.53 (±1.85) | 9.10 (±0.66) |
| OD (600 nm) | 8.90 (±0.18) | 8.72 (±0.95) |
| Succinic acid accumulation (g/L) | 3.40 (±0.56) | 6.37 (±0.51) |
| Succinic acid yield based on consumed glucose (%) | 35.80 (±1.82) | 69.70 (±1.79) |

Explanation of Sequence Listing

SEQ ID NO: 1: ybjL gene of *Pantoea ananatis*

SEQ ID NO: 2: YbjL of *Pantoea ananatis*

SEQ ID NO: 3: ybjL gene of *Escherichia coli*

SEQ ID NO: 4: YbjL of *Escherichia coli*

SEQ ID NO: 5: Consensus sequence of YbjL of *Pantoea ananatis* and *Escherichia coli*

SEQ ID NO: 6: Primer for ams gene disruption

SEQ ID NO: 7: Primer for ams gene disruption

SEQ ID NO: 8: Primer for amplification of ybjL of *P. ananatis*

SEQ ID NO: 9: Primer for amplification of ybjL of *P. ananatis*

SEQ ID NO: 10: Sequence of RSFCPG plasmid

SEQ ID NO: 11: Primer for amplification of ybjL of *E. coli* W3110

SEQ ID NO: 12: Primer for amplification of ybjL of *E. coli* W3110

SEQ ID NO: 13: Primer for deletion of ldhA

SEQ ID NO: 14: Primer for deletion of ldhA

SEQ ID NO: 15: Primer for confirming deletion of ldhA

SEQ ID NO: 16: Primer for confirming deletion of ldhA

SEQ ID NO: 17: Primer for deletion of lldD

SEQ ID NO: 18: Primer for deletion of lldD

SEQ ID NO: 19: Primer for confirming deletion of lldD

SEQ ID NO: 20: Primer for confirming deletion of lldD

SEQ ID NO: 21: Threonine promoter sequence

SEQ ID NO: 22: Primer for amplification of ybjL of *E. coli* MG1655

SEQ ID NO: 23: Primer for amplification of ybjL of *E. coli* MG1655

SEQ ID NO: 24: ybjL gene of *Salmonella typhimurium*

SEQ ID NO: 25: YbjL of *Salmonella typhimurium*

SEQ ID NO: 26: ybjL gene of *Yersinia pestis*

SEQ ID NO: 27: YbjL of *Yersinia pestis*

SEQ ID NO: 28: ybjL gene of *Erwinia carotovora*

SEQ ID NO: 29: YbjL of *Erwinia carotovora*

SEQ ID NO: 30: ybjL gene of *Vibrio cholerae*

SEQ ID NO: 31: YbjL of *Vibrio cholerae*

SEQ ID NO: 32: ybjL gene of *Aeromonas hydrophia*

SEQ ID NO: 33: YbjL of *Aeromonas hydrophia*

SEQ ID NO: 34: ybjL gene of *Photobacterium profundum*

SEQ ID NO: 35: YbjL of *Photobacterium profundum*

SEQ ID NO: 36: ldhA gene of *Escherichia coli*

SEQ ID NO: 37: LdhA of *Escherichia coli*

SEQ ID NO: 38: lldD gene of *Escherichia coli*

SEQ ID NO: 39: LldD of *Escherichia coli*

SEQ ID NO: 40: Nucleotide sequence of hisD gene of *Pantoea ananatis*

SEQ ID NO: 41: Primer for amplification of fragment for incorporation of $Km^r$ gene into hisD gene SEQ ID NO: 42: Primer for amplification of fragment for incorporation of $Km^r$ gene into hisD gene SEQ ID NO: 43: Primer for amplification of cat gene SEQ ID NO: 44: Primer for amplification of cat gene SEQ ID NO: 45: Primer for amplification of sacB gene SEQ ID NO: 46: Primer for amplification of sacB gene SEQ ID NO: 47: Primer for amplification of DNA fragment containing PlacUV5 promoter SEQ ID NO: 48: Primer for amplification of DNA fragment containing PlacUV5 promoter SEQ ID NO: 49: Primer for amplification of DNA fragment containing λRedαβγ gene and tL3

SEQ ID NO: 50: Primer for amplification of DNA fragment containing λRedαβγ gene and tL3

SEQ ID NO: 51: Primer for amplification of DNA fragment containing PlacUV5 promoter and TrrnB SEQ ID NO: 52: Primer for amplification of DNA fragment containing PlacUV5 promoter and TrrnB SEQ ID NO: 53: Primer for amplification of attL SEQ ID NO: 54: Primer for amplification of attL SEQ ID NO: 55: Nucleotide sequence of attL SEQ ID NO: 56: Primer for amplification of attR SEQ ID NO: 57: Primer for amplification of attR SEQ ID NO: 58: Nucleotide sequence of attR SEQ ID NO: 59: Primer for amplification of DNA fragment containing bla gene SEQ ID NO: 60: Primer for amplification of DNA fragment containing bla gene SEQ ID NO: 61: Primer for amplification of DNA fragment containing ter_rrnB SEQ ID NO: 62: Primer for amplification of DNA fragment containing ter_rrnB SEQ ID NO: 63: Nucleotide sequence of the DNA fragment containing ter_thrL terminator SEQ ID NO: 64: Primer for amplification of DNA fragment containing ter_thrL terminator SEQ ID NO: 65: Primer for amplification of DNA fragment containing ter_thrL terminator SEQ ID NO: 66: ams operon of *Pantoea ananatis*

SEQ ID NO: 67: AmsH of *Pantoea ananatis*

SEQ ID NO: 68: AmsI of *Pantoea ananatis*

SEQ ID NO: 69: AmsA of *Pantoea ananatis*

SEQ ID NO: 70: AmsC of *Pantoea ananatis*

SEQ ID NO: 71: AmsB of *Pantoea ananatis*

SEQ ID NO: 72: Nucleotide sequence of primer for deletion of adhE

SEQ ID NO: 73: Nucleotide sequence of primer for deletion of adhE

SEQ ID NO: 74: Nucleotide sequence of adhE of *Enterobacter aerogenes AJ*110637 partial sequence)

SEQ ID NO: 75: Primer for amplification of threonine promoter

SEQ ID NO: 76: Primer for amplification of threonine promoter

SEQ ID NO: 77: Threonine promoter gene fragment

SEQ ID NO: 78: Primer for amplification of pyruvate carboxylase gene

SEQ ID NO: 79: Primer for amplification of pyruvate carboxylase gene

SEQ ID NO: 80: Pyruvate carboxylase gene fragment

SEQ ID NO: 81: Primer for amplification of threonine promoter

SEQ ID NO: 82: Primer for amplification of threonine promoter

SEQ ID NO: 83: Threonine promoter gene fragment

SEQ ID NO: 84: Nucleotide sequence of primer for amplification of ybjL of *Enterobacter aerogenes* AJ110637

SEQ ID NO: 85: Nucleotide sequence of primer for amplification of ybjL of *Enterobacter aerogenes* AJ110637

SEQ ID NO: 86: Nucleotide sequence of ybjL of *Enterobacter aerogenes* AJ110637

SEQ ID NO: 87: Amino acid sequence of YbjL of *Enterobacter aerogenes* AJ110637

SEQ ID NO: 88: Consensus sequence of YbjL of *Escherichia, Pantoea* and *Enterobacter*

INDUSTRIAL APPLICABILITY

Production efficiency of an acidic substance having a carboxyl group can be improved by using the microorganism of the present invention.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

---

The invention claimed is:

1. A method for producing an acidic substance having a carboxyl group comprising culturing in a medium a microorganism, having an ability to produce the acidic substance having a carboxyl group, to produce and accumulate the acidic substance having a carboxyl group in the medium, collecting the acidic substance having a carboxyl group from the medium, wherein the acidic substance is L-glutamic acid and/or L-aspartic acid, wherein the microorganism has been modified to enhance expression of an ybjL gene, and wherein the ybjL gene encodes a protein selected from the group consisting of:

(A) a protein comprising the amino acid sequence of SEQ ID NO: 2; and (B) a protein comprising a variant of the amino acid sequence of SEQ ID NO: 2, wherein one to 5 amino acid residues are substituted, deleted, inserted or added, and wherein, upon expression, said variant improves the ability of the microorganism to produce the acidic substance having a carboxyl group.

2. The method according to claim 1, wherein said enhanced expression is obtained by a method selected from the group consisting of: A) increasing copy number of the ybjL gene, B) modifying an expression control sequence of the ybjL gene, and C) combinations thereof.

3. The method according to claim 1, wherein the microorganism is a bacterium belonging to the family Enterobacteriaceae.

4. The method according to claim 3, wherein the bacterium belongs to a genus selected from the group consisting of *Escherichia, Enterobacter, Raoultella, Pantoea*, and *Klebsiella*.

5. The method according to claim 1, wherein the microorganism is a rumen bacterium.

6. The method according to claim 5, wherein the microorganism is *Mannheimia*.

* * * * *

SEQUENCE LISTING

```
<160> NUMBER OF SEQ ID NOS: 88

<210> SEQ ID NO 1
<211> LENGTH: 2229
<212> TYPE: DNA
<213> ORGANISM: Pantoea ananatis
<220> FEATURE:
<221> NAME/KEY: CDS
<222> LOCATION: (298)..(1986)

<400> SEQUENCE: 1

acgccacctg atacgcaggt tgcccagaaa taataacgct gcggcataac tccccactca      60

ttaaaaacat gccaaaactt cgcctttgac cttgccgagc ctggtggaaa taaaaagaaa     120

cagtcgtttt gagaacgaat gaaagtcgcc aatggctgag aatgattttt ctgattagaa     180

tattggccgc gttacctttt cagacatcag tgatagctgg aggtaatctt acggcctgct     240

caagatagcg aaaaacaggc ctctcttcaa taggttacaa gtaaacaaga agttaaa        297

atg ttg aat gtt aac atc gca gaa ttg tta aga ggt aat gac att ctg       345
Met Leu Asn Val Asn Ile Ala Glu Leu Leu Arg Gly Asn Asp Ile Leu
1               5                   10                  15

tta tta ttt ttc gta ctg gca ctg gga ctt tgc ctg gga aaa tta cgt       393
Leu Leu Phe Phe Val Leu Ala Leu Gly Leu Cys Leu Gly Lys Leu Arg
            20                  25                  30

ttt ggc tcg ata caa ctc gga aat tcc att ggc gta tta gtg gtt tca       441
Phe Gly Ser Ile Gln Leu Gly Asn Ser Ile Gly Val Leu Val Val Ser
        35                  40                  45

tta tta tta ggt cag caa cac ttc tcg atg aat acg gat gcc ctg agc       489
Leu Leu Leu Gly Gln Gln His Phe Ser Met Asn Thr Asp Ala Leu Ser
    50                  55                  60

ctg ggt ttc atg ttg ttt att ttc tgc gtc ggc att gaa gca ggc ccc       537
Leu Gly Phe Met Leu Phe Ile Phe Cys Val Gly Ile Glu Ala Gly Pro
65                  70                  75                  80

aac ttt ttt tcc att ttc ttt cgg gat ggc aaa aat tat ttc atg ctc       585
Asn Phe Phe Ser Ile Phe Phe Arg Asp Gly Lys Asn Tyr Phe Met Leu
                85                  90                  95

gcc att gtg atg gtg gtc agc gcc ctg ctg ctg gcc ctg gga ttc ggc       633
Ala Ile Val Met Val Val Ser Ala Leu Leu Leu Ala Leu Gly Phe Gly
            100                 105                 110

aag ctt ttt ggc tgg gac atc ggc ctg acc gca ggc gta ctg gcc ggc       681
Lys Leu Phe Gly Trp Asp Ile Gly Leu Thr Ala Gly Val Leu Ala Gly
        115                 120                 125

tcc atg acg tcc acg ccg gtc ctg gtt ggc gcg ggt gat acg ctg cgc       729
Ser Met Thr Ser Thr Pro Val Leu Val Gly Ala Gly Asp Thr Leu Arg
    130                 135                 140

cag agc atc agc gat ccc aga cag ctg agc atc atg cag gat caa ctc       777
Gln Ser Ile Ser Asp Pro Arg Gln Leu Ser Ile Met Gln Asp Gln Leu
145                 150                 155                 160

agc ctg ggt tat gcc gta acc tat ctt gtc ggg tta gtc agc ctg att       825
```

-continued

```
Ser Leu Gly Tyr Ala Val Thr Tyr Leu Val Gly Leu Val Ser Leu Ile
                165                 170                 175

ttc ggc gca cgc tat ctg ccc cgt tta caa cat cag gac tta ccc acc      873
Phe Gly Ala Arg Tyr Leu Pro Arg Leu Gln His Gln Asp Leu Pro Thr
            180                 185                 190

tgc gcc cag cag att gcg cgc gaa cgc ggt ctt gac gct gac agc cag      921
Cys Ala Gln Gln Ile Ala Arg Glu Arg Gly Leu Asp Ala Asp Ser Gln
        195                 200                 205

cgc aaa gtg ttt ctg ccg gtg att cgc gct tac cgc gtt ggc ccg gaa      969
Arg Lys Val Phe Leu Pro Val Ile Arg Ala Tyr Arg Val Gly Pro Glu
    210                 215                 220

ctg gtg gcg tgg agc ggc ggc aaa aac ttg cgc gag ctc ggt att tac     1017
Leu Val Ala Trp Ser Gly Gly Lys Asn Leu Arg Glu Leu Gly Ile Tyr
225                 230                 235                 240

cgg cag acc ggc tgc tat atc gaa cga att cgc cgc aat ggc atc ctt     1065
Arg Gln Thr Gly Cys Tyr Ile Glu Arg Ile Arg Arg Asn Gly Ile Leu
                245                 250                 255

gcc agc ccg gat ggt gat gcg gtg ctg caa ctg ggg gac gat att tcc     1113
Ala Ser Pro Asp Gly Asp Ala Val Leu Gln Leu Gly Asp Asp Ile Ser
            260                 265                 270

ctg gtg ggc tat ccg gat gcc cac gcg cgc ctg gat gcc agc ttt cgt     1161
Leu Val Gly Tyr Pro Asp Ala His Ala Arg Leu Asp Ala Ser Phe Arg
        275                 280                 285

aac ggc aaa gaa gtt ttt gac cgc gat ctg ctg gat atg cgg att gtg     1209
Asn Gly Lys Glu Val Phe Asp Arg Asp Leu Leu Asp Met Arg Ile Val
    290                 295                 300

acg gaa gag atc gtg gtg aaa aac cac aat gcc gtc aac aaa cgg cta     1257
Thr Glu Glu Ile Val Val Lys Asn His Asn Ala Val Asn Lys Arg Leu
305                 310                 315                 320

agc aaa ctc aac ctt acc gat cac ggc tgc ttt ctc aac cgc gtg att     1305
Ser Lys Leu Asn Leu Thr Asp His Gly Cys Phe Leu Asn Arg Val Ile
                325                 330                 335

cgc agc cag atc gag atg cct att gat gac aac atc atg ctg aac aaa     1353
Arg Ser Gln Ile Glu Met Pro Ile Asp Asp Asn Ile Met Leu Asn Lys
            340                 345                 350

ggt gat gtg ttg cag gtc agc ggc gag gcg cga cgg gtg aag agc gta     1401
Gly Asp Val Leu Gln Val Ser Gly Glu Ala Arg Arg Val Lys Ser Val
        355                 360                 365

gcg gat cgc atc ggc ttt gtg gcg att cac agt cag atg acc gac ctg     1449
Ala Asp Arg Ile Gly Phe Val Ala Ile His Ser Gln Met Thr Asp Leu
    370                 375                 380

ctg gca ttc tgt gct ttt ttt atc atc ggt ctg atg gtc ggg tta att     1497
Leu Ala Phe Cys Ala Phe Phe Ile Ile Gly Leu Met Val Gly Leu Ile
385                 390                 395                 400

acg ttc cag ttc agc aac ttt agc ttt ggc atc ggt aat gcc gca ggg     1545
Thr Phe Gln Phe Ser Asn Phe Ser Phe Gly Ile Gly Asn Ala Ala Gly
                405                 410                 415

ttg ttg ttt gcc ggc att atg ctg ggc ttc ctg cgc gct aac cat cct     1593
Leu Leu Phe Ala Gly Ile Met Leu Gly Phe Leu Arg Ala Asn His Pro
            420                 425                 430

acc ttt ggc tat att ccg cag ggt gcg ctg acg atg gtg aaa gag ttc     1641
Thr Phe Gly Tyr Ile Pro Gln Gly Ala Leu Thr Met Val Lys Glu Phe
        435                 440                 445

ggg ctg atg gta ttc atg gcg ggc gtc ggg ctg agc gcc ggc agc ggt     1689
Gly Leu Met Val Phe Met Ala Gly Val Gly Leu Ser Ala Gly Ser Gly
    450                 455                 460

atc gac cac ggt ata tcg ggt aac ggc gca ctg atg ctc ttg tgc ggc     1737
Ile Asp His Gly Ile Ser Gly Asn Gly Ala Leu Met Leu Leu Cys Gly
465                 470                 475                 480
```

```
ctg ctg gtc agc ctg tta ccg gtg gtg att tgc tac ctg ttt ggc gcc     1785
Leu Leu Val Ser Leu Leu Pro Val Val Ile Cys Tyr Leu Phe Gly Ala
                485                 490                 495

tat gtt ctg cgc atg aac cgc gcg ctg ctg ttt ggc gcc att atg ggt     1833
Tyr Val Leu Arg Met Asn Arg Ala Leu Leu Phe Gly Ala Ile Met Gly
            500                 505                 510

gca cgc acc tgc gcg cca gcc atg gag ata atc agc gac aca gct cgc     1881
Ala Arg Thr Cys Ala Pro Ala Met Glu Ile Ile Ser Asp Thr Ala Arg
        515                 520                 525

agt aac atc ccg gca ctc ggc tac gcc ggg acc tat gct atc gcg aac     1929
Ser Asn Ile Pro Ala Leu Gly Tyr Ala Gly Thr Tyr Ala Ile Ala Asn
    530                 535                 540

gtt ttg cta acg ctg gcg gga aca tta atc gtt att atc tgg ccg tta     1977
Val Leu Leu Thr Leu Ala Gly Thr Leu Ile Val Ile Ile Trp Pro Leu
545                 550                 555                 560

ttg ccc tta taaaattttt ttactgacgt ccagaacttt ttttcccgac             2026
Leu Pro Leu

cacagtctga ataagtgcca ctgcttttct ttgaaatccc caaattgtgg agcccgctgg   2086

tctttttccc agcgggtttt tttatgcctt tctcctgccc gccctgcctg gacactaaaa   2146

catcattaaa cttaaaccgt tttgcaacct taacgcagat taagaacctt gtgatggact   2206

ctctgaccgt ctgcacgcag gat                                           2229


<210> SEQ ID NO 2
<211> LENGTH: 563
<212> TYPE: PRT
<213> ORGANISM: Pantoea ananatis

<400> SEQUENCE: 2

Met Leu Asn Val Asn Ile Ala Glu Leu Leu Arg Gly Asn Asp Ile Leu
1               5                   10                  15

Leu Leu Phe Phe Val Leu Ala Leu Gly Leu Cys Leu Gly Lys Leu Arg
            20                  25                  30

Phe Gly Ser Ile Gln Leu Gly Asn Ser Ile Gly Val Leu Val Val Ser
        35                  40                  45

Leu Leu Leu Gly Gln Gln His Phe Ser Met Asn Thr Asp Ala Leu Ser
    50                  55                  60

Leu Gly Phe Met Leu Phe Ile Phe Cys Val Gly Ile Glu Ala Gly Pro
65                  70                  75                  80

Asn Phe Phe Ser Ile Phe Phe Arg Asp Gly Lys Asn Tyr Phe Met Leu
                85                  90                  95

Ala Ile Val Met Val Val Ser Ala Leu Leu Leu Ala Leu Gly Phe Gly
            100                 105                 110

Lys Leu Phe Gly Trp Asp Ile Gly Leu Thr Ala Gly Val Leu Ala Gly
        115                 120                 125

Ser Met Thr Ser Thr Pro Val Leu Val Gly Ala Gly Asp Thr Leu Arg
    130                 135                 140

Gln Ser Ile Ser Asp Pro Arg Gln Leu Ser Ile Met Gln Asp Gln Leu
145                 150                 155                 160

Ser Leu Gly Tyr Ala Val Thr Tyr Leu Val Gly Leu Val Ser Leu Ile
                165                 170                 175

Phe Gly Ala Arg Tyr Leu Pro Arg Leu Gln His Gln Asp Leu Pro Thr
            180                 185                 190

Cys Ala Gln Gln Ile Ala Arg Glu Arg Gly Leu Asp Ala Asp Ser Gln
        195                 200                 205

Arg Lys Val Phe Leu Pro Val Ile Arg Ala Tyr Arg Val Gly Pro Glu
```

```
    210                 215                 220

Leu Val Ala Trp Ser Gly Gly Lys Asn Leu Arg Glu Leu Gly Ile Tyr
225                 230                 235                 240

Arg Gln Thr Gly Cys Tyr Ile Glu Arg Ile Arg Arg Asn Gly Ile Leu
                245                 250                 255

Ala Ser Pro Asp Gly Asp Ala Val Leu Gln Leu Gly Asp Asp Ile Ser
            260                 265                 270

Leu Val Gly Tyr Pro Asp Ala His Ala Arg Leu Asp Ala Ser Phe Arg
        275                 280                 285

Asn Gly Lys Glu Val Phe Asp Arg Asp Leu Leu Asp Met Arg Ile Val
    290                 295                 300

Thr Glu Glu Ile Val Val Lys Asn His Asn Ala Val Asn Lys Arg Leu
305                 310                 315                 320

Ser Lys Leu Asn Leu Thr Asp His Gly Cys Phe Leu Asn Arg Val Ile
                325                 330                 335

Arg Ser Gln Ile Glu Met Pro Ile Asp Asp Asn Ile Met Leu Asn Lys
            340                 345                 350

Gly Asp Val Leu Gln Val Ser Gly Glu Ala Arg Arg Val Lys Ser Val
        355                 360                 365

Ala Asp Arg Ile Gly Phe Val Ala Ile His Ser Gln Met Thr Asp Leu
    370                 375                 380

Leu Ala Phe Cys Ala Phe Phe Ile Ile Gly Leu Met Val Gly Leu Ile
385                 390                 395                 400

Thr Phe Gln Phe Ser Asn Phe Ser Phe Gly Ile Gly Asn Ala Ala Gly
                405                 410                 415

Leu Leu Phe Ala Gly Ile Met Leu Gly Phe Leu Arg Ala Asn His Pro
            420                 425                 430

Thr Phe Gly Tyr Ile Pro Gln Gly Ala Leu Thr Met Val Lys Glu Phe
        435                 440                 445

Gly Leu Met Val Phe Met Ala Gly Val Gly Leu Ser Ala Gly Ser Gly
    450                 455                 460

Ile Asp His Gly Ile Ser Gly Asn Gly Ala Leu Met Leu Leu Cys Gly
465                 470                 475                 480

Leu Leu Val Ser Leu Leu Pro Val Val Ile Cys Tyr Leu Phe Gly Ala
                485                 490                 495

Tyr Val Leu Arg Met Asn Arg Ala Leu Leu Phe Gly Ala Ile Met Gly
            500                 505                 510

Ala Arg Thr Cys Ala Pro Ala Met Glu Ile Ile Ser Asp Thr Ala Arg
        515                 520                 525

Ser Asn Ile Pro Ala Leu Gly Tyr Ala Gly Thr Tyr Ala Ile Ala Asn
    530                 535                 540

Val Leu Leu Thr Leu Ala Gly Thr Leu Ile Val Ile Ile Trp Pro Leu
545                 550                 555                 560

Leu Pro Leu
```

<210> SEQ ID NO 3
<211> LENGTH: 1886
<212> TYPE: DNA
<213> ORGANISM: Escherichia coli
<220> FEATURE:
<221> NAME/KEY: CDS
<222> LOCATION: (101)..(1783)

<400> SEQUENCE: 3

```
ggtgcgctga atgaatctgc gccctgaatt ctggtaaaaa acattatcgt aaattaccat      60
```

-continued

```
ttctttcaac agcttactag taaacaagaa gttagcctcc gtg aat ata aac gtc      115
                                            Val Asn Ile Asn Val
                                            1               5

gcc gaa ttg tta aat ggg aat tac att ctg tta tta ttt gtg gtc ctc      163
Ala Glu Leu Leu Asn Gly Asn Tyr Ile Leu Leu Leu Phe Val Val Leu
                10                  15                  20

gcg ctt ggg cta tgt ctc gga aag tta cga ctt ggt tcg atc caa ctg      211
Ala Leu Gly Leu Cys Leu Gly Lys Leu Arg Leu Gly Ser Ile Gln Leu
            25                  30                  35

ggt aat tcc att ggc gtt tta gtc gta tcg ctg tta tta ggc caa caa      259
Gly Asn Ser Ile Gly Val Leu Val Val Ser Leu Leu Leu Gly Gln Gln
        40                  45                  50

cat ttc agc att aac acc gat gcg ctt aat ctt ggc ttt atg ctg ttt      307
His Phe Ser Ile Asn Thr Asp Ala Leu Asn Leu Gly Phe Met Leu Phe
    55                  60                  65

att ttc tgc gtc ggg gtc gaa gcc gga ccg aac ttt ttt tcc att ttt      355
Ile Phe Cys Val Gly Val Glu Ala Gly Pro Asn Phe Phe Ser Ile Phe
70                  75                  80                  85

ttt cgc gat ggg aaa aat tac cta atg tta gca ctg gtg atg gtt ggc      403
Phe Arg Asp Gly Lys Asn Tyr Leu Met Leu Ala Leu Val Met Val Gly
                90                  95                  100

agt gcg ctg gtg atc gcc tta ggg tta ggt aag ctg ttt ggc tgg gat      451
Ser Ala Leu Val Ile Ala Leu Gly Leu Gly Lys Leu Phe Gly Trp Asp
            105                 110                 115

att ggc ctg acg gcc ggt atg tta gca ggc tct atg acg tcg aca ccg      499
Ile Gly Leu Thr Ala Gly Met Leu Ala Gly Ser Met Thr Ser Thr Pro
        120                 125                 130

gtt ctg gtc ggt gct ggc gat aca ctg cgt cat tcc ggc atg gaa agc      547
Val Leu Val Gly Ala Gly Asp Thr Leu Arg His Ser Gly Met Glu Ser
    135                 140                 145

agg cag ctc tca ctg gca ctg gat aat ctg agc ctc ggg tat gcc tta      595
Arg Gln Leu Ser Leu Ala Leu Asp Asn Leu Ser Leu Gly Tyr Ala Leu
150                 155                 160                 165

acc tat tta atc ggt ctg gtg agt ttg att gtt ggt gcg cgt tac ttg      643
Thr Tyr Leu Ile Gly Leu Val Ser Leu Ile Val Gly Ala Arg Tyr Leu
                170                 175                 180

ccg aaa ttg cag cat cag gac tta cag acc agc gcc cag caa atc gcc      691
Pro Lys Leu Gln His Gln Asp Leu Gln Thr Ser Ala Gln Gln Ile Ala
            185                 190                 195

cgc gaa cgt ggc ctg gac act gat gcc aac cgt aag gtt tat tta ccg      739
Arg Glu Arg Gly Leu Asp Thr Asp Ala Asn Arg Lys Val Tyr Leu Pro
        200                 205                 210

gtg atc cgc gcc tat cgc gtc ggc ccg gaa ctg gtg gcc tgg acc gac      787
Val Ile Arg Ala Tyr Arg Val Gly Pro Glu Leu Val Ala Trp Thr Asp
    215                 220                 225

ggc aaa aat ctg cgt gaa ctg ggt att tat cga caa acc ggc tgc tac      835
Gly Lys Asn Leu Arg Glu Leu Gly Ile Tyr Arg Gln Thr Gly Cys Tyr
230                 235                 240                 245

att gaa cgt att cga cgt aac ggg att ctg gca aat cca gac ggt gat      883
Ile Glu Arg Ile Arg Arg Asn Gly Ile Leu Ala Asn Pro Asp Gly Asp
                250                 255                 260

gcc gtg cta caa atg ggc gat gaa ata gcg ttg gta ggc tat ccc gac      931
Ala Val Leu Gln Met Gly Asp Glu Ile Ala Leu Val Gly Tyr Pro Asp
            265                 270                 275

gcc cat gcc cga ctc gat ccc agc ttc cgt aac ggt aaa gaa gtt ttc      979
Ala His Ala Arg Leu Asp Pro Ser Phe Arg Asn Gly Lys Glu Val Phe
        280                 285                 290

gat cgt gac ctt ctc gac atg cgt atc gtc act gaa gaa gtg gtc gtt     1027
Asp Arg Asp Leu Leu Asp Met Arg Ile Val Thr Glu Glu Val Val Val
```

-continued

```
    295                 300                 305

aaa aac cat aac gct gta ggt aaa cgt ctc gca caa ctg aag ttg acc     1075
Lys Asn His Asn Ala Val Gly Lys Arg Leu Ala Gln Leu Lys Leu Thr
310                 315                 320                 325

gat cac ggt tgc ttc ctt aac cgc gtc att cgt agc cag att gag atg     1123
Asp His Gly Cys Phe Leu Asn Arg Val Ile Arg Ser Gln Ile Glu Met
                330                 335                 340

ccg ata gat gac aac gtc gtg ctt aac aaa ggt gac gtt tta caa gtc     1171
Pro Ile Asp Asp Asn Val Val Leu Asn Lys Gly Asp Val Leu Gln Val
            345                 350                 355

agc ggc gat gcc cgc cgc gta aaa acc atc gcc gat cgc atc ggc ttt     1219
Ser Gly Asp Ala Arg Arg Val Lys Thr Ile Ala Asp Arg Ile Gly Phe
        360                 365                 370

atc tcg att cac agc cag gtc act gac ctg ctg gca ttc tgc gcc ttc     1267
Ile Ser Ile His Ser Gln Val Thr Asp Leu Leu Ala Phe Cys Ala Phe
    375                 380                 385

ttt gtt att ggg ctg atg atc ggg atg atc acc ttc cag ttc agc aca     1315
Phe Val Ile Gly Leu Met Ile Gly Met Ile Thr Phe Gln Phe Ser Thr
390                 395                 400                 405

ttc agt ttc ggc atg ggg aac gct gcc ggg ttg tta ttc gcc gga att     1363
Phe Ser Phe Gly Met Gly Asn Ala Ala Gly Leu Leu Phe Ala Gly Ile
                410                 415                 420

atg ctg ggc ttt atg cgt gct aac cac ccg acc ttc ggt tac att ccg     1411
Met Leu Gly Phe Met Arg Ala Asn His Pro Thr Phe Gly Tyr Ile Pro
            425                 430                 435

cag ggt gca tta agc atg gtg aaa gag ttc ggc ttg atg gtg ttt atg     1459
Gln Gly Ala Leu Ser Met Val Lys Glu Phe Gly Leu Met Val Phe Met
        440                 445                 450

gca ggc gtt ggt ctg agc gcc ggt agc ggt att aat aac ggc ctg ggc     1507
Ala Gly Val Gly Leu Ser Ala Gly Ser Gly Ile Asn Asn Gly Leu Gly
    455                 460                 465

gcg att ggc ggt cag atg ttg att gcc gga ttg att gtc agt ctg gtg     1555
Ala Ile Gly Gly Gln Met Leu Ile Ala Gly Leu Ile Val Ser Leu Val
470                 475                 480                 485

ccc gtg gtt atc tgt ttc ttg ttc ggt gct tat gta ttg cga atg aac     1603
Pro Val Val Ile Cys Phe Leu Phe Gly Ala Tyr Val Leu Arg Met Asn
                490                 495                 500

cgc gcg ctg ttg ttc ggc gca atg atg ggc gca cgt acc tgc gcg ccg     1651
Arg Ala Leu Leu Phe Gly Ala Met Met Gly Ala Arg Thr Cys Ala Pro
            505                 510                 515

gca atg gag atc atc agt gat aca gct cgc agt aac atc ccg gcg ctg     1699
Ala Met Glu Ile Ile Ser Asp Thr Ala Arg Ser Asn Ile Pro Ala Leu
        520                 525                 530

ggc tat gcg ggc acc tat gca atc gcc aac gtc ctg ctg acg ctg gca     1747
Gly Tyr Ala Gly Thr Tyr Ala Ile Ala Asn Val Leu Leu Thr Leu Ala
    535                 540                 545

ggg aca atc atc gtc atg gta tgg cca gga tta gga taaaactgaa          1793
Gly Thr Ile Ile Val Met Val Trp Pro Gly Leu Gly
550                 555                 560

gttgccctga aaatgaaatt tttttgcaca accgcagaac ttttccgcag ggcatcagtc   1853

ttaattagtg ccactgcttt tctttgatgt ccc                                1886


<210> SEQ ID NO 4
<211> LENGTH: 561
<212> TYPE: PRT
<213> ORGANISM: Escherichia coli

<400> SEQUENCE: 4

Val Asn Ile Asn Val Ala Glu Leu Leu Asn Gly Asn Tyr Ile Leu Leu
```

-continued

```
1               5                   10                  15

Leu Phe Val Val Leu Ala Leu Gly Leu Cys Leu Gly Lys Leu Arg Leu
            20                  25                  30

Gly Ser Ile Gln Leu Gly Asn Ser Ile Gly Val Leu Val Val Ser Leu
        35                  40                  45

Leu Leu Gly Gln Gln His Phe Ser Ile Asn Thr Asp Ala Leu Asn Leu
    50                  55                  60

Gly Phe Met Leu Phe Ile Phe Cys Val Gly Val Glu Ala Gly Pro Asn
65                  70                  75                  80

Phe Phe Ser Ile Phe Phe Arg Asp Gly Lys Asn Tyr Leu Met Leu Ala
                85                  90                  95

Leu Val Met Val Gly Ser Ala Leu Val Ile Ala Leu Gly Leu Gly Lys
            100                 105                 110

Leu Phe Gly Trp Asp Ile Gly Leu Thr Ala Gly Met Leu Ala Gly Ser
        115                 120                 125

Met Thr Ser Thr Pro Val Leu Val Gly Ala Gly Asp Thr Leu Arg His
    130                 135                 140

Ser Gly Met Glu Ser Arg Gln Leu Ser Leu Ala Leu Asp Asn Leu Ser
145                 150                 155                 160

Leu Gly Tyr Ala Leu Thr Tyr Leu Ile Gly Leu Val Ser Leu Ile Val
                165                 170                 175

Gly Ala Arg Tyr Leu Pro Lys Leu Gln His Gln Asp Leu Gln Thr Ser
            180                 185                 190

Ala Gln Gln Ile Ala Arg Glu Arg Gly Leu Asp Thr Asp Ala Asn Arg
        195                 200                 205

Lys Val Tyr Leu Pro Val Ile Arg Ala Tyr Arg Val Gly Pro Glu Leu
    210                 215                 220

Val Ala Trp Thr Asp Gly Lys Asn Leu Arg Glu Leu Gly Ile Tyr Arg
225                 230                 235                 240

Gln Thr Gly Cys Tyr Ile Glu Arg Ile Arg Arg Asn Gly Ile Leu Ala
                245                 250                 255

Asn Pro Asp Gly Asp Ala Val Leu Gln Met Gly Asp Glu Ile Ala Leu
            260                 265                 270

Val Gly Tyr Pro Asp Ala His Ala Arg Leu Asp Pro Ser Phe Arg Asn
        275                 280                 285

Gly Lys Glu Val Phe Asp Arg Asp Leu Leu Asp Met Arg Ile Val Thr
    290                 295                 300

Glu Glu Val Val Val Lys Asn His Asn Ala Val Gly Lys Arg Leu Ala
305                 310                 315                 320

Gln Leu Lys Leu Thr Asp His Gly Cys Phe Leu Asn Arg Val Ile Arg
                325                 330                 335

Ser Gln Ile Glu Met Pro Ile Asp Asp Asn Val Val Leu Asn Lys Gly
            340                 345                 350

Asp Val Leu Gln Val Ser Gly Asp Ala Arg Arg Val Lys Thr Ile Ala
        355                 360                 365

Asp Arg Ile Gly Phe Ile Ser Ile His Ser Gln Val Thr Asp Leu Leu
    370                 375                 380

Ala Phe Cys Ala Phe Phe Val Ile Gly Leu Met Ile Gly Met Ile Thr
385                 390                 395                 400

Phe Gln Phe Ser Thr Phe Ser Phe Gly Met Gly Asn Ala Ala Gly Leu
                405                 410                 415

Leu Phe Ala Gly Ile Met Leu Gly Phe Met Arg Ala Asn His Pro Thr
            420                 425                 430
```

```
Phe Gly Tyr Ile Pro Gln Gly Ala Leu Ser Met Val Lys Glu Phe Gly
        435                 440                 445

Leu Met Val Phe Met Ala Gly Val Gly Leu Ser Ala Gly Ser Gly Ile
    450                 455                 460

Asn Asn Gly Leu Gly Ala Ile Gly Gly Gln Met Leu Ile Ala Gly Leu
465                 470                 475                 480

Ile Val Ser Leu Val Pro Val Val Ile Cys Phe Leu Phe Gly Ala Tyr
                485                 490                 495

Val Leu Arg Met Asn Arg Ala Leu Leu Phe Gly Ala Met Met Gly Ala
            500                 505                 510

Arg Thr Cys Ala Pro Ala Met Glu Ile Ile Ser Asp Thr Ala Arg Ser
        515                 520                 525

Asn Ile Pro Ala Leu Gly Tyr Ala Gly Thr Tyr Ala Ile Ala Asn Val
    530                 535                 540

Leu Leu Thr Leu Ala Gly Thr Ile Ile Val Met Val Trp Pro Gly Leu
545                 550                 555                 560

Gly
```

```
<210> SEQ ID NO 5
<211> LENGTH: 563
<212> TYPE: PRT
<213> ORGANISM: Artificial Sequence
<220> FEATURE:
<223> OTHER INFORMATION: Concensus between E.coli and P.ananatis
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (94)..(94)
<223> OTHER INFORMATION: Xaa can be any naturally occurring amino acid
<220> FEATURE:
```

<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: misc_feature
<222> LOCATION: (106)..(107)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (145)..(145)
<223> OTHER INFORMATION: Xaa can be any naturally occurring amino acid
<220> FEATURE:
<221> NAME/KEY: misc_feature
<222> LOCATION: (147)..(150)
<223> OTHER INFORMATION: Xaa can be any naturally occurring amino acid
<220> FEATURE:
<221> NAME/KEY: misc_feature
<222> LOCATION: (155)..(157)
<223> OTHER INFORMATION: Xaa can be any naturally occurring amino acid
<220> FEATURE:
<221> NAME/KEY: misc_feature
<222> LOCATION: (159)..(159)
<223> OTHER INFORMATION: Xaa can be any naturally occurring amino acid
<220> FEATURE:
<221> NAME/KEY: misc_feature
<222> LOCATION: (166)..(166)
<223> OTHER INFORMATION: Xaa can be any naturally occurring amino acid
<220> FEATURE:
<221> NAME/KEY: misc_feature
<222> LOCATION: (170)..(170)
<223> OTHER INFORMATION: Xaa can be any naturally occurring amino acid
<220> FEATURE:
<221> NAME/KEY: misc_feature
<222> LOCATION: (177)..(177)
<223> OTHER INFORMATION: Xaa can be any naturally occurring amino acid
<220> FEATURE:
<221> NAME/KEY: misc_feature
<222> LOCATION: (184)..(184)
<223> OTHER INFORMATION: Xaa can be any naturally occurring amino acid
<220> FEATURE:
<221> NAME/KEY: misc_feature
<222> LOCATION: (191)..(191)
<223> OTHER INFORMATION: Xaa can be any naturally occurring amino acid
<220> FEATURE:
<221> NAME/KEY: misc_feature
<222> LOCATION: (193)..(193)
<223> OTHER INFORMATION: Xaa can be any naturally occurring amino acid
<220> FEATURE:
<221> NAME/KEY: misc_feature
<222> LOCATION: (205)..(205)
<223> OTHER INFORMATION: Xaa can be any naturally occurring amino acid
<220> FEATURE:
<221> NAME/KEY: misc_feature
<222> LOCATION: (207)..(208)
<223> OTHER INFORMATION: Xaa can be any naturally occurring amino acid
<220> FEATURE:
<221> NAME/KEY: misc_feature
<222> LOCATION: (212)..(212)
<223> OTHER INFORMATION: Xaa can be any naturally occurring amino acid
<220> FEATURE:
<221> NAME/KEY: misc_feature
<222> LOCATION: (229)..(230)
<223> OTHER INFORMATION: Xaa can be any naturally occurring amino acid
<220> FEATURE:
<221> NAME/KEY: misc_feature
<222> LOCATION: (258)..(258)
<223> OTHER INFORMATION: Xaa can be any naturally occurring amino acid
<220> FEATURE:
<221> NAME/KEY: misc_feature
<222> LOCATION: (267)..(267)
<223> OTHER INFORMATION: Xaa can be any naturally occurring amino acid
<220> FEATURE:
<221> NAME/KEY: misc_feature
<222> LOCATION: (270)..(270)
<223> OTHER INFORMATION: Xaa can be any naturally occurring amino acid
<220> FEATURE:
<221> NAME/KEY: misc_feature
<222> LOCATION: (272)..(272)
<223> OTHER INFORMATION: Xaa can be any naturally occurring amino acid
<220> FEATURE:
<221> NAME/KEY: misc_feature
<222> LOCATION: (285)..(285)
<223> OTHER INFORMATION: Xaa can be any naturally occurring amino acid
<220> FEATURE:
<221> NAME/KEY: misc_feature
<222> LOCATION: (308)..(308)
<223> OTHER INFORMATION: Xaa can be any naturally occurring amino acid
<220> FEATURE:
<221> NAME/KEY: misc_feature
<222> LOCATION: (317)..(317)
<223> OTHER INFORMATION: Xaa can be any naturally occurring amino acid
<220> FEATURE:
<221> NAME/KEY: misc_feature
<222> LOCATION: (321)..(322)
<223> OTHER INFORMATION: Xaa can be any naturally occurring amino acid
<220> FEATURE:
<221> NAME/KEY: misc_feature
<222> LOCATION: (324)..(324)
<223> OTHER INFORMATION: Xaa can be any naturally occurring amino acid
<220> FEATURE:
<221> NAME/KEY: misc_feature
<222> LOCATION: (348)..(349)
<223> OTHER INFORMATION: Xaa can be any naturally occurring amino acid
<220> FEATURE:
<221> NAME/KEY: misc_feature
<222> LOCATION: (361)..(361)
<223> OTHER INFORMATION: Xaa can be any naturally occurring amino acid
<220> FEATURE:
<221> NAME/KEY: misc_feature
<222> LOCATION: (367)..(368)
<223> OTHER INFORMATION: Xaa can be any naturally occurring amino acid
<220> FEATURE:
<221> NAME/KEY: misc_feature
<222> LOCATION: (375)..(376)
<223> OTHER INFORMATION: Xaa can be any naturally occurring amino acid
<220> FEATURE:
<221> NAME/KEY: misc_feature
<222> LOCATION: (381)..(381)
<223> OTHER INFORMATION: Xaa can be any naturally occurring amino acid
<220> FEATURE:
<221> NAME/KEY: misc_feature
<222> LOCATION: (392)..(392)
<223> OTHER INFORMATION: Xaa can be any naturally occurring amino acid
<220> FEATURE:
<221> NAME/KEY: misc_feature
<222> LOCATION: (397)..(397)
<223> OTHER INFORMATION: Xaa can be any naturally occurring amino acid
<220> FEATURE:
<221> NAME/KEY: misc_feature
<222> LOCATION: (399)..(399)
<223> OTHER INFORMATION: Xaa can be any naturally occurring amino acid
<220> FEATURE:
<221> NAME/KEY: misc_feature
<222> LOCATION: (406)..(406)
<223> OTHER INFORMATION: Xaa can be any naturally occurring amino acid
<220> FEATURE:
<221> NAME/KEY: misc_feature
<222> LOCATION: (411)..(411)
<223> OTHER INFORMATION: Xaa can be any naturally occurring amino acid
<220> FEATURE:
<221> NAME/KEY: misc_feature
<222> LOCATION: (427)..(427)
<223> OTHER INFORMATION: Xaa can be any naturally occurring amino acid
<220> FEATURE:
<221> NAME/KEY: misc_feature
<222> LOCATION: (443)..(443)

<223> OTHER INFORMATION: Xaa can be any naturally occurring amino acid
<220> FEATURE:
<221> NAME/KEY: misc_feature
<222> LOCATION: (466)..(467)
<223> OTHER INFORMATION: Xaa can be any naturally occurring amino acid
<220> FEATURE:
<221> NAME/KEY: misc_feature
<222> LOCATION: (469)..(472)
<223> OTHER INFORMATION: Xaa can be any naturally occurring amino acid
<220> FEATURE:
<221> NAME/KEY: misc_feature
<222> LOCATION: (474)..(475)
<223> OTHER INFORMATION: Xaa can be any naturally occurring amino acid
<220> FEATURE:
<221> NAME/KEY: misc_feature
<222> LOCATION: (478)..(479)
<223> OTHER INFORMATION: Xaa can be any naturally occurring amino acid
<220> FEATURE:
<221> NAME/KEY: misc_feature
<222> LOCATION: (482)..(482)
<223> OTHER INFORMATION: Xaa can be any naturally occurring amino acid
<220> FEATURE:
<221> NAME/KEY: misc_feature
<222> LOCATION: (486)..(486)
<223> OTHER INFORMATION: Xaa can be any naturally occurring amino acid
<220> FEATURE:
<221> NAME/KEY: misc_feature
<222> LOCATION: (492)..(492)
<223> OTHER INFORMATION: Xaa can be any naturally occurring amino acid
<220> FEATURE:
<221> NAME/KEY: misc_feature
<222> LOCATION: (510)..(510)
<223> OTHER INFORMATION: Xaa can be any naturally occurring amino acid
<220> FEATURE:
<221> NAME/KEY: misc_feature
<222> LOCATION: (553)..(553)
<223> OTHER INFORMATION: Xaa can be any naturally occurring amino acid
<220> FEATURE:
<221> NAME/KEY: misc_feature
<222> LOCATION: (556)..(557)
<223> OTHER INFORMATION: Xaa can be any naturally occurring amino acid
<220> FEATURE:
<221> NAME/KEY: misc_feature
<222> LOCATION: (560)..(560)
<223> OTHER INFORMATION: Xaa can be any naturally occurring amino acid
<220> FEATURE:
<221> NAME/KEY: misc_feature
<222> LOCATION: (562)..(562)
<223> OTHER INFORMATION: Xaa can be any naturally occurring amino acid

<400> SEQUENCE: 5

```
Met Xaa Asn Xaa Asn Xaa Ala Glu Leu Leu Xaa Gly Asn Xaa Ile Leu
1               5                   10                  15

Leu Leu Phe Xaa Val Leu Ala Leu Gly Leu Cys Leu Gly Lys Leu Arg
            20                  25                  30

Xaa Gly Ser Ile Gln Leu Gly Asn Ser Ile Gly Val Leu Val Val Ser
        35                  40                  45

Leu Leu Leu Gly Gln Gln His Phe Ser Xaa Asn Thr Asp Ala Leu Xaa
    50                  55                  60

Leu Gly Phe Met Leu Phe Ile Phe Cys Val Gly Xaa Glu Ala Gly Pro
65                  70                  75                  80

Asn Phe Phe Ser Ile Phe Phe Arg Asp Gly Lys Asn Tyr Xaa Met Leu
                85                  90                  95

Ala Xaa Val Met Val Xaa Ser Ala Leu Xaa Xaa Ala Leu Gly Xaa Gly
            100                 105                 110

Lys Leu Phe Gly Trp Asp Ile Gly Leu Thr Ala Gly Xaa Leu Ala Gly
        115                 120                 125

Ser Met Thr Ser Thr Pro Val Leu Val Gly Ala Gly Asp Thr Leu Arg
    130                 135                 140
```

```
Xaa Ser Xaa Xaa Xaa Xaa Arg Gln Leu Ser Xaa Xaa Xaa Asp Xaa Leu
145                 150                 155                 160

Ser Leu Gly Tyr Ala Xaa Thr Tyr Leu Xaa Gly Leu Val Ser Leu Ile
                165                 170                 175

Xaa Gly Ala Arg Tyr Leu Pro Xaa Leu Gln His Gln Asp Leu Xaa Thr
            180                 185                 190

Xaa Ala Gln Gln Ile Ala Arg Glu Arg Gly Leu Asp Xaa Asp Xaa Xaa
        195                 200                 205

Arg Lys Val Xaa Leu Pro Val Ile Arg Ala Tyr Arg Val Gly Pro Glu
    210                 215                 220

Leu Val Ala Trp Xaa Xaa Gly Lys Asn Leu Arg Glu Leu Gly Ile Tyr
225                 230                 235                 240

Arg Gln Thr Gly Cys Tyr Ile Glu Arg Ile Arg Arg Asn Gly Ile Leu
                245                 250                 255

Ala Xaa Pro Asp Gly Asp Ala Val Leu Gln Xaa Gly Asp Xaa Ile Xaa
            260                 265                 270

Leu Val Gly Tyr Pro Asp Ala His Ala Arg Leu Asp Xaa Ser Phe Arg
        275                 280                 285

Asn Gly Lys Glu Val Phe Asp Arg Asp Leu Leu Asp Met Arg Ile Val
    290                 295                 300

Thr Glu Glu Xaa Val Val Lys Asn His Asn Ala Val Xaa Lys Arg Leu
305                 310                 315                 320

Xaa Xaa Leu Xaa Leu Thr Asp His Gly Cys Phe Leu Asn Arg Val Ile
                325                 330                 335

Arg Ser Gln Ile Glu Met Pro Ile Asp Asp Asn Xaa Xaa Leu Asn Lys
            340                 345                 350

Gly Asp Val Leu Gln Val Ser Gly Xaa Ala Arg Arg Val Lys Xaa Xaa
        355                 360                 365

Ala Asp Arg Ile Gly Phe Xaa Xaa Ile His Ser Gln Xaa Thr Asp Leu
    370                 375                 380

Leu Ala Phe Cys Ala Phe Phe Xaa Ile Gly Leu Met Xaa Gly Xaa Ile
385                 390                 395                 400

Thr Phe Gln Phe Ser Xaa Phe Ser Phe Gly Xaa Gly Asn Ala Ala Gly
                405                 410                 415

Leu Leu Phe Ala Gly Ile Met Leu Gly Phe Xaa Arg Ala Asn His Pro
            420                 425                 430

Thr Phe Gly Tyr Ile Pro Gln Gly Ala Leu Xaa Met Val Lys Glu Phe
        435                 440                 445

Gly Leu Met Val Phe Met Ala Gly Val Gly Leu Ser Ala Gly Ser Gly
    450                 455                 460

Ile Xaa Xaa Gly Xaa Xaa Xaa Xaa Gly Xaa Xaa Met Leu Xaa Xaa Gly
465                 470                 475                 480

Leu Xaa Val Ser Leu Xaa Pro Val Val Ile Cys Xaa Leu Phe Gly Ala
                485                 490                 495

Tyr Val Leu Arg Met Asn Arg Ala Leu Leu Phe Gly Ala Xaa Met Gly
            500                 505                 510

Ala Arg Thr Cys Ala Pro Ala Met Glu Ile Ile Ser Asp Thr Ala Arg
        515                 520                 525

Ser Asn Ile Pro Ala Leu Gly Tyr Ala Gly Thr Tyr Ala Ile Ala Asn
    530                 535                 540

Val Leu Leu Thr Leu Ala Gly Thr Xaa Ile Val Xaa Xaa Trp Pro Xaa
545                 550                 555                 560

Leu Xaa Leu
```

<210> SEQ ID NO 6
<211> LENGTH: 80
<212> TYPE: DNA
<213> ORGANISM: Artificial Sequence
<220> FEATURE:
<223> OTHER INFORMATION: primer

<400> SEQUENCE: 6
agcggcgtat tcgcctctat caaacattaa ctgatagcga agatctaaat tgaagcctgc 60 tttttatac taagttggca 80

<210> SEQ ID NO 7
<211> LENGTH: 80
<212> TYPE: DNA
<213> ORGANISM: Artificial Sequence
<220> FEATURE:
<223> OTHER INFORMATION: primer

<400> SEQUENCE: 7
ccaccagata accttccggt agcgttaaaa cgtcacgaca ttcaatagaa cgctcaagtt 60
agtataaaaa agctgaacga 80

<210> SEQ ID NO 8
<211> LENGTH: 45
<212> TYPE: DNA
<213> ORGANISM: Artificial Sequence
<220> FEATURE:
<223> OTHER INFORMATION: primer

<400> SEQUENCE: 8
gatcggtacc cagacatcag tgatagctgg aggtaatctt acggc 45

<210> SEQ ID NO 9
<211> LENGTH: 50
<212> TYPE: DNA
<213> ORGANISM: Artificial Sequence
<220> FEATURE:
<223> OTHER INFORMATION: primer

<400> SEQUENCE: 9
gatcgcatgc gacgtcagta aaaaaatttt ataagggcaa taacggccag 50

<210> SEQ ID NO 10
<211> LENGTH: 16214
<212> TYPE: DNA
<213> ORGANISM: Artificial Sequence
<220> FEATURE:
<223> OTHER INFORMATION: RSFCPG

<400> SEQUENCE: 10
gaattccgcc agaaccttca tcagcagcat aaacaggtgc agtgaacagc agagatacgg 60
ccagtgcggc caatgttttt tgtcctttaa acataacaga gtcctttaag gatatagaat 120
aggggtatag ctacgccaga atatcgtatt tgattattgc tagtttttag ttttgcttaa 180
aaaatattgt tagttttatt aaattggaaa actaaattat tggtatcatg aattgttgta 240
tgatgataaa tatagggggg atatgataga cgtcattttc atagggttat aaaatgcgac 300
taccatgaag tttttaattc aaagtattgg gttgctgata atttgagctg ttctattctt 360
tttaaatatc tatataggtc tgttaatgga ttttattttt acaagttttt tgtgtttagg 420
catataaaaa tcaagcccgc catatgaacg gcgggttaaa atatttacaa cttagcaatc 480

-continued gaaccattaa cgcttgatat cgcttttaaa gtcgcgtttt tcatatcctg tatacagctg 540
acgcggacgg gcaatcttca taccgtcact gtgcatttcg ctccagtggg cgatccagcc 600
aacggtacgt gccattgcga aaatgacggt gaacatggaa gacggaatac ccatcgcttt 660
caggatgata ccagagtaga aatcgacgtt cgggtacagt ttcttctcga taaagtacgg 720
gtcgttcagc gcgatgtttt ccagctccat agccacttcc agcaggtcat ccttcgtgcc 780
cagctctttc agcacttcat ggcaggtttc acgcattacg gtggcgcgcg ggtcgtaatt 840
tttgtacacg cggtgaccga agcccatcag gcggaaagaa tcatttttgt ctttcgcacg 900
acgaaaaaat tccggaatgt gtttaacgga gctgatttct tccagcattt tcagcgccgc 960
ttcgttagca ccgccgtgcg caggtcccca cagtgaagca atacctgctg cgatacaggc 1020
aaacgggttc gcacccgaag agccagcggt acgcacggtg gaggtagagg cgttctgttc 1080
atggtcagcg tgcaggatca gaatacggtc catagcacgt tccagaatcg gattaacttc 1140
atacggttcg cacggcgtgg agaacatcat attcaggaag ttaccggcgt aggagagatc 1200
gttgcgcggg taaacaaatg gctgaccaat ggaatacttg taacacatcg cggccatggt 1260
cggcattttc gacagcaggc ggaacgcggc aatttcacgg tgacgaggat tgttaacatc 1320
cagcgagtcg tgatagaacg ccgccagcgc gccggtaata ccacacatga ctgccattgg 1380
atgcgagtcg cgacggaaag catggaacag acgggtaatc tgctcgtgga tcatggtatg 1440
acgggtcacc gtagttttaa attcgtcata ctgttcctga gtcggttttt caccattcag 1500
caggatgtaa caaacttcca ggtagttaga atcggtcgcc agctgatcga tcgggaaacc 1560
gcggtgcagc aaaatacctt catcaccatc aataaaagta attttagatt cgcaggatgc 1620
ggttgaagtg aagcctgggt caaaggtgaa cacacctttt gaaccgagag tacggatatc 1680
aataacatct tgacccagcg tgcctttcag cacatccagt tcaacagctg tatccccgtt 1740
gagggtgagt tttgcttttg tatcagccat ttaaggtctc cttagcgcct tattgcgtaa 1800
gactgccgga acttaaattt gccttcgcac atcaacctgg ctttacccgt tttttatttg 1860
gctcgccgct ctgtgaaaga ggggaaaacc tgggtacaga gctctgggcg cttgcaggta 1920
aaggatccat tgatgacgaa taaatggcga atcaagtact tagcaatccg aattattaaa 1980
cttgtctacc actaataact gtcccgaatg aattggtcaa tactccacac tgttacataa 2040
gttaatctta ggtgaaatac cgacttcata acttttacgc attatatgct tttcctggta 2100
atgtttgtaa caactttgtt gaatgattgt caaattagat gattaaaaat taaataaatg 2160
ttgttatcgt gacctggatc actgttcagg ataaaacccg acaaactata tgtaggttaa 2220
ttgtaatgat tttgtgaaca gcctatactg ccgccagtct ccggaacacc ctgcaatccc 2280
gagccaccca gcgttgtaac gtgtcgtttt cgcatctgga agcagtgttt tgcatgacgc 2340
gcagttatag aaaggacgct gtctgacccg caagcagacc ggaggaagga aatcccgacg 2400
tcggggatcc tctagagctt tagcgtctga ggttatcgca atttggttat gagattactc 2460
tcgttattaa tttgctttcc tgggtcattt ttttcttgct taccgtcaca ttcttgatgg 2520
tatagtcgaa aactgcaaaa gcacatgaca taaacaacat aagcacaatc gtattaatat 2580
ataagggttt tatatctatg gatcagacat attctctgga gtcattcctc aaccatgtcc 2640
aaaagcgcga cccgaatcaa accgagttcg cgcaagccgt tcgtgaagta atgaccacac 2700
tctggccttt tcttgaacaa aatccaaaat atcgccagat gtcattactg gagcgtctgg 2760
ttgaaccgga gcgcgtgatc cagtttcgcg tggtatgggt tgatgatcgc aaccagatac 2820
aggtcaaccg tgcatggcgt gtgcagttca gctctgccat cggcccgtac aaaggcggta 2880
tgcgcttcca tccgtcagtt aacctttcca ttctcaaatt cctcggcttt gaacaaacct 2940
tcaaaaatgc cctgactact ctgccgatgg gcggtggtaa aggcggcagc gatttcgatc 3000
cgaaaggaaa aagcgaaggt gaagtgatgc gtttttgcca ggcgctgatg actgaactgt 3060
atcgccacct gggcgcggat accgacgttc cggcaggtga tatcggggtt ggtggtcgtg 3120
aagtcggctt tatggcgggg atgatgaaaa agctctccaa caataccgcc tgcgtcttca 3180
ccggtaaggg cctttcattt ggcggcagtc ttattcgccc ggaagctacc ggctacggtc 3240
tggtttattt cacagaagca atgctaaaac gccacggtat gggttttgaa gggatgcgcg 3300
tttccgtttc tggctccggc aacgtcgccc agtacgctat cgaaaaagcg atggaatttg 3360
gtgctcgtgt gatcactgcg tcagactcca gcggcactgt agttgatgaa agcggattca 3420
cgaaagagaa actggcacgt cttatcgaaa tcaaagccag ccgcgatggt cgagtggcag 3480
attacgccaa agaatttggt ctggtctatc tcgaaggcca acagccgtgg tctctaccgg 3540
ttgatatcgc cctgccttgc gccacccaga atgaactgga tgttgacgcc gcgcatcagc 3600
ttatcgctaa tggcgttaaa gccgtcgccg aaggggcaaa tatgccgacc accatcgaag 3660
cgactgaact gttccagcag gcaggcgtac tatttgcacc gggtaaagcg gctaatgctg 3720
gtggcgtcgc tacatcgggc ctggaaatgc cacaaaacgc tgcgcgcctg ggctggaaag 3780
ccgagaaagt tgacgcacgt ttgcatcaca tcatgctgga tatccaccat gcctgtgttg 3840
agcatggtgg tgaaggtgag caaaccaact acgtgcaggg cgcgaacatt gccggttttg 3900
tgaaggttgc cgatgcgatg ctggcgcagg gtgtgattta agttgtaaat gcctgatggc 3960
gctacgctta tcaggcctac aaatgggcac aattcattgc agttacgctc taatgtaggc 4020
cgggcaagcg cagcgccccc ggcaaaattt caggcgttta tgagtattta acggatgatg 4080
ctccccacgg aacatttctt atgggccaac ggcatttctt actgtagtgc tcccaaaact 4140
gcttgtcgta acgataacac gcttcaagtt cagcatccgt taactttctg cggactcacg 4200
cgcgcagcac tatgccagta aagaaatccc atttgactat ttttttgata atcttcttcg 4260
ctttcgaaca actcgtgcgc ctttcgagaa gctagagtcg actcgccaat caccagcact 4320
aaagtgcgcg gttcgttacc cgattcatct ttgaaattag ccagtggcgg caaggcatta 4380
ttttcattca gtaactttgt tagcgagttt agttgctgac gatactgata atagccggtc 4440
aggaattgcc acggtgcggc aggctccata cgcgaggcca ggttatccaa cgttttctca 4500
aacggcttgt ttttgataaa cgtattcatg gcgatcggat gcagaatcaa gccataaagc 4560
agggcaaaag agacaacata acgccacggc tttggaatat agaccgggcg caggcgtgtc 4620
cacagcagaa ctgccaccgc cgtataggcc agcgcgataa gcacaatttt caggctgaaa 4680
tactggctta aatactcgct ggcttcgttg gtgttggttt cgaacatcac aaacagaacg 4740
ctctgcgaga actcctgacc gtagatgacg tagtagcaca gcgccgccag agaggccgcc 4800
catagcacca cgccgattac tgcggcaata attttaatcc gcttcggaaa gaggaatacc 4860
gggatcaacc acagcgaact gaataacagc gagtcgcgaa tgccgttagt gccactataa 4920
ccactgatgt aaataatggc ctgtagcaga gtagagaaaa accaaaagta gagcagtgcc 4980
caacccaggg ctttccagct aaaaagaggt ttagcctgga cttctgtgga atgcatagta 5040
agaacctgtc ttgaaaaaat atcgccgaat gtaacgacaa ttccttaagg atatctgaag 5100
gtatattcag aatttgaata aaatgcagac agaaatatat tgaaaacgag ggtgttagaa 5160
cagaagtatt tcagaaaacc ctcgcgcaaa agcacgaggg tttgcagaag aggaagatta 5220
gccggtatta cgcatacctg ccgcaatccc ggcaatagtg accattaacg cttgttcgac 5280
gcgaggatcc ggttcctggc cttctttttc tgcctggcgg gagcggtgca gcaactcggc 5340
ctgcaatacg ttcagcgggt cggtgtaaat attccgtagc tgaatagact ctgcaatcca 5400
cggcagatcg gccatcagat gggaatcgtt ggcaatcgcc agcaccactt tgatgtcttc 5460
ttcttgcagg ttgcgtaact ctttacctaa cggccacagt gctttgtcta ccaggcgttg 5520
gtcatagtat tccgccagcc acaggtctgc tttggcgaag accatctcca gcatgccgag 5580
acgcgtcgag aagaatggcc aatcgcggca catagcctcc agctcgctct gtttgccgtc 5640
ttcgaccact ttttgcagcg ccgtacctgc acccagccag gcggggagca tcagacggtt 5700
ttgcgtccag gcgaagatcc acggaatggc gcgtagtgac tcgacgccgc cggttgggcg 5760
acgtttcgcc ggacgtgaac ccaacggcag tttgcccagt tcttgttccg gcgtagcgga 5820
gcggaagtaa ggcacaaaat ctttgttttc acgtacgtag ccgcggtaga catcgcagga 5880
gatgactgac agttcatcca taatgcgacg ccagctctct ttcggctccg gcggtggcag 5940
caggttggct tccagaatcg ccccggtata aagcgacagg ctgctgacgg tgatttctgg 6000
cagaccatat ttaaagcgga tcatctcgcc ctgttcggtt acgcgcaggc cgcctttcag 6060
gcttcctggc ggttgtgaca gcagcgccgc atgagcaggt gcgccgccgc gaccaatgga 6120
accgccgcga ccgtggaaca acgtcagctc aatacccgct ttttcgcagg ttttgattaa 6180
tgcatcctgt gcctgatatt gcgcccagga agctgccatc actcccgcat cttttgctga 6240
gtcggaatag ccaatcatca ccatctgttt gccctgaatc aggccacgat accagtcaat 6300
attgagcagc tgggtcatga catcgttggc gttgttcaga tcatcgaggg tttcaaacag 6360
cggagcaacc ggcatcgcaa acccgatacc cgcttctttc agcagcaggt ggacagccag 6420
tacgtcggac ggcgttttcg ccatcgagat cacgtaggcg gcaatggagc cttgcggtgc 6480
ttcggcaatc acctggcagg tatcgagcac ttcgcgcgtt tcggcgcttg gttgccagtt 6540
gcgcggcaga agcggacgtt tggagttcag ttcgcggatc aggaacgcct gtttgtcggc 6600
ctctgaccag ctttcgtagt cgccgatacc gaggtagcgg gtcagctcgc ccagcgcttc 6660
ggtatgacgc gtgctctcct gacggatatc aatacggacc agcggtacgc cgaaacattt 6720
cacgcggcgc agggtgtcga gcagatcgcc gttggcgata atacccatgc cacacgcctg 6780
aagtgactgg tagcaagcgt agagcggttc ccacagttct tcgttttgtg tcagcaggcc 6840
ttctggtttt ggcagttctt cgcctttcag gcgcgcttcc agccatgcct gtgtcgccat 6900
caggcgagaa cgcaggtttt tcatcagata gcgatacggt tctgcggcac cttcttcgcc 6960
aaccagcgcc agcagttcag ggtcgcttc aaccatcgac agttcagaaa ccagcacctg 7020
aatatctttc aggaacaaat cggtggcttt ccagcggctg agtagcagga cgtggcgggt 7080
gatatcggca gtgacgttcg ggttgccgtc gcggtcgccg cccatccacg aagtaaaacg 7140
gaccggaaca aattcgacgg gcagtttgta gccgaggttc tcttccagtt gttcgttcag 7200
ttcgcgcagg taatttggta cgccttgcca caggctgttt tccactacgg caaagcccca 7260
tttggcttca tctaccgggc ttggacgcag cttacggatt tcatcggtat gccatgactg 7320
ggcgatcaac tggcgcaggc gacgcatcag ctggttgtgt tcgtagtcag cgatatcttt 7380
gttatcgagc tgttttaaac aggcgttcac ttccaccatt ttgtggatca gtgtacgacg 7440
ggtaatttcg gttgggtgag ccgtgaggac cagttccagc gacagcgatt ccactgcttt 7500
tttgatggtg tcttcgctca gttccggctg gtttttcagt ttacgcaggg tgcgggcgat 7560
cacttccggg ttgctggcag cttcgccttt cggcgaaatg ctgtggtatt gctcggcggt 7620
gttggccagg ttcaggaact gactaaacgc acgcgcaacg ggcagcagct cgtcgttcga 7680
caaattttgt aaggtggtga gcaactcctg gcggttagca tcattgccag cgcgtgaaga 7740
tttcgacaac ttacggatag tttctacgcg ttcaagaatg tgttctccca acgcatcctt 7800
gatggtttct cccagcactt tgccgagcat actgacatta ctacgcaatg cggaatattg 7860
ttcgttcata ttaccccaga caccccatct tatcgtttga tagccctgta tccttcacgt 7920
cgcattggcg cgaatatgct cgggctttgc ttttcgtcgt cttttataaa gccacgtaaa 7980
agcggtgacg tcaaatgctg cgaaatcgct tcagcaaacg aataaatagc aggaatttac 8040
gtcattaaat tcacgacgct ttaaataagc gtaacttatg gaaatgttaa aaaatcgccc 8100
caagtaacac caaaggtgta ggtcggataa gatgcgcaag tatcgcatcc gacattattg 8160
cggcactgga gtttggcaac agtgccggat gcggcgcgag cgccttatcc ggcctacagt 8220
tgggcatcgt ttgagtcact gtcggtcgga taagatgcgc aagtatcgca tccgacatta 8280
ttgcggcact ggagtttggc aacagtgccg gatgcggcgc gagcgcctta tccggcctac 8340
ggttgggcat cgtttgagtc actgtaggtc ggataagatg cgcaagcatc gcatccgaca 8400
ttattgcggc actggagttt ggcaacagcg ccggatgcgg cgcgagcgcc ttatccggcc 8460
tacgttttaa tgccagcaaa aatggtgaat tacctgggtt atcagttcgc gggtgggctt 8520
gataaaccgt gtttccagat attcatcagg ttgatgagcc tgattaattg agccaggccc 8580
caacaccagc gtcgggcata acgtttgaat aaacggcgct tcggtacagt agttcaccac 8640
ttcggttttt gctccgagca atttctcaac cacttcaacc agttgatgat tcggtgggca 8700
ttcatagcca gggatcggcg gatgcagctc gtcgacctgc aggagcagaa gagcatacat 8760
ctggaagcaa agccaggaaa gcggcctatg gagctgtgcg gcagcgctca gtaggcaatt 8820
tttcaaaata ttgttaagcc ttttctgagc atggtatttt tcatggtatt accaattagc 8880
aggaaaataa gccattgaat ataaaagata aaaatgtctt gtttacaata gagtgggggg 8940
ggtcagcctg ccgccttggg ccgggtgatg tcgtacttgc ccgccgcgaa ctcggttacc 9000
gtccagccca gcgcgaccag ctccggcaac gcctcgcgca cccgctggcg gcgcttgcgc 9060
atggtcgaac cactggcctc tgacggccag acatagccgc acaaggtatc tatggaagcc 9120
ttgccggttt tgccggggtc gatccagcca cacagccgct ggtgcagcag gcgggcggtt 9180
tcgctgtcca gcgcccgcac ctcgtccatg ctgatgcgca catgctggcc gccacccatg 9240
acggcctgcg cgatcaaggg gttcagggcc acgtacaggc gcccgtccgc ctcgtcgctg 9300
gcgtactccg acagcagccg aaacccctgc cgcttgcggc cattctgggc gatgatggat 9360
accttccaaa ggcgctcgat gcagtcctgt atgtgcttga gcgccccacc actatcgacc 9420
tctgccccga tttcctttgc cagcgcccga tagctacctt tgaccacatg gcattcagcg 9480
gtgacggcct cccacttggg ttccaggaac agccggagct gccgtccgcc ttcggtcttg 9540
ggttccgggc caagcactag gccattaggc ccagccatgg ccaccagccc ttgcaggatg 9600
cgcagatcat cagcgcccag cggctccggg ccgctgaact cgatccgctt gccgtcgccg 9660
tagtcatacg tcacgtccag cttgctgcgc ttgcgctcgc cccgcttgag ggcacggaac 9720
aggccggggg ccagacagtg cgccgggtcg tgccggacgt ggctgaggct gtgcttgttc 9780
ttaggcttca ccacggggca ccccccttgct cttgcgctgc ctctccagca cggcgggctt 9840
gagcaccccg ccgtcatgcc gcctgaacca ccgatcagcg aacggtgcgc catagttggc 9900
cttgctcaca ccgaagcgga cgaagaaccg gcgctggtcg tcgtccacac cccattcctc 9960

```
ggcctcggcg ctggtcatgc tcgacaggta ggactgccag cggatgttat cgaccagtac  10020
cgagctgccc cggctggcct gctgctggtc gcctgcgccc atcatggccg cgcccttgct  10080
ggcatggtgc aggaacacga tagagcaccc ggtatcggcg gcgatggcct ccatgcgacc  10140
gatgacctgg gccatggggc cgctggcgtt ttcttcctcg atgtggaacc ggcgcagcgt  10200
gtccagcacc atcaggcggc ggccctcggc ggcgcgcttg aggccgtcga accactccgg  10260
ggccatgatg ttgggcaggc tgccgatcag cggctggatc agcaggccgt cagccacggc  10320
ttgccgttcc tcggcgctga ggtgcgcccc aagggcgtgc aggcggtgat gaatggcggt  10380
gggcgggtct tcggcgggca ggtagatcac cgggccggtg ggcagttcgc ccacctccag  10440
cagatccggc ccgcctgcaa tctgtgcggc cagttgcagg gccagcatgg atttaccggc  10500
accaccgggc gacaccagcg ccccgaccgt accggccacc atgttgggca aaacgtagtc  10560
cagcggtggc ggcgctgctg cgaacgcctc cagaatattg ataggcttat gggtagccat  10620
tgattgcctc ctttgcaggc agttggtggt taggcgctgg cggggtcact acccccgccc  10680
tgcgccgctc tgagttcttc caggcactcg cgcagcgcct cgtattcgtc gtcggtcagc  10740
cagaacttgc gctgacgcat ccctttggcc ttcatgcgct cggcatatcg cgcttggcgt  10800
acagcgtcag ggctggccag caggtcgccg gtctgcttgt ccttttggtc tttcatatca  10860
gtcaccgaga aacttgccgg ggccgaaagg cttgtcttcg cggaacaagg acaaggtgca  10920
gccgtcaagg ttaaggctgg ccatatcagc gactgaaaag cggccagcct cggccttgtt  10980
tgacgtataa ccaaagccac cgggcaacca atagcccttg tcacttttga tcaggtagac  11040
cgaccctgaa gcgctttttt cgtattccat aaaacccccct tctgtgcgtg agtactcata  11100
gtataacagg cgtgagtacc aacgcaagca ctacatgctg aaatctggcc cgcccctgtc  11160
catgcctcgc tggcggggtg ccggtgcccg tgccagctcg gcccgcgcaa gctggacgct  11220
gggcagaccc atgaccttgc tgacggtgcg ctcgatgtaa tccgcttcgt ggccgggctt  11280
gcgctctgcc agcgctgggc tggcctcggc catggccttg ccgatttcct cggcactgcg  11340
gccccggctg gccagcttct gcgcggcgat aaagtcgcac ttgctgaggt catcaccgaa  11400
gcgcttgacc agcccggcca tctcgctgcg gtactcgtcc agcgccgtgc gccggtggcg  11460
gctaagctgc cgctcgggca gttcgaggct ggccagcctg cgggccttct cctgctgccg  11520
ctgggcctgc tcgatctgct ggccagcctg ctgcaccagc gccgggccag cggtggcggt  11580
cttgcccttg gattcacgca gcagcaccca cggctgataa ccggcgcggg tggtgtgctt  11640
gtccttgcgg ttggtgaagc ccgccaagcg gccatagtgg cggctgtcgg cgctggccgg  11700
gtcggcgtcg tactcgctgg ccagcgtccg ggcaatctgc ccccgaagtt caccgcctgc  11760
ggcgtcggcc accttgaccc atgcctgata gttcttcggg ctggtttcca ctaccagggc  11820
aggctcccgg ccctcggctt tcatgtcatc caggtcaaac tcgctgaggt cgtccaccag  11880
caccagacca tgccgctcct gctcggcggg cctgatatac acgtcattgc cctgggcatt  11940
catccgcttg agccatggcg tgttctggag cacttcggcg gctgaccatt cccggttcat  12000
catctggccg gtggtggcgt ccctgacgcc gatatcgaag cgctcacagc ccatggcctt  12060
gagctgtcgg cctatggcct gcaaagtcct gtcgttcttc atcgggccac caagcgcagc  12120
cagatcgagc cgtcctcggt tgtcagtggc gtcaggtcga gcaagagcaa cgatgcgatc  12180
agcagcacca ccgtaggcat catggaagcc agcatcacgg ttagccatag cttccagtgc  12240
cacccccgcg acgcgctccg ggcgctctgc gcggcgctgc tcacctcggc ggctacctcc  12300
cgcaactctt tggccagctc cacccatgcc gcccctgtct ggcgctgggc tttcagccac  12360
```

tccgccgcct gcgcctcgct ggcctgctgg gtctggctca tgacctgccg ggcttcgtcg 12420
gccagtgtcg ccatgctctg ggccagcggt tcgatctgct ccgctaactc gttgatgcct 12480
ctggatttct tcactctgtc gattgcgttc atggtctatt gcctcccggt attcctgtaa 12540
gtcgatgatc tgggcgttgg cggtgtcgat gttcagggcc acgtctgccc ggtcggtgcg 12600
gatgccccgg ccttccatct ccaccacgtt cggccccagg tgaacaccgg gcaggcgctc 12660
gatgccctgc gcctcaagtg ttctgtggtc aatgcgggcg tcgtggccag cccgctctaa 12720
tgcccggttg gcatggtcgg cccatgcctc gcgggtctgc tcaagccatg ccttgggctt 12780
gagcgcttcg gtcttctgtg ccccgccctt ctccggggtc ttgccgttgt accgcttgaa 12840
ccactgagcg gcgggccgct cgatgccgtc attgatccgc tcggagatca tcaggtggca 12900
gtgcgggttc tcgccgccac cggcatggat ggccagcgta tacggcaggc gctcggcacc 12960
ggtcaggtgc tgggcgaact cggacgccag cgccttctgc tggtcgaggg tcagctcgac 13020
cggcagggca aattcgacct ccttgaacag ccgcccattg gcgcgttcat acaggtcggc 13080
agcatcccag tagtcggcgg gccgctcgac gaactccggc atgtgcccgg attcggcgtg 13140
caagacttca tccatgtcgc gggcatactt gccttcgcgc tggatgtagt cggccttggc 13200
cctggccgat tggccgcccg acctgctgcc ggttttcgcc gtaaggtgat aaatcgccat 13260
gctgcctcgc tgttgctttt gcttttcggc tccatgcaat ggccctcgga gagcgcaccg 13320
cccgaagggt ggccgttagg ccagtttctc gaagagaaac cggtaagtgc gccctcccct 13380
acaaagtagg gtcgggattg ccgccgctgt gcctccatga tagcctacga gacagcacat 13440
taacaatggg gtgtcaagat ggttaagggg agcaacaagg cggcggatcg gctggccaag 13500
ctcgaagaac aacgagcgcg aatcaatgcc gaaattcagc gggtgcgggc aagggaacag 13560
cagcaagagc gcaagaacga aacaaggcgc aaggtgctgg tgggggccat gatttggcc 13620
aaggtgaaca gcagcgagtg gccggaggat cggctcatgg cggcaatgga tgcgtacctt 13680
gaacgcgacc acgaccgcgc cttgttcggt ctgccgccac gccagaagga tgagccgggc 13740
tgaatgatcg accgagacag gccctgcggg gctgcacacg cgcccccacc cttcgggtag 13800
ggggaaaggc cgctaaagcg gctaaaagcg ctccagcgta tttctgcggg gtttggtgtg 13860
gggtttagcg ggctttgccc gcctttcccc ctgccgcgca gcggtggggc ggtgtgtagc 13920
ctagcgcagc gaatagacca gctatccggc ctctggccgg gcatattggg caagggcagc 13980
agcgccccac aagggcgctg ataaccgcgc ctagtggatt attcttagat aatcatggat 14040
ggatttttcc aacaccccgc cagcccccgc ccctgctggg tttgcaggtt tgggggcgtg 14100
acagttattg caggggttcg tgacagttat tgcagggggg cgtgacagtt attgcagggg 14160
ttcgtgacag ttagtacggg agtgacgggc actggctggc aatgtctagc aacggcaggc 14220
atttcggctg agggtaaaag aactttccgc taagcgatag actgtatgta aacacagtat 14280
tgcaaggacg cggaacatgc ctcatgtggc ggccaggacg gccagccggg atcgggatac 14340
tggtcgttac cagagccacc gacccgagca aacccttctc tatcagatcg ttgacgagta 14400
ttacccggca ttcgctgcgc ttatggcaga gcagggaaag gaattgccgg gctatgtgca 14460
acgggaattt gaagaatttc tccaatgcgg gcggctggag catggctttc tacgggttcg 14520
ctgcgagtct tgccacgccg agcacctggt cgctttcagc tgtaagcgtc gcggtttctg 14580
cccgagctgt ggggcgcggc ggatggccga aagtgccgcc ttgctggttg atgaagtact 14640
gcctgaacaa cccatgcgtc agtgggtgtt gagcttcccg tttcagctgc gtttcctgtt 14700

-continued

```
tggggtcgtt tgcgggaagg ggcggaatcc tacgctaagg ctttggccag cgatattctc  14760

cggtgagatt gatgtgttcc caggggatag gagaagtcgc ttgatatcta gtatgacgtc  14820

tgtcgcacct gcttgatcgc ggcccaaggg ttggtttgcg cattcacagt tctccgcaag  14880

aattgattgg ctccaattct tggagtggtg aatccgttag cgaggtgccg ccggcttcca  14940

ttcaggtcga ggtggcccgg ctccatgcac cgcgacgcaa cgcggggagg cagacaaggt  15000

atagggcggc gcctacaatc catgccaacc cgttccatgt gctcgccgag gcggcataaa  15060

tcgccgtgac gatcagcggt ccagtgatcg aagttaggct ggtaagagcc gcgagcgatc  15120

cttgaagctg tccctgatgg tcgtcatcta cctgcctgga cagcatggcc tgcaacgcgg  15180

gcatcccgat gccgccggaa gcgagaagaa tcataatggg gaaggccatc cagcctcgcg  15240

tcgcgaacgc cagcaagacg tagcccagcg cgtcggccgc catgccggcg ataatggcct  15300

gcttctcgcc gaaacgtttg gtggcgggac cagtgacgaa ggcttgagcg agggcgtgca  15360

agattccgaa taccgcaagc gacaggccga tcatcgtcgc gctccagcga aagcggtcct  15420

cgccgaaaat gacccagagc gctgccggca cctgtcctac gagttgcatg ataaagaaga  15480

cagtcataag tgcggcgacg atagtcatgc cccgcgccca ccggaaggag ctgactgggt  15540

tgaaggctct caagggcatc ggtcgacgct ctcccttatg cgactcctgc attaggaagc  15600

agcccagtag taggttgagg ccgttgagca ccgccgccgc aaggaatggt gcatgcaagg  15660

agatggcgcc caacagtccc ccggccacgg ggcctgccac catacccacg ccgaaacaag  15720

cgctcatgag cccgaagtgg cgagcccgat cttccccatc ggtgatgtcg gcgatatagg  15780

cgccagcaac cgcacctgtg gcgccggtga tgccggccac gatgcgtccg gcgtagagga  15840

tccacaggac gggtgtggtc gccatgatcg cgtagtcgat agtggctcca agtagcgaag  15900

cgagcaggac tgggcggcgg ccaaagcggt cggacagtgc tccgagaacg ggtgcgcata  15960

gaaattgcat caacgcatat agcgctagca gcacgccata gtgactggcg atgctgtcgg  16020

aatggacgat atcccgcaag aggcccggca gtaccggcat aaccaagcct atgcctacag  16080

catccagggt gacggtgccg aggatgacga tgagcgcatt gttagatttc atacacggtg  16140

cctgactgcg ttagcaattt aactgtgata aactaccgca ttaaagctta tcgatgataa  16200

gctgtcaaac atga                                                    16214
```

<210> SEQ ID NO 11
<211> LENGTH: 40
<212> TYPE: DNA
<213> ORGANISM: Artificial Sequence
<220> FEATURE:
<223> OTHER INFORMATION: primer

<400> SEQUENCE: 11

```
gatcggtacc ggtgcgctga atgaatctgc gccctgaatt                             40
```

<210> SEQ ID NO 12
<211> LENGTH: 40
<212> TYPE: DNA
<213> ORGANISM: Artificial Sequence
<220> FEATURE:
<223> OTHER INFORMATION: primer

<400> SEQUENCE: 12

```
gatcgcatgc ggcaacttca gttttatcct aatcctggcc                             40
```

<210> SEQ ID NO 13
<211> LENGTH: 55

-continued

<212> TYPE: DNA
<213> ORGANISM: Artificial Sequence
<220> FEATURE:
<223> OTHER INFORMATION: primer

<400> SEQUENCE: 13
gtgattcaac atcactggag aaagtcttat gaaactctga agcctgcttt tttat 55

<210> SEQ ID NO 14
<211> LENGTH: 55
<212> TYPE: DNA
<213> ORGANISM: Artificial Sequence
<220> FEATURE:
<223> OTHER INFORMATION: primer

<400> SEQUENCE: 14
cctggaatgc aggggagcgg caagattaaa ccagttccgc tcaagttagt ataaa 55

<210> SEQ ID NO 15
<211> LENGTH: 22
<212> TYPE: DNA
<213> ORGANISM: Artificial Sequence
<220> FEATURE:
<223> OTHER INFORMATION: primer

<400> SEQUENCE: 15
gcgcctacac taagcatagt tg 22

<210> SEQ ID NO 16
<211> LENGTH: 22
<212> TYPE: DNA
<213> ORGANISM: Artificial Sequence
<220> FEATURE:
<223> OTHER INFORMATION: Artificial Sequence

<400> SEQUENCE: 16
ccatcagcag gcttagcgca ac 22

<210> SEQ ID NO 17
<211> LENGTH: 55
<212> TYPE: DNA
<213> ORGANISM: Artificial Sequence
<220> FEATURE:
<223> OTHER INFORMATION: primer

<400> SEQUENCE: 17
gagggagaaa aacgcatgat tatttccgca gccagcgtga agcctgcttt tttat 55

<210> SEQ ID NO 18
<211> LENGTH: 54
<212> TYPE: DNA
<213> ORGANISM: Artificial Sequence
<220> FEATURE:
<223> OTHER INFORMATION: primer

<400> SEQUENCE: 18
gcgcaaacga ctatgccgca ttccctttcg ccatggcgct caagttagta taaa 54

<210> SEQ ID NO 19
<211> LENGTH: 23
<212> TYPE: DNA
<213> ORGANISM: Artificial Sequence
<220> FEATURE:
<223> OTHER INFORMATION: primer

<400> SEQUENCE: 19
gcgtaaagca atgatggcgc acc 23

<210> SEQ ID NO 20
<211> LENGTH: 23
<212> TYPE: DNA
<213> ORGANISM: Artificial Sequence
<220> FEATURE:
<223> OTHER INFORMATION: primer

<400> SEQUENCE: 20
gcggtgtcgt ttcagagtga ggg 23

<210> SEQ ID NO 21
<211> LENGTH: 348
<212> TYPE: DNA
<213> ORGANISM: Escherichia coli

<400> SEQUENCE: 21
aagctttacg cgaacgagcc atgacattgc tgacgactct ggcagtggca gatgacataa 60
aactggtcga ctggttacaa caacgcctgg ggcttttaga gcaacgagac acggcaatgt 120
tgcaccgttt gctgcatgat attgaaaaaa atatcaccaa ataaaaaacg ccttagtaag 180
tatttttcag cttttcattc tgactgcaac gggcaatatg tctctgtgtg gattaaaaaa 240
agagtgtctg atagcagctt ctgaactggt tacctgccgt gagtaaatta aaattttatt 300
gacttaggtc actaaatact ttaaccaata taggcgactc taggatcc 348

<210> SEQ ID NO 22
<211> LENGTH: 24
<212> TYPE: DNA
<213> ORGANISM: Artificial Sequence
<220> FEATURE:
<223> OTHER INFORMATION: primer

<400> SEQUENCE: 22
cgggatccca gcttactagt aaac 24

<210> SEQ ID NO 23
<211> LENGTH: 32
<212> TYPE: DNA
<213> ORGANISM: Artificial Sequence
<220> FEATURE:
<223> OTHER INFORMATION: primer

<400> SEQUENCE: 23
gggaaaggat ccgatgggct ccacaaaatg gg 32

<210> SEQ ID NO 24
<211> LENGTH: 1686
<212> TYPE: DNA
<213> ORGANISM: Salmonella typhimurium
<220> FEATURE:
<221> NAME/KEY: CDS
<222> LOCATION: (1)..(1686)

<400> SEQUENCE: 24

```
gtg aat ata aac gtc gca gat ttg tta aat ggg aat tac atc ctg tta       48
Val Asn Ile Asn Val Ala Asp Leu Leu Asn Gly Asn Tyr Ile Leu Leu
1               5                   10                  15

tta ttt gtg gtc ctg gct ctt ggc ctg tgt ctt ggc aag tta cgt ctg       96
Leu Phe Val Val Leu Ala Leu Gly Leu Cys Leu Gly Lys Leu Arg Leu
            20                  25                  30

ggt tca gtc caa ctt ggt aat tcc att ggc gtt tta gtg gtc tct cta      144
Gly Ser Val Gln Leu Gly Asn Ser Ile Gly Val Leu Val Val Ser Leu
```

-continued

```
        35                  40                  45

tta tta ggg cag caa cac ttc agt att aac acc gac gcg cta aat ctg      192
Leu Leu Gly Gln Gln His Phe Ser Ile Asn Thr Asp Ala Leu Asn Leu
    50                  55                  60

gga ttt atg ctg ttt att ttt tgt gtc ggc gtc gag gct ggc ccc aac      240
Gly Phe Met Leu Phe Ile Phe Cys Val Gly Val Glu Ala Gly Pro Asn
65                  70                  75                  80

ttt ttt tcg att ttt ttt cgc gac ggt aaa aat tat ctg atg ctt gcc      288
Phe Phe Ser Ile Phe Phe Arg Asp Gly Lys Asn Tyr Leu Met Leu Ala
                85                  90                  95

ctg gtc atg gtc ggt agc gct ctg cta atc gcc tta ggc ctt ggt aag      336
Leu Val Met Val Gly Ser Ala Leu Leu Ile Ala Leu Gly Leu Gly Lys
            100                 105                 110

cta ttc ggc tgg gat atc ggc ctg acg gcc ggt atg ctg gcc ggc tca      384
Leu Phe Gly Trp Asp Ile Gly Leu Thr Ala Gly Met Leu Ala Gly Ser
        115                 120                 125

atg acc tcc acg ccc gtg ctg gtt ggc gca ggc gat acc ctg cga cat      432
Met Thr Ser Thr Pro Val Leu Val Gly Ala Gly Asp Thr Leu Arg His
    130                 135                 140

tcc ggc atc gcc agc acc caa ctc tcc tcc gct ctt gat aat ctg agc      480
Ser Gly Ile Ala Ser Thr Gln Leu Ser Ser Ala Leu Asp Asn Leu Ser
145                 150                 155                 160

ctg ggc tat gcc ctg acc tat ctg att ggg ttg gtc agt ctg atc gtg      528
Leu Gly Tyr Ala Leu Thr Tyr Leu Ile Gly Leu Val Ser Leu Ile Val
                165                 170                 175

ggc gcg cgc tac ttg cct aaa cta cag cat cag gat ttg caa acc agc      576
Gly Ala Arg Tyr Leu Pro Lys Leu Gln His Gln Asp Leu Gln Thr Ser
            180                 185                 190

gcc cag caa att gct cgc gag cgc ggt ctg gat acc gat gct aat cgc      624
Ala Gln Gln Ile Ala Arg Glu Arg Gly Leu Asp Thr Asp Ala Asn Arg
        195                 200                 205

aag gtt tat ttg ccg gtt atc cgc gcc tat cgg gtt ggc ccg gaa ctg      672
Lys Val Tyr Leu Pro Val Ile Arg Ala Tyr Arg Val Gly Pro Glu Leu
    210                 215                 220

gtg gcc tgg act gac ggt aaa aac ctg cgc gag ctg ggt att tac cgc      720
Val Ala Trp Thr Asp Gly Lys Asn Leu Arg Glu Leu Gly Ile Tyr Arg
225                 230                 235                 240

cag aca ggc tgc tat atc gaa cgt att cgc cgt aac ggt att ctg gcg      768
Gln Thr Gly Cys Tyr Ile Glu Arg Ile Arg Arg Asn Gly Ile Leu Ala
                245                 250                 255

aac ccg gat ggc gat gcg gtg ctg caa atg ggc gat gag att gcg ctg      816
Asn Pro Asp Gly Asp Ala Val Leu Gln Met Gly Asp Glu Ile Ala Leu
            260                 265                 270

gtc ggc tat ccg gac gcg cac gcc agg ctc gat ccc agc ttc cgt aat      864
Val Gly Tyr Pro Asp Ala His Ala Arg Leu Asp Pro Ser Phe Arg Asn
        275                 280                 285

ggt aag gaa gta ttt gat cgc gat ctg ctt gat atg cgc atc gtg acg      912
Gly Lys Glu Val Phe Asp Arg Asp Leu Leu Asp Met Arg Ile Val Thr
    290                 295                 300

gaa gaa att gtg gtg aaa aac cac aat gcg gtc ggt cgc cgc ctc gct      960
Glu Glu Ile Val Val Lys Asn His Asn Ala Val Gly Arg Arg Leu Ala
305                 310                 315                 320

cag ctc aag ctg acc gat cat ggc tgc ttc ctt aac cgc gtc atc cgc     1008
Gln Leu Lys Leu Thr Asp His Gly Cys Phe Leu Asn Arg Val Ile Arg
                325                 330                 335

agc cag atc gaa atg cct atc gac gat aac gtc gtg ctg aat aaa ggc     1056
Ser Gln Ile Glu Met Pro Ile Asp Asp Asn Val Val Leu Asn Lys Gly
            340                 345                 350

gac gtg tta cag gtg agc ggc gac gcc aga cgc gta aaa acc atc gcc     1104
```

-continued

Asp Val Leu Gln Val Ser Gly Asp Ala Arg Arg Val Lys Thr Ile Ala
355 360 365 gat cgc att ggt ttt att tcg att cat agt cag gtg acg gac ctg ctt 1152
Asp Arg Ile Gly Phe Ile Ser Ile His Ser Gln Val Thr Asp Leu Leu
370 375 380 gcc ttc tgc gct ttt ttt atc atc ggg tta atg atc ggg atg att acc 1200
Ala Phe Cys Ala Phe Phe Ile Ile Gly Leu Met Ile Gly Met Ile Thr
385 390 395 400 ttc cag ttc agc aat ttt agt ttc ggt atc ggc aac gcg gcc gga ttg 1248
Phe Gln Phe Ser Asn Phe Ser Phe Gly Ile Gly Asn Ala Ala Gly Leu
405 410 415 ctg ttc gcc ggg atc atg ctc ggt ttc ctg cgc gct aac cat cct acc 1296
Leu Phe Ala Gly Ile Met Leu Gly Phe Leu Arg Ala Asn His Pro Thr
420 425 430 ttt ggt tat att ccg cag ggc gcg ctt aat atg gtg aaa gaa ttc ggc 1344
Phe Gly Tyr Ile Pro Gln Gly Ala Leu Asn Met Val Lys Glu Phe Gly
435 440 445 ttg atg gtg ttt atg gca ggc gtt ggt tta agc gcc ggc agc ggt atc 1392
Leu Met Val Phe Met Ala Gly Val Gly Leu Ser Ala Gly Ser Gly Ile
450 455 460 agc aac ggt ctg ggc gcg gtc ggc gga caa atg ctg atc gcc ggg ctt 1440
Ser Asn Gly Leu Gly Ala Val Gly Gly Gln Met Leu Ile Ala Gly Leu
465 470 475 480 gtc gtc agc ctg gta ccg gtg gtg atc tgc ttc ttg ttt ggc gct tat 1488
Val Val Ser Leu Val Pro Val Val Ile Cys Phe Leu Phe Gly Ala Tyr
485 490 495 gtg ctg cgc atg aac cgg gcg ctg ctg ttc ggt gcc atg atg ggc gcg 1536
Val Leu Arg Met Asn Arg Ala Leu Leu Phe Gly Ala Met Met Gly Ala
500 505 510 cgt acc tgc gcc ccg gcg atg gaa atc att agc gat acg gcg cgc agt 1584
Arg Thr Cys Ala Pro Ala Met Glu Ile Ile Ser Asp Thr Ala Arg Ser
515 520 525 aat att cca gcg ctg ggt tat gcg ggg act tac gcc atc gcc aac gtt 1632
Asn Ile Pro Ala Leu Gly Tyr Ala Gly Thr Tyr Ala Ile Ala Asn Val
530 535 540 ctg cta acg ctg gcg ggg acg ctt att gtc atc atc tgg ccg ggg tta 1680
Leu Leu Thr Leu Ala Gly Thr Leu Ile Val Ile Ile Trp Pro Gly Leu
545 550 555 560 gga taa 1686
Gly

<210> SEQ ID NO 25
<211> LENGTH: 561
<212> TYPE: PRT
<213> ORGANISM: Salmonella typhimurium

<400> SEQUENCE: 25

Val Asn Ile Asn Val Ala Asp Leu Leu Asn Gly Asn Tyr Ile Leu Leu
1 5 10 15

Leu Phe Val Val Leu Ala Leu Gly Leu Cys Leu Gly Lys Leu Arg Leu
20 25 30

Gly Ser Val Gln Leu Gly Asn Ser Ile Gly Val Leu Val Val Ser Leu
35 40 45

Leu Leu Gly Gln Gln His Phe Ser Ile Asn Thr Asp Ala Leu Asn Leu
50 55 60

Gly Phe Met Leu Phe Ile Phe Cys Val Gly Val Glu Ala Gly Pro Asn
65 70 75 80

Phe Phe Ser Ile Phe Phe Arg Asp Gly Lys Asn Tyr Leu Met Leu Ala
85 90 95

```
Leu Val Met Val Gly Ser Ala Leu Leu Ile Ala Leu Gly Leu Gly Lys
            100                 105                 110

Leu Phe Gly Trp Asp Ile Gly Leu Thr Ala Gly Met Leu Ala Gly Ser
        115                 120                 125

Met Thr Ser Thr Pro Val Leu Val Gly Ala Gly Asp Thr Leu Arg His
    130                 135                 140

Ser Gly Ile Ala Ser Thr Gln Leu Ser Ser Ala Leu Asp Asn Leu Ser
145                 150                 155                 160

Leu Gly Tyr Ala Leu Thr Tyr Leu Ile Gly Leu Val Ser Leu Ile Val
                165                 170                 175

Gly Ala Arg Tyr Leu Pro Lys Leu Gln His Gln Asp Leu Gln Thr Ser
            180                 185                 190

Ala Gln Gln Ile Ala Arg Glu Arg Gly Leu Asp Thr Asp Ala Asn Arg
        195                 200                 205

Lys Val Tyr Leu Pro Val Ile Arg Ala Tyr Arg Val Gly Pro Glu Leu
    210                 215                 220

Val Ala Trp Thr Asp Gly Lys Asn Leu Arg Glu Leu Gly Ile Tyr Arg
225                 230                 235                 240

Gln Thr Gly Cys Tyr Ile Glu Arg Ile Arg Arg Asn Gly Ile Leu Ala
                245                 250                 255

Asn Pro Asp Gly Asp Ala Val Leu Gln Met Gly Asp Glu Ile Ala Leu
            260                 265                 270

Val Gly Tyr Pro Asp Ala His Ala Arg Leu Asp Pro Ser Phe Arg Asn
        275                 280                 285

Gly Lys Glu Val Phe Asp Arg Asp Leu Leu Asp Met Arg Ile Val Thr
    290                 295                 300

Glu Glu Ile Val Val Lys Asn His Asn Ala Val Gly Arg Arg Leu Ala
305                 310                 315                 320

Gln Leu Lys Leu Thr Asp His Gly Cys Phe Leu Asn Arg Val Ile Arg
                325                 330                 335

Ser Gln Ile Glu Met Pro Ile Asp Asp Asn Val Val Leu Asn Lys Gly
            340                 345                 350

Asp Val Leu Gln Val Ser Gly Asp Ala Arg Arg Val Lys Thr Ile Ala
        355                 360                 365

Asp Arg Ile Gly Phe Ile Ser Ile His Ser Gln Val Thr Asp Leu Leu
    370                 375                 380

Ala Phe Cys Ala Phe Phe Ile Ile Gly Leu Met Ile Gly Met Ile Thr
385                 390                 395                 400

Phe Gln Phe Ser Asn Phe Ser Phe Gly Ile Gly Asn Ala Ala Gly Leu
                405                 410                 415

Leu Phe Ala Gly Ile Met Leu Gly Phe Leu Arg Ala Asn His Pro Thr
            420                 425                 430

Phe Gly Tyr Ile Pro Gln Gly Ala Leu Asn Met Val Lys Glu Phe Gly
        435                 440                 445

Leu Met Val Phe Met Ala Gly Val Gly Leu Ser Ala Gly Ser Gly Ile
    450                 455                 460

Ser Asn Gly Leu Gly Ala Val Gly Gly Gln Met Leu Ile Ala Gly Leu
465                 470                 475                 480

Val Val Ser Leu Val Pro Val Val Ile Cys Phe Leu Phe Gly Ala Tyr
                485                 490                 495

Val Leu Arg Met Asn Arg Ala Leu Leu Phe Gly Ala Met Met Gly Ala
            500                 505                 510
```

-continued

```
Arg Thr Cys Ala Pro Ala Met Glu Ile Ile Ser Asp Thr Ala Arg Ser
        515                 520                 525

Asn Ile Pro Ala Leu Gly Tyr Ala Gly Thr Tyr Ala Ile Ala Asn Val
    530                 535                 540

Leu Leu Thr Leu Ala Gly Thr Leu Ile Val Ile Ile Trp Pro Gly Leu
545                 550                 555                 560

Gly


<210> SEQ ID NO 26
<211> LENGTH: 1689
<212> TYPE: DNA
<213> ORGANISM: Yersinia pestis
<220> FEATURE:
<221> NAME/KEY: CDS
<222> LOCATION: (1)..(1689)

<400> SEQUENCE: 26

gtg aat ata aac gtc gca aat ttg tta aac ggc aac tat atc ttg ctg       48
Val Asn Ile Asn Val Ala Asn Leu Leu Asn Gly Asn Tyr Ile Leu Leu
1               5                   10                  15

tta ttc gtc gtc tta gcg ttg ggg tta tgc tta ggt aaa ttg cgc ctt       96
Leu Phe Val Val Leu Ala Leu Gly Leu Cys Leu Gly Lys Leu Arg Leu
            20                  25                  30

ggc tct atc caa tta ggt aac gct att ggt gta ctg gtg gta tca ctg      144
Gly Ser Ile Gln Leu Gly Asn Ala Ile Gly Val Leu Val Val Ser Leu
        35                  40                  45

ttg cta ggg caa cag cat ttc gcc atc aat act gaa gcg cta aat ctg      192
Leu Leu Gly Gln Gln His Phe Ala Ile Asn Thr Glu Ala Leu Asn Leu
    50                  55                  60

ggc ttt atg ttg ttt att ttt tgt gtc ggt gtt gaa gcc ggt cca aac      240
Gly Phe Met Leu Phe Ile Phe Cys Val Gly Val Glu Ala Gly Pro Asn
65                  70                  75                  80

ttc ttt tct att ttc ttc cgt gat ggc aaa aat tac ctg atg ctc gcc      288
Phe Phe Ser Ile Phe Phe Arg Asp Gly Lys Asn Tyr Leu Met Leu Ala
                85                  90                  95

ttg gtt atg gtg ggc agc gcg atg att tta gcg ttg ggg ctt ggc aaa      336
Leu Val Met Val Gly Ser Ala Met Ile Leu Ala Leu Gly Leu Gly Lys
            100                 105                 110

tta ttt ggt tgg gat atc ggt ctg acc gcc ggg atg ctg gca ggg tca      384
Leu Phe Gly Trp Asp Ile Gly Leu Thr Ala Gly Met Leu Ala Gly Ser
        115                 120                 125

atg aca tcg acc ccc gtt ttg gtt ggg gcc ggt gat acg cta cgc cat      432
Met Thr Ser Thr Pro Val Leu Val Gly Ala Gly Asp Thr Leu Arg His
    130                 135                 140

acc atg gct aat ggt tcg tca ctg caa caa gca cag gat aat ttg agc      480
Thr Met Ala Asn Gly Ser Ser Leu Gln Gln Ala Gln Asp Asn Leu Ser
145                 150                 155                 160

ctc ggc tat gcc ctg act tat ctt atc ggg ctg gtt agc ctg att tta      528
Leu Gly Tyr Ala Leu Thr Tyr Leu Ile Gly Leu Val Ser Leu Ile Leu
                165                 170                 175

ggt gcg cgc tat tta cct aag ctt cag cat cag gat tta ccg acc agc      576
Gly Ala Arg Tyr Leu Pro Lys Leu Gln His Gln Asp Leu Pro Thr Ser
            180                 185                 190

gcc caa caa att gcc cgc gaa cga ggg ctg gac acc gat agc cag cgt      624
Ala Gln Gln Ile Ala Arg Glu Arg Gly Leu Asp Thr Asp Ser Gln Arg
        195                 200                 205

aaa gtg tat ttg cct gtc atc cgt gct tat cgt gta ggc ccg gag ctg      672
Lys Val Tyr Leu Pro Val Ile Arg Ala Tyr Arg Val Gly Pro Glu Leu
    210                 215                 220

gtt gcc tgg gca gat ggt aaa aac ttg cgt gaa tta ggg att tac cgc      720
```

-continued

```
Val Ala Trp Ala Asp Gly Lys Asn Leu Arg Glu Leu Gly Ile Tyr Arg
225                 230                 235                 240

caa acc ggt tgc tat atc gag cgt atc cgc cgc aac ggt att ctc gcg      768
Gln Thr Gly Cys Tyr Ile Glu Arg Ile Arg Arg Asn Gly Ile Leu Ala
                245                 250                 255

aat ccg gat ggt gac gcc gtg cta caa gtc ggt gat gaa atc tcg ttg      816
Asn Pro Asp Gly Asp Ala Val Leu Gln Val Gly Asp Glu Ile Ser Leu
            260                 265                 270

gtg ggt tac cca gat gcc cat tcc cgc ctt gac ccc agc ttc cgt aat      864
Val Gly Tyr Pro Asp Ala His Ser Arg Leu Asp Pro Ser Phe Arg Asn
        275                 280                 285

ggc aaa gaa gtt ttc gac cgt gat ctg ttg gat atg cgt atc gtc acc      912
Gly Lys Glu Val Phe Asp Arg Asp Leu Leu Asp Met Arg Ile Val Thr
    290                 295                 300

gaa gag atc gtg gtc aaa aat agc aat gct gtc ggt aaa cgc ctc agc      960
Glu Glu Ile Val Val Lys Asn Ser Asn Ala Val Gly Lys Arg Leu Ser
305                 310                 315                 320

cat tta aaa ctc acc gat cac ggt tgc ttc ctt aat cgg gtc att cgt     1008
His Leu Lys Leu Thr Asp His Gly Cys Phe Leu Asn Arg Val Ile Arg
                325                 330                 335

agc caa att gaa atg ccc att gat gat aac gtg gtg ttg aat aaa ggt     1056
Ser Gln Ile Glu Met Pro Ile Asp Asp Asn Val Val Leu Asn Lys Gly
            340                 345                 350

gat gtg ctg caa gtc agc ggt gat gcc cgg cga gtc aaa agc gtg gca     1104
Asp Val Leu Gln Val Ser Gly Asp Ala Arg Arg Val Lys Ser Val Ala
        355                 360                 365

gaa aaa att ggc ttt atc tct att cac agt cag gtc act gac ctg ctg     1152
Glu Lys Ile Gly Phe Ile Ser Ile His Ser Gln Val Thr Asp Leu Leu
    370                 375                 380

gcc ttc tgc tca ttc ttt att ctt ggg tta atg att ggc ctg att act     1200
Ala Phe Cys Ser Phe Phe Ile Leu Gly Leu Met Ile Gly Leu Ile Thr
385                 390                 395                 400

ttc cag ttc agc aat ttc agc ttc ggt att ggc aat gcc gca ggg ctg     1248
Phe Gln Phe Ser Asn Phe Ser Phe Gly Ile Gly Asn Ala Ala Gly Leu
                405                 410                 415

tta tta gca ggg atc atg ctg gga ttt tta cgt gcc aac cac cct act     1296
Leu Leu Ala Gly Ile Met Leu Gly Phe Leu Arg Ala Asn His Pro Thr
            420                 425                 430

ttt ggc tat atc ccg caa ggc gcc ttg aat atg gtg aaa gag ttc ggg     1344
Phe Gly Tyr Ile Pro Gln Gly Ala Leu Asn Met Val Lys Glu Phe Gly
        435                 440                 445

tta atg gtc ttt atg gca ggt gtc ggg tta agt gcc ggg ggc ggc att     1392
Leu Met Val Phe Met Ala Gly Val Gly Leu Ser Ala Gly Gly Gly Ile
    450                 455                 460

aat agc agc ctg ggc gcc gtc ggt gga caa atg ttg att tcc ggt ttg     1440
Asn Ser Ser Leu Gly Ala Val Gly Gly Gln Met Leu Ile Ser Gly Leu
465                 470                 475                 480

ata gtc agt ttg gtt ccg gtg gtg atc tgc ttt gtt ttt ggt gct tat     1488
Ile Val Ser Leu Val Pro Val Val Ile Cys Phe Val Phe Gly Ala Tyr
                485                 490                 495

gtt ctg cgt atg aac cgt gca ctg ctt ttt ggt gcc att atg ggg gcc     1536
Val Leu Arg Met Asn Arg Ala Leu Leu Phe Gly Ala Ile Met Gly Ala
            500                 505                 510

aga acc tgt gca ccc gcc atg gac atc atc agt gat acc gcg cgt agc     1584
Arg Thr Cys Ala Pro Ala Met Asp Ile Ile Ser Asp Thr Ala Arg Ser
        515                 520                 525

aat att ccc gca tta ggc tac gcg ggg act tac gct atc gcc aac gtc     1632
Asn Ile Pro Ala Leu Gly Tyr Ala Gly Thr Tyr Ala Ile Ala Asn Val
    530                 535                 540
```

```
tta ctg acc ttg gct ggc tcg ttg att gtc atc ctc tgg cca ggg ata      1680
Leu Leu Thr Leu Ala Gly Ser Leu Ile Val Ile Leu Trp Pro Gly Ile
545                 550                 555                 560

tta ggt tag                                                          1689
Leu Gly


<210> SEQ ID NO 27
<211> LENGTH: 562
<212> TYPE: PRT
<213> ORGANISM: Yersinia pestis

<400> SEQUENCE: 27

Val Asn Ile Asn Val Ala Asn Leu Leu Asn Gly Asn Tyr Ile Leu Leu
1               5                   10                  15

Leu Phe Val Val Leu Ala Leu Gly Leu Cys Leu Gly Lys Leu Arg Leu
            20                  25                  30

Gly Ser Ile Gln Leu Gly Asn Ala Ile Gly Val Leu Val Val Ser Leu
        35                  40                  45

Leu Leu Gly Gln Gln His Phe Ala Ile Asn Thr Glu Ala Leu Asn Leu
    50                  55                  60

Gly Phe Met Leu Phe Ile Phe Cys Val Gly Val Glu Ala Gly Pro Asn
65                  70                  75                  80

Phe Phe Ser Ile Phe Phe Arg Asp Gly Lys Asn Tyr Leu Met Leu Ala
                85                  90                  95

Leu Val Met Val Gly Ser Ala Met Ile Leu Ala Leu Gly Leu Gly Lys
            100                 105                 110

Leu Phe Gly Trp Asp Ile Gly Leu Thr Ala Gly Met Leu Ala Gly Ser
        115                 120                 125

Met Thr Ser Thr Pro Val Leu Val Gly Ala Gly Asp Thr Leu Arg His
    130                 135                 140

Thr Met Ala Asn Gly Ser Ser Leu Gln Gln Ala Gln Asp Asn Leu Ser
145                 150                 155                 160

Leu Gly Tyr Ala Leu Thr Tyr Leu Ile Gly Leu Val Ser Leu Ile Leu
                165                 170                 175

Gly Ala Arg Tyr Leu Pro Lys Leu Gln His Gln Asp Leu Pro Thr Ser
            180                 185                 190

Ala Gln Gln Ile Ala Arg Glu Arg Gly Leu Asp Thr Asp Ser Gln Arg
        195                 200                 205

Lys Val Tyr Leu Pro Val Ile Arg Ala Tyr Arg Val Gly Pro Glu Leu
    210                 215                 220

Val Ala Trp Ala Asp Gly Lys Asn Leu Arg Glu Leu Gly Ile Tyr Arg
225                 230                 235                 240

Gln Thr Gly Cys Tyr Ile Glu Arg Ile Arg Arg Asn Gly Ile Leu Ala
                245                 250                 255

Asn Pro Asp Gly Asp Ala Val Leu Gln Val Gly Asp Glu Ile Ser Leu
            260                 265                 270

Val Gly Tyr Pro Asp Ala His Ser Arg Leu Asp Pro Ser Phe Arg Asn
        275                 280                 285

Gly Lys Glu Val Phe Asp Arg Asp Leu Leu Asp Met Arg Ile Val Thr
    290                 295                 300

Glu Glu Ile Val Val Lys Asn Ser Asn Ala Val Gly Lys Arg Leu Ser
305                 310                 315                 320

His Leu Lys Leu Thr Asp His Gly Cys Phe Leu Asn Arg Val Ile Arg
                325                 330                 335

Ser Gln Ile Glu Met Pro Ile Asp Asp Asn Val Val Leu Asn Lys Gly
```

```
            340                 345                 350

Asp Val Leu Gln Val Ser Gly Asp Ala Arg Arg Val Lys Ser Val Ala
        355                 360                 365

Glu Lys Ile Gly Phe Ile Ser Ile His Ser Gln Val Thr Asp Leu Leu
    370                 375                 380

Ala Phe Cys Ser Phe Phe Ile Leu Gly Leu Met Ile Gly Leu Ile Thr
385                 390                 395                 400

Phe Gln Phe Ser Asn Phe Ser Phe Gly Ile Gly Asn Ala Ala Gly Leu
                405                 410                 415

Leu Leu Ala Gly Ile Met Leu Gly Phe Leu Arg Ala Asn His Pro Thr
            420                 425                 430

Phe Gly Tyr Ile Pro Gln Gly Ala Leu Asn Met Val Lys Glu Phe Gly
        435                 440                 445

Leu Met Val Phe Met Ala Gly Val Gly Leu Ser Ala Gly Gly Gly Ile
    450                 455                 460

Asn Ser Ser Leu Gly Ala Val Gly Gly Gln Met Leu Ile Ser Gly Leu
465                 470                 475                 480

Ile Val Ser Leu Val Pro Val Val Ile Cys Phe Val Phe Gly Ala Tyr
                485                 490                 495

Val Leu Arg Met Asn Arg Ala Leu Leu Phe Gly Ala Ile Met Gly Ala
            500                 505                 510

Arg Thr Cys Ala Pro Ala Met Asp Ile Ile Ser Asp Thr Ala Arg Ser
        515                 520                 525

Asn Ile Pro Ala Leu Gly Tyr Ala Gly Thr Tyr Ala Ile Ala Asn Val
    530                 535                 540

Leu Leu Thr Leu Ala Gly Ser Leu Ile Val Ile Leu Trp Pro Gly Ile
545                 550                 555                 560

Leu Gly


<210> SEQ ID NO 28
<211> LENGTH: 1689
<212> TYPE: DNA
<213> ORGANISM: Erwinia carotovora
<220> FEATURE:
<221> NAME/KEY: CDS
<222> LOCATION: (1)..(1689)

<400> SEQUENCE: 28

atg aat ata aac gtc gct gat ttg tta aac ggg aat tac att ctg ctt       48
Met Asn Ile Asn Val Ala Asp Leu Leu Asn Gly Asn Tyr Ile Leu Leu
1               5                   10                  15

tta ttc gtg gtt ctt tca tta gga ctc tgt ctg ggg aaa ttg cgc ctc       96
Leu Phe Val Val Leu Ser Leu Gly Leu Cys Leu Gly Lys Leu Arg Leu
            20                  25                  30

ggg cca gta caa ctc ggt aat tct att ggc gtt tta gtg gtt tct tta      144
Gly Pro Val Gln Leu Gly Asn Ser Ile Gly Val Leu Val Val Ser Leu
        35                  40                  45

tta ctc ggc caa caa cat ttt tcg att aat acc gaa gca ctg agc ctc      192
Leu Leu Gly Gln Gln His Phe Ser Ile Asn Thr Glu Ala Leu Ser Leu
    50                  55                  60

ggt ttt atg tta ttt att ttt tgc gtg gga gta gaa gcc ggg ccg aat      240
Gly Phe Met Leu Phe Ile Phe Cys Val Gly Val Glu Ala Gly Pro Asn
65                  70                  75                  80

ttc ttt tct att ttc ttc cgc gac ggg aaa aat tat ttc atg ctg gcg      288
Phe Phe Ser Ile Phe Phe Arg Asp Gly Lys Asn Tyr Phe Met Leu Ala
                85                  90                  95

ctg gtg atg gtc ggc agc gcc atg tta ctg gcg tta ggg tta ggc aaa      336
```

```
Leu Val Met Val Gly Ser Ala Met Leu Leu Ala Leu Gly Leu Gly Lys
            100                 105                 110

ctt ttc ggc tgg gga atc ggc ctg acc gcg ggg atg ctg gca gga tcc      384
Leu Phe Gly Trp Gly Ile Gly Leu Thr Ala Gly Met Leu Ala Gly Ser
        115                 120                 125

atg aca tcg aca ccg gtg ctg gtc ggt gca ggc gac aca cta cgc aat      432
Met Thr Ser Thr Pro Val Leu Val Gly Ala Gly Asp Thr Leu Arg Asn
    130                 135                 140

acc gcc agt ttg ggt ggt caa ctc ggt gtt gaa caa gat cat ttg agc      480
Thr Ala Ser Leu Gly Gly Gln Leu Gly Val Glu Gln Asp His Leu Ser
145                 150                 155                 160

ctg ggc tat gcg ctg acg tat ctg gtc ggg ctg gtc agt ctc att ttt      528
Leu Gly Tyr Ala Leu Thr Tyr Leu Val Gly Leu Val Ser Leu Ile Phe
                165                 170                 175

ggt gca cgc tat ctg ccc aaa ctt cag cat cag gat ctt ccc acc agt      576
Gly Ala Arg Tyr Leu Pro Lys Leu Gln His Gln Asp Leu Pro Thr Ser
            180                 185                 190

gcg cag caa att gca cgc gag cgc ggg ctg gat gta gac agc caa aga      624
Ala Gln Gln Ile Ala Arg Glu Arg Gly Leu Asp Val Asp Ser Gln Arg
        195                 200                 205

aaa gtg tat ctg cca gtg att cgt gcc tat cgc gtc ggg cca gag ttg      672
Lys Val Tyr Leu Pro Val Ile Arg Ala Tyr Arg Val Gly Pro Glu Leu
    210                 215                 220

gtt gac tgg gcg gct ggc aaa aac ttg cgc gaa ctg gga atc tat cgc      720
Val Asp Trp Ala Ala Gly Lys Asn Leu Arg Glu Leu Gly Ile Tyr Arg
225                 230                 235                 240

cag acc ggt tgc tac atc gag cgc att cga cgc aac gga att ctg gca      768
Gln Thr Gly Cys Tyr Ile Glu Arg Ile Arg Arg Asn Gly Ile Leu Ala
                245                 250                 255

aat ccc gac ggg gat gcc gtc ttg caa atc ggc gac gag atc gcg ctg      816
Asn Pro Asp Gly Asp Ala Val Leu Gln Ile Gly Asp Glu Ile Ala Leu
            260                 265                 270

gtc ggt tat ccc gat gca cac tct cgt ctg aac tcc aat ttc cgc gat      864
Val Gly Tyr Pro Asp Ala His Ser Arg Leu Asn Ser Asn Phe Arg Asp
        275                 280                 285

ggc aaa gaa gtt ttc gac cgt aat ttg ttg gac atg cgc atc gtg acg      912
Gly Lys Glu Val Phe Asp Arg Asn Leu Leu Asp Met Arg Ile Val Thr
    290                 295                 300

gaa gag att gtc gtc aag aat cac aac gcc gtc ggt aag cgc ctc agc      960
Glu Glu Ile Val Val Lys Asn His Asn Ala Val Gly Lys Arg Leu Ser
305                 310                 315                 320

caa ttg aag ctg act gac cac ggc tgt ttc ctt aac cgt att gtt cgc     1008
Gln Leu Lys Leu Thr Asp His Gly Cys Phe Leu Asn Arg Ile Val Arg
                325                 330                 335

agc cag ata gaa atg ccg ctc gac gat aac gtc gtg ctg aat aaa ggc     1056
Ser Gln Ile Glu Met Pro Leu Asp Asp Asn Val Val Leu Asn Lys Gly
            340                 345                 350

gat gtc tta cag gtc agc ggt gac gcc cgt cgg gta aaa agc att gct     1104
Asp Val Leu Gln Val Ser Gly Asp Ala Arg Arg Val Lys Ser Ile Ala
        355                 360                 365

gag cga atc ggg ttc att tct att cac agt cag gtc acc gat tta ctg     1152
Glu Arg Ile Gly Phe Ile Ser Ile His Ser Gln Val Thr Asp Leu Leu
    370                 375                 380

gcc ttc tgc gcc ttt ttt gtt atc ggc gtg atg gtc ggg ctg atc acc     1200
Ala Phe Cys Ala Phe Phe Val Ile Gly Val Met Val Gly Leu Ile Thr
385                 390                 395                 400

atc cag ttc agc aac ttc acc ttt ggc atc ggt aac gcg gct ggg ttg     1248
Ile Gln Phe Ser Asn Phe Thr Phe Gly Ile Gly Asn Ala Ala Gly Leu
                405                 410                 415
```

-continued

```
ctc ttc gcc ggt atc atg ctg ggc ttc ctg cgc gcc aac cac ccg acc     1296
Leu Phe Ala Gly Ile Met Leu Gly Phe Leu Arg Ala Asn His Pro Thr
            420                 425                 430

ttc ggc tat att ccg caa ggc gcg ctt aac atg gtc aaa gag ttt ggc     1344
Phe Gly Tyr Ile Pro Gln Gly Ala Leu Asn Met Val Lys Glu Phe Gly
        435                 440                 445

ctg atg gtc ttt atg gcg ggc gta gga ctg agt gcc ggt agc acc atc     1392
Leu Met Val Phe Met Ala Gly Val Gly Leu Ser Ala Gly Ser Thr Ile
    450                 455                 460

aac agt agc cta gga gaa gtc ggt atc cag atg ctg gct tca ggg ctg     1440
Asn Ser Ser Leu Gly Glu Val Gly Ile Gln Met Leu Ala Ser Gly Leu
465                 470                 475                 480

att gtc agt ctc gtg cca gtg gtg att tgt ttt ctg ttc ggc gcg tat     1488
Ile Val Ser Leu Val Pro Val Val Ile Cys Phe Leu Phe Gly Ala Tyr
                485                 490                 495

gtg ctg aaa atg aat cga gcg ctg ctg ttt ggt gcc atg atg ggc gct     1536
Val Leu Lys Met Asn Arg Ala Leu Leu Phe Gly Ala Met Met Gly Ala
            500                 505                 510

cgg acc tgc gcg cca gcc atg gag atc atc agc gat acc gct cgc agt     1584
Arg Thr Cys Ala Pro Ala Met Glu Ile Ile Ser Asp Thr Ala Arg Ser
        515                 520                 525

aat att cct gct ctc ggc tat gcg ggt acc tac gcc atc gct aac gtt     1632
Asn Ile Pro Ala Leu Gly Tyr Ala Gly Thr Tyr Ala Ile Ala Asn Val
    530                 535                 540

ctg ctc aca tta gca ggt tca ctt atc gtg gtt atc tgg cct gaa ttg     1680
Leu Leu Thr Leu Ala Gly Ser Leu Ile Val Val Ile Trp Pro Glu Leu
545                 550                 555                 560

ccc ggc tga                                                         1689
Pro Gly


<210> SEQ ID NO 29
<211> LENGTH: 562
<212> TYPE: PRT
<213> ORGANISM: Erwinia carotovora

<400> SEQUENCE: 29

Met Asn Ile Asn Val Ala Asp Leu Leu Asn Gly Asn Tyr Ile Leu Leu
1               5                   10                  15

Leu Phe Val Val Leu Ser Leu Gly Leu Cys Leu Gly Lys Leu Arg Leu
            20                  25                  30

Gly Pro Val Gln Leu Gly Asn Ser Ile Gly Val Leu Val Val Ser Leu
        35                  40                  45

Leu Leu Gly Gln Gln His Phe Ser Ile Asn Thr Glu Ala Leu Ser Leu
    50                  55                  60

Gly Phe Met Leu Phe Ile Phe Cys Val Gly Val Glu Ala Gly Pro Asn
65                  70                  75                  80

Phe Phe Ser Ile Phe Phe Arg Asp Gly Lys Asn Tyr Phe Met Leu Ala
                85                  90                  95

Leu Val Met Val Gly Ser Ala Met Leu Leu Ala Leu Gly Leu Gly Lys
            100                 105                 110

Leu Phe Gly Trp Gly Ile Gly Leu Thr Ala Gly Met Leu Ala Gly Ser
        115                 120                 125

Met Thr Ser Thr Pro Val Leu Val Gly Ala Gly Asp Thr Leu Arg Asn
    130                 135                 140

Thr Ala Ser Leu Gly Gly Gln Leu Gly Val Glu Gln Asp His Leu Ser
145                 150                 155                 160

Leu Gly Tyr Ala Leu Thr Tyr Leu Val Gly Leu Val Ser Leu Ile Phe
                165                 170                 175
```

```
Gly Ala Arg Tyr Leu Pro Lys Leu Gln His Gln Asp Leu Pro Thr Ser
            180                 185                 190

Ala Gln Gln Ile Ala Arg Glu Arg Gly Leu Asp Val Asp Ser Gln Arg
        195                 200                 205

Lys Val Tyr Leu Pro Val Ile Arg Ala Tyr Arg Val Gly Pro Glu Leu
    210                 215                 220

Val Asp Trp Ala Ala Gly Lys Asn Leu Arg Glu Leu Gly Ile Tyr Arg
225                 230                 235                 240

Gln Thr Gly Cys Tyr Ile Glu Arg Ile Arg Arg Asn Gly Ile Leu Ala
                245                 250                 255

Asn Pro Asp Gly Asp Ala Val Leu Gln Ile Gly Asp Glu Ile Ala Leu
            260                 265                 270

Val Gly Tyr Pro Asp Ala His Ser Arg Leu Asn Ser Asn Phe Arg Asp
        275                 280                 285

Gly Lys Glu Val Phe Asp Arg Asn Leu Leu Asp Met Arg Ile Val Thr
    290                 295                 300

Glu Glu Ile Val Val Lys Asn His Asn Ala Val Gly Lys Arg Leu Ser
305                 310                 315                 320

Gln Leu Lys Leu Thr Asp His Gly Cys Phe Leu Asn Arg Ile Val Arg
                325                 330                 335

Ser Gln Ile Glu Met Pro Leu Asp Asp Asn Val Val Leu Asn Lys Gly
            340                 345                 350

Asp Val Leu Gln Val Ser Gly Asp Ala Arg Arg Val Lys Ser Ile Ala
        355                 360                 365

Glu Arg Ile Gly Phe Ile Ser Ile His Ser Gln Val Thr Asp Leu Leu
    370                 375                 380

Ala Phe Cys Ala Phe Phe Val Ile Gly Val Met Val Gly Leu Ile Thr
385                 390                 395                 400

Ile Gln Phe Ser Asn Phe Thr Phe Gly Ile Gly Asn Ala Ala Gly Leu
                405                 410                 415

Leu Phe Ala Gly Ile Met Leu Gly Phe Leu Arg Ala Asn His Pro Thr
            420                 425                 430

Phe Gly Tyr Ile Pro Gln Gly Ala Leu Asn Met Val Lys Glu Phe Gly
        435                 440                 445

Leu Met Val Phe Met Ala Gly Val Gly Leu Ser Ala Gly Ser Thr Ile
    450                 455                 460

Asn Ser Ser Leu Gly Glu Val Gly Ile Gln Met Leu Ala Ser Gly Leu
465                 470                 475                 480

Ile Val Ser Leu Val Pro Val Val Ile Cys Phe Leu Phe Gly Ala Tyr
                485                 490                 495

Val Leu Lys Met Asn Arg Ala Leu Leu Phe Gly Ala Met Met Gly Ala
            500                 505                 510

Arg Thr Cys Ala Pro Ala Met Glu Ile Ile Ser Asp Thr Ala Arg Ser
        515                 520                 525

Asn Ile Pro Ala Leu Gly Tyr Ala Gly Thr Tyr Ala Ile Ala Asn Val
    530                 535                 540

Leu Leu Thr Leu Ala Gly Ser Leu Ile Val Val Ile Trp Pro Glu Leu
545                 550                 555                 560

Pro Gly
```

<210> SEQ ID NO 30
<211> LENGTH: 1677
<212> TYPE: DNA

```
<213> ORGANISM: Vibrio cholerae
<220> FEATURE:
<221> NAME/KEY: CDS
<222> LOCATION: (1)..(1677)

<400> SEQUENCE: 30

gtg aac atc gac gtc gtt ttg ttg cta gag caa aat cca att ttg ctg       48
Val Asn Ile Asp Val Val Leu Leu Leu Glu Gln Asn Pro Ile Leu Leu
1               5                   10                  15

ata ttt gtt gtc ctc gcc atc ggt ctc tct ttc ggg aaa att cgc ttt       96
Ile Phe Val Val Leu Ala Ile Gly Leu Ser Phe Gly Lys Ile Arg Phe
            20                  25                  30

ggc agc ttc caa ttg ggt aat tcg att gga gtg ctc atc acc tct ctg      144
Gly Ser Phe Gln Leu Gly Asn Ser Ile Gly Val Leu Ile Thr Ser Leu
        35                  40                  45

atc atg ggg cat ctt ggt ttt tcc ttt aca ccg gaa gca tta acc atc      192
Ile Met Gly His Leu Gly Phe Ser Phe Thr Pro Glu Ala Leu Thr Ile
    50                  55                  60

ggc ttt atg ctc ttt att tat tgt gtc ggc att gaa gcg ggt cct aac      240
Gly Phe Met Leu Phe Ile Tyr Cys Val Gly Ile Glu Ala Gly Pro Asn
65                  70                  75                  80

ttc ttt ggt att ttc ttc cgc gat ggt aaa cac tac tta att cta agc      288
Phe Phe Gly Ile Phe Phe Arg Asp Gly Lys His Tyr Leu Ile Leu Ser
                85                  90                  95

tta gtg gtc ttg atc act gcg act tgg att gcc tac ttt ggt ggt tac      336
Leu Val Val Leu Ile Thr Ala Thr Trp Ile Ala Tyr Phe Gly Gly Tyr
            100                 105                 110

tat ctt aat ctg gat tat ggc tta gcc gcc ggg atg atg gcg ggc gca      384
Tyr Leu Asn Leu Asp Tyr Gly Leu Ala Ala Gly Met Met Ala Gly Ala
        115                 120                 125

tta acc tca aca ccc gta ctg gtt ggt gct cag gat gcg ctc aat tct      432
Leu Thr Ser Thr Pro Val Leu Val Gly Ala Gln Asp Ala Leu Asn Ser
    130                 135                 140

ggg ctt gcc gcg gta cca aga cat atg gat tta tca ctg att tta gat      480
Gly Leu Ala Ala Val Pro Arg His Met Asp Leu Ser Leu Ile Leu Asp
145                 150                 155                 160

aat gtc tcg gtc ggt tat gcg atg gcc tac ttg atc ggc ctt atc agc      528
Asn Val Ser Val Gly Tyr Ala Met Ala Tyr Leu Ile Gly Leu Ile Ser
                165                 170                 175

atg atc atg ttt gct aaa tta ctc cct aag ttg caa aag caa aac ctg      576
Met Ile Met Phe Ala Lys Leu Leu Pro Lys Leu Gln Lys Gln Asn Leu
            180                 185                 190

tcc gat tcg gct caa caa atc gcg caa gaa cga ggg tta ggc agt cag      624
Ser Asp Ser Ala Gln Gln Ile Ala Gln Glu Arg Gly Leu Gly Ser Gln
        195                 200                 205

cgt aaa gtc tat ctg ccg atc atc cgt gcc tat cga gtc gga cct gaa      672
Arg Lys Val Tyr Leu Pro Ile Ile Arg Ala Tyr Arg Val Gly Pro Glu
    210                 215                 220

ctg att aac tgg atc gac ggt cgt aat ctg cgc gag ctg ggt atc tac      720
Leu Ile Asn Trp Ile Asp Gly Arg Asn Leu Arg Glu Leu Gly Ile Tyr
225                 230                 235                 240

cgt caa aca ggc tgt tat att gag cgt atc cgc cga cat ggc att ttg      768
Arg Gln Thr Gly Cys Tyr Ile Glu Arg Ile Arg Arg His Gly Ile Leu
                245                 250                 255

gcc cat cct gat ggt gat gcc att ttg caa gaa ggg gat gaa att gct      816
Ala His Pro Asp Gly Asp Ala Ile Leu Gln Glu Gly Asp Glu Ile Ala
            260                 265                 270

ctc gta ggt ttc cca gat agt cac gct cgt ctt gac ccg agc ttt cgc      864
Leu Val Gly Phe Pro Asp Ser His Ala Arg Leu Asp Pro Ser Phe Arg
        275                 280                 285
```

-continued

```
aat ggc aaa gaa gtg ttt gac cgt aac tta ctc gac cta cga att tca      912
Asn Gly Lys Glu Val Phe Asp Arg Asn Leu Leu Asp Leu Arg Ile Ser
    290                 295                 300

gaa gaa gag atc gtg gta aaa agt gac agc att gcg gga aaa cgt ctc      960
Glu Glu Glu Ile Val Val Lys Ser Asp Ser Ile Ala Gly Lys Arg Leu
305                 310                 315                 320

tcc gat ctt aat ctt tcg gaa tac ggc tgc ttc ctt aac cga gtc gtt     1008
Ser Asp Leu Asn Leu Ser Glu Tyr Gly Cys Phe Leu Asn Arg Val Val
                325                 330                 335

cgt gcg caa atc gaa atg ccg atg gat ctg gat atc gtg ctc gcc aaa     1056
Arg Ala Gln Ile Glu Met Pro Met Asp Leu Asp Ile Val Leu Ala Lys
            340                 345                 350

ggc gat gtc ctg caa gtc agc ggc gag aaa agc aaa gta aag ggg ctg     1104
Gly Asp Val Leu Gln Val Ser Gly Glu Lys Ser Lys Val Lys Gly Leu
        355                 360                 365

gca gat aaa atc ggt ttt atc tct gta cac agc caa atg gct gat ctg     1152
Ala Asp Lys Ile Gly Phe Ile Ser Val His Ser Gln Met Ala Asp Leu
    370                 375                 380

ctt gct ttc tgt agc ttt ttt att ctt ggc att ctg ttt ggt ttg gtc     1200
Leu Ala Phe Cys Ser Phe Phe Ile Leu Gly Ile Leu Phe Gly Leu Val
385                 390                 395                 400

acc atg acc ttt ggc caa gtg tcg ttt agc tta ggt aat gcg gtg ggg     1248
Thr Met Thr Phe Gly Gln Val Ser Phe Ser Leu Gly Asn Ala Val Gly
                405                 410                 415

tta ctg ctc tct ggt atc act ttg ggc ttt ttg cga gcc aac cac ccg     1296
Leu Leu Leu Ser Gly Ile Thr Leu Gly Phe Leu Arg Ala Asn His Pro
            420                 425                 430

act ttc ggt tat gtt ccg caa ggc gca ctc aat atg gtc aaa gac ctt     1344
Thr Phe Gly Tyr Val Pro Gln Gly Ala Leu Asn Met Val Lys Asp Leu
        435                 440                 445

ggt cta gcc atc ttc atg gtc ggt att ggg ctc aat gca ggt agc aaa     1392
Gly Leu Ala Ile Phe Met Val Gly Ile Gly Leu Asn Ala Gly Ser Lys
    450                 455                 460

atg ttc cag cat ctc tcc gaa gta ggt gtg caa gtg atc ggt tta gcc     1440
Met Phe Gln His Leu Ser Glu Val Gly Val Gln Val Ile Gly Leu Ala
465                 470                 475                 480

ttt tta gtg agc gtt gta cct gtc gtg ttc gct tac ttg gtt ggc gcc     1488
Phe Leu Val Ser Val Val Pro Val Val Phe Ala Tyr Leu Val Gly Ala
                485                 490                 495

tac att cta aag atg aac cgc gct cta ttg ttt ggt gcg att att ggc     1536
Tyr Ile Leu Lys Met Asn Arg Ala Leu Leu Phe Gly Ala Ile Ile Gly
            500                 505                 510

gcg cgc acc tgt gct ccg gcg atg gat gtg gtt aat gaa tac gct aag     1584
Ala Arg Thr Cys Ala Pro Ala Met Asp Val Val Asn Glu Tyr Ala Lys
        515                 520                 525

tct acc att cca gca ctg ggt tat gcg ggc acc tac gcg att gcc aat     1632
Ser Thr Ile Pro Ala Leu Gly Tyr Ala Gly Thr Tyr Ala Ile Ala Asn
    530                 535                 540

atc tta atg acc tta acg ggt acc atc ttt atc ttg ctc agt taa         1677
Ile Leu Met Thr Leu Thr Gly Thr Ile Phe Ile Leu Leu Ser
545                 550                 555


<210> SEQ ID NO 31
<211> LENGTH: 558
<212> TYPE: PRT
<213> ORGANISM: Vibrio cholerae

<400> SEQUENCE: 31

Val Asn Ile Asp Val Val Leu Leu Leu Glu Gln Asn Pro Ile Leu Leu
1               5                   10                  15
```

-continued

```
Ile Phe Val Val Leu Ala Ile Gly Leu Ser Phe Gly Lys Ile Arg Phe
            20                  25                  30

Gly Ser Phe Gln Leu Gly Asn Ser Ile Gly Val Leu Ile Thr Ser Leu
        35                  40                  45

Ile Met Gly His Leu Gly Phe Ser Phe Thr Pro Glu Ala Leu Thr Ile
    50                  55                  60

Gly Phe Met Leu Phe Ile Tyr Cys Val Gly Ile Glu Ala Gly Pro Asn
65                  70                  75                  80

Phe Phe Gly Ile Phe Phe Arg Asp Gly Lys His Tyr Leu Ile Leu Ser
                85                  90                  95

Leu Val Val Leu Ile Thr Ala Thr Trp Ile Ala Tyr Phe Gly Gly Tyr
            100                 105                 110

Tyr Leu Asn Leu Asp Tyr Gly Leu Ala Ala Gly Met Met Ala Gly Ala
        115                 120                 125

Leu Thr Ser Thr Pro Val Leu Val Gly Ala Gln Asp Ala Leu Asn Ser
    130                 135                 140

Gly Leu Ala Ala Val Pro Arg His Met Asp Leu Ser Leu Ile Leu Asp
145                 150                 155                 160

Asn Val Ser Val Gly Tyr Ala Met Ala Tyr Leu Ile Gly Leu Ile Ser
                165                 170                 175

Met Ile Met Phe Ala Lys Leu Leu Pro Lys Leu Gln Lys Gln Asn Leu
            180                 185                 190

Ser Asp Ser Ala Gln Gln Ile Ala Gln Glu Arg Gly Leu Gly Ser Gln
        195                 200                 205

Arg Lys Val Tyr Leu Pro Ile Ile Arg Ala Tyr Arg Val Gly Pro Glu
    210                 215                 220

Leu Ile Asn Trp Ile Asp Gly Arg Asn Leu Arg Glu Leu Gly Ile Tyr
225                 230                 235                 240

Arg Gln Thr Gly Cys Tyr Ile Glu Arg Ile Arg Arg His Gly Ile Leu
                245                 250                 255

Ala His Pro Asp Gly Asp Ala Ile Leu Gln Glu Gly Asp Glu Ile Ala
            260                 265                 270

Leu Val Gly Phe Pro Asp Ser His Ala Arg Leu Asp Pro Ser Phe Arg
        275                 280                 285

Asn Gly Lys Glu Val Phe Asp Arg Asn Leu Leu Asp Leu Arg Ile Ser
    290                 295                 300

Glu Glu Glu Ile Val Val Lys Ser Asp Ser Ile Ala Gly Lys Arg Leu
305                 310                 315                 320

Ser Asp Leu Asn Leu Ser Glu Tyr Gly Cys Phe Leu Asn Arg Val Val
                325                 330                 335

Arg Ala Gln Ile Glu Met Pro Met Asp Leu Asp Ile Val Leu Ala Lys
            340                 345                 350

Gly Asp Val Leu Gln Val Ser Gly Glu Lys Ser Lys Val Lys Gly Leu
        355                 360                 365

Ala Asp Lys Ile Gly Phe Ile Ser Val His Ser Gln Met Ala Asp Leu
    370                 375                 380

Leu Ala Phe Cys Ser Phe Phe Ile Leu Gly Ile Leu Phe Gly Leu Val
385                 390                 395                 400

Thr Met Thr Phe Gly Gln Val Ser Phe Ser Leu Gly Asn Ala Val Gly
                405                 410                 415

Leu Leu Leu Ser Gly Ile Thr Leu Gly Phe Leu Arg Ala Asn His Pro
            420                 425                 430

Thr Phe Gly Tyr Val Pro Gln Gly Ala Leu Asn Met Val Lys Asp Leu
```

```
        435                 440                 445

Gly Leu Ala Ile Phe Met Val Gly Ile Gly Leu Asn Ala Gly Ser Lys
    450                 455                 460

Met Phe Gln His Leu Ser Glu Val Gly Val Gln Val Ile Gly Leu Ala
465                 470                 475                 480

Phe Leu Val Ser Val Val Pro Val Val Phe Ala Tyr Leu Val Gly Ala
                485                 490                 495

Tyr Ile Leu Lys Met Asn Arg Ala Leu Leu Phe Gly Ala Ile Ile Gly
            500                 505                 510

Ala Arg Thr Cys Ala Pro Ala Met Asp Val Val Asn Glu Tyr Ala Lys
        515                 520                 525

Ser Thr Ile Pro Ala Leu Gly Tyr Ala Gly Thr Tyr Ala Ile Ala Asn
    530                 535                 540

Ile Leu Met Thr Leu Thr Gly Thr Ile Phe Ile Leu Leu Ser
545                 550                 555


<210> SEQ ID NO 32
<211> LENGTH: 1686
<212> TYPE: DNA
<213> ORGANISM: Aeromonas hydrophila
<220> FEATURE:
<221> NAME/KEY: CDS
<222> LOCATION: (1)..(1686)

<400> SEQUENCE: 32

atg acc ata gat ttt gtg aca ctg cta cat caa agc gac tcc ctg ctg       48
Met Thr Ile Asp Phe Val Thr Leu Leu His Gln Ser Asp Ser Leu Leu
1               5                   10                  15

ctg ttc gtg gta ctg gcc ttc ggc ctg ctg ctc ggt aaa gtc agg ttc       96
Leu Phe Val Val Leu Ala Phe Gly Leu Leu Leu Gly Lys Val Arg Phe
            20                  25                  30

ggc aac ttc cag atc ggc aac acc atc ggc gtg ctg ttt acc gcc ctg      144
Gly Asn Phe Gln Ile Gly Asn Thr Ile Gly Val Leu Phe Thr Ala Leu
        35                  40                  45

ctg ttc ggc cag atg ggc ttc gaa ttc acc gcc acc acg gag aac gtc      192
Leu Phe Gly Gln Met Gly Phe Glu Phe Thr Ala Thr Thr Glu Asn Val
    50                  55                  60

ggc ttc atg ctg ttc atc ttc tgc gtg ggg ata gaa gcg ggg ccg cac      240
Gly Phe Met Leu Phe Ile Phe Cys Val Gly Ile Glu Ala Gly Pro His
65                  70                  75                  80

ttc ttc agc gtc ttc ctg cgt gac ggc atc cac tac atc acc ctc acc      288
Phe Phe Ser Val Phe Leu Arg Asp Gly Ile His Tyr Ile Thr Leu Thr
                85                  90                  95

ctg gtg atc ctg ctg acc gcc ctc ttc ctc acc gtg ggg ctc gcc aag      336
Leu Val Ile Leu Leu Thr Ala Leu Phe Leu Thr Val Gly Leu Ala Lys
            100                 105                 110

ttc ttc aac ctg ggg ccg ggc atg gcg gcc ggc atc ctg gcc ggc tcg      384
Phe Phe Asn Leu Gly Pro Gly Met Ala Ala Gly Ile Leu Ala Gly Ser
        115                 120                 125

ctc acc tcg acc ccg gcg ctg gtg ggt gcg cag gat gcc ctg cgc agc      432
Leu Thr Ser Thr Pro Ala Leu Val Gly Ala Gln Asp Ala Leu Arg Ser
    130                 135                 140

ggc ctg ctc aac ctg ccc cat cag acc gac atg cag tcg gtg ctc gac      480
Gly Leu Leu Asn Leu Pro His Gln Thr Asp Met Gln Ser Val Leu Asp
145                 150                 155                 160

aac atg ggc atc ggc tat gcg ttg acc tat ctg gtg ggg ctg gtc ggc      528
Asn Met Gly Ile Gly Tyr Ala Leu Thr Tyr Leu Val Gly Leu Val Gly
                165                 170                 175

ctg atg ctg gtg gtg cgc tac ctg cct tcg ctg gca cgg ctc gac ctc      576
```

-continued

```
Leu Met Leu Val Val Arg Tyr Leu Pro Ser Leu Ala Arg Leu Asp Leu
            180                 185                 190

aac acc gag gcg cag aag atc gcc cgt gag cgc ggc ctc tcc gac aac      624
Asn Thr Glu Ala Gln Lys Ile Ala Arg Glu Arg Gly Leu Ser Asp Asn
        195                 200                 205

gag agc cgc aag acc tac ctg ccc atc atc cgt gcc tac cgg gtt ggt      672
Glu Ser Arg Lys Thr Tyr Leu Pro Ile Ile Arg Ala Tyr Arg Val Gly
    210                 215                 220

ccc gag ctc gcc gcc tgg atc ggc ggc cgc acc ctg cgc gag acc ggc      720
Pro Glu Leu Ala Ala Trp Ile Gly Gly Arg Thr Leu Arg Glu Thr Gly
225                 230                 235                 240

atc tac ccc cac acc ggc tgc tac gtg gag cgg atc cgc cgc aac ggc      768
Ile Tyr Pro His Thr Gly Cys Tyr Val Glu Arg Ile Arg Arg Asn Gly
                245                 250                 255

atc ctg gcg agc ccg gat ggc gac gcc gtc atc cag gaa ggg gac gag      816
Ile Leu Ala Ser Pro Asp Gly Asp Ala Val Ile Gln Glu Gly Asp Glu
            260                 265                 270

atc gcc ctg gtg ggt tac ccc gag agc cac gag aag ctc gac gtc aac      864
Ile Ala Leu Val Gly Tyr Pro Glu Ser His Glu Lys Leu Asp Val Asn
        275                 280                 285

tac cgc aac ggc aag gag gtg ttc gac cgc aac ctg ctt gac ctg cag      912
Tyr Arg Asn Gly Lys Glu Val Phe Asp Arg Asn Leu Leu Asp Leu Gln
    290                 295                 300

atc gtc acc gaa gag ata gtg gtg aaa aac gat gcg gtg gtg ggt cgc      960
Ile Val Thr Glu Glu Ile Val Val Lys Asn Asp Ala Val Val Gly Arg
305                 310                 315                 320

cat ctg gtg gag ctc aac ctc acc gag aag ggc tgc ttc ctc aac cgg     1008
His Leu Val Glu Leu Asn Leu Thr Glu Lys Gly Cys Phe Leu Asn Arg
                325                 330                 335

gtg gtg cgc tcc cag atc gag atg ccg ttc gat cgc aac atc atg ctg     1056
Val Val Arg Ser Gln Ile Glu Met Pro Phe Asp Arg Asn Ile Met Leu
            340                 345                 350

caa aag ggc gac gtg ctg cag atc agc ggc gag aag cag cgg gtc aag     1104
Gln Lys Gly Asp Val Leu Gln Ile Ser Gly Glu Lys Gln Arg Val Lys
        355                 360                 365

ctg ctg gcc aac aag att ggc ttc atc agc atc cac agc cag acc acg     1152
Leu Leu Ala Asn Lys Ile Gly Phe Ile Ser Ile His Ser Gln Thr Thr
    370                 375                 380

gat ctg gtg gcc ttc acc acc ttc ttc gtg ctg ggg ctg ctg ata ggc     1200
Asp Leu Val Ala Phe Thr Thr Phe Phe Val Leu Gly Leu Leu Ile Gly
385                 390                 395                 400

tcc gtc tcc ctg gtg ttc ggc cag ctc gag ttt ggg ctg ggc aac gcc     1248
Ser Val Ser Leu Val Phe Gly Gln Leu Glu Phe Gly Leu Gly Asn Ala
                405                 410                 415

gtc ggc ctg ctg ctg gcg ggg atc ctg atg ggc tac ctg cgc gcc aac     1296
Val Gly Leu Leu Leu Ala Gly Ile Leu Met Gly Tyr Leu Arg Ala Asn
            420                 425                 430

cac ccc acc gtc ggc tac gtg ccg ccg ggc gcc ctg cgt ctg gcc aag     1344
His Pro Thr Val Gly Tyr Val Pro Pro Gly Ala Leu Arg Leu Ala Lys
        435                 440                 445

gat ctc ggt ctg gcg gtg ttc atg gtg agc acc ggc ctc aaa gct ggc     1392
Asp Leu Gly Leu Ala Val Phe Met Val Ser Thr Gly Leu Lys Ala Gly
    450                 455                 460

ggc ggc att ctg gac cac ctg agc cag gtc ggt gcc gtg gtg ctc ttt     1440
Gly Gly Ile Leu Asp His Leu Ser Gln Val Gly Ala Val Val Leu Phe
465                 470                 475                 480

tcc ggc atg ctg gtg acc acc ctg ccg gtg ctg gtg ggc tac ctg ttc     1488
Ser Gly Met Leu Val Thr Thr Leu Pro Val Leu Val Gly Tyr Leu Phe
                485                 490                 495
```

```
gga gtc tgg gtg ctg aag atg aac ccg gcc ctg ctg ctc ggc gcc atc      1536
Gly Val Trp Val Leu Lys Met Asn Pro Ala Leu Leu Leu Gly Ala Ile
            500                 505                 510

acg ggg gcc cgc acc tgc gcc ccg gcc atg gac gtg gtg aac gag gcg      1584
Thr Gly Ala Arg Thr Cys Ala Pro Ala Met Asp Val Val Asn Glu Ala
        515                 520                 525

gcc aac agc tcc atc ccg gcg ctc ggc tat gcc ggc acc tat gcg gtg      1632
Ala Asn Ser Ser Ile Pro Ala Leu Gly Tyr Ala Gly Thr Tyr Ala Val
    530                 535                 540

gcc aac gtc atg ctg acc ttg gcg ggc tcc ttc atc atc ggc ttc tgg      1680
Ala Asn Val Met Leu Thr Leu Ala Gly Ser Phe Ile Ile Gly Phe Trp
545                 550                 555                 560

ttc tag                                                              1686
Phe


<210> SEQ ID NO 33
<211> LENGTH: 561
<212> TYPE: PRT
<213> ORGANISM: Aeromonas hydrophila

<400> SEQUENCE: 33

Met Thr Ile Asp Phe Val Thr Leu Leu His Gln Ser Asp Ser Leu Leu
1               5                   10                  15

Leu Phe Val Val Leu Ala Phe Gly Leu Leu Leu Gly Lys Val Arg Phe
            20                  25                  30

Gly Asn Phe Gln Ile Gly Asn Thr Ile Gly Val Leu Phe Thr Ala Leu
        35                  40                  45

Leu Phe Gly Gln Met Gly Phe Glu Phe Thr Ala Thr Thr Glu Asn Val
    50                  55                  60

Gly Phe Met Leu Phe Ile Phe Cys Val Gly Ile Glu Ala Gly Pro His
65                  70                  75                  80

Phe Phe Ser Val Phe Leu Arg Asp Gly Ile His Tyr Ile Thr Leu Thr
                85                  90                  95

Leu Val Ile Leu Leu Thr Ala Leu Phe Leu Thr Val Gly Leu Ala Lys
            100                 105                 110

Phe Phe Asn Leu Gly Pro Gly Met Ala Ala Gly Ile Leu Ala Gly Ser
        115                 120                 125

Leu Thr Ser Thr Pro Ala Leu Val Gly Ala Gln Asp Ala Leu Arg Ser
    130                 135                 140

Gly Leu Leu Asn Leu Pro His Gln Thr Asp Met Gln Ser Val Leu Asp
145                 150                 155                 160

Asn Met Gly Ile Gly Tyr Ala Leu Thr Tyr Leu Val Gly Leu Val Gly
                165                 170                 175

Leu Met Leu Val Val Arg Tyr Leu Pro Ser Leu Ala Arg Leu Asp Leu
            180                 185                 190

Asn Thr Glu Ala Gln Lys Ile Ala Arg Glu Arg Gly Leu Ser Asp Asn
        195                 200                 205

Glu Ser Arg Lys Thr Tyr Leu Pro Ile Ile Arg Ala Tyr Arg Val Gly
    210                 215                 220

Pro Glu Leu Ala Ala Trp Ile Gly Gly Arg Thr Leu Arg Glu Thr Gly
225                 230                 235                 240

Ile Tyr Pro His Thr Gly Cys Tyr Val Glu Arg Ile Arg Arg Asn Gly
                245                 250                 255

Ile Leu Ala Ser Pro Asp Gly Asp Ala Val Ile Gln Glu Gly Asp Glu
            260                 265                 270

Ile Ala Leu Val Gly Tyr Pro Glu Ser His Glu Lys Leu Asp Val Asn
```

```
        275                 280                 285

Tyr Arg Asn Gly Lys Glu Val Phe Asp Arg Asn Leu Leu Asp Leu Gln
    290                 295                 300

Ile Val Thr Glu Glu Ile Val Val Lys Asn Asp Ala Val Val Gly Arg
305                 310                 315                 320

His Leu Val Glu Leu Asn Leu Thr Glu Lys Gly Cys Phe Leu Asn Arg
                325                 330                 335

Val Val Arg Ser Gln Ile Glu Met Pro Phe Asp Arg Asn Ile Met Leu
            340                 345                 350

Gln Lys Gly Asp Val Leu Gln Ile Ser Gly Glu Lys Gln Arg Val Lys
        355                 360                 365

Leu Leu Ala Asn Lys Ile Gly Phe Ile Ser Ile His Ser Gln Thr Thr
    370                 375                 380

Asp Leu Val Ala Phe Thr Thr Phe Phe Val Leu Gly Leu Leu Ile Gly
385                 390                 395                 400

Ser Val Ser Leu Val Phe Gly Gln Leu Glu Phe Gly Leu Gly Asn Ala
                405                 410                 415

Val Gly Leu Leu Leu Ala Gly Ile Leu Met Gly Tyr Leu Arg Ala Asn
            420                 425                 430

His Pro Thr Val Gly Tyr Val Pro Pro Gly Ala Leu Arg Leu Ala Lys
        435                 440                 445

Asp Leu Gly Leu Ala Val Phe Met Val Ser Thr Gly Leu Lys Ala Gly
    450                 455                 460

Gly Gly Ile Leu Asp His Leu Ser Gln Val Gly Ala Val Val Leu Phe
465                 470                 475                 480

Ser Gly Met Leu Val Thr Thr Leu Pro Val Leu Val Gly Tyr Leu Phe
                485                 490                 495

Gly Val Trp Val Leu Lys Met Asn Pro Ala Leu Leu Leu Gly Ala Ile
            500                 505                 510

Thr Gly Ala Arg Thr Cys Ala Pro Ala Met Asp Val Val Asn Glu Ala
        515                 520                 525

Ala Asn Ser Ser Ile Pro Ala Leu Gly Tyr Ala Gly Thr Tyr Ala Val
    530                 535                 540

Ala Asn Val Met Leu Thr Leu Ala Gly Ser Phe Ile Ile Gly Phe Trp
545                 550                 555                 560

Phe


<210> SEQ ID NO 34
<211> LENGTH: 1638
<212> TYPE: DNA
<213> ORGANISM: Photobacterium profundum
<220> FEATURE:
<221> NAME/KEY: CDS
<222> LOCATION: (1)..(1638)

<400> SEQUENCE: 34

ttg ctt ttt gtt gtt ctc gct gtt ggt cta agt ttt ggt aaa att cgt       48
Leu Leu Phe Val Val Leu Ala Val Gly Leu Ser Phe Gly Lys Ile Arg
1               5                   10                  15

ttt gct aag atg caa gta ggc aat tct att ggt gtt tta ctg act gcc       96
Phe Ala Lys Met Gln Val Gly Asn Ser Ile Gly Val Leu Leu Thr Ala
            20                  25                  30

ata ctg ttc ggt aat gcc ggg ttt acc ttt aat act gaa gca tta aat      144
Ile Leu Phe Gly Asn Ala Gly Phe Thr Phe Asn Thr Glu Ala Leu Asn
        35                  40                  45

att ggc ttt atg ctg ttt att ttt tgt gtg ggt ata gag gct ggc ccc      192
```

-continued

```
Ile Gly Phe Met Leu Phe Ile Phe Cys Val Gly Ile Glu Ala Gly Pro
    50                  55                  60

aac ttt ttt ggt att ttc ttc cga gat ggt aaa cat tac ctt tta ctc      240
Asn Phe Phe Gly Ile Phe Phe Arg Asp Gly Lys His Tyr Leu Leu Leu
65                  70                  75                  80

gcc ctt gtt gtg ctg ctt tcc gcc ata gct atc act tta gcc atg act      288
Ala Leu Val Val Leu Leu Ser Ala Ile Ala Ile Thr Leu Ala Met Thr
            85                  90                  95

cat tat ctt ggg ctt gat ata ggt tta gcg aca ggc tta atg gct ggt      336
His Tyr Leu Gly Leu Asp Ile Gly Leu Ala Thr Gly Leu Met Ala Gly
            100                 105                 110

tca ttg aca gca aca cct gtt ctt gta ggt gca aaa gac gca ttg aat      384
Ser Leu Thr Ala Thr Pro Val Leu Val Gly Ala Lys Asp Ala Leu Asn
        115                 120                 125

tcc gga tta tct ggc att agc gat cct gat atc att aaa caa acc att      432
Ser Gly Leu Ser Gly Ile Ser Asp Pro Asp Ile Ile Lys Gln Thr Ile
    130                 135                 140

gat agc cta agc gtt ggc tat gct atg tct tat tta atg ggc tta atc      480
Asp Ser Leu Ser Val Gly Tyr Ala Met Ser Tyr Leu Met Gly Leu Ile
145                 150                 155                 160

agt ctt att ttt ctc gct aaa cta atg cct aaa tta cag aaa caa gac      528
Ser Leu Ile Phe Leu Ala Lys Leu Met Pro Lys Leu Gln Lys Gln Asp
            165                 170                 175

ctg gct gaa tcg tcg caa caa att gcc cgt gaa cgc ggt att ggt gaa      576
Leu Ala Glu Ser Ser Gln Gln Ile Ala Arg Glu Arg Gly Ile Gly Glu
            180                 185                 190

gtg ggg caa cgt aaa gta tat ttg cca atc att cgc gct tac cgt gtt      624
Val Gly Gln Arg Lys Val Tyr Leu Pro Ile Ile Arg Ala Tyr Arg Val
        195                 200                 205

ggc cct gag ctt att aac tgg att gat agt cgt aac tta cgt gag ttg      672
Gly Pro Glu Leu Ile Asn Trp Ile Asp Ser Arg Asn Leu Arg Glu Leu
    210                 215                 220

ggc atc tac cgc caa aca ggc tgc tac atc gaa cgt ata cgg cga aac      720
Gly Ile Tyr Arg Gln Thr Gly Cys Tyr Ile Glu Arg Ile Arg Arg Asn
225                 230                 235                 240

ggt ata tta gct aac cca gat ggt gat gct att tta caa gaa ggt gat      768
Gly Ile Leu Ala Asn Pro Asp Gly Asp Ala Ile Leu Gln Glu Gly Asp
            245                 250                 255

gag att gcc tta gtg ggt tac cca gac agc cat gca cgt ttg gat ccc      816
Glu Ile Ala Leu Val Gly Tyr Pro Asp Ser His Ala Arg Leu Asp Pro
            260                 265                 270

agc ttt cga aac ggc aaa gaa gtt ttc gac cgt gat ctt ctc gac ctt      864
Ser Phe Arg Asn Gly Lys Glu Val Phe Asp Arg Asp Leu Leu Asp Leu
        275                 280                 285

cgt att gtt gaa gaa gag att gta gtt aag aat gac aac atc tct ggc      912
Arg Ile Val Glu Glu Glu Ile Val Val Lys Asn Asp Asn Ile Ser Gly
    290                 295                 300

aaa cgc cta tct gag cta aat tta tca gaa tac ggt tgt ttc ttg aac      960
Lys Arg Leu Ser Glu Leu Asn Leu Ser Glu Tyr Gly Cys Phe Leu Asn
305                 310                 315                 320

cgt gtt gtt cgc gca caa ata gaa atg ccg atg gac cat aat att ctt     1008
Arg Val Val Arg Ala Gln Ile Glu Met Pro Met Asp His Asn Ile Leu
            325                 330                 335

ttg aat aaa ggg gat att ttg caa gtc agt gga gaa aaa agt cga gta     1056
Leu Asn Lys Gly Asp Ile Leu Gln Val Ser Gly Glu Lys Ser Arg Val
            340                 345                 350

ctt ggt ctt gct gaa cgt att ggt ttt atc tcg att cac agt caa att     1104
Leu Gly Leu Ala Glu Arg Ile Gly Phe Ile Ser Ile His Ser Gln Ile
        355                 360                 365
```

-continued

```
gcc gat cta tta gca ttc tgc tgt ttt ttt atc atc ggg tta ctt atc      1152
Ala Asp Leu Leu Ala Phe Cys Cys Phe Phe Ile Ile Gly Leu Leu Ile
    370                 375                 380

ggt tcg att aca tta gca ttt ggt cac gtt gca ttt ggt tta ggt agt      1200
Gly Ser Ile Thr Leu Ala Phe Gly His Val Ala Phe Gly Leu Gly Ser
385                 390                 395                 400

gct gca ggg ctt ctg att gcc ggt att aca tta gga ttc cta cgt gct      1248
Ala Ala Gly Leu Leu Ile Ala Gly Ile Thr Leu Gly Phe Leu Arg Ala
                405                 410                 415

aac cac cct act ttt ggc tat gta ccc caa ggt gcg ctt aat atg gcg      1296
Asn His Pro Thr Phe Gly Tyr Val Pro Gln Gly Ala Leu Asn Met Ala
            420                 425                 430

aaa gat ctt ggc tta atg gtc ttc atg gta gga att ggt ttg agt gcg      1344
Lys Asp Leu Gly Leu Met Val Phe Met Val Gly Ile Gly Leu Ser Ala
        435                 440                 445

ggt tct aat tta ttc gat tca ttt gca cat att ggc cct atg gtc tta      1392
Gly Ser Asn Leu Phe Asp Ser Phe Ala His Ile Gly Pro Met Val Leu
    450                 455                 460

gtc acc agc tta atg gtg agt gtg atc cct gtt gta ttg gca tac ctg      1440
Val Thr Ser Leu Met Val Ser Val Ile Pro Val Val Leu Ala Tyr Leu
465                 470                 475                 480

ttt ggt gct tac gta ctg aag atg aac cgt gca ctt tta ttt ggt gcc      1488
Phe Gly Ala Tyr Val Leu Lys Met Asn Arg Ala Leu Leu Phe Gly Ala
                485                 490                 495

atc att ggt gct cga act tgt gca cct gcg atg gat atg atc aat gaa      1536
Ile Ile Gly Ala Arg Thr Cys Ala Pro Ala Met Asp Met Ile Asn Glu
            500                 505                 510

cat gct cga agc aca att cca gct tta ggc tat gct ggt act tat gcc      1584
His Ala Arg Ser Thr Ile Pro Ala Leu Gly Tyr Ala Gly Thr Tyr Ala
        515                 520                 525

att gcc aac gta ctg tta acg att gcc ggt acg tta atc atc atc atg      1632
Ile Ala Asn Val Leu Leu Thr Ile Ala Gly Thr Leu Ile Ile Ile Met
    530                 535                 540

aat taa                                                              1638
Asn
545


<210> SEQ ID NO 35
<211> LENGTH: 545
<212> TYPE: PRT
<213> ORGANISM: Photobacterium profundum

<400> SEQUENCE: 35

Leu Leu Phe Val Val Leu Ala Val Gly Leu Ser Phe Gly Lys Ile Arg
1               5                   10                  15

Phe Ala Lys Met Gln Val Gly Asn Ser Ile Gly Val Leu Leu Thr Ala
            20                  25                  30

Ile Leu Phe Gly Asn Ala Gly Phe Thr Phe Asn Thr Glu Ala Leu Asn
        35                  40                  45

Ile Gly Phe Met Leu Phe Ile Phe Cys Val Gly Ile Glu Ala Gly Pro
    50                  55                  60

Asn Phe Phe Gly Ile Phe Phe Arg Asp Gly Lys His Tyr Leu Leu Leu
65                  70                  75                  80

Ala Leu Val Val Leu Leu Ser Ala Ile Ala Ile Thr Leu Ala Met Thr
                85                  90                  95

His Tyr Leu Gly Leu Asp Ile Gly Leu Ala Thr Gly Leu Met Ala Gly
            100                 105                 110

Ser Leu Thr Ala Thr Pro Val Leu Val Gly Ala Lys Asp Ala Leu Asn
        115                 120                 125
```

-continued

```
Ser Gly Leu Ser Gly Ile Ser Asp Pro Asp Ile Ile Lys Gln Thr Ile
    130                 135                 140

Asp Ser Leu Ser Val Gly Tyr Ala Met Ser Tyr Leu Met Gly Leu Ile
145                 150                 155                 160

Ser Leu Ile Phe Leu Ala Lys Leu Met Pro Lys Leu Gln Lys Gln Asp
                165                 170                 175

Leu Ala Glu Ser Ser Gln Gln Ile Ala Arg Glu Arg Gly Ile Gly Glu
            180                 185                 190

Val Gly Gln Arg Lys Val Tyr Leu Pro Ile Ile Arg Ala Tyr Arg Val
        195                 200                 205

Gly Pro Glu Leu Ile Asn Trp Ile Asp Ser Arg Asn Leu Arg Glu Leu
    210                 215                 220

Gly Ile Tyr Arg Gln Thr Gly Cys Tyr Ile Glu Arg Ile Arg Arg Asn
225                 230                 235                 240

Gly Ile Leu Ala Asn Pro Asp Gly Asp Ala Ile Leu Gln Glu Gly Asp
                245                 250                 255

Glu Ile Ala Leu Val Gly Tyr Pro Asp Ser His Ala Arg Leu Asp Pro
            260                 265                 270

Ser Phe Arg Asn Gly Lys Glu Val Phe Asp Arg Asp Leu Leu Asp Leu
        275                 280                 285

Arg Ile Val Glu Glu Glu Ile Val Val Lys Asn Asp Asn Ile Ser Gly
    290                 295                 300

Lys Arg Leu Ser Glu Leu Asn Leu Ser Glu Tyr Gly Cys Phe Leu Asn
305                 310                 315                 320

Arg Val Val Arg Ala Gln Ile Glu Met Pro Met Asp His Asn Ile Leu
                325                 330                 335

Leu Asn Lys Gly Asp Ile Leu Gln Val Ser Gly Glu Lys Ser Arg Val
            340                 345                 350

Leu Gly Leu Ala Glu Arg Ile Gly Phe Ile Ser Ile His Ser Gln Ile
        355                 360                 365

Ala Asp Leu Leu Ala Phe Cys Cys Phe Phe Ile Ile Gly Leu Leu Ile
    370                 375                 380

Gly Ser Ile Thr Leu Ala Phe Gly His Val Ala Phe Gly Leu Gly Ser
385                 390                 395                 400

Ala Ala Gly Leu Leu Ile Ala Gly Ile Thr Leu Gly Phe Leu Arg Ala
                405                 410                 415

Asn His Pro Thr Phe Gly Tyr Val Pro Gln Gly Ala Leu Asn Met Ala
            420                 425                 430

Lys Asp Leu Gly Leu Met Val Phe Met Val Gly Ile Gly Leu Ser Ala
        435                 440                 445

Gly Ser Asn Leu Phe Asp Ser Phe Ala His Ile Gly Pro Met Val Leu
    450                 455                 460

Val Thr Ser Leu Met Val Ser Val Ile Pro Val Val Leu Ala Tyr Leu
465                 470                 475                 480

Phe Gly Ala Tyr Val Leu Lys Met Asn Arg Ala Leu Leu Phe Gly Ala
                485                 490                 495

Ile Ile Gly Ala Arg Thr Cys Ala Pro Ala Met Asp Met Ile Asn Glu
            500                 505                 510

His Ala Arg Ser Thr Ile Pro Ala Leu Gly Tyr Ala Gly Thr Tyr Ala
        515                 520                 525

Ile Ala Asn Val Leu Leu Thr Ile Ala Gly Thr Leu Ile Ile Ile Met
    530                 535                 540
```

```
Asn
545


<210> SEQ ID NO 36
<211> LENGTH: 990
<212> TYPE: DNA
<213> ORGANISM: Escherichia coli
<220> FEATURE:
<221> NAME/KEY: CDS
<222> LOCATION: (1)..(990)

<400> SEQUENCE: 36

atg aaa ctc gcc gtt tat agc aca aaa cag tac gac aag aag tac ctg       48
Met Lys Leu Ala Val Tyr Ser Thr Lys Gln Tyr Asp Lys Lys Tyr Leu
1               5                   10                  15

caa cag gtg aac gag tcc ttt ggc ttt gag ctg gaa ttt ttt gac ttt       96
Gln Gln Val Asn Glu Ser Phe Gly Phe Glu Leu Glu Phe Phe Asp Phe
            20                  25                  30

ctg ctg acg gaa aaa acc gct aaa act gcc aat ggc tgc gaa gcg gta      144
Leu Leu Thr Glu Lys Thr Ala Lys Thr Ala Asn Gly Cys Glu Ala Val
        35                  40                  45

tgt att ttc gta aac gat gac ggc agc cgc ccg gtg ctg gaa gag ctg      192
Cys Ile Phe Val Asn Asp Asp Gly Ser Arg Pro Val Leu Glu Glu Leu
    50                  55                  60

aaa aag cac ggc gtt aaa tat atc gcc ctg cgc tgt gcc ggt ttc aat      240
Lys Lys His Gly Val Lys Tyr Ile Ala Leu Arg Cys Ala Gly Phe Asn
65                  70                  75                  80

aac gtc gac ctt gac gcg gca aaa gaa ctg ggg ctg aaa gta gtc cgt      288
Asn Val Asp Leu Asp Ala Ala Lys Glu Leu Gly Leu Lys Val Val Arg
                85                  90                  95

gtt cca gcc tat gat cca gag gcc gtt gct gaa cac gcc atc ggt atg      336
Val Pro Ala Tyr Asp Pro Glu Ala Val Ala Glu His Ala Ile Gly Met
            100                 105                 110

atg atg acg ctg aac cgc cgt att cac cgc gcg tat cag cgt acc cgt      384
Met Met Thr Leu Asn Arg Arg Ile His Arg Ala Tyr Gln Arg Thr Arg
        115                 120                 125

gat gct aac ttc tct ctg gaa ggt ctg acc ggc ttt act atg tat ggc      432
Asp Ala Asn Phe Ser Leu Glu Gly Leu Thr Gly Phe Thr Met Tyr Gly
    130                 135                 140

aaa acg gca ggc gtt atc ggt acc ggt aaa atc ggt gtg gcg atg ctg      480
Lys Thr Ala Gly Val Ile Gly Thr Gly Lys Ile Gly Val Ala Met Leu
145                 150                 155                 160

cgc att ctg aaa ggt ttt ggt atg cgt ctg ctg gcg ttc gat ccg tat      528
Arg Ile Leu Lys Gly Phe Gly Met Arg Leu Leu Ala Phe Asp Pro Tyr
                165                 170                 175

cca agt gca gcg gcg ctg gaa ctc ggt gtg gag tat gtc gat ctg cca      576
Pro Ser Ala Ala Ala Leu Glu Leu Gly Val Glu Tyr Val Asp Leu Pro
            180                 185                 190

acc ctg ttc tct gaa tca gac gtt atc tct ctg cac tgc ccg ctg aca      624
Thr Leu Phe Ser Glu Ser Asp Val Ile Ser Leu His Cys Pro Leu Thr
        195                 200                 205

ccg gaa aac tat cat ctg ttg aac gaa gcc gcc ttc gaa cag atg aaa      672
Pro Glu Asn Tyr His Leu Leu Asn Glu Ala Ala Phe Glu Gln Met Lys
    210                 215                 220

aat ggc gtg atg atc gtc aat acc agt cgc ggt gca ttg att gat tct      720
Asn Gly Val Met Ile Val Asn Thr Ser Arg Gly Ala Leu Ile Asp Ser
225                 230                 235                 240

cag gca gca att gaa gcg ctg aaa aat cag aaa att ggt tcg ttg ggt      768
Gln Ala Ala Ile Glu Ala Leu Lys Asn Gln Lys Ile Gly Ser Leu Gly
                245                 250                 255

atg gac gtg tat gag aac gaa cgc gat cta ttc ttt gaa gat aaa tcc      816
```

-continued

```
Met Asp Val Tyr Glu Asn Glu Arg Asp Leu Phe Phe Glu Asp Lys Ser
            260                 265                 270

aac gac gtg atc cag gat gac gta ttc cgt cgc ctg tct gcc tgc cac      864
Asn Asp Val Ile Gln Asp Asp Val Phe Arg Arg Leu Ser Ala Cys His
        275                 280                 285

aac gtg ctg ttt acc ggg cac cag gca ttc ctg aca gca gaa gct ctg      912
Asn Val Leu Phe Thr Gly His Gln Ala Phe Leu Thr Ala Glu Ala Leu
    290                 295                 300

acc agt att tct cag act acg ctg caa aac tta agc aat ctg gaa aaa      960
Thr Ser Ile Ser Gln Thr Thr Leu Gln Asn Leu Ser Asn Leu Glu Lys
305                 310                 315                 320

ggc gaa acc tgc ccg aac gaa ctg gtt taa                              990
Gly Glu Thr Cys Pro Asn Glu Leu Val
                325


<210> SEQ ID NO 37
<211> LENGTH: 329
<212> TYPE: PRT
<213> ORGANISM: Escherichia coli

<400> SEQUENCE: 37

Met Lys Leu Ala Val Tyr Ser Thr Lys Gln Tyr Asp Lys Lys Tyr Leu
1               5                   10                  15

Gln Gln Val Asn Glu Ser Phe Gly Phe Glu Leu Glu Phe Phe Asp Phe
            20                  25                  30

Leu Leu Thr Glu Lys Thr Ala Lys Thr Ala Asn Gly Cys Glu Ala Val
        35                  40                  45

Cys Ile Phe Val Asn Asp Asp Gly Ser Arg Pro Val Leu Glu Glu Leu
    50                  55                  60

Lys Lys His Gly Val Lys Tyr Ile Ala Leu Arg Cys Ala Gly Phe Asn
65                  70                  75                  80

Asn Val Asp Leu Asp Ala Ala Lys Glu Leu Gly Leu Lys Val Val Arg
                85                  90                  95

Val Pro Ala Tyr Asp Pro Glu Ala Val Ala Glu His Ala Ile Gly Met
            100                 105                 110

Met Met Thr Leu Asn Arg Arg Ile His Arg Ala Tyr Gln Arg Thr Arg
        115                 120                 125

Asp Ala Asn Phe Ser Leu Glu Gly Leu Thr Gly Phe Thr Met Tyr Gly
    130                 135                 140

Lys Thr Ala Gly Val Ile Gly Thr Gly Lys Ile Gly Val Ala Met Leu
145                 150                 155                 160

Arg Ile Leu Lys Gly Phe Gly Met Arg Leu Leu Ala Phe Asp Pro Tyr
                165                 170                 175

Pro Ser Ala Ala Ala Leu Glu Leu Gly Val Glu Tyr Val Asp Leu Pro
            180                 185                 190

Thr Leu Phe Ser Glu Ser Asp Val Ile Ser Leu His Cys Pro Leu Thr
        195                 200                 205

Pro Glu Asn Tyr His Leu Leu Asn Glu Ala Ala Phe Glu Gln Met Lys
    210                 215                 220

Asn Gly Val Met Ile Val Asn Thr Ser Arg Gly Ala Leu Ile Asp Ser
225                 230                 235                 240

Gln Ala Ala Ile Glu Ala Leu Lys Asn Gln Lys Ile Gly Ser Leu Gly
                245                 250                 255

Met Asp Val Tyr Glu Asn Glu Arg Asp Leu Phe Phe Glu Asp Lys Ser
            260                 265                 270

Asn Asp Val Ile Gln Asp Asp Val Phe Arg Arg Leu Ser Ala Cys His
```

-continued

```
        275                 280                 285

Asn Val Leu Phe Thr Gly His Gln Ala Phe Leu Thr Ala Glu Ala Leu
    290                 295                 300

Thr Ser Ile Ser Gln Thr Thr Leu Gln Asn Leu Ser Asn Leu Glu Lys
305                 310                 315                 320

Gly Glu Thr Cys Pro Asn Glu Leu Val
                325


<210> SEQ ID NO 38
<211> LENGTH: 1191
<212> TYPE: DNA
<213> ORGANISM: Escherichia coli
<220> FEATURE:
<221> NAME/KEY: CDS
<222> LOCATION: (1)..(1191)

<400> SEQUENCE: 38

atg att att tcc gca gcc agc gat tat cgc gcc gca gcg caa cgc att       48
Met Ile Ile Ser Ala Ala Ser Asp Tyr Arg Ala Ala Ala Gln Arg Ile
1               5                   10                  15

ctg ccg ccg ttc ctg ttc cac tat atg gat ggt ggt gca tat tct gaa       96
Leu Pro Pro Phe Leu Phe His Tyr Met Asp Gly Gly Ala Tyr Ser Glu
            20                  25                  30

tac acg ctg cgc cgc aac gtg gaa gat ttg tca gaa gtg gcg ctg cgc      144
Tyr Thr Leu Arg Arg Asn Val Glu Asp Leu Ser Glu Val Ala Leu Arg
        35                  40                  45

cag cgt att ctg aaa aac atg tcc gac tta agc ctg gaa acg acg ctg      192
Gln Arg Ile Leu Lys Asn Met Ser Asp Leu Ser Leu Glu Thr Thr Leu
    50                  55                  60

ttt aat gag aaa ttg tcg atg ccg gtg gca ctg gct ccg gtg ggt ttg      240
Phe Asn Glu Lys Leu Ser Met Pro Val Ala Leu Ala Pro Val Gly Leu
65                  70                  75                  80

tgt ggc atg tat gcg cgt cgt ggc gaa gtt cag gca gcc aaa gcg gcg      288
Cys Gly Met Tyr Ala Arg Arg Gly Glu Val Gln Ala Ala Lys Ala Ala
                85                  90                  95

gac gcg cat ggt att ccg ttt act ctc tcg acg gtt tcc gtt tgc ccg      336
Asp Ala His Gly Ile Pro Phe Thr Leu Ser Thr Val Ser Val Cys Pro
            100                 105                 110

att gaa gaa gtc gcg cca gcc atc aag cgc cca atg tgg ttc cag ctt      384
Ile Glu Glu Val Ala Pro Ala Ile Lys Arg Pro Met Trp Phe Gln Leu
        115                 120                 125

tat gta ctg cgc gat cgc ggc ttt atg cgt aac gcg ctg gag cga gca      432
Tyr Val Leu Arg Asp Arg Gly Phe Met Arg Asn Ala Leu Glu Arg Ala
    130                 135                 140

aaa gca gcg ggt tgt tcg acg ctg gtt ttc acc gtg gat atg ccg aca      480
Lys Ala Ala Gly Cys Ser Thr Leu Val Phe Thr Val Asp Met Pro Thr
145                 150                 155                 160

ccg ggc gca cgc tac cgt gat gcg cat tca ggt atg agc ggc ccg aac      528
Pro Gly Ala Arg Tyr Arg Asp Ala His Ser Gly Met Ser Gly Pro Asn
                165                 170                 175

gcg gca atg cgc cgc tac ttg caa gcg gtg aca cat ccg caa tgg gcg      576
Ala Ala Met Arg Arg Tyr Leu Gln Ala Val Thr His Pro Gln Trp Ala
            180                 185                 190

tgg gat gtg ggc ctg aac ggt cgt cca cat gat tta ggt aat atc tca      624
Trp Asp Val Gly Leu Asn Gly Arg Pro His Asp Leu Gly Asn Ile Ser
        195                 200                 205

gct tat ctc ggc aaa ccg acc gga ctg gaa gat tac atc ggc tgg ctg      672
Ala Tyr Leu Gly Lys Pro Thr Gly Leu Glu Asp Tyr Ile Gly Trp Leu
    210                 215                 220

ggg aat aac ttc gat ccg tcc atc tca tgg aaa gac ctt gaa tgg atc      720
```

```
Gly Asn Asn Phe Asp Pro Ser Ile Ser Trp Lys Asp Leu Glu Trp Ile
225                 230                 235                 240

cgc gat ttc tgg gat ggc ccg atg gtg atc aaa ggg atc ctc gat ccg      768
Arg Asp Phe Trp Asp Gly Pro Met Val Ile Lys Gly Ile Leu Asp Pro
                245                 250                 255

gaa gat gcg cgc gat gca gta cgt ttt ggt gct gat gga att gtg gtt      816
Glu Asp Ala Arg Asp Ala Val Arg Phe Gly Ala Asp Gly Ile Val Val
            260                 265                 270

tct aac cac ggt ggc cgc cag ctg gac ggt gta ctc tct tcc gcc cgt      864
Ser Asn His Gly Gly Arg Gln Leu Asp Gly Val Leu Ser Ser Ala Arg
        275                 280                 285

gca ctg cct gct att gca gat gcg gtg aaa ggt gat ata gcc att ctg      912
Ala Leu Pro Ala Ile Ala Asp Ala Val Lys Gly Asp Ile Ala Ile Leu
    290                 295                 300

gcg gat agc gga att cgt aac ggg ctt gat gtc gtg cgt atg att gcg      960
Ala Asp Ser Gly Ile Arg Asn Gly Leu Asp Val Val Arg Met Ile Ala
305                 310                 315                 320

ctc ggt gcc gac acc gta ctg ctg ggt cgt gct ttc ttg tat gcg ctg     1008
Leu Gly Ala Asp Thr Val Leu Leu Gly Arg Ala Phe Leu Tyr Ala Leu
                325                 330                 335

gca aca gcg ggc cag gcg ggt gta gct aac ctg cta aat ctg atc gaa     1056
Ala Thr Ala Gly Gln Ala Gly Val Ala Asn Leu Leu Asn Leu Ile Glu
            340                 345                 350

aaa gag atg aaa gtg gcg atg acg ctg act ggc gcg aaa tcg atc agc     1104
Lys Glu Met Lys Val Ala Met Thr Leu Thr Gly Ala Lys Ser Ile Ser
        355                 360                 365

gaa att acg caa gat tcg ctg gtg cag ggg ctg ggt aaa gag ttg cct     1152
Glu Ile Thr Gln Asp Ser Leu Val Gln Gly Leu Gly Lys Glu Leu Pro
    370                 375                 380

gcg gca ctg gct ccc atg gcg aaa ggg aat gcg gca tag                 1191
Ala Ala Leu Ala Pro Met Ala Lys Gly Asn Ala Ala
385                 390                 395


<210> SEQ ID NO 39
<211> LENGTH: 396
<212> TYPE: PRT
<213> ORGANISM: Escherichia coli

<400> SEQUENCE: 39

Met Ile Ile Ser Ala Ala Ser Asp Tyr Arg Ala Ala Ala Gln Arg Ile
1               5                   10                  15

Leu Pro Pro Phe Leu Phe His Tyr Met Asp Gly Gly Ala Tyr Ser Glu
            20                  25                  30

Tyr Thr Leu Arg Arg Asn Val Glu Asp Leu Ser Glu Val Ala Leu Arg
        35                  40                  45

Gln Arg Ile Leu Lys Asn Met Ser Asp Leu Ser Leu Glu Thr Thr Leu
    50                  55                  60

Phe Asn Glu Lys Leu Ser Met Pro Val Ala Leu Ala Pro Val Gly Leu
65                  70                  75                  80

Cys Gly Met Tyr Ala Arg Arg Gly Glu Val Gln Ala Ala Lys Ala Ala
                85                  90                  95

Asp Ala His Gly Ile Pro Phe Thr Leu Ser Thr Val Ser Val Cys Pro
            100                 105                 110

Ile Glu Glu Val Ala Pro Ala Ile Lys Arg Pro Met Trp Phe Gln Leu
        115                 120                 125

Tyr Val Leu Arg Asp Arg Gly Phe Met Arg Asn Ala Leu Glu Arg Ala
    130                 135                 140

Lys Ala Ala Gly Cys Ser Thr Leu Val Phe Thr Val Asp Met Pro Thr
```

-continued

```
145                 150                 155                 160

Pro Gly Ala Arg Tyr Arg Asp Ala His Ser Gly Met Ser Gly Pro Asn
                165                 170                 175

Ala Ala Met Arg Arg Tyr Leu Gln Ala Val Thr His Pro Gln Trp Ala
            180                 185                 190

Trp Asp Val Gly Leu Asn Gly Arg Pro His Asp Leu Gly Asn Ile Ser
        195                 200                 205

Ala Tyr Leu Gly Lys Pro Thr Gly Leu Glu Asp Tyr Ile Gly Trp Leu
    210                 215                 220

Gly Asn Asn Phe Asp Pro Ser Ile Ser Trp Lys Asp Leu Glu Trp Ile
225                 230                 235                 240

Arg Asp Phe Trp Asp Gly Pro Met Val Ile Lys Gly Ile Leu Asp Pro
                245                 250                 255

Glu Asp Ala Arg Asp Ala Val Arg Phe Gly Ala Asp Gly Ile Val Val
            260                 265                 270

Ser Asn His Gly Gly Arg Gln Leu Asp Gly Val Leu Ser Ser Ala Arg
        275                 280                 285

Ala Leu Pro Ala Ile Ala Asp Ala Val Lys Gly Asp Ile Ala Ile Leu
    290                 295                 300

Ala Asp Ser Gly Ile Arg Asn Gly Leu Asp Val Val Arg Met Ile Ala
305                 310                 315                 320

Leu Gly Ala Asp Thr Val Leu Leu Gly Arg Ala Phe Leu Tyr Ala Leu
                325                 330                 335

Ala Thr Ala Gly Gln Ala Gly Val Ala Asn Leu Leu Asn Leu Ile Glu
            340                 345                 350

Lys Glu Met Lys Val Ala Met Thr Leu Thr Gly Ala Lys Ser Ile Ser
        355                 360                 365

Glu Ile Thr Gln Asp Ser Leu Val Gln Gly Leu Gly Lys Glu Leu Pro
    370                 375                 380

Ala Ala Leu Ala Pro Met Ala Lys Gly Asn Ala Ala
385                 390                 395


<210> SEQ ID NO 40
<211> LENGTH: 1308
<212> TYPE: DNA
<213> ORGANISM: Pantoea ananatis

<400> SEQUENCE: 40

atgagcagaa tcatgacgcc cgtgaactgg gaagcctgca gcagcgaggc gcagcaggcg      60

ctgttggcac gccctgcgct cgcctcgtct gacagcatca gccagatcgt gcgcgatgtg     120

ttggtcagag tgaaagagga aggcgatgcg gctttacgag aattcagcgc gcgctttgac     180

aaggttgaaa cagacgacct gcgcgttacg ccacagcaga tgcaggcggc cagcgatcgc     240

cttggtgacg agctgaaaca ggcgatggcc gtggccattg gcaatattga aacctttcac     300

cgtgcgcaga tcctgccgcc ggtggatgtg gaaacgcagc ccggcgtgcg ctgtcagcaa     360

attacgcgcc cgatgaaatc ggtgggcttg tatattccgg gcggttctgc cccgctgttt     420

tctaccgttc tgatgctggc taccccggcg cggattgcgg gctgtggtcg cgtggtgctg     480

tgctcgcccc cgccgattgc tgatgaaatt ctctacgcgg ccaaactttg cggtgtggaa     540

gaagtgttcc aggtgggtgg atcacaggcg attgccgccc tggcttttgg caccgaaagc     600

atccctaagg tagataaaat ttttggtccg ggcaacgcgt gggttaccga agccaaacgt     660

caggtcagcc agcgccttga tggcgcggcg attgatatgc ccgctggccc gtcggaagtg     720
```

```
ctggtgattg ccgatgaagg tgccacaccg gccttcgttg cctctgatct gctgtcgcag    780

gcggaacacg gccctgactc gcaggtgatt ttactgacgc cttcgctggc gctggccgag    840

cgcgtcgccg aggcggtgga ggatcagctg gcccagttgc cacgtgcggc gacagcccgc    900

caggcactgg aaagcagccg cctgatcgtc gcccgggata tgcagcaatg cattgcgatc    960

tccaaccgct atggtccgga gcacctgatt ctgcaaaccc gcacgccacg ggatctggtg   1020

gaacagatta ccagcgccgg ttcggttttc ctgggcgact ggtcaccgga atccgcagga   1080

gattatgctt cgggcaccaa ccacgtgctg ccgacctacg gctataccgc gacatgctcc   1140

agcctgggcc tggccgactt tcagaaacgc atgacggtac aggagctgac gccgcagggc   1200

ttcctgaacc tggcggcgac catcgaaacc ctggcggccg ctgaacagct gcacgcccac   1260

aaaaatgccg tcacgttgcg cgttgccgca ctcaaggagc aagcatga              1308
```

<210> SEQ ID NO 41
<211> LENGTH: 68
<212> TYPE: DNA
<213> ORGANISM: Artificial Sequence
<220> FEATURE:
<223> OTHER INFORMATION: primer

<400> SEQUENCE: 41

```
ccatagcggt tggagatcgc aatgcattgc tgcatatccc tgaagcctgc ttttttatac     60

taagttgg                                                             68
```

<210> SEQ ID NO 42
<211> LENGTH: 68
<212> TYPE: DNA
<213> ORGANISM: Artificial Sequence
<220> FEATURE:
<223> OTHER INFORMATION: primer

<400> SEQUENCE: 42

```
gcccgccagg cactggaaag cagccgcctg atcgtcgccc cgctcaagtt agtataaaaa     60

agctgaac                                                             68
```

<210> SEQ ID NO 43
<211> LENGTH: 33
<212> TYPE: DNA
<213> ORGANISM: Artificial Sequence
<220> FEATURE:
<223> OTHER INFORMATION: primer

<400> SEQUENCE: 43

```
tagcgagatc tctgatgtcc ggcggtgctt ttg                                  33
```

<210> SEQ ID NO 44
<211> LENGTH: 32
<212> TYPE: DNA
<213> ORGANISM: Artificial Sequence
<220> FEATURE:
<223> OTHER INFORMATION: primer

<400> SEQUENCE: 44

```
aaaaagagct cttacgcccc gccctgccac tc                                   32
```

<210> SEQ ID NO 45
<211> LENGTH: 34
<212> TYPE: DNA
<213> ORGANISM: Artificial Sequence
<220> FEATURE:
<223> OTHER INFORMATION: primer

<400> SEQUENCE: 45
caggatctag aaggagacat gaacgatgaa catc 34

<210> SEQ ID NO 46
<211> LENGTH: 36
<212> TYPE: DNA
<213> ORGANISM: Artificial Sequence
<220> FEATURE:
<223> OTHER INFORMATION: primer

<400> SEQUENCE: 46
gataaggatc cgaaataaaa gaaaatgcca atagga 36

<210> SEQ ID NO 47
<211> LENGTH: 31
<212> TYPE: DNA
<213> ORGANISM: Artificial Sequence
<220> FEATURE:
<223> OTHER INFORMATION: primer

<400> SEQUENCE: 47
cctttgagct cgcgggcagt gagcgcaacg c 31

<210> SEQ ID NO 48
<211> LENGTH: 48
<212> TYPE: DNA
<213> ORGANISM: Artificial Sequence
<220> FEATURE:
<223> OTHER INFORMATION: primer

<400> SEQUENCE: 48
ctagagcggc cgccgatcgg gatcctcctg tgtgaaattg ttatccgc 48

<210> SEQ ID NO 49
<211> LENGTH: 42
<212> TYPE: DNA
<213> ORGANISM: Artificial Sequence
<220> FEATURE:
<223> OTHER INFORMATION: primer

<400> SEQUENCE: 49
ctctacgatc gaggaggtta taaaaaatgg atattaatac tg 42

<210> SEQ ID NO 50
<211> LENGTH: 36
<212> TYPE: DNA
<213> ORGANISM: Artificial Sequence
<220> FEATURE:
<223> OTHER INFORMATION: primer

<400> SEQUENCE: 50
tcaaagcggc cgcttcttcg tctgtttcta ctggta 36

<210> SEQ ID NO 51
<211> LENGTH: 31
<212> TYPE: DNA
<213> ORGANISM: Artificial Sequence
<220> FEATURE:
<223> OTHER INFORMATION: primer

<400> SEQUENCE: 51
cctttggtac cgcgggcagt gagcgcaacg c 31

<210> SEQ ID NO 52

```
<211> LENGTH: 34
<212> TYPE: DNA
<213> ORGANISM: Artificial Sequence
<220> FEATURE:
<223> OTHER INFORMATION: primer

<400> SEQUENCE: 52

aacaggaatt ctttgcctgg cggcagtagc gcgg                                34

<210> SEQ ID NO 53
<211> LENGTH: 40
<212> TYPE: DNA
<213> ORGANISM: Artificial Sequence
<220> FEATURE:
<223> OTHER INFORMATION: primer P1

<400> SEQUENCE: 53

ctagtaagat cttgaagcct gcttttttat actaagttgg                          40

<210> SEQ ID NO 54
<211> LENGTH: 41
<212> TYPE: DNA
<213> ORGANISM: Artificial Sequence
<220> FEATURE:
<223> OTHER INFORMATION: primer P2

<400> SEQUENCE: 54

atgatcgaat tcgaaatcaa ataatgattt tattttgact g                        41

<210> SEQ ID NO 55
<211> LENGTH: 120
<212> TYPE: DNA
<213> ORGANISM: Artificial Sequence
<220> FEATURE:
<223> OTHER INFORMATION: DNA fragment containing attL

<400> SEQUENCE: 55

agatcttgaa gcctgctttt ttatactaag ttggcattat aaaaaagcat tgcttatcaa    60

tttgttgcaa cgaacaggtc actatcagtc aaaataaaat cattatttga tttcgaattc   120

<210> SEQ ID NO 56
<211> LENGTH: 41
<212> TYPE: DNA
<213> ORGANISM: Artificial Sequence
<220> FEATURE:
<223> OTHER INFORMATION: primer P3

<400> SEQUENCE: 56

atgccactgc agtctgttac aggtcactaa taccatctaa g                        41

<210> SEQ ID NO 57
<211> LENGTH: 46
<212> TYPE: DNA
<213> ORGANISM: Artificial Sequence
<220> FEATURE:
<223> OTHER INFORMATION: primer P4

<400> SEQUENCE: 57

accgttaagc tttctagacg ctcaagttag tataaaaaag ctgaac                   46

<210> SEQ ID NO 58
<211> LENGTH: 184
<212> TYPE: DNA
<213> ORGANISM: Artificial Sequence
<220> FEATURE:
<223> OTHER INFORMATION: DNA fragment containing attR
```

<400> SEQUENCE: 58
ctgcagtctg ttacaggtca ctaataccat ctaagtagtt gattcatagt gactgcatat 60
gttgtgtttt acagtattat gtagtctgtt ttttatgcaa aatctaattt aatatattga 120
tatttatatc attttacgtt tctcgttcag ctttttttata ctaacttgag cgtctagaaa 180
gctt 184

<210> SEQ ID NO 59
<211> LENGTH: 38
<212> TYPE: DNA
<213> ORGANISM: Artificial Sequence
<220> FEATURE:
<223> OTHER INFORMATION: primer P5

<400> SEQUENCE: 59
ttcttagacg tcaggtggca cttttcgggg aaatgtgc 38

<210> SEQ ID NO 60
<211> LENGTH: 37
<212> TYPE: DNA
<213> ORGANISM: Artificial Sequence
<220> FEATURE:
<223> OTHER INFORMATION: primer P6

<400> SEQUENCE: 60
taacagagat ctcgcgcaga aaaaaaggat ctcaaga 37

<210> SEQ ID NO 61
<211> LENGTH: 46
<212> TYPE: DNA
<213> ORGANISM: Artificial Sequence
<220> FEATURE:
<223> OTHER INFORMATION: primer P7

<400> SEQUENCE: 61
aacagagatc taagcttaga tcctttgcct ggcggcagta gcgcgg 46

<210> SEQ ID NO 62
<211> LENGTH: 35
<212> TYPE: DNA
<213> ORGANISM: Artificial Sequence
<220> FEATURE:
<223> OTHER INFORMATION: primer P8

<400> SEQUENCE: 62
ataaactgca gcaaaaagag tttgtagaaa cgcaa 35

<210> SEQ ID NO 63
<211> LENGTH: 1388
<212> TYPE: DNA
<213> ORGANISM: Artificial Sequence
<220> FEATURE:
<223> OTHER INFORMATION: DNA fragment containing Tc gene and ter_thrL

<400> SEQUENCE: 63
gaattctcat gtttgacagc ttatcatcga taagctttaa tgcggtagtt tatcacagtt 60
aaattgctaa cgcagtcagg caccgtgtat gaaatctaac aatgcgctca tcgtcatcct 120
cggcaccgtc accctggatg ctgtaggcat aggcttggtt atgccggtac tgccgggcct 180
cttgcgggat atcgtccatt ccgacagcat cgccagtcac tatggcgtgc tgctagcgct 240
atatgcgttg atgcaatttc tatgcgcacc cgttctcgga gcactgtccg accgctttgg 300

```
ccgccgccca gtcctgctcg cttcgctact tggagccact atcgactacg cgatcatggc    360

gaccacaccc gtcctgtgga tcctctacgc cggacgcatc gtggccggca tcaccggcgc    420

cacaggtgcg gttgctggcg cctatatcgc cgacatcacc gatggggaag atcgggctcg    480

ccacttcggg ctcatgagcg cttgtttcgg cgtgggtatg gtggcaggcc ccgtggccgg    540

gggactgttg ggcgccatct ccttgcatgc accattcctt gcggcggcgg tgctcaacgg    600

cctcaaccta ctactgggct gcttcctaat gcaggagtcg cataagggag agcgtcgacc    660

gatgcccttg agagccttca acccagtcag ctccttccgg tgggcgcggg gcatgactat    720

cgtcgccgca cttatgactg tcttctttat catgcaactc gtaggacagg tgccggcagc    780

gctctgggtc attttcggcg aggaccgctt tcgctggagc gcgacgatga tcggcctgtc    840

gcttgcggta ttcggaatct tgcacgccct cgctcaagcc ttcgtcactg gtcccgccac    900

caaacgtttc ggcgagaagc aggccattat cgccggcatg gcggccgacg cgctgggcta    960

cgtcttgctg gcgttcgcga cgcgaggctg gatggccttc cccattatga ttcttctcgc   1020

ttccggcggc atcgggatgc ccgcgttgca ggccatgctg tccaggcagg tagatgacga   1080

ccatcaggga cagcttcaag gatcgctcgc ggctcttacc agcctaactt cgatcactgg   1140

accgctgatc gtcacggcga tttatgccgc ctcggcgagc acatggaacg ggttggcatg   1200

gattgtaggc gccgccctat accttgtctg cctccccgcg ttgcgtcgcg gtgcatggag   1260

ccgggccacc tcgacctgaa tggaagccgg cggcacctcg ctaacggatt caccactcca   1320

actagaaagc ttaacacaga aaaaagcccg cacctgacag tgcgggcttt tttttcgac    1380

cactgcag                                                             1388
```

<210> SEQ ID NO 64
<211> LENGTH: 36
<212> TYPE: DNA
<213> ORGANISM: Artificial Sequence
<220> FEATURE:
<223> OTHER INFORMATION: primer P9

<400> SEQUENCE: 64

```
agtaattcta gaaagcttaa cacagaaaaa agcccg                               36
```

<210> SEQ ID NO 65
<211> LENGTH: 43
<212> TYPE: DNA
<213> ORGANISM: Artificial Sequence
<220> FEATURE:
<223> OTHER INFORMATION: primer P10

<400> SEQUENCE: 65

```
ctagtaggat ccctgcagtg gtcgaaaaaa aaagcccgca ctg                       43
```

<210> SEQ ID NO 66
<211> LENGTH: 6550
<212> TYPE: DNA
<213> ORGANISM: Pantoea ananatis
<220> FEATURE:
<221> NAME/KEY: CDS
<222> LOCATION: (231)..(1370)
<220> FEATURE:
<221> NAME/KEY: CDS
<222> LOCATION: (1380)..(1814)
<220> FEATURE:
<221> NAME/KEY: CDS
<222> LOCATION: (1827)..(4004)
<220> FEATURE:
<221> NAME/KEY: CDS
<222> LOCATION: (4260)..(5396)

```
<220> FEATURE:
<221> NAME/KEY: CDS
<222> LOCATION: (5526)..(6443)

<400> SEQUENCE: 66

aggttccggc gggcagattt ctctaaaaaa aagcggtacg gcattgataa accgaaatgt      60

tctgctttgc tttattccgt tccgggtaaa gcgcgtgatg ggtacaagac aggagctaag     120

aataatgaac gacatgttca gggcctgagt caggatagct tactttttttc gagcgcttac    180

acagcggcgt attcgcctct atcaaacatt aactgatagc gaagatctaa atg att       236
                                                        Met Ile
                                                        1

aca atg aaa atg aag atg ata cct gtt ctg gta tct gca act ttt atg      284
Thr Met Lys Met Lys Met Ile Pro Val Leu Val Ser Ala Thr Phe Met
        5                   10                  15

gcc ggg tgt act gtc gtg ccg ggg caa aat tta tcc act tcg gga aaa      332
Ala Gly Cys Thr Val Val Pro Gly Gln Asn Leu Ser Thr Ser Gly Lys
    20                  25                  30

gat gtc att gag cag cag gac agc aat ttt gac atc gac aag tac gtt      380
Asp Val Ile Glu Gln Gln Asp Ser Asn Phe Asp Ile Asp Lys Tyr Val
35                  40                  45                  50

aac gtt tat ccg tta acg cca ggc ctg gtg gag aaa atg cgt cct aag      428
Asn Val Tyr Pro Leu Thr Pro Gly Leu Val Glu Lys Met Arg Pro Lys
                55                  60                  65

cca ctt gtg gca cag gct aat ccg tcg tta caa acc gaa att cag aac      476
Pro Leu Val Ala Gln Ala Asn Pro Ser Leu Gln Thr Glu Ile Gln Asn
            70                  75                  80

tac gaa tac cgc atc ggc atc ggt gat gtt ctc acc gtc acc gtg tgg      524
Tyr Glu Tyr Arg Ile Gly Ile Gly Asp Val Leu Thr Val Thr Val Trp
        85                  90                  95

gat cac ccc gaa ctc acc acg cct gcc ggt cag tac cgt agc gcc agt      572
Asp His Pro Glu Leu Thr Thr Pro Ala Gly Gln Tyr Arg Ser Ala Ser
    100                 105                 110

gac acc ggt aac tgg gtc cat tcc gac ggc acg att ttc tat cct tac      620
Asp Thr Gly Asn Trp Val His Ser Asp Gly Thr Ile Phe Tyr Pro Tyr
115                 120                 125                 130

atc ggc cgc gtc cgt gtt gcc ggc cgt acc gta ggt gac gtg cgt aat      668
Ile Gly Arg Val Arg Val Ala Gly Arg Thr Val Gly Asp Val Arg Asn
                135                 140                 145

gaa gtg gcg cgt cgt ctg gcg cag tac atc gaa agc ccc cag gtt gac      716
Glu Val Ala Arg Arg Leu Ala Gln Tyr Ile Glu Ser Pro Gln Val Asp
            150                 155                 160

gtc agc att gcc tcg ttt aag tca cag aag act tac gtg acc ggt gcc      764
Val Ser Ile Ala Ser Phe Lys Ser Gln Lys Thr Tyr Val Thr Gly Ala
        165                 170                 175

gtg acg acc tca ggc cag cag cct atc acc aac gta ccg ctg act atc      812
Val Thr Thr Ser Gly Gln Gln Pro Ile Thr Asn Val Pro Leu Thr Ile
    180                 185                 190

ctg gat gcg att aac gca gcg ggc ggc tta gcg gcg gac gca gac tgg      860
Leu Asp Ala Ile Asn Ala Ala Gly Gly Leu Ala Ala Asp Ala Asp Trp
195                 200                 205                 210

cgc aac gtt atc ctg acc cac aac ggc cgt gag cag cgc gtg tca ctg      908
Arg Asn Val Ile Leu Thr His Asn Gly Arg Glu Gln Arg Val Ser Leu
                215                 220                 225

cag gcc ctg atg caa aac ggc gat ctg agc cag aac cac ctg ctt tat      956
Gln Ala Leu Met Gln Asn Gly Asp Leu Ser Gln Asn His Leu Leu Tyr
            230                 235                 240

ccg ggt gac atc ctg tat gtg ccg cgt aac gac gac ctg aaa gtg ttt     1004
Pro Gly Asp Ile Leu Tyr Val Pro Arg Asn Asp Asp Leu Lys Val Phe
        245                 250                 255
```

```
gtc atg ggc gaa gtg aaa cag cag gcc acc ctg aaa atg gac cgc agc     1052
Val Met Gly Glu Val Lys Gln Gln Ala Thr Leu Lys Met Asp Arg Ser
    260                 265                 270

ggt atg acc ctg gct gaa gcg ctg ggt aat gcg gca ggc atg gat caa     1100
Gly Met Thr Leu Ala Glu Ala Leu Gly Asn Ala Ala Gly Met Asp Gln
275                 280                 285                 290

acc acg tcc gac gcg acc ggg gtc ttt gtt atc cga ccg acg cgc ggc     1148
Thr Thr Ser Asp Ala Thr Gly Val Phe Val Ile Arg Pro Thr Arg Gly
                295                 300                 305

tcc gat cgc agc aaa atc gcc aat atc tac cag ctg aat acc aaa gat     1196
Ser Asp Arg Ser Lys Ile Ala Asn Ile Tyr Gln Leu Asn Thr Lys Asp
            310                 315                 320

gcg gca tcc atg gtg atg ggt acc gaa ttc caa ctt gaa cct tac gat     1244
Ala Ala Ser Met Val Met Gly Thr Glu Phe Gln Leu Glu Pro Tyr Asp
        325                 330                 335

atc gtc tac gtg aca tcg acg ccg ctg acg cgt tgg aac cgc gtg ata     1292
Ile Val Tyr Val Thr Ser Thr Pro Leu Thr Arg Trp Asn Arg Val Ile
    340                 345                 350

tcg cag ttg ata cca acc ata gcc ggt gtt aac gat gcg acg cag gct     1340
Ser Gln Leu Ile Pro Thr Ile Ala Gly Val Asn Asp Ala Thr Gln Ala
355                 360                 365                 370

gca cag cgc atc cgc aac tgg tcg aac taa ggtttcgcc atg att aag tcc   1391
Ala Gln Arg Ile Arg Asn Trp Ser Asn              Met Ile Lys Ser
                375                              380

gtg tta gtc gtc tgc gta ggc aac atc tgc cgc tct cct acg gga gag     1439
Val Leu Val Val Cys Val Gly Asn Ile Cys Arg Ser Pro Thr Gly Glu
    385                 390                 395

cgc ctg ttc aaa cgc gcg ctg ccg cac ctg cct gtg gcc tcc gcc gga     1487
Arg Leu Phe Lys Arg Ala Leu Pro His Leu Pro Val Ala Ser Ala Gly
400                 405                 410                 415

ctc ggc gcc ctg gtt ggg cac gcg gcg gat aaa acg gcg acg gag gtg     1535
Leu Gly Ala Leu Val Gly His Ala Ala Asp Lys Thr Ala Thr Glu Val
                420                 425                 430

gca gcc gaa aaa ggc tta tcg ctg gaa ggt cat gag gct cag cag cta     1583
Ala Ala Glu Lys Gly Leu Ser Leu Glu Gly His Glu Ala Gln Gln Leu
            435                 440                 445

acg gcc agc ctg tgc cgg gag tat gac ctg att ctg gtg atg gaa aag     1631
Thr Ala Ser Leu Cys Arg Glu Tyr Asp Leu Ile Leu Val Met Glu Lys
        450                 455                 460

cgc cac att gaa cag gta aac cgc atc gat ccg gct gca cgc ggc aaa     1679
Arg His Ile Glu Gln Val Asn Arg Ile Asp Pro Ala Ala Arg Gly Lys
    465                 470                 475

acg atg ctg ctt ggg cac tgg ctc aat cag aag gaa att gcg gat ccg     1727
Thr Met Leu Leu Gly His Trp Leu Asn Gln Lys Glu Ile Ala Asp Pro
480                 485                 490                 495

tac aga aaa agc cgt gag gcc ttt gaa gag gtt tac ggg tta ctg gaa     1775
Tyr Arg Lys Ser Arg Glu Ala Phe Glu Glu Val Tyr Gly Leu Leu Glu
                500                 505                 510

cac gcc act cag aaa tgg gtc agc gta cta agc cga tag ttgggattat cc   1826
His Ala Thr Gln Lys Trp Val Ser Val Leu Ser Arg
            515                 520

atg aat ata aaa aac aaa gtc atg acc gcg ccg cgc gag gaa tcg aat     1874
Met Asn Ile Lys Asn Lys Val Met Thr Ala Pro Arg Glu Glu Ser Asn
    525                 530                 535

ggg tgg gat ctg gcg cat ctt gtg gga cag ctt att gat cac cgc tgg     1922
Gly Trp Asp Leu Ala His Leu Val Gly Gln Leu Ile Asp His Arg Trp
540                 545                 550                 555

gtt atc gtc gct gtc acc gct ttt ttc atg ctg gta gca acg ctc tac     1970
Val Ile Val Ala Val Thr Ala Phe Phe Met Leu Val Ala Thr Leu Tyr
```

```
                560                 565                 570

aca ctg ttt gcg acg cct att tac agc gcc gat gcc atg gtt cag gtg     2018
Thr Leu Phe Ala Thr Pro Ile Tyr Ser Ala Asp Ala Met Val Gln Val
            575                 580                 585

gag cag aag aat acc agc acc gtc ctg aat gaa tta cag acg ctg atg     2066
Glu Gln Lys Asn Thr Ser Thr Val Leu Asn Glu Leu Gln Thr Leu Met
        590                 595                 600

ccc acg acg cca gca tcg gat acc gaa atc cag att ctt gaa tca cgc     2114
Pro Thr Thr Pro Ala Ser Asp Thr Glu Ile Gln Ile Leu Glu Ser Arg
    605                 610                 615

atg gtg ctg gga aaa acc gtt cag gat ctt ggc ctg gat gca gtg gtt     2162
Met Val Leu Gly Lys Thr Val Gln Asp Leu Gly Leu Asp Ala Val Val
620                 625                 630                 635

tca cag aac tat ttc ccg gtt atc ggc aaa ggt ctg tcg cgc ctg atg     2210
Ser Gln Asn Tyr Phe Pro Val Ile Gly Lys Gly Leu Ser Arg Leu Met
                640                 645                 650

ggc aac aag cct ggc aat gtt gcg atc tcc cgt ctg gag att ccg cgt     2258
Gly Asn Lys Pro Gly Asn Val Ala Ile Ser Arg Leu Glu Ile Pro Arg
            655                 660                 665

acg atc gag aag cgc agt gtt gag ctc gag gtt acg ggt aaa gac agc     2306
Thr Ile Glu Lys Arg Ser Val Glu Leu Glu Val Thr Gly Lys Asp Ser
        670                 675                 680

tat acc gtt tct gcc gat ggc gat gag ctg ttc aaa ggc aaa gtg ggg     2354
Tyr Thr Val Ser Ala Asp Gly Asp Glu Leu Phe Lys Gly Lys Val Gly
    685                 690                 695

cag ttc gaa aaa cac ggc gat gtg agc atg ctg gtc agc gat atc aat     2402
Gln Phe Glu Lys His Gly Asp Val Ser Met Leu Val Ser Asp Ile Asn
700                 705                 710                 715

gcg gag ccg ggc acc acg ttt acc gtc acc aaa ctc aac gat ctg cag     2450
Ala Glu Pro Gly Thr Thr Phe Thr Val Thr Lys Leu Asn Asp Leu Gln
                720                 725                 730

gca att aac agc atc ctg tct aac ctg acc gtt gca gac aaa ggg aaa     2498
Ala Ile Asn Ser Ile Leu Ser Asn Leu Thr Val Ala Asp Lys Gly Lys
            735                 740                 745

gac acc ggc gta ctg gga ctg cag tat gtg ggt gaa gat cag gag cag     2546
Asp Thr Gly Val Leu Gly Leu Gln Tyr Val Gly Glu Asp Gln Glu Gln
        750                 755                 760

atc agc aaa gtt ctg aac cag atc gtg aat aac tac ctg ttg cag aac     2594
Ile Ser Lys Val Leu Asn Gln Ile Val Asn Asn Tyr Leu Leu Gln Asn
    765                 770                 775

gtg cag cgt aaa tcc gaa cag gcc gag aaa agc ctg gag ttc ctg aaa     2642
Val Gln Arg Lys Ser Glu Gln Ala Glu Lys Ser Leu Glu Phe Leu Lys
780                 785                 790                 795

cag caa ctg ccg gaa gtg cgt ggc aaa ctg gat cag gcg gaa gac aaa     2690
Gln Gln Leu Pro Glu Val Arg Gly Lys Leu Asp Gln Ala Glu Asp Lys
                800                 805                 810

ctt aac gcc ttc cgc cgt gag aac gag tcc gtt gac ctg tcg ctt gaa     2738
Leu Asn Ala Phe Arg Arg Glu Asn Glu Ser Val Asp Leu Ser Leu Glu
            815                 820                 825

gct aag tct gcg ttg gat tca tcc gtt agc gtg cag agc cag ctt aac     2786
Ala Lys Ser Ala Leu Asp Ser Ser Val Ser Val Gln Ser Gln Leu Asn
        830                 835                 840

gag ctg acg ttc cgc gaa gcc gaa gtt tcg cag ctg ttc acc aaa gat     2834
Glu Leu Thr Phe Arg Glu Ala Glu Val Ser Gln Leu Phe Thr Lys Asp
    845                 850                 855

cac cct acc tat cgg gcc ctg tta gaa aag cgt aaa acg ctg gaa gat     2882
His Pro Thr Tyr Arg Ala Leu Leu Glu Lys Arg Lys Thr Leu Glu Asp
860                 865                 870                 875

gag cag gcg cag ctg aac aag aaa att gcg cag atg ccg aaa act cag     2930
```

-continued

```
Glu Gln Ala Gln Leu Asn Lys Lys Ile Ala Gln Met Pro Lys Thr Gln
            880                 885                 890

cag gag att ctg cgt ctg acc cgc gat gtg cag tca ggt cag gaa atc      2978
Gln Glu Ile Leu Arg Leu Thr Arg Asp Val Gln Ser Gly Gln Glu Ile
        895                 900                 905

tac atg cag tta ctg aac cgc cag caa gag ctg agc atc agt aag gcc      3026
Tyr Met Gln Leu Leu Asn Arg Gln Gln Glu Leu Ser Ile Ser Lys Ala
    910                 915                 920

agc acc gtg ggt gat gtt cgc atc atc gat cag gcc gcc acg gca aac      3074
Ser Thr Val Gly Asp Val Arg Ile Ile Asp Gln Ala Ala Thr Ala Asn
    925                 930                 935

tcg ccg gtt gcg ccg aaa aag ctg ctg atc atc gca gcc agc ctg att      3122
Ser Pro Val Ala Pro Lys Lys Leu Leu Ile Ile Ala Ala Ser Leu Ile
940                 945                 950                 955

ctg ggg ctg atg gtg tcc gtc ggt gtg gtt ctg ctt aaa gcg ctg ttg      3170
Leu Gly Leu Met Val Ser Val Gly Val Val Leu Leu Lys Ala Leu Leu
            960                 965                 970

cat cac gga atc gag aac ccg gaa cag ctg gaa gag ctg ggc atg aac      3218
His His Gly Ile Glu Asn Pro Glu Gln Leu Glu Glu Leu Gly Met Asn
        975                 980                 985

gtc tat gcc agc gta ccg ctc tct gag tgg cag cgt aag  aag gat acc     3266
Val Tyr Ala Ser Val Pro Leu Ser Glu Trp Gln Arg Lys  Lys Asp Thr
    990                 995                 1000

gaa gca  ctg gcg cgt cgc ggt  cac aaa ggc aaa acc  gat ccg cat      3311
Glu Ala  Leu Ala Arg Arg Gly  His Lys Gly Lys Thr  Asp Pro His
    1005                 1010                 1015

gag acg  ctg ttg gca ctg ggt  aat cca acc gac ctc  tct att gaa      3356
Glu Thr  Leu Leu Ala Leu Gly  Asn Pro Thr Asp Leu  Ser Ile Glu
    1020                 1025                 1030

gcg att  cgt agc ctg cgt acc  agc ctg cac ttc gcc  atg atg gaa      3401
Ala Ile  Arg Ser Leu Arg Thr  Ser Leu His Phe Ala  Met Met Glu
    1035                 1040                 1045

gcg aaa  aac aac att ctg atg  atc acc ggc gcc agc  ccg ggt att      3446
Ala Lys  Asn Asn Ile Leu Met  Ile Thr Gly Ala Ser  Pro Gly Ile
    1050                 1055                 1060

ggt aaa  acc ttt atc tgc gtt  aac ctc gct acc ctg  gtg gcc aag      3491
Gly Lys  Thr Phe Ile Cys Val  Asn Leu Ala Thr Leu  Val Ala Lys
    1065                 1070                 1075

gcc ggt  cag aag gtg ttg ttt  atc gat ggt gac atg  cgc cgc ggt      3536
Ala Gly  Gln Lys Val Leu Phe  Ile Asp Gly Asp Met  Arg Arg Gly
    1080                 1085                 1090

tac acc  cac gaa ctg ctg ggg  gcg gac aat aaa tcc  ggt ctg tct      3581
Tyr Thr  His Glu Leu Leu Gly  Ala Asp Asn Lys Ser  Gly Leu Ser
    1095                 1100                 1105

aac gtc  ctg tct ggc aaa acc  gag ttt acg ccg acc  atg att cag      3626
Asn Val  Leu Ser Gly Lys Thr  Glu Phe Thr Pro Thr  Met Ile Gln
    1110                 1115                 1120

caa ggg  cca tac ggt ttt gat  ttc ctg ccg cgc gga  cag gtt cca      3671
Gln Gly  Pro Tyr Gly Phe Asp  Phe Leu Pro Arg Gly  Gln Val Pro
    1125                 1130                 1135

ccg aac  ccg tca gag ctg ttg  atg cac cgc cgc atg  ggc gag ctg      3716
Pro Asn  Pro Ser Glu Leu Leu  Met His Arg Arg Met  Gly Glu Leu
    1140                 1145                 1150

ctg gag  tgg gca agc aaa aac  tat gat tta gtc ctg  att gat aca      3761
Leu Glu  Trp Ala Ser Lys Asn  Tyr Asp Leu Val Leu  Ile Asp Thr
    1155                 1160                 1165

cca ccg  att ctg gcc gta acg  gat gcg tcc atc atc  ggt aag ctg      3806
Pro Pro  Ile Leu Ala Val Thr  Asp Ala Ser Ile Ile  Gly Lys Leu
    1170                 1175                 1180
```

-continued

```
gcc ggt  acc tcg ctg atg gtg  gcg cgt ttt gaa acc  aac acc aca      3851
Ala Gly  Thr Ser Leu Met Val  Ala Arg Phe Glu Thr  Asn Thr Thr
    1185                 1190                 1195

aaa gaa  gtg gat gtc agc ttc  aaa cgc ttc gcg cag  aac ggt atc      3896
Lys Glu  Val Asp Val Ser Phe  Lys Arg Phe Ala Gln  Asn Gly Ile
    1200                 1205                 1210

gaa atc  aaa ggg gtt atc ctg  aac gcc gtg gta cgt  aaa gcg gct      3941
Glu Ile  Lys Gly Val Ile Leu  Asn Ala Val Val Arg  Lys Ala Ala
    1215                 1220                 1225

aac tcg  tac ggt tat ggt tat  gac tac tac gac tac  gag tac ggt      3986
Asn Ser  Tyr Gly Tyr Gly Tyr  Asp Tyr Tyr Asp Tyr  Glu Tyr Gly
    1230                 1235                 1240

aaa cca  acg aaa agc taa gagctgaaag aaaaggggcg ggtttgaccg           4034
Lys Pro  Thr Lys Ser
    1245

cccctttga tccctggctc atgataacga cacgtaacga tttgcacagg tgattctgga   4094

tacaacgcac aataagcgac gatctaacgt caatcatcag aattcatcat caacacgctt   4154

ttgtctgtcg cgatgtcggc gcagacctgc tgagagatca acccggaagg taatcagcac   4214

tggccactgt tggcatgaga acttgtggat ttaaggaatc acacc atg gct  cca      4268
                                                  Met Ala  Pro
                                                      1250

tat tgg tat ata  tca ggg ttt ttg ctg  ctg att tcg ctg ttc  gaa      4313
Tyr Trp Tyr Ile  Ser Gly Phe Leu Leu  Leu Ile Ser Leu Phe  Glu
            1255                 1260                 1265

atc ctg gtg aaa  aaa gac gaa cgc aca  aat tat att ttg acc  tgg      4358
Ile Leu Val Lys  Lys Asp Glu Arg Thr  Asn Tyr Ile Leu Thr  Trp
            1270                 1275                 1280

ctg ctg tgc ttt  gcg gcc att att ctg  atc gta ttc ggg ggg  att      4403
Leu Leu Cys Phe  Ala Ala Ile Ile Leu  Ile Val Phe Gly Gly  Ile
            1285                 1290                 1295

cgt ggc ctc ggc  acc ggc atg gat gac  ttc cag tac cgc agt  ttc      4448
Arg Gly Leu Gly  Thr Gly Met Asp Asp  Phe Gln Tyr Arg Ser  Phe
            1300                 1305                 1310

ttt gag gac ttt  gta cgg cgt att cag  atc aac ggt ttt ttc  aat      4493
Phe Glu Asp Phe  Val Arg Arg Ile Gln  Ile Asn Gly Phe Phe  Asn
            1315                 1320                 1325

acc gtc gcg ttt  ttc cgc tac gaa ccg  ctg att ttt gcg atg  gcg      4538
Thr Val Ala Phe  Phe Arg Tyr Glu Pro  Leu Ile Phe Ala Met  Ala
            1330                 1335                 1340

tgg ata acg agt  ctg ttt tcg cat aac  gcc agc gtg ttt ctg  ttc      4583
Trp Ile Thr Ser  Leu Phe Ser His Asn  Ala Ser Val Phe Leu  Phe
            1345                 1350                 1355

gtc ttc tgt gcg  att gcg gta tcc att  aac gcc ttc ttt ttc  aga      4628
Val Phe Cys Ala  Ile Ala Val Ser Ile  Asn Ala Phe Phe Phe  Arg
            1360                 1365                 1370

aag atg tcg cct  tat ccg gta ctg gcg  ctg gcg ctg tat tcg  gcg      4673
Lys Met Ser Pro  Tyr Pro Val Leu Ala  Leu Ala Leu Tyr Ser  Ala
            1375                 1380                 1385

cac atc ttt att  aac aaa gac atc aac  cag ata cgt ttt ggc  tta      4718
His Ile Phe Ile  Asn Lys Asp Ile Asn  Gln Ile Arg Phe Gly  Leu
            1390                 1395                 1400

agc tcc gcc ctg  ttc ctc ggc gtg ctg  tgg acg atc tac ctg  aag      4763
Ser Ser Ala Leu  Phe Leu Gly Val Leu  Trp Thr Ile Tyr Leu  Lys
            1405                 1410                 1415

cgt tac tgg tgg  gcc ttt acc ttt ttt  atc ctg tcg ttc atg  agt      4808
Arg Tyr Trp Trp  Ala Phe Thr Phe Phe  Ile Leu Ser Phe Met  Ser
            1420                 1425                 1430

cac aac acc gcc  gtt atg gtg ata acg  ctg gtg cct ttc ctg  ttt      4853
```

-continued

```
His Asn Thr Ala  Val Met Val Ile Thr  Leu Val Pro Phe Leu  Phe
            1435                 1440                 1445

att cgt gac tgg  cgc tgg tgg ccg gtg  gtg atc atc gtt gtc  agc      4898
Ile Arg Asp Trp  Arg Trp Trp Pro Val  Val Ile Ile Val Val  Ser
            1450                 1455                 1460

ctg ccg ctc tcg  gtc gtc ggg ggt tca  agc ttc atc gcc ctg  att      4943
Leu Pro Leu Ser  Val Val Gly Gly Ser  Ser Phe Ile Ala Leu  Ile
            1465                 1470                 1475

gcc gga cac ctc  gga tcg ctg ggg gaa  agg gca tcg ggc tat  aac      4988
Ala Gly His Leu  Gly Ser Leu Gly Glu  Arg Ala Ser Gly Tyr  Asn
            1480                 1485                 1490

aac gat ccc tcc  tat gca atg gat ggc  agc atc ctg tca gtc  tcg      5033
Asn Asp Pro Ser  Tyr Ala Met Asp Gly  Ser Ile Leu Ser Val  Ser
            1495                 1500                 1505

aac ctg aag aac  atc atg ctg gtg ttt  att ttc ttc tat ttc  atg      5078
Asn Leu Lys Asn  Ile Met Leu Val Phe  Ile Phe Phe Tyr Phe  Met
            1510                 1515                 1520

ctg act gaa gaa  ctg aag cgc gaa aac  tat gcc cag tat cgt  ctg      5123
Leu Thr Glu Glu  Leu Lys Arg Glu Asn  Tyr Ala Gln Tyr Arg  Leu
            1525                 1530                 1535

aac tac ttg ctg  att tta agt ttt gct  atc ggc ggg gcg atc  cgc      5168
Asn Tyr Leu Leu  Ile Leu Ser Phe Ala  Ile Gly Gly Ala Ile  Arg
            1540                 1545                 1550

atc ttc ctg tat  aac ttc ccg tca ggt  tcg cgt ctt tcc aac  tat      5213
Ile Phe Leu Tyr  Asn Phe Pro Ser Gly  Ser Arg Leu Ser Asn  Tyr
            1555                 1560                 1565

ttg caa cag gtt  gaa ccc atc att ctg  acc tcg ctt atc tac  cag      5258
Leu Gln Gln Val  Glu Pro Ile Ile Leu  Thr Ser Leu Ile Tyr  Gln
            1570                 1575                 1580

gcc aga cgc gtc  tgg aag ccg gcg ctg  ttt ggc atg ctg ttt  ttc      5303
Ala Arg Arg Val  Trp Lys Pro Ala Leu  Phe Gly Met Leu Phe  Phe
            1585                 1590                 1595

ttc ctg ctc tat  tac ctc tac tac aac  acc atc tca acc aag  cag      5348
Phe Leu Leu Tyr  Tyr Leu Tyr Tyr Asn  Thr Ile Ser Thr Lys  Gln
            1600                 1605                 1610

gcg gtt gta ggg  tac gaa gtg gcc cag  gag ttc tgg ctg att  cgg      5393
Ala Val Val Gly  Tyr Glu Val Ala Gln  Glu Phe Trp Leu Ile  Arg
            1615                 1620                 1625

taa cggacccggc ggcgcgcccc cagtgaacgg cttcacttcg cggggcggtc          5446

gcctgtaaca acacaggttt ttcttcggcg tttgtcgatt gaattgttta tttttgaata   5506

ctttaatgag gtgctggca atg aag gac att  cgt ttc tcc atc gta  att      5555
                     Met Lys Asp Ile  Arg Phe Ser Ile Val  Ile
                                 1630                 1635

ccg gct tat aac  gcg tca gaa tcg att  gtc acg acg ctg gat  tgc      5600
Pro Ala Tyr Asn  Ala Ser Glu Ser Ile  Val Thr Thr Leu Asp  Cys
            1640                 1645                 1650

gtt aaa gca caa  act tat cgc cat ttc  gaa gtc atc atc gtg  gat      5645
Val Lys Ala Gln  Thr Tyr Arg His Phe  Glu Val Ile Ile Val  Asp
            1655                 1660                 1665

gac aaa tct gcc  gat gcc gcc gcg ctg  gcg gaa gtg gtg cgc  agt      5690
Asp Lys Ser Ala  Asp Ala Ala Ala Leu  Ala Glu Val Val Arg  Ser
            1670                 1675                 1680

gag cgc tat cag  gac ctg gac atc aat  ctg gtc ttg tct gag  gtt      5735
Glu Arg Tyr Gln  Asp Leu Asp Ile Asn  Leu Val Leu Ser Glu  Val
            1685                 1690                 1695

aaa ctc aac ggt  gcc ggc gcg cgt aac  aaa ggc att gag ctg  gca      5780
Lys Leu Asn Gly  Ala Gly Ala Arg Asn  Lys Gly Ile Glu Leu  Ala
            1700                 1705                 1710
```

-continued

```
acg ggc gac tat  gtc agt ttt ctg gat  gcc gat gac gag tgg  cat      5825
Thr Gly Asp Tyr  Val Ser Phe Leu Asp  Ala Asp Asp Glu Trp  His
            1715                 1720                 1725

gcc gac aag ctt  ctg cag gtc agt gaa  aag att gcg gag cta  gag      5870
Ala Asp Lys Leu  Leu Gln Val Ser Glu  Lys Ile Ala Glu Leu  Glu
            1730                 1735                 1740

gcg cag ggt cag  cac aat acc att atc  ttc agc cag gta aat  atc      5915
Ala Gln Gly Gln  His Asn Thr Ile Ile  Phe Ser Gln Val Asn  Ile
            1745                 1750                 1755

tat cag gac ggt  gcg ttc ctg aag gtt  atg ccg atg cag cct  ccg      5960
Tyr Gln Asp Gly  Ala Phe Leu Lys Val  Met Pro Met Gln Pro  Pro
            1760                 1765                 1770

gca aaa aac gaa  act gtc gca gag tat  ctg ttt ggc tgt tat  ggc      6005
Ala Lys Asn Glu  Thr Val Ala Glu Tyr  Leu Phe Gly Cys Tyr  Gly
            1775                 1780                 1785

ttt att caa acc  agc acc atc gtg ctg  aag cgt gaa gat gcc  gct      6050
Phe Ile Gln Thr  Ser Thr Ile Val Leu  Lys Arg Glu Asp Ala  Ala
            1790                 1795                 1800

aaa att cag ttc  gat gcg cgt ttt atc  cgc cat cag gac tat  gac      6095
Lys Ile Gln Phe  Asp Ala Arg Phe Ile  Arg His Gln Asp Tyr  Asp
            1805                 1810                 1815

ttc tgc atc cgt  gcc gac cgc atg ggt  tac cgg ttt gaa atg  atc      6140
Phe Cys Ile Arg  Ala Asp Arg Met Gly  Tyr Arg Phe Glu Met  Ile
            1820                 1825                 1830

gcc gcc ccg ctg  gcc aac tac cac ctg  gtg acg aag ttt ggc  tcc      6185
Ala Ala Pro Leu  Ala Asn Tyr His Leu  Val Thr Lys Phe Gly  Ser
            1835                 1840                 1845

aaa cac aaa ggt  gaa tcg gtc aag tac  tcc ctg ttc tgg ctg  gat      6230
Lys His Lys Gly  Glu Ser Val Lys Tyr  Ser Leu Phe Trp Leu  Asp
            1850                 1855                 1860

acg atg aaa ccg  cac ctt acc gca cga  gat att cac acc tac  aaa      6275
Thr Met Lys Pro  His Leu Thr Ala Arg  Asp Ile His Thr Tyr  Lys
            1865                 1870                 1875

gca ttc aag ctg  ccc ctg cgc tac aaa  atg gac ggt aac tcg  ctg      6320
Ala Phe Lys Leu  Pro Leu Arg Tyr Lys  Met Asp Gly Asn Ser  Leu
            1880                 1885                 1890

atg gcg agc gtc  agc ttc gcg cgc tac  ttc ctg ctc acc aat  aaa      6365
Met Ala Ser Val  Ser Phe Ala Arg Tyr  Phe Leu Leu Thr Asn  Lys
            1895                 1900                 1905

gat aat cgc acc  tac ttc ctg aac cgc  gtg aaa gac aaa ctg  aaa      6410
Asp Asn Arg Thr  Tyr Phe Leu Asn Arg  Val Lys Asp Lys Leu  Lys
            1910                 1915                 1920

gcg cgg ttg ggt  ggc gaa aag gca ctc  tcc tga ttctattgaa            6453
Ala Arg Leu Gly  Gly Glu Lys Ala Leu  Ser
            1925                 1930

tgtcgtgacg ttttaacgct accggaaggt tatctggtgg ccccgtctat tttatttatt   6513

caggtatgaa aatgaataat cactctggta ccgtcgg                            6550


<210> SEQ ID NO 67
<211> LENGTH: 379
<212> TYPE: PRT
<213> ORGANISM: Pantoea ananatis

<400> SEQUENCE: 67

Met Ile Thr Met Lys Met Lys Met Ile Pro Val Leu Val Ser Ala Thr
1               5                   10                  15

Phe Met Ala Gly Cys Thr Val Val Pro Gly Gln Asn Leu Ser Thr Ser
            20                  25                  30

Gly Lys Asp Val Ile Glu Gln Gln Asp Ser Asn Phe Asp Ile Asp Lys
```

-continued

```
        35                  40                  45

Tyr Val Asn Val Tyr Pro Leu Thr Pro Gly Leu Val Glu Lys Met Arg
    50                  55                  60

Pro Lys Pro Leu Val Ala Gln Ala Asn Pro Ser Leu Gln Thr Glu Ile
65                  70                  75                  80

Gln Asn Tyr Glu Tyr Arg Ile Gly Ile Gly Asp Val Leu Thr Val Thr
                85                  90                  95

Val Trp Asp His Pro Glu Leu Thr Thr Pro Ala Gly Gln Tyr Arg Ser
            100                 105                 110

Ala Ser Asp Thr Gly Asn Trp Val His Ser Asp Gly Thr Ile Phe Tyr
        115                 120                 125

Pro Tyr Ile Gly Arg Val Arg Val Ala Gly Arg Thr Val Gly Asp Val
    130                 135                 140

Arg Asn Glu Val Ala Arg Arg Leu Ala Gln Tyr Ile Glu Ser Pro Gln
145                 150                 155                 160

Val Asp Val Ser Ile Ala Ser Phe Lys Ser Gln Lys Thr Tyr Val Thr
                165                 170                 175

Gly Ala Val Thr Thr Ser Gly Gln Gln Pro Ile Thr Asn Val Pro Leu
            180                 185                 190

Thr Ile Leu Asp Ala Ile Asn Ala Ala Gly Gly Leu Ala Ala Asp Ala
        195                 200                 205

Asp Trp Arg Asn Val Ile Leu Thr His Asn Gly Arg Glu Gln Arg Val
    210                 215                 220

Ser Leu Gln Ala Leu Met Gln Asn Gly Asp Leu Ser Gln Asn His Leu
225                 230                 235                 240

Leu Tyr Pro Gly Asp Ile Leu Tyr Val Pro Arg Asn Asp Asp Leu Lys
                245                 250                 255

Val Phe Val Met Gly Glu Val Lys Gln Gln Ala Thr Leu Lys Met Asp
            260                 265                 270

Arg Ser Gly Met Thr Leu Ala Glu Ala Leu Gly Asn Ala Ala Gly Met
        275                 280                 285

Asp Gln Thr Thr Ser Asp Ala Thr Gly Val Phe Val Ile Arg Pro Thr
    290                 295                 300

Arg Gly Ser Asp Arg Ser Lys Ile Ala Asn Ile Tyr Gln Leu Asn Thr
305                 310                 315                 320

Lys Asp Ala Ala Ser Met Val Met Gly Thr Glu Phe Gln Leu Glu Pro
                325                 330                 335

Tyr Asp Ile Val Tyr Val Thr Ser Thr Pro Leu Thr Arg Trp Asn Arg
            340                 345                 350

Val Ile Ser Gln Leu Ile Pro Thr Ile Ala Gly Val Asn Asp Ala Thr
        355                 360                 365

Gln Ala Ala Gln Arg Ile Arg Asn Trp Ser Asn
    370                 375


<210> SEQ ID NO 68
<211> LENGTH: 144
<212> TYPE: PRT
<213> ORGANISM: Pantoea ananatis

<400> SEQUENCE: 68

Met Ile Lys Ser Val Leu Val Val Cys Val Gly Asn Ile Cys Arg Ser
1               5                   10                  15

Pro Thr Gly Glu Arg Leu Phe Lys Arg Ala Leu Pro His Leu Pro Val
            20                  25                  30
```

Ala Ser Ala Gly Leu Gly Ala Leu Val Gly His Ala Ala Asp Lys Thr
35 40 45

Ala Thr Glu Val Ala Ala Glu Lys Gly Leu Ser Leu Glu Gly His Glu
50 55 60

Ala Gln Gln Leu Thr Ala Ser Leu Cys Arg Glu Tyr Asp Leu Ile Leu
65 70 75 80

Val Met Glu Lys Arg His Ile Glu Gln Val Asn Arg Ile Asp Pro Ala
85 90 95

Ala Arg Gly Lys Thr Met Leu Leu Gly His Trp Leu Asn Gln Lys Glu
100 105 110

Ile Ala Asp Pro Tyr Arg Lys Ser Arg Glu Ala Phe Glu Glu Val Tyr
115 120 125

Gly Leu Leu Glu His Ala Thr Gln Lys Trp Val Ser Val Leu Ser Arg
130 135 140

<210> SEQ ID NO 69
<211> LENGTH: 725
<212> TYPE: PRT
<213> ORGANISM: Pantoea ananatis

<400> SEQUENCE: 69

Met Asn Ile Lys Asn Lys Val Met Thr Ala Pro Arg Glu Glu Ser Asn
1 5 10 15

Gly Trp Asp Leu Ala His Leu Val Gly Gln Leu Ile Asp His Arg Trp
20 25 30

Val Ile Val Ala Val Thr Ala Phe Phe Met Leu Val Ala Thr Leu Tyr
35 40 45

Thr Leu Phe Ala Thr Pro Ile Tyr Ser Ala Asp Ala Met Val Gln Val
50 55 60

Glu Gln Lys Asn Thr Ser Thr Val Leu Asn Glu Leu Gln Thr Leu Met
65 70 75 80

Pro Thr Thr Pro Ala Ser Asp Thr Glu Ile Gln Ile Leu Glu Ser Arg
85 90 95

Met Val Leu Gly Lys Thr Val Gln Asp Leu Gly Leu Asp Ala Val Val
100 105 110

Ser Gln Asn Tyr Phe Pro Val Ile Gly Lys Gly Leu Ser Arg Leu Met
115 120 125

Gly Asn Lys Pro Gly Asn Val Ala Ile Ser Arg Leu Glu Ile Pro Arg
130 135 140

Thr Ile Glu Lys Arg Ser Val Glu Leu Glu Val Thr Gly Lys Asp Ser
145 150 155 160

Tyr Thr Val Ser Ala Asp Gly Asp Glu Leu Phe Lys Gly Lys Val Gly
165 170 175

Gln Phe Glu Lys His Gly Asp Val Ser Met Leu Val Ser Asp Ile Asn
180 185 190

Ala Glu Pro Gly Thr Thr Phe Thr Val Thr Lys Leu Asn Asp Leu Gln
195 200 205

Ala Ile Asn Ser Ile Leu Ser Asn Leu Thr Val Ala Asp Lys Gly Lys
210 215 220

Asp Thr Gly Val Leu Gly Leu Gln Tyr Val Gly Glu Asp Gln Glu Gln
225 230 235 240

Ile Ser Lys Val Leu Asn Gln Ile Val Asn Asn Tyr Leu Leu Gln Asn
245 250 255

Val Gln Arg Lys Ser Glu Gln Ala Glu Lys Ser Leu Glu Phe Leu Lys
260 265 270

-continued

```
Gln Gln Leu Pro Glu Val Arg Gly Lys Leu Asp Gln Ala Glu Asp Lys
        275                 280                 285

Leu Asn Ala Phe Arg Arg Glu Asn Glu Ser Val Asp Leu Ser Leu Glu
    290                 295                 300

Ala Lys Ser Ala Leu Asp Ser Ser Val Ser Val Gln Ser Gln Leu Asn
305                 310                 315                 320

Glu Leu Thr Phe Arg Glu Ala Glu Val Ser Gln Leu Phe Thr Lys Asp
                325                 330                 335

His Pro Thr Tyr Arg Ala Leu Leu Glu Lys Arg Lys Thr Leu Glu Asp
            340                 345                 350

Glu Gln Ala Gln Leu Asn Lys Lys Ile Ala Gln Met Pro Lys Thr Gln
        355                 360                 365

Gln Glu Ile Leu Arg Leu Thr Arg Asp Val Gln Ser Gly Gln Glu Ile
    370                 375                 380

Tyr Met Gln Leu Leu Asn Arg Gln Gln Glu Leu Ser Ile Ser Lys Ala
385                 390                 395                 400

Ser Thr Val Gly Asp Val Arg Ile Ile Asp Gln Ala Ala Thr Ala Asn
                405                 410                 415

Ser Pro Val Ala Pro Lys Lys Leu Leu Ile Ile Ala Ala Ser Leu Ile
            420                 425                 430

Leu Gly Leu Met Val Ser Val Gly Val Val Leu Leu Lys Ala Leu Leu
        435                 440                 445

His His Gly Ile Glu Asn Pro Glu Gln Leu Glu Glu Leu Gly Met Asn
    450                 455                 460

Val Tyr Ala Ser Val Pro Leu Ser Glu Trp Gln Arg Lys Lys Asp Thr
465                 470                 475                 480

Glu Ala Leu Ala Arg Arg Gly His Lys Gly Lys Thr Asp Pro His Glu
                485                 490                 495

Thr Leu Leu Ala Leu Gly Asn Pro Thr Asp Leu Ser Ile Glu Ala Ile
            500                 505                 510

Arg Ser Leu Arg Thr Ser Leu His Phe Ala Met Met Glu Ala Lys Asn
        515                 520                 525

Asn Ile Leu Met Ile Thr Gly Ala Ser Pro Gly Ile Gly Lys Thr Phe
    530                 535                 540

Ile Cys Val Asn Leu Ala Thr Leu Val Ala Lys Ala Gly Gln Lys Val
545                 550                 555                 560

Leu Phe Ile Asp Gly Asp Met Arg Arg Gly Tyr Thr His Glu Leu Leu
                565                 570                 575

Gly Ala Asp Asn Lys Ser Gly Leu Ser Asn Val Leu Ser Gly Lys Thr
            580                 585                 590

Glu Phe Thr Pro Thr Met Ile Gln Gln Gly Pro Tyr Gly Phe Asp Phe
        595                 600                 605

Leu Pro Arg Gly Gln Val Pro Pro Asn Pro Ser Glu Leu Leu Met His
    610                 615                 620

Arg Arg Met Gly Glu Leu Leu Glu Trp Ala Ser Lys Asn Tyr Asp Leu
625                 630                 635                 640

Val Leu Ile Asp Thr Pro Pro Ile Leu Ala Val Thr Asp Ala Ser Ile
                645                 650                 655

Ile Gly Lys Leu Ala Gly Thr Ser Leu Met Val Ala Arg Phe Glu Thr
            660                 665                 670

Asn Thr Thr Lys Glu Val Asp Val Ser Phe Lys Arg Phe Ala Gln Asn
        675                 680                 685
```

-continued

Gly Ile Glu Ile Lys Gly Val Ile Leu Asn Ala Val Val Arg Lys Ala
    690                 695                 700

Ala Asn Ser Tyr Gly Tyr Gly Tyr Asp Tyr Tyr Asp Tyr Glu Tyr Gly
705                 710                 715                 720

Lys Pro Thr Lys Ser
                725

<210> SEQ ID NO 70
<211> LENGTH: 378
<212> TYPE: PRT
<213> ORGANISM: Pantoea ananatis

<400> SEQUENCE: 70

Met Ala Pro Tyr Trp Tyr Ile Ser Gly Phe Leu Leu Leu Ile Ser Leu
1               5                   10                  15

Phe Glu Ile Leu Val Lys Lys Asp Glu Arg Thr Asn Tyr Ile Leu Thr
            20                  25                  30

Trp Leu Leu Cys Phe Ala Ala Ile Ile Leu Ile Val Phe Gly Gly Ile
        35                  40                  45

Arg Gly Leu Gly Thr Gly Met Asp Asp Phe Gln Tyr Arg Ser Phe Phe
    50                  55                  60

Glu Asp Phe Val Arg Arg Ile Gln Ile Asn Gly Phe Phe Asn Thr Val
65                  70                  75                  80

Ala Phe Phe Arg Tyr Glu Pro Leu Ile Phe Ala Met Ala Trp Ile Thr
                85                  90                  95

Ser Leu Phe Ser His Asn Ala Ser Val Phe Leu Phe Val Phe Cys Ala
            100                 105                 110

Ile Ala Val Ser Ile Asn Ala Phe Phe Phe Arg Lys Met Ser Pro Tyr
        115                 120                 125

Pro Val Leu Ala Leu Ala Leu Tyr Ser Ala His Ile Phe Ile Asn Lys
    130                 135                 140

Asp Ile Asn Gln Ile Arg Phe Gly Leu Ser Ser Ala Leu Phe Leu Gly
145                 150                 155                 160

Val Leu Trp Thr Ile Tyr Leu Lys Arg Tyr Trp Trp Ala Phe Thr Phe
                165                 170                 175

Phe Ile Leu Ser Phe Met Ser His Asn Thr Ala Val Met Val Ile Thr
            180                 185                 190

Leu Val Pro Phe Leu Phe Ile Arg Asp Trp Arg Trp Trp Pro Val Val
        195                 200                 205

Ile Ile Val Val Ser Leu Pro Leu Ser Val Val Gly Gly Ser Ser Phe
    210                 215                 220

Ile Ala Leu Ile Ala Gly His Leu Gly Ser Leu Gly Glu Arg Ala Ser
225                 230                 235                 240

Gly Tyr Asn Asn Asp Pro Ser Tyr Ala Met Asp Gly Ser Ile Leu Ser
                245                 250                 255

Val Ser Asn Leu Lys Asn Ile Met Leu Val Phe Ile Phe Phe Tyr Phe
            260                 265                 270

Met Leu Thr Glu Glu Leu Lys Arg Glu Asn Tyr Ala Gln Tyr Arg Leu
        275                 280                 285

Asn Tyr Leu Leu Ile Leu Ser Phe Ala Ile Gly Gly Ala Ile Arg Ile
    290                 295                 300

Phe Leu Tyr Asn Phe Pro Ser Gly Ser Arg Leu Ser Asn Tyr Leu Gln
305                 310                 315                 320

Gln Val Glu Pro Ile Ile Leu Thr Ser Leu Ile Tyr Gln Ala Arg Arg
                325                 330                 335

```
Val Trp Lys Pro Ala Leu Phe Gly Met Leu Phe Phe Phe Leu Leu Tyr
            340                 345                 350

Tyr Leu Tyr Tyr Asn Thr Ile Ser Thr Lys Gln Ala Val Val Gly Tyr
        355                 360                 365

Glu Val Ala Gln Glu Phe Trp Leu Ile Arg
    370                 375


<210> SEQ ID NO 71
<211> LENGTH: 305
<212> TYPE: PRT
<213> ORGANISM: Pantoea ananatis

<400> SEQUENCE: 71

Met Lys Asp Ile Arg Phe Ser Ile Val Ile Pro Ala Tyr Asn Ala Ser
1               5                   10                  15

Glu Ser Ile Val Thr Thr Leu Asp Cys Val Lys Ala Gln Thr Tyr Arg
            20                  25                  30

His Phe Glu Val Ile Ile Val Asp Asp Lys Ser Ala Asp Ala Ala Ala
        35                  40                  45

Leu Ala Glu Val Val Arg Ser Glu Arg Tyr Gln Asp Leu Asp Ile Asn
    50                  55                  60

Leu Val Leu Ser Glu Val Lys Leu Asn Gly Ala Gly Ala Arg Asn Lys
65                  70                  75                  80

Gly Ile Glu Leu Ala Thr Gly Asp Tyr Val Ser Phe Leu Asp Ala Asp
                85                  90                  95

Asp Glu Trp His Ala Asp Lys Leu Leu Gln Val Ser Glu Lys Ile Ala
            100                 105                 110

Glu Leu Glu Ala Gln Gly Gln His Asn Thr Ile Ile Phe Ser Gln Val
        115                 120                 125

Asn Ile Tyr Gln Asp Gly Ala Phe Leu Lys Val Met Pro Met Gln Pro
    130                 135                 140

Pro Ala Lys Asn Glu Thr Val Ala Glu Tyr Leu Phe Gly Cys Tyr Gly
145                 150                 155                 160

Phe Ile Gln Thr Ser Thr Ile Val Leu Lys Arg Glu Asp Ala Ala Lys
                165                 170                 175

Ile Gln Phe Asp Ala Arg Phe Ile Arg His Gln Asp Tyr Asp Phe Cys
            180                 185                 190

Ile Arg Ala Asp Arg Met Gly Tyr Arg Phe Glu Met Ile Ala Ala Pro
        195                 200                 205

Leu Ala Asn Tyr His Leu Val Thr Lys Phe Gly Ser Lys His Lys Gly
    210                 215                 220

Glu Ser Val Lys Tyr Ser Leu Phe Trp Leu Asp Thr Met Lys Pro His
225                 230                 235                 240

Leu Thr Ala Arg Asp Ile His Thr Tyr Lys Ala Phe Lys Leu Pro Leu
                245                 250                 255

Arg Tyr Lys Met Asp Gly Asn Ser Leu Met Ala Ser Val Ser Phe Ala
            260                 265                 270

Arg Tyr Phe Leu Leu Thr Asn Lys Asp Asn Arg Thr Tyr Phe Leu Asn
        275                 280                 285

Arg Val Lys Asp Lys Leu Lys Ala Arg Leu Gly Gly Glu Lys Ala Leu
    290                 295                 300

Ser
305
```

<210> SEQ ID NO 72
<211> LENGTH: 89
<212> TYPE: DNA
<213> ORGANISM: Artificial Sequence
<220> FEATURE:
<223> OTHER INFORMATION: primer

<400> SEQUENCE: 72
caagttgata agatcttccg tgccgccgct ctggccgctg cagatgctcg aatccctctc 60
tgaagcctgc ttttttatac taagttggc 89

<210> SEQ ID NO 73
<211> LENGTH: 89
<212> TYPE: DNA
<213> ORGANISM: Artificial Sequence
<220> FEATURE:
<223> OTHER INFORMATION: primer

<400> SEQUENCE: 73
acgtgagcca ggaaatcagc ttcctgaacg ccggcttcgc gaatagattt cggaataccc 60
gctcaagtta gtataaaaaa gctgaacga 89

<210> SEQ ID NO 74
<211> LENGTH: 2688
<212> TYPE: DNA
<213> ORGANISM: Enterobacter aerogenes
<220> FEATURE:
<221> NAME/KEY: misc_feature
<222> LOCATION: (663)..(663)
<223> OTHER INFORMATION: n is a, c, g, or t
<220> FEATURE:
<221> NAME/KEY: misc_feature
<222> LOCATION: (1303)..(1303)
<223> OTHER INFORMATION: n is a, c, g, or t
<220> FEATURE:
<221> NAME/KEY: misc_feature
<222> LOCATION: (1869)..(1869)
<223> OTHER INFORMATION: n is a, c, g, or t
<220> FEATURE:
<221> NAME/KEY: misc_feature
<222> LOCATION: (2609)..(2610)
<223> OTHER INFORMATION: n is a, c, g, or t
<220> FEATURE:
<221> NAME/KEY: misc_feature
<222> LOCATION: (2618)..(2618)
<223> OTHER INFORMATION: n is a, c, g, or t

<400> SEQUENCE: 74
tcgcatgctc ccggccgcca tggccgcggg attctcgttg agcgtgtaaa aaaagcccag 60
cattgaatat gccagtttca ctcaagaaca agttgataag atcttccgtg ccgccgctct 120
ggccgctgca gatgctcgaa tccctctcgc taaaatggct gttgccgaat ccggcatggg 180
tattattgaa gataaagtga tcaaaaacca cttcgcttcc gaatatatct acaacgccta 240
taaagatgaa aagacctgtg gcgtcctgtc tgaagacgac actttcggta ccatcaccat 300
tgctgagcca atcggtatta tttgcggtat cgtcccgact accaacccga cttctactgc 360
tatcttcaaa tcgctgatca gcctgaagac gcgtaacgcc atcatcttct ctccgcaccc 420
gcgtgctgct aaagacgcga ctaacaaagc ggcggacatc gtattgcagg cagctattgc 480
cgcaggcgcg ccgaaagatc tgatcggttg gatcgaccag ccttccgtag aactgtctaa 540
cgcactgatg catcatcctg acatcaacct gatcctcgcc accggcggcc caggtatggt 600
taaggccgct tatagctccg gtaaaccagc tatcggcgtt ggcgcgggca acacgccggt 660
tgntattgat gaaacggctg atatcaaacg cgctgtggcg tccgtactga tgtcaaaaac 720

-continued

```
cttcgataac ggcgttatct gtgcttctga acaatccgtg gtggttgtcg actccgtcta    780

cgacgccgtc cgcgagcgtt ttgccagcca tggcggctac ctgctgcagg gtaaagagct    840

gaaagccgtt caggacatca tcctgaaaaa tggcgcgctg aatgcggcga tcgttggtca    900

accagcggca aaaatcgctg aactggcagg cttcaccgtg ccagccacca ctaagattct    960

gatcggcgaa gttaccgacg ttgacgaaag cgaaccgttc gctcacgaaa aactgtctcc   1020

gacgctggca atgtaccgtg cgaaagattt cgaagacgcg gtcaataaag cagaaaaact   1080

ggtcgccatg ggcggtatcg gtcacacctc ttgcctgtac accgaccagg acaaccagcc   1140

ggctcgcgtg gcctacttcg gccagatgat gaaaaccgcg cgtatcctga tcaacacccc   1200

ggcttcccag ggtggtatcg gcgacctgta taacttcaag ctcgcacctt ccctgactct   1260

gggttgtggt tcctggggtg gtaactccat ctctgaaaac gtnggtccga aacacctgat   1320

caacaagaaa accgttgcta agcgagctga aaacatgttg tggcataaac ttccgaaatc   1380

tatctacttc cgtcgtggct cactgccaat cgcactggat gaagtgatta ctgatggtca   1440

caaacgcgcg ctgattgtga ctgaccgctt cctgttcaac aacggttacg cggaccagat   1500

cacttccgta ctgaaagcgg ctggcgtaga aaccgaagtg ttctttgaag ttgaagctga   1560

cccaacgctg actatcgtgc gtaaaggcgc ggatctggcc aactccttca aaccagacgt   1620

aatcatcgcc ctgggcggcg gttccccgat ggatgcggca aaaatcatgt gggtcatgta   1680

cgagcacccg gaaacccact tcgaagaact ggcgctgcgc tttatggata tccgtaaacg   1740

tatctacaag ttcccgaaaa tgggcgtcaa agccaagatg gttgccatta ccaccacctc   1800

cggtaccggt tctgaagtta ccccgttcgc cgtagtaacc gacgatgcaa ctggacagaa   1860

atatccgcng gctgactacg ctctgactcc ggatatggcg attgtcgatg ccaacctggt   1920

catggatatg ccgaagtctc tctgtgcctt cggtggtctg gatgccgtga ctcacgctct   1980

ggaagcttac gtctccgtac tggcttctga gttctccgat ggtcaggctc tgcaggcgct   2040

gaaactgctg aaagagtatc tgccggcctc ttaccatgaa ggttctaaga acccggtagc   2100

ccgcgaacgt gtgcacagcg ccgccactat cgccggtatc gcgtttgcta acgccttcct   2160

cggcgtgtgc cactcaatgg cgcacaaact gggctcgcag ttccacattc ctcacggtct   2220

ggcaaacgcc ctgctgatca gcaacgttat ccgctataac gcgaatgaca acccgaccaa   2280

gcagaccgca ttcagccagt atgaccgtcc gcaggcgcgc cgtcgctacg ctgagatcgc   2340

agaccacctg ggcctgagcg ctccgggcga ccgcactgcg gcgaaaatcg agaaactgct   2400

ggcatggctg gaaagcctca aagctgaact gggtattccg aaatctatcc gtgaagctgg   2460

cgttcaggaa gcagacttcc tggcgaacgt ggataaactg tctgaagatg cattcgatga   2520

ccagtgcacc ggcgctaacc cgcgttaccc gctgatctcc gagctgaaac agattctgct   2580

ggatacctac tacggtcgtg atttatgtnn agaaggtnga aactgcagcg aagaaagaag   2640

ctgctccggc taaagctgag aaaaaagcga aaaaatccgc ttaatcag                2688
```

<210> SEQ ID NO 75
<211> LENGTH: 30
<212> TYPE: DNA
<213> ORGANISM: Artificial Sequence
<220> FEATURE:
<223> OTHER INFORMATION: primer

<400> SEQUENCE: 75

```
aagagctccg cgaacgagcc atgacattgc                                      30
```

<210> SEQ ID NO 76
<211> LENGTH: 43
<212> TYPE: DNA
<213> ORGANISM: Artificial Sequence
<220> FEATURE:
<223> OTHER INFORMATION: primer

<400> SEQUENCE: 76
gtcgacacac gtcattcctc cttgtcgcct atattggtta aag 43

<210> SEQ ID NO 77
<211> LENGTH: 361
<212> TYPE: DNA
<213> ORGANISM: Enterobacter aerogenes

<400> SEQUENCE: 77
aagagctccg cgaacgagcc atgacattgc tgacgactct ggcagtggca gatgacataa 60
aactggtcga ctggttacaa caacgcctgg ggcttttaga gcaacgagac acggcaatgt 120
tgcaccgttt gctgcatgat attgaaaaaa atatcaccaa ataaaaaacg ccttagtaag 180
tatttttcag cttttcattc tgactgcaac gggcaatatg tctctgtgtg gattaaaaaa 240
agagtgtctg atagcagctt ctgaactggt tacctgccgt gagtaaatta aaattttatt 300
gacttaggtc actaaatact ttaaccaata taggcgacaa ggaggaatga cgtgtgtcga 360
c 361

<210> SEQ ID NO 78
<211> LENGTH: 44
<212> TYPE: DNA
<213> ORGANISM: Artificial Sequence
<220> FEATURE:
<223> OTHER INFORMATION: primer

<400> SEQUENCE: 78
aaggaggaat gacgtgtgtc gactcacaca tcttcaacgc ttcc 44

<210> SEQ ID NO 79
<211> LENGTH: 28
<212> TYPE: DNA
<213> ORGANISM: Artificial Sequence
<220> FEATURE:
<223> OTHER INFORMATION: primer

<400> SEQUENCE: 79
ttgagctctt tttacagaaa ggtttagg 28

<210> SEQ ID NO 80
<211> LENGTH: 3461
<212> TYPE: DNA
<213> ORGANISM: Corynebacterium glutamicum

<400> SEQUENCE: 80
aaggaggaat gacgtgtgtc gactcacaca tcttcaacgc ttccagcatt caaaaagatc 60
ttggtagcaa accgcggcga aatcgcggtc cgtgctttcc gtgcagcact cgaaaccggt 120
gcagccacgg tagctattta cccccgtgaa gatcggggat cattccaccg ctcttttgct 180
tctgaagctg tccgcattgg taccgaaggc tcaccagtca aggcgtacct ggacatcgat 240
gaaattatcg gtgcagctaa aaaagttaaa gcagatgcca tttacccggg atacggcttc 300
ctgtctgaaa atgcccagct tgcccgcgag tgtgcggaaa acggcattac ttttattggc 360
ccaaccccag aggttcttga tctcaccggt gataagtctc gcgcggtaac cgccgcgaag 420

-continued

```
aaggctggtc tgccagtttt ggcggaatcc accccgagca aaaacatcga tgagatcgtt    480
aaaagcgctg aaggccagac ttaccccatc tttgtgaagg cagttgccgg tggtggcgga    540
cgcggtatgc gttttgttgc ttcacctgat gagcttcgca aattagcaac agaagcatct    600
cgtgaagctg aagcggcttt cggcgatggc gcggtatatg tcgaacgtgc tgtgattaac    660
cctcagcata ttgaagtgca gatccttggc gatcacactg gagaagttgt acacctttat    720
gaacgtgact gctcactgca gcgtcgtcac caaaaagttg tcgaaattgc gccagcacag    780
catttggatc cagaactgcg tgatcgcatt tgtgcggatg cagtaaagtt ctgccgctcc    840
attggttacc agggcgcggg aaccgtggaa ttcttggtcg atgaaaaggg caaccacgtc    900
ttcatcgaaa tgaacccacg tatccaggtt gagcacaccg tgactgaaga agtcaccgag    960
gtggacctgg tgaaggcgca gatgcgcttg gctgctggtg caaccttgaa ggaattgggt   1020
ctgacccaag ataagatcaa gacccacggt gcagcactgc agtgccgcat caccacggaa   1080
gatccaaaca acggcttccg cccagatacc ggaactatca ccgcgtaccg ctcaccaggc   1140
ggagctggcg ttcgtcttga cggtgcagct cagctcggtg gcgaaatcac cgcacacttt   1200
gactccatgc tggtgaaaat gacctgccgt ggttccgact ttgaaactgc tgttgctcgt   1260
gcacagcgcg cgttggctga gttcaccgtg tctggtgttg caaccaacat tggtttcttg   1320
cgtgcgttgc tgcgggaaga ggacttcact tccaagcgca tcgccaccgg attcattgcc   1380
gatcacccgc acctccttca ggctccacct gctgatgatg agcagggacg catcctggat   1440
tacttggcag atgtcaccgt gaacaagcct catggtgtgc gtccaaagga tgttgcagct   1500
cctatcgata agctgcctaa catcaaggat ctgccactgc cacgcggttc ccgtgaccgc   1560
ctgaagcagc ttggcccagc cgcgtttgct cgtgatctcc gtgagcagga cgcactggca   1620
gttactgata ccaccttccg cgatgcacac cagtctttgc ttgcgacccg agtccgctca   1680
ttcgcactga agcctgcggc agaggccgtc gcaaagctga ctcctgagct tttgtccgtg   1740
gaggcctggg gcggcgcgac ctacgatgtg gcgatgcgtt tcctctttga ggatccgtgg   1800
gacaggctcg acgagctgcg cgaggcgatg ccgaatgtaa acattcagat gctgcttcgc   1860
ggccgcaaca ccgtgggata caccccgtac ccagactccg tctgccgcgc gtttgttaag   1920
gaagctgcca gctccggcgt ggacatcttc cgcatcttcg acgcgcttaa cgacgtctcc   1980
cagatgcgtc cagcaatcga cgcagtcctg gagaccaaca ccgcggtagc cgaggtggct   2040
atggcttatt ctggtgatct ctctgatcca aatgaaaagc tctacaccct ggattactac   2100
ctaaagatgg cagaggagat cgtcaagtct ggcgctcaca tcttggccat taaggatatg   2160
gctggtctgc ttcgcccagc tgcggtaacc aagctggtca ccgcactgcg ccgtgaattc   2220
gatctgccag tgcacgtgca cacccacgac actgcgggtg gccagctggc aacctacttt   2280
gctgcagctc aagctggtgc agatgctgtt gacggtgctt ccgcaccact gtctggcacc   2340
acctcccagc catccctgtc tgccattgtt gctgcattcg cgcacacccg tcgcgatacc   2400
ggtttgagcc tcgaggctgt ttctgacctc gagccgtact gggaagcagt gcgcggactg   2460
tacctgccat ttgagtctgg aaccccaggc ccaaccggtc gcgtctaccg ccacgaaatc   2520
ccaggcggac agttgtccaa cctgcgtgca caggccaccg cactgggcct tgcggatcgt   2580
ttcgaactca tcgaagacaa ctacgcagcc gttaatgaga tgctgggacg cccaaccaag   2640
gtcaccccat cctccaaggt tgttggcgac ctcgcactcc acctcgttgg tgcgggtgtg   2700
gatccagcag actttgctgc cgatccacaa aagtacgaca tcccagactc tgtcatcgcg   2760
ttcctgcgcg gcgagcttgg taaccctcca ggtggctggc cagagccact gcgcacccgc   2820
```

gcactggaag gccgctccga aggcaaggca cctctgacgg aagttcctga ggaagagcag 2880
gcgcacctcg acgctgatga ttccaaggaa cgtcgcaata gcctcaaccg cctgctgttc 2940
ccgaagccaa ccgaagagtt cctcgagcac cgtcgccgct tcggcaacac ctctgcgctg 3000
gatgatcgtg aattcttcta cggcctggtc gaaggccgcg agactttgat ccgcctgcca 3060
gatgtgcgca ccccactgct tgttcgcctg gatgcgatct ctgagccaga cgataagggt 3120
atgcgcaatg ttgtggccaa cgtcaacggc cagatccgcc caatgcgtgt gcgtgaccgc 3180
tccgttgagt ctgtcaccgc aaccgcagaa aaggcagatt cctccaacaa gggccatgtt 3240
gctgcaccat tcgctggtgt tgtcaccgtg actgttgctg aaggtgatga ggtcaaggct 3300
ggagatgcag tcgcaatcat cgaggctatg aagatggaag caacaatcac tgcttctgtt 3360
gacggcaaaa tcgatcgcgt tgtggttcct gctgcaacga aggtggaagg tggcgacttg 3420
atcgtcgtcg tttcctaaac ctttctgtaa aaagagctca a 3461

<210> SEQ ID NO 81
<211> LENGTH: 32
<212> TYPE: DNA
<213> ORGANISM: Artificial Sequence
<220> FEATURE:
<223> OTHER INFORMATION: primer

<400> SEQUENCE: 81
aagcatgcta cgcgaacgag ccatgacatt gc 32

<210> SEQ ID NO 82
<211> LENGTH: 38
<212> TYPE: DNA
<213> ORGANISM: Artificial Sequence
<220> FEATURE:
<223> OTHER INFORMATION: primer

<400> SEQUENCE: 82
catacgtcat tcctccttgt cgcctatatt ggttaaag 38

<210> SEQ ID NO 83
<211> LENGTH: 357
<212> TYPE: DNA
<213> ORGANISM: Eschericia coli

<400> SEQUENCE: 83
aagcatgctc gcgaacgagc catgacattg ctgacgactc tggcagtggc agatgacata 60
aaactggtcg actggttaca acaacgcctg gggcttttag agcaacgaga cacggcaatg 120
ttgcaccgtt tgctgcatga tattgaaaaa aatatcacca aataaaaaac gccttagtaa 180
gtatttttca gcttttcatt ctgactgcaa cgggcaatat gtctctgtgt ggattaaaaa 240
aagagtgtct gatagcagct tctgaactgg ttacctgccg tgagtaaatt aaaattttat 300
tgacttaggt cactaaatac tttaaccaat ataggcgaca aggaggaatg acgtatg 357

<210> SEQ ID NO 84
<211> LENGTH: 37
<212> TYPE: DNA
<213> ORGANISM: Artificial Sequence
<220> FEATURE:
<223> OTHER INFORMATION: primer

<400> SEQUENCE: 84
gacaaggagg aatgacgtat gaatataaac gtcgcag 37

<210> SEQ ID NO 85
<211> LENGTH: 30
<212> TYPE: DNA
<213> ORGANISM: Artificial Sequence
<220> FEATURE:
<223> OTHER INFORMATION: primer

<400> SEQUENCE: 85

```
gggaaggatc catcctggga aaaagttctg                                  30


<210> SEQ ID NO 86
<211> LENGTH: 1781
<212> TYPE: DNA
<213> ORGANISM: Enterobacter aerogenes
<220> FEATURE:
<221> NAME/KEY: CDS
<222> LOCATION: (19)..(1704)

<400> SEQUENCE: 86

gacaaggagg aatgacgt atg aat ata aac gtc gca gat ttg tta aac ggg       51
                    Met Asn Ile Asn Val Ala Asp Leu Leu Asn Gly
                    1               5                   10

aat tac atc ctg tta ttg ttt gtt gta ctc gca ctg ggt ctt tgc ctg       99
Asn Tyr Ile Leu Leu Leu Phe Val Val Leu Ala Leu Gly Leu Cys Leu
            15                  20                  25

ggg aaa ctt cgc ctc ggg tca gta caa ctt ggt aat tcc att ggc gtt      147
Gly Lys Leu Arg Leu Gly Ser Val Gln Leu Gly Asn Ser Ile Gly Val
        30                  35                  40

tta gtc gtt tct tta tta tta ggt cag cag cac ttc gcc att aac aca      195
Leu Val Val Ser Leu Leu Leu Gly Gln Gln His Phe Ala Ile Asn Thr
    45                  50                  55

gat gcg cta aat ctt ggc ttt atg ctg ttt att ttc tgc gtc ggc gtc      243
Asp Ala Leu Asn Leu Gly Phe Met Leu Phe Ile Phe Cys Val Gly Val
60                  65                  70                  75

gaa gcg ggc ccc aac ttt ttt tcg att ttt ttc cgc gac ggc aaa aac      291
Glu Ala Gly Pro Asn Phe Phe Ser Ile Phe Phe Arg Asp Gly Lys Asn
                80                  85                  90

tat cta atg ctg gcg ctg gtg atg gtg gcc agc gcg atg tta atc gct      339
Tyr Leu Met Leu Ala Leu Val Met Val Ala Ser Ala Met Leu Ile Ala
            95                  100                 105

atg ggg ctg ggc aaa ttg ttt ggc tgg gac atc ggc ctg acc gcc ggg      387
Met Gly Leu Gly Lys Leu Phe Gly Trp Asp Ile Gly Leu Thr Ala Gly
        110                 115                 120

atg ctg gcg ggc gct atg acc tcc acc ccg gtg ctg gtg ggc gct ggc      435
Met Leu Ala Gly Ala Met Thr Ser Thr Pro Val Leu Val Gly Ala Gly
    125                 130                 135

gat acc cta cgc cac ttt ggc ctg ccc agc gat cag ctg gcg cag tcg      483
Asp Thr Leu Arg His Phe Gly Leu Pro Ser Asp Gln Leu Ala Gln Ser
140                 145                 150                 155

ctt gac cac ctg agc ctg ggt tac gcc ctg act tac ctg gtt ggc ctg      531
Leu Asp His Leu Ser Leu Gly Tyr Ala Leu Thr Tyr Leu Val Gly Leu
                160                 165                 170

gtg agc ctg atc gtc ggc gcg cgc tat atg ccg aag ctg cag cat cag      579
Val Ser Leu Ile Val Gly Ala Arg Tyr Met Pro Lys Leu Gln His Gln
            175                 180                 185

gat ctg cag acc agc gcc cag cag atc gcc cgc gag cgc ggt ctg gat      627
Asp Leu Gln Thr Ser Ala Gln Gln Ile Ala Arg Glu Arg Gly Leu Asp
        190                 195                 200

acc gac tcc aag cgt aaa gtc tat ctg ccg gtt atc cgc gcc tac cgc      675
Thr Asp Ser Lys Arg Lys Val Tyr Leu Pro Val Ile Arg Ala Tyr Arg
    205                 210                 215
```

-continued

```
gtc ggc ccg gaa ttg gtc gcg tgg gcg gac ggc aaa aat ctt cgt gag      723
Val Gly Pro Glu Leu Val Ala Trp Ala Asp Gly Lys Asn Leu Arg Glu
220                 225                 230                 235

ctg gga att tac cgc cag acc ggc tgc tat atc gag cgt att cgt cgt      771
Leu Gly Ile Tyr Arg Gln Thr Gly Cys Tyr Ile Glu Arg Ile Arg Arg
                240                 245                 250

aac ggt atc ctg gcg aac ccg gat ggc gac gcg gta ctg cag atg ggc      819
Asn Gly Ile Leu Ala Asn Pro Asp Gly Asp Ala Val Leu Gln Met Gly
            255                 260                 265

gac gat atc gcg ctg gtt ggc tac ccg gac gcc cat gcc cgc ctc gac      867
Asp Asp Ile Ala Leu Val Gly Tyr Pro Asp Ala His Ala Arg Leu Asp
        270                 275                 280

cca agc ttc cgt aac ggt aaa gag gtg ttt gac cgc gac ctg ctc gat      915
Pro Ser Phe Arg Asn Gly Lys Glu Val Phe Asp Arg Asp Leu Leu Asp
    285                 290                 295

atg cgt atc gtc acc gaa gag att gtg gtt aag aat cat aac gcc gtc      963
Met Arg Ile Val Thr Glu Glu Ile Val Val Lys Asn His Asn Ala Val
300                 305                 310                 315

ggc cgc cgc ctg gcg cag ctg aag ctg acc gat cac ggc tgt ttc tta     1011
Gly Arg Arg Leu Ala Gln Leu Lys Leu Thr Asp His Gly Cys Phe Leu
                320                 325                 330

aac cgg gtg atc cgc agc cag att gag atg cca atc gac gat aac gtg     1059
Asn Arg Val Ile Arg Ser Gln Ile Glu Met Pro Ile Asp Asp Asn Val
            335                 340                 345

gtg ctc aat aaa ggc gac gtg ctg cag gtg agc ggc gac gcc cgc cgc     1107
Val Leu Asn Lys Gly Asp Val Leu Gln Val Ser Gly Asp Ala Arg Arg
        350                 355                 360

gta aaa acc gtc gct gac cgc atc ggc ttt att tcg att cac agc cag     1155
Val Lys Thr Val Ala Asp Arg Ile Gly Phe Ile Ser Ile His Ser Gln
    365                 370                 375

gtg acc gat ctg ctg gct ttc tgc gcc ttc ttt atc gtc ggc ctg atg     1203
Val Thr Asp Leu Leu Ala Phe Cys Ala Phe Phe Ile Val Gly Leu Met
380                 385                 390                 395

atc ggc atg atc act ttc cag ttc agc tcg ttc agc ttc ggc atc ggt     1251
Ile Gly Met Ile Thr Phe Gln Phe Ser Ser Phe Ser Phe Gly Ile Gly
                400                 405                 410

aac gcc gcc ggc ctg ctg ttc gcc ggc att atg ctt ggc ttc ctg cgc     1299
Asn Ala Ala Gly Leu Leu Phe Ala Gly Ile Met Leu Gly Phe Leu Arg
            415                 420                 425

gcc aac cat ccg acc ttc ggc tat atc ccg cag ggc gca ttg aac atg     1347
Ala Asn His Pro Thr Phe Gly Tyr Ile Pro Gln Gly Ala Leu Asn Met
        430                 435                 440

gtt aag gag ttc ggt ctg atg gtg ttt atg gcc ggg gtc ggc ctg agc     1395
Val Lys Glu Phe Gly Leu Met Val Phe Met Ala Gly Val Gly Leu Ser
    445                 450                 455

gcc ggc gcg ggt att aat aac ggt ctg ggc gcc att ggc ggg caa atg     1443
Ala Gly Ala Gly Ile Asn Asn Gly Leu Gly Ala Ile Gly Gly Gln Met
460                 465                 470                 475

ctg gct gcc ggt ctt atc gtc agc ctg gtg ccg gtg gtg atc tgc ttc     1491
Leu Ala Ala Gly Leu Ile Val Ser Leu Val Pro Val Val Ile Cys Phe
                480                 485                 490

ctg ttc ggc gcc tat gtg cta cgc atg aac cgc gcg atg ctg ttc ggc     1539
Leu Phe Gly Ala Tyr Val Leu Arg Met Asn Arg Ala Met Leu Phe Gly
            495                 500                 505

gcg atg atg ggc gcg cgc acc tgc gcc ccg gcg atg gaa att atc agc     1587
Ala Met Met Gly Ala Arg Thr Cys Ala Pro Ala Met Glu Ile Ile Ser
        510                 515                 520

gat acc gcg cgc agc aac att ccc gca ctc ggc tat gct ggc act tac     1635
Asp Thr Ala Arg Ser Asn Ile Pro Ala Leu Gly Tyr Ala Gly Thr Tyr
    525                 530                 535
```

```
gct atc gcc aac gtg ctg ctc acc ctt gcc ggt acg cta atc gtc atc     1683
Ala Ile Ala Asn Val Leu Leu Thr Leu Ala Gly Thr Leu Ile Val Ile
540                 545                 550                 555

atc tgg ccg ggc ctt ggc tag ccccggccga aaatttttaa ctttttcgca        1734
Ile Trp Pro Gly Leu Gly
                560

aaaaaatcgg tgatgaacag aactttttcc caggatggat ccttccc                 1781


<210> SEQ ID NO 87
<211> LENGTH: 561
<212> TYPE: PRT
<213> ORGANISM: Enterobacter aerogenes

<400> SEQUENCE: 87

Met Asn Ile Asn Val Ala Asp Leu Leu Asn Gly Asn Tyr Ile Leu Leu
1               5                   10                  15

Leu Phe Val Val Leu Ala Leu Gly Leu Cys Leu Gly Lys Leu Arg Leu
            20                  25                  30

Gly Ser Val Gln Leu Gly Asn Ser Ile Gly Val Leu Val Val Ser Leu
        35                  40                  45

Leu Leu Gly Gln Gln His Phe Ala Ile Asn Thr Asp Ala Leu Asn Leu
    50                  55                  60

Gly Phe Met Leu Phe Ile Phe Cys Val Gly Val Glu Ala Gly Pro Asn
65                  70                  75                  80

Phe Phe Ser Ile Phe Phe Arg Asp Gly Lys Asn Tyr Leu Met Leu Ala
                85                  90                  95

Leu Val Met Val Ala Ser Ala Met Leu Ile Ala Met Gly Leu Gly Lys
            100                 105                 110

Leu Phe Gly Trp Asp Ile Gly Leu Thr Ala Gly Met Leu Ala Gly Ala
        115                 120                 125

Met Thr Ser Thr Pro Val Leu Val Gly Ala Gly Asp Thr Leu Arg His
    130                 135                 140

Phe Gly Leu Pro Ser Asp Gln Leu Ala Gln Ser Leu Asp His Leu Ser
145                 150                 155                 160

Leu Gly Tyr Ala Leu Thr Tyr Leu Val Gly Leu Val Ser Leu Ile Val
                165                 170                 175

Gly Ala Arg Tyr Met Pro Lys Leu Gln His Gln Asp Leu Gln Thr Ser
            180                 185                 190

Ala Gln Gln Ile Ala Arg Glu Arg Gly Leu Asp Thr Asp Ser Lys Arg
        195                 200                 205

Lys Val Tyr Leu Pro Val Ile Arg Ala Tyr Arg Val Gly Pro Glu Leu
    210                 215                 220

Val Ala Trp Ala Asp Gly Lys Asn Leu Arg Glu Leu Gly Ile Tyr Arg
225                 230                 235                 240

Gln Thr Gly Cys Tyr Ile Glu Arg Ile Arg Arg Asn Gly Ile Leu Ala
                245                 250                 255

Asn Pro Asp Gly Asp Ala Val Leu Gln Met Gly Asp Asp Ile Ala Leu
            260                 265                 270

Val Gly Tyr Pro Asp Ala His Ala Arg Leu Asp Pro Ser Phe Arg Asn
        275                 280                 285

Gly Lys Glu Val Phe Asp Arg Asp Leu Leu Asp Met Arg Ile Val Thr
    290                 295                 300

Glu Glu Ile Val Val Lys Asn His Asn Ala Val Gly Arg Arg Leu Ala
305                 310                 315                 320
```

-continued

```
Gln Leu Lys Leu Thr Asp His Gly Cys Phe Leu Asn Arg Val Ile Arg
                325                 330                 335

Ser Gln Ile Glu Met Pro Ile Asp Asp Asn Val Val Leu Asn Lys Gly
            340                 345                 350

Asp Val Leu Gln Val Ser Gly Asp Ala Arg Arg Val Lys Thr Val Ala
        355                 360                 365

Asp Arg Ile Gly Phe Ile Ser Ile His Ser Gln Val Thr Asp Leu Leu
    370                 375                 380

Ala Phe Cys Ala Phe Phe Ile Val Gly Leu Met Ile Gly Met Ile Thr
385                 390                 395                 400

Phe Gln Phe Ser Ser Phe Ser Phe Gly Ile Gly Asn Ala Ala Gly Leu
                405                 410                 415

Leu Phe Ala Gly Ile Met Leu Gly Phe Leu Arg Ala Asn His Pro Thr
            420                 425                 430

Phe Gly Tyr Ile Pro Gln Gly Ala Leu Asn Met Val Lys Glu Phe Gly
        435                 440                 445

Leu Met Val Phe Met Ala Gly Val Gly Leu Ser Ala Gly Ala Gly Ile
    450                 455                 460

Asn Asn Gly Leu Gly Ala Ile Gly Gly Gln Met Leu Ala Ala Gly Leu
465                 470                 475                 480

Ile Val Ser Leu Val Pro Val Val Ile Cys Phe Leu Phe Gly Ala Tyr
                485                 490                 495

Val Leu Arg Met Asn Arg Ala Met Leu Phe Gly Ala Met Met Gly Ala
            500                 505                 510

Arg Thr Cys Ala Pro Ala Met Glu Ile Ile Ser Asp Thr Ala Arg Ser
        515                 520                 525

Asn Ile Pro Ala Leu Gly Tyr Ala Gly Thr Tyr Ala Ile Ala Asn Val
    530                 535                 540

Leu Leu Thr Leu Ala Gly Thr Leu Ile Val Ile Ile Trp Pro Gly Leu
545                 550                 555                 560

Gly
```

<210> SEQ ID NO 88
<211> LENGTH: 561
<212> TYPE: PRT
<213> ORGANISM: Artificial Sequence
<220> FEATURE:
<223> OTHER INFORMATION: conserved sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:

<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: misc_feature
<222> LOCATION: (104)..(106)
<223> OTHER INFORMATION: Xaa can be any naturally occurring amino acid
<220> FEATURE:
<221> NAME/KEY: misc_feature
<222> LOCATION: (108)..(108)
<223> OTHER INFORMATION: Xaa can be any naturally occurring amino acid
<220> FEATURE:
<221> NAME/KEY: misc_feature
<222> LOCATION: (110)..(110)
<223> OTHER INFORMATION: Xaa can be any naturally occurring amino acid
<220> FEATURE:
<221> NAME/KEY: misc_feature
<222> LOCATION: (124)..(124)
<223> OTHER INFORMATION: Xaa can be any naturally occurring amino acid
<220> FEATURE:
<221> NAME/KEY: misc_feature
<222> LOCATION: (128)..(128)
<223> OTHER INFORMATION: Xaa can be any naturally occurring amino acid
<220> FEATURE:
<221> NAME/KEY: misc_feature
<222> LOCATION: (144)..(146)
<223> OTHER INFORMATION: Xaa can be any naturally occurring amino acid
<220> FEATURE:
<221> NAME/KEY: misc_feature
<222> LOCATION: (149)..(150)
<223> OTHER INFORMATION: Xaa can be any naturally occurring amino acid
<220> FEATURE:
<221> NAME/KEY: misc_feature
<222> LOCATION: (153)..(156)
<223> OTHER INFORMATION: Xaa can be any naturally occurring amino acid
<220> FEATURE:
<221> NAME/KEY: misc_feature
<222> LOCATION: (158)..(158)
<223> OTHER INFORMATION: Xaa can be any naturally occurring amino acid
<220> FEATURE:
<221> NAME/KEY: misc_feature
<222> LOCATION: (165)..(165)
<223> OTHER INFORMATION: Xaa can be any naturally occurring amino acid
<220> FEATURE:
<221> NAME/KEY: misc_feature
<222> LOCATION: (169)..(169)
<223> OTHER INFORMATION: Xaa can be any naturally occurring amino acid -continued
<220> FEATURE:
<221> NAME/KEY: misc_feature
<222> LOCATION: (176)..(176)
<223> OTHER INFORMATION: Xaa can be any naturally occurring amino acid
<220> FEATURE:
<221> NAME/KEY: misc_feature
<222> LOCATION: (181)..(181)
<223> OTHER INFORMATION: Xaa can be any naturally occurring amino acid
<220> FEATURE:
<221> NAME/KEY: misc_feature
<222> LOCATION: (183)..(183)
<223> OTHER INFORMATION: Xaa can be any naturally occurring amino acid
<220> FEATURE:
<221> NAME/KEY: misc_feature
<222> LOCATION: (190)..(190)
<223> OTHER INFORMATION: Xaa can be any naturally occurring amino acid
<220> FEATURE:
<221> NAME/KEY: misc_feature
<222> LOCATION: (192)..(192)
<223> OTHER INFORMATION: Xaa can be any naturally occurring amino acid
<220> FEATURE:
<221> NAME/KEY: misc_feature
<222> LOCATION: (204)..(204)
<223> OTHER INFORMATION: Xaa can be any naturally occurring amino acid
<220> FEATURE:
<221> NAME/KEY: misc_feature
<222> LOCATION: (206)..(207)
<223> OTHER INFORMATION: Xaa can be any naturally occurring amino acid
<220> FEATURE:
<221> NAME/KEY: misc_feature
<222> LOCATION: (211)..(211)
<223> OTHER INFORMATION: Xaa can be any naturally occurring amino acid
<220> FEATURE:
<221> NAME/KEY: misc_feature
<222> LOCATION: (228)..(229)
<223> OTHER INFORMATION: Xaa can be any naturally occurring amino acid
<220> FEATURE:
<221> NAME/KEY: misc_feature
<222> LOCATION: (257)..(257)
<223> OTHER INFORMATION: Xaa can be any naturally occurring amino acid
<220> FEATURE:
<221> NAME/KEY: misc_feature
<222> LOCATION: (266)..(266)
<223> OTHER INFORMATION: Xaa can be any naturally occurring amino acid
<220> FEATURE:
<221> NAME/KEY: misc_feature
<222> LOCATION: (269)..(269)
<223> OTHER INFORMATION: Xaa can be any naturally occurring amino acid
<220> FEATURE:
<221> NAME/KEY: misc_feature
<222> LOCATION: (271)..(271)
<223> OTHER INFORMATION: Xaa can be any naturally occurring amino acid
<220> FEATURE:
<221> NAME/KEY: misc_feature
<222> LOCATION: (284)..(284)
<223> OTHER INFORMATION: Xaa can be any naturally occurring amino acid
<220> FEATURE:
<221> NAME/KEY: misc_feature
<222> LOCATION: (307)..(307)
<223> OTHER INFORMATION: Xaa can be any naturally occurring amino acid
<220> FEATURE:
<221> NAME/KEY: misc_feature
<222> LOCATION: (316)..(317)
<223> OTHER INFORMATION: Xaa can be any naturally occurring amino acid
<220> FEATURE:
<221> NAME/KEY: misc_feature
<222> LOCATION: (320)..(321)
<223> OTHER INFORMATION: Xaa can be any naturally occurring amino acid
<220> FEATURE:
<221> NAME/KEY: misc_feature
<222> LOCATION: (323)..(323)
<223> OTHER INFORMATION: Xaa can be any naturally occurring amino acid
<220> FEATURE:
<221> NAME/KEY: misc_feature
<222> LOCATION: (347)..(348)
<223> OTHER INFORMATION: Xaa can be any naturally occurring amino acid
<220> FEATURE:
<221> NAME/KEY: misc_feature
<222> LOCATION: (360)..(360)

<223> OTHER INFORMATION: Xaa can be any naturally occurring amino acid
<220> FEATURE:
<221> NAME/KEY: misc_feature
<222> LOCATION: (366)..(367)
<223> OTHER INFORMATION: Xaa can be any naturally occurring amino acid
<220> FEATURE:
<221> NAME/KEY: misc_feature
<222> LOCATION: (374)..(375)
<223> OTHER INFORMATION: Xaa can be any naturally occurring amino acid
<220> FEATURE:
<221> NAME/KEY: misc_feature
<222> LOCATION: (380)..(380)
<223> OTHER INFORMATION: Xaa can be any naturally occurring amino acid
<220> FEATURE:
<221> NAME/KEY: misc_feature
<222> LOCATION: (391)..(392)
<223> OTHER INFORMATION: Xaa can be any naturally occurring amino acid
<220> FEATURE:
<221> NAME/KEY: misc_feature
<222> LOCATION: (396)..(396)
<223> OTHER INFORMATION: Xaa can be any naturally occurring amino acid
<220> FEATURE:
<221> NAME/KEY: misc_feature
<222> LOCATION: (398)..(398)
<223> OTHER INFORMATION: Xaa can be any naturally occurring amino acid
<220> FEATURE:
<221> NAME/KEY: misc_feature
<222> LOCATION: (405)..(405)
<223> OTHER INFORMATION: Xaa can be any naturally occurring amino acid
<220> FEATURE:
<221> NAME/KEY: misc_feature
<222> LOCATION: (410)..(410)
<223> OTHER INFORMATION: Xaa can be any naturally occurring amino acid
<220> FEATURE:
<221> NAME/KEY: misc_feature
<222> LOCATION: (426)..(426)
<223> OTHER INFORMATION: Xaa can be any naturally occurring amino acid
<220> FEATURE:
<221> NAME/KEY: misc_feature
<222> LOCATION: (442)..(442)
<223> OTHER INFORMATION: Xaa can be any naturally occurring amino acid
<220> FEATURE:
<221> NAME/KEY: misc_feature
<222> LOCATION: (462)..(462)
<223> OTHER INFORMATION: Xaa can be any naturally occurring amino acid
<220> FEATURE:
<221> NAME/KEY: misc_feature
<222> LOCATION: (465)..(466)
<223> OTHER INFORMATION: Xaa can be any naturally occurring amino acid
<220> FEATURE:
<221> NAME/KEY: misc_feature
<222> LOCATION: (468)..(471)
<223> OTHER INFORMATION: Xaa can be any naturally occurring amino acid
<220> FEATURE:
<221> NAME/KEY: misc_feature
<222> LOCATION: (473)..(474)
<223> OTHER INFORMATION: Xaa can be any naturally occurring amino acid
<220> FEATURE:
<221> NAME/KEY: misc_feature
<222> LOCATION: (477)..(478)
<223> OTHER INFORMATION: Xaa can be any naturally occurring amino acid
<220> FEATURE:
<221> NAME/KEY: misc_feature
<222> LOCATION: (481)..(481)
<223> OTHER INFORMATION: Xaa can be any naturally occurring amino acid
<220> FEATURE:
<221> NAME/KEY: misc_feature
<222> LOCATION: (485)..(485)
<223> OTHER INFORMATION: Xaa can be any naturally occurring amino acid
<220> FEATURE:
<221> NAME/KEY: misc_feature
<222> LOCATION: (491)..(491)
<223> OTHER INFORMATION: Xaa can be any naturally occurring amino acid
<220> FEATURE:
<221> NAME/KEY: misc_feature
<222> LOCATION: (504)..(504)
<223> OTHER INFORMATION: Xaa can be any naturally occurring amino acid
<220> FEATURE:
<221> NAME/KEY: misc_feature
<222> LOCATION: (509)..(509)
<223> OTHER INFORMATION: Xaa can be any naturally occurring amino acid
<220> FEATURE:
<221> NAME/KEY: misc_feature
<222> LOCATION: (552)..(552)
<223> OTHER INFORMATION: Xaa can be any naturally occurring amino acid
<220> FEATURE:
<221> NAME/KEY: misc_feature
<222> LOCATION: (555)..(556)
<223> OTHER INFORMATION: Xaa can be any naturally occurring amino acid
<220> FEATURE:
<221> NAME/KEY: misc_feature
<222> LOCATION: (559)..(559)
<223> OTHER INFORMATION: Xaa can be any naturally occurring amino acid
<220> FEATURE:
<221> NAME/KEY: misc_feature
<222> LOCATION: (561)..(561)
<223> OTHER INFORMATION: Xaa can be any naturally occurring amino acid

<400> SEQUENCE: 88

```
Xaa Asn Xaa Asn Xaa Ala Xaa Leu Leu Xaa Gly Asn Xaa Ile Leu Leu
1               5                   10                  15

Leu Phe Xaa Val Leu Ala Leu Gly Leu Cys Leu Gly Lys Leu Arg Xaa
            20                  25                  30

Gly Ser Xaa Gln Leu Gly Asn Ser Ile Gly Val Leu Val Val Ser Leu
        35                  40                  45

Leu Leu Gly Gln Gln His Phe Xaa Xaa Asn Thr Asp Ala Leu Xaa Leu
    50                  55                  60

Gly Phe Met Leu Phe Ile Phe Cys Val Gly Xaa Glu Ala Gly Pro Asn
65                  70                  75                  80

Phe Phe Ser Ile Phe Phe Arg Asp Gly Lys Asn Tyr Xaa Met Leu Ala
                85                  90                  95

Xaa Val Met Val Xaa Ser Ala Xaa Xaa Xaa Ala Xaa Gly Xaa Gly Lys
            100                 105                 110

Leu Phe Gly Trp Asp Ile Gly Leu Thr Ala Gly Xaa Leu Ala Gly Xaa
        115                 120                 125

Met Thr Ser Thr Pro Val Leu Val Gly Ala Gly Asp Thr Leu Arg Xaa
    130                 135                 140

Xaa Xaa Met Glu Xaa Xaa Gln Leu Xaa Xaa Xaa Xaa Asp Xaa Leu Ser
145                 150                 155                 160

Leu Gly Tyr Ala Xaa Thr Tyr Leu Xaa Gly Leu Val Ser Leu Ile Xaa
                165                 170                 175

Gly Ala Arg Tyr Xaa Pro Xaa Leu Gln His Gln Asp Leu Xaa Thr Xaa
            180                 185                 190

Ala Gln Gln Ile Ala Arg Glu Arg Gly Leu Asp Xaa Asp Xaa Xaa Arg
        195                 200                 205

Lys Val Xaa Leu Pro Val Ile Arg Ala Tyr Arg Val Gly Pro Glu Leu
    210                 215                 220

Val Ala Trp Xaa Xaa Gly Lys Asn Leu Arg Glu Leu Gly Ile Tyr Arg
225                 230                 235                 240

Gln Thr Gly Cys Tyr Ile Glu Arg Ile Arg Arg Asn Gly Ile Leu Ala
                245                 250                 255

Xaa Pro Asp Gly Asp Ala Val Leu Gln Xaa Gly Asp Xaa Ile Xaa Leu
            260                 265                 270

Val Gly Tyr Pro Asp Ala His Ala Arg Leu Asp Xaa Ser Phe Arg Asn
        275                 280                 285

Gly Lys Glu Val Phe Asp Arg Asp Leu Leu Asp Met Arg Ile Val Thr
    290                 295                 300

Glu Glu Xaa Val Val Lys Asn His Asn Ala Val Xaa Xaa Arg Leu Xaa
```

-continued

```
305                 310                 315                 320

Xaa Leu Xaa Leu Thr Asp His Gly Cys Phe Leu Asn Arg Val Ile Arg
                325                 330                 335

Ser Gln Ile Glu Met Pro Ile Asp Asp Asn Xaa Xaa Leu Asn Lys Gly
            340                 345                 350

Asp Val Leu Gln Val Ser Gly Xaa Ala Arg Arg Val Lys Xaa Xaa Ala
        355                 360                 365

Asp Arg Ile Gly Phe Xaa Xaa Ile His Ser Gln Xaa Thr Asp Leu Leu
    370                 375                 380

Ala Phe Cys Ala Phe Phe Xaa Xaa Gly Leu Met Xaa Gly Xaa Ile Thr
385                 390                 395                 400

Phe Gln Phe Ser Xaa Phe Ser Phe Gly Xaa Gly Asn Ala Ala Gly Leu
                405                 410                 415

Leu Phe Ala Gly Ile Met Leu Gly Phe Xaa Arg Ala Asn His Pro Thr
            420                 425                 430

Phe Gly Tyr Ile Pro Gln Gly Ala Leu Xaa Met Val Lys Glu Phe Gly
        435                 440                 445

Leu Met Val Phe Met Ala Gly Val Gly Leu Ser Ala Gly Xaa Gly Ile
    450                 455                 460

Xaa Xaa Gly Xaa Xaa Xaa Xaa Gly Xaa Xaa Met Leu Xaa Xaa Gly Leu
465                 470                 475                 480

Xaa Val Ser Leu Xaa Pro Val Val Ile Cys Xaa Leu Phe Gly Ala Tyr
                485                 490                 495

Val Leu Arg Met Asn Arg Ala Xaa Leu Phe Gly Ala Xaa Met Gly Ala
            500                 505                 510

Arg Thr Cys Ala Pro Ala Met Glu Ile Ile Ser Asp Thr Ala Arg Ser
        515                 520                 525

Asn Ile Pro Ala Leu Gly Tyr Ala Gly Thr Tyr Ala Ile Ala Asn Val
    530                 535                 540

Leu Leu Thr Leu Ala Gly Thr Xaa Ile Val Xaa Xaa Trp Pro Xaa Leu
545                 550                 555                 560

Xaa
```